(12) United States Patent
Callewaert et al.

(10) Patent No.: US 8,026,083 B2
(45) Date of Patent: Sep. 27, 2011

(54) YARROWIA LIPOLYTICA AND PICHIA PASTORIS HAC1 NUCLEIC ACIDS

(75) Inventors: Nico Luc Marc Callewaert, Hansbeke-Nevele (BE); Wouter Vervecken, Ghent-Ledeberg (BE); Karen Jacqueline Marcel De Pourcq, Merelbeke (BE); Steven Christian Jozef Geysens, Kruishoutem (BE); Mouna Guerfal, Ghent-Drongen (BE)

(73) Assignees: Oxyrane UK Limited, Manchester (GB); VIB vzw, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 12/062,469

(22) Filed: Apr. 3, 2008

(65) Prior Publication Data

US 2009/0069232 A1 Mar. 12, 2009

Related U.S. Application Data

(60) Provisional application No. 60/909,904, filed on Apr. 3, 2007, provisional application No. 60/940,212, filed on May 25, 2007.

(51) Int. Cl.
*C12N 15/63* (2006.01)
*C12N 15/04* (2006.01)
*C12N 15/11* (2006.01)
*C12P 21/06* (2006.01)

(52) U.S. Cl. ............... 435/69.1; 435/254.2; 435/254.23; 435/320.1; 536/23.1; 536/23.74; 530/350

(58) Field of Classification Search ........................ None
See application file for complete search history.

(56) References Cited

U.S. PATENT DOCUMENTS

2006/0148039 A1 7/2006 Kobayashi et al.

FOREIGN PATENT DOCUMENTS

| WO | WO 01/49830 | 7/2001 |
| WO | WO 03/056914 A | 7/2003 |
| WO | WO 2004/074458 A | 9/2004 |

OTHER PUBLICATIONS

Song et al, Yeast, 2003, 9-23.*
Callewaert et al, FEBS Letters, 2001, V. 503, pp. 173-178.*
Bobrowicz et al., "Engineering of an artificial glycosylation pathway blocked in core oligosaccharide assembly in the yeast *Pichia pastoris*: production of complex humanized glycoproteins with terminal galactose", Glycobiology, 14(9):757-766 (2004).
Burda et al., "Ordered assembly of the asymmetrically branched lipid-linked oligosaccharide in the endoplasmic reticulum is ensured by the substrate specificity of the individual glycosyltransferases", Glycobiology, 9(6):617-625 (1999).
Chiba et al., "Production in yeast of alpha-galactosidase A, a lysomal enzyme applicable to enzyme replacement therapy for Fabry disease", Glycobiology, 12(12):821-828 (2002).
Madzak et al., "Heterologous Protein Expression and Secretion in the Non-conventional Yeast *Yarrowia lipolytica*: A Review", J. Biotechnol., 109:63-81 (2004).
Barnay-Verdier et al., "Identification and characterization of two alpha-1,6-mannosyltransferases, Anl1p and Och1p, in the yeast *Yarrowia lipolytica*", Microbiology, 150;2185-2195 (2004).
Database Accession No. P41546, UniProt (online), "RecName: Full Transcriptional Activator HAC1"; XP002509286, Nov. 1, 1995; Nojima et al.
Authorized Officer Cecile Chatel, International Preliminary Report on Patentability in PCT/IB2008/001814 mailed Oct. 15, 2009, 16 pages.
Song, Y, et al., "Engineering of the Yeast *Yarrowia lipolytica* for the Production of Glycoproteins Lacking the Outer-Chain Mannose Residue of N-Glycans," *Applied and Environmental Microbiology*, Jul. 2007, pp. 4446-4454.
Gellissen, et al., New yeast expression platforms based on methylotrophic *Hansenula polymorpha* and *Pichia pastoris* and on dimorphic *Arxula adeninivorans* and *Yarrowia lipolytica*—A comparison, *FEMS Yeast Research*, Aug. 24, 2005, pp. 1079-1096.
Caroline, Berger, European Patent Office, Examination Report, EP Application No. 08-776-351.2, dated Jan. 22, 2010, 4 pages.
Eric Toh Hock Chye, Assistant Registrar for Registrar of Patents Singapore, Singapore Search Report & Written Opinion, dated Oct. 26, 2010.
Fickers, P. et al. "Hydrophobic substrate utilization by the yeast *Yarrowia lipolytica* and its potential applications," FEMS Yeast Research, Apr. 2005, vol. 5, No. 6-7, pp. 527-543.
Akeboshi et al., "Production of Recombinant Beta-Hexosaminidase A, a Potential Enzyme for Replacement Therapy for Tay-Sachs and Sandhoff Diseases, in the Methylotrophic Yeast *Ogataea minuta*", Appl. Environ. Microbiol., 73(15):4805-4812 (2007).
Kuroda et al., "Production of Man5GlcNAc2-type sugar chain by the methylotrophic yeast *Ogataea minuta*", FEMS Yeast Res. 6:1052-1062 (2006).

* cited by examiner

*Primary Examiner* — Bridget E Bunner
*Assistant Examiner* — Fozia Hamud
(74) *Attorney, Agent, or Firm* — Fish & Richardson P.C.

(57) ABSTRACT

Described herein are methods and genetically engineered cells useful for producing an altered N-glycosylation form of a target molecule. Also described are methods and molecules with altered N-glycosylation useful for treating a variety of disorders such as metabolic disorders.

22 Claims, 82 Drawing Sheets

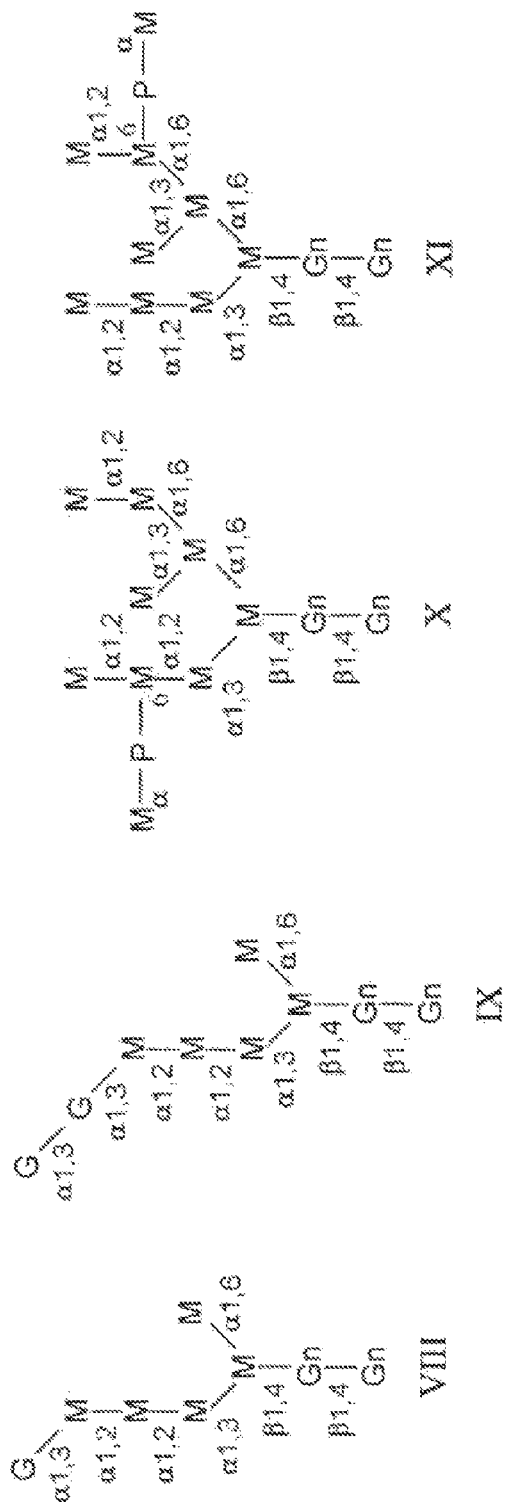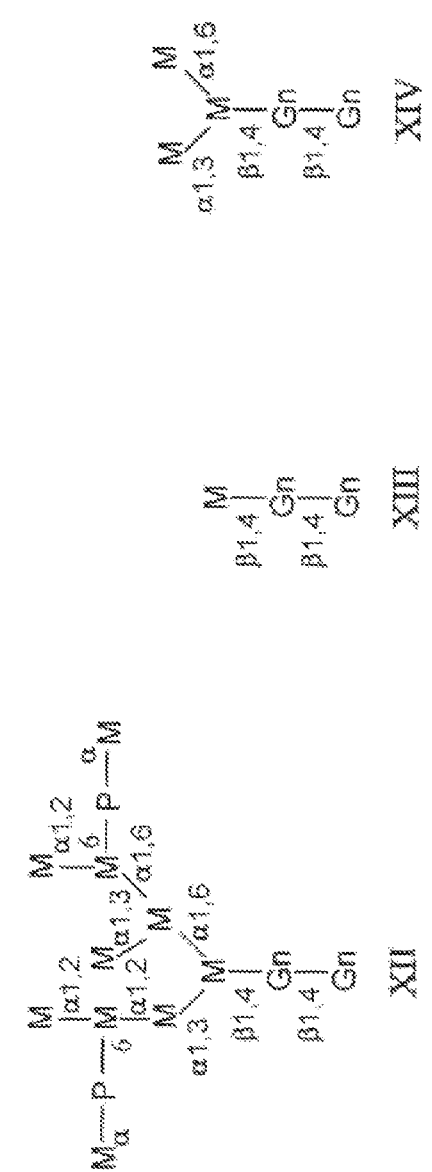
FIG. 4B
M: Mannose  G: Glucose  Gn: N-acetylglucosamine  P: Phosphate

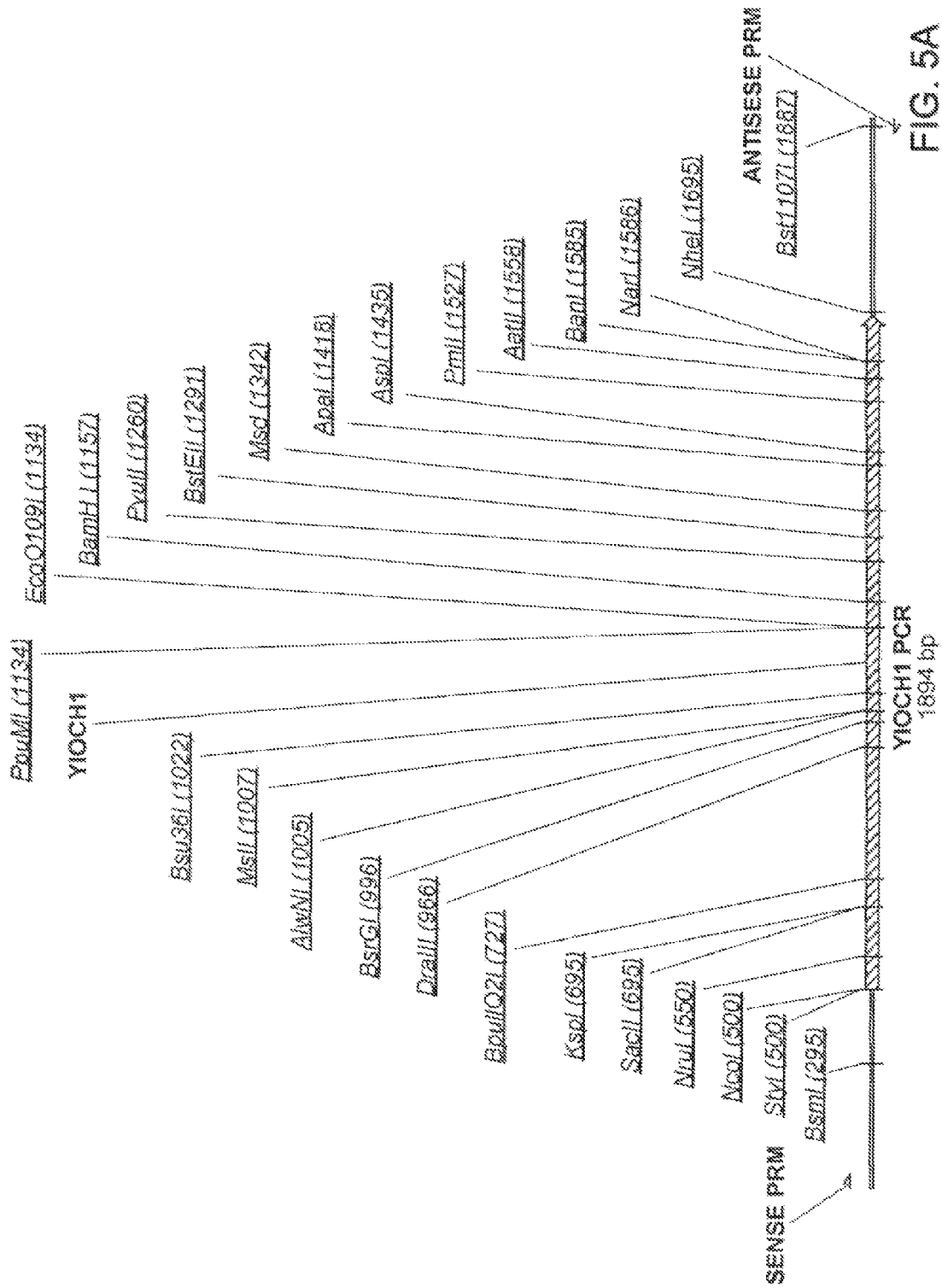

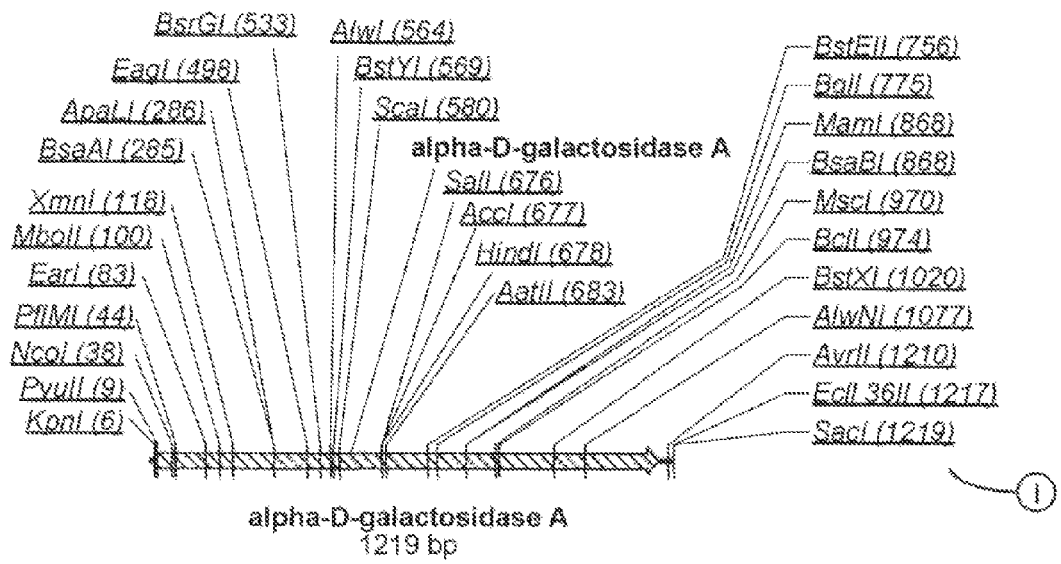
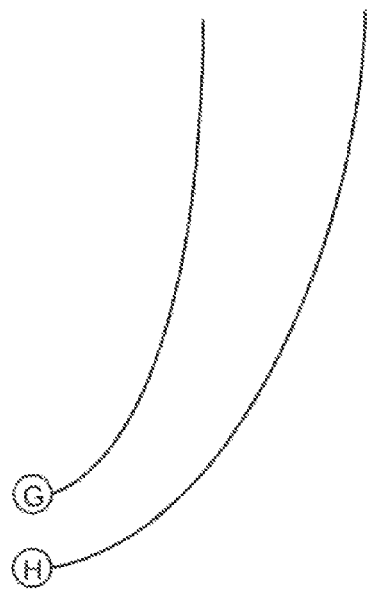
FIG. 12F

FIG. 15

5' splice site

P. pastoris    atccagcagtgatgacg
S. cerevisiae  atccagccgtgattacg
               ****  *

3' splice site

P. pastoris    ggtctgcagcaccat
S. cerevisiae  tgtccgaagcgcagt
               *** * *** * *

FIG. 16

```
NL      1  atgcccgtagattcttctcataagacagctagcccacttccacctcgtaa   50
           ||||||||||||||||||||||||||||||||||||||||||||||||||
L       1  atgcccgtagattcttctcataagacagctagcccacttccacctcgtaa   50

NL     51  aagagcaaagacggaagaagaaaaggagcagcgtcgagtggaacgtatcc  100
           ||||||||||||||||||||||||||||||||||||||||||||||||||
L      51  aagagcaaagacggaagaagaaaaggagcagcgtcgagtggaacgtatcc  100

NL    101  tacgtaataggagagcggcccatgcttcagagagaagaaacgaagacac   150
           ||||||||||||||||||||||||||||||||||||||||||||||||||
L     101  tacgtaataggagagcggcccatgcttcagagagaagaaacgaagacac   150

NL    151  gttgaatttctggaaaaccacgtcgtcgacctggaatctgcacttcaaga  200
           ||||||||||||||||||||||||||||||||||||||||||||||||||
L     151  gttgaatttctggaaaaccacgtcgtcgacctggaatctgcacttcaaga  200

NL    201  atcagccaaagccactaacaagttgaaagaaatacaagatatcattgttt  250
           ||||||||||||||||||||||||||||||||||||||||||||||||||
L     201  atcagccaaagccactaacaagttgaaagaaatacaagatatcattgttt  250

NL    251  caaggttggaagccttaggtggtaccgtctcagatttggatttaacagtt  300
           ||||||||||||||||||||||||||||||||||||||||||||||||||
L     251  caaggttggaagccttaggtggtaccgtctcagatttggatttaacagtt  300

NL    301  ccggaagtcgattttcccaaatcttctgatttggaacccatgtctgatct  350
           ||||||||||||||||||||||||||||||||||||||||||||||||||
L     301  ccggaagtcgattttcccaaatcttctgatttggaacccatgtctgatct  350

NL    351  ctcaacttcttcgaaatcggagaaagcatctacatccactcgcagatctt  400
           ||||||||||||||||||||||||||||||||||||||||||||||||||
L     351  ctcaacttcttcgaaatcggagaaagcatctacatccactcgcagatctt  400

NL    401  tgactgaggatctggacgaagatgacgtcgctgaatatgacgacgaagaa  450
           ||||||||||||||||||||||||||||||||||||||||||||||||||
L     401  tgactgaggatctggacgaagatgacgtcgctgaatatgacgacgaagaa  450

NL    451  gaggacgaagagttacccaggaaatgaaagtcttaaacgacaaaaacaa   500
           ||||||||||||||||||||||||||||||||||||||||||||||||||
L     451  gaggacgaagagttacccaggaaatgaaagtcttaaacgacaaaaacaa   500

NL    501  gagcacatctatcaagcaggagaagttgaatgaacttccatctcctttgt  550
           ||||||||||||||||||||||||||||||||||||||||||||||||||
L     501  gagcacatctatcaagcaggagaagttgaatgaacttccatctcctttgt  550

NL    551  catccgattttcagacgtagatgaagaaagtcaactctcacacattta   600
           ||||||||||||||||||||||||||||||||||||||||||||||||||
L     551  catccgattttcagacgtagatgaagaaagtcaactctcacacattta   600

NL    601  aagttgcaacagcaacaacaacaaccagtagacaattatgtttctactcc  650
           ||||||||||||||||||||||||||||||||||||||||||||||||||
L     601  aagttgcaacagcaacaacaacaaccagtagacaattatgtttctactcc  650
```

FIG. 17A

```
NI.   651  tttgagtcttccggaggattcagttgatttattaacccaggtaacttaa  700
           |||||||||||||||||||||||||||||||||||||||||||||||||
I.    651  tttgagtcttccggaggattcagttgatttattaacccaggtaacttaa  700

NI.   701  aaatagagtccgatgagaacttcttgttgagttcaaatactttacaaata  750
           |||||||||||||||||||||||||||||||||||||||||||||||||
I.    701  aaatagagtccgatgagaacttcttgttgagttcaaatactttacaaata  750

NI.   751  aaacacgaaaatgacaccgactacattactacagctccatcaggttccat  800
           |||||||||||||||||||||||||||||||||||||||||||||||||
I.    751  aaacacgaaaatgacaccgactacattactacagctccatcaggttccat  800

NI.   801  caatgatttttttaattcttatgacattagcgagtcgaatcggttgcatc  850
           |||||||||||||||||||||||||||||||||||||||||||||||||
I.    801  caatgatttttttaattcttatgacattagcgagtcgaatcggttgcatc  850

NI.   851  atccagcagtgatgacggattcatctttacacattacagcaggctccatc  900
           ||||||
I.    851  atccag--------------------------------------------  855

NI.   901  ggcttttctctttgattgggggggggaaagttctgtagcagggaggcg    950
I.    856  -------------------------------------------------  855

NI.   951  cagttcagttggcacatatcagttgacatgcatagcgatcaggtgattgc 1000
I.    856  -------------------------------------------------  855

NI.  1001  tcttgttaactggtatgccaagtcaaccgttttcggcgtacctactactc 1050
I.    856  -------------------------------------------------  855

NI.  1051  tactttaactcttgaattgagatgaaacaatcgcccttgttcgagacgcg 1100
I.    856  -------------------------------------------------  855

NI.  1101  tagttaatttaagatgaatcaatttgcacaaaagaacaaacgaaaaga   1150
I.    856  -------------------------------------------------  855

NI.  1151  taacagcaaacttaagtttcgtggtctgcagcaccatttaccgctaatgc 1200
                                              ||||||||||||||||||
I.    856  -----------------------------cagcaccatttaccgctaatgc  878

NI.  1201  atttgatttaaatgactttgtattcttccaggaatag 1237
           |||||||||||||||||||||||||||||||||||||
I.    879  atttgatttaaatgactttgtattcttccaggaatag  915
```

FIG. 17B

```
P.pastoris       1  APFTANAFDLNDFVFPQE
18
                    |....|:|:||||....
S.cerevisiae     1  EAQSGLNSFELNDFFITS
18
```

FIG. 18

MSIKREESFTPTPEDLGSPLTADSPQSPESGDKRKKDLTLP
LPAGALPPRKRAKTENEKEQRRIERIMRNRQAAHASREKKRRH
LEDLEKKCSELSSENNDLHHQVTESKKTNMHLMEQHYSLVAK
LQQLSSLVNMAKSSGALAGVDVPDMSDVSMAPKLEMPTAAPS
QPMGLASAPTLFNHDNETVVPDSPIVKTEEVDSTNFLLHTESSS
PPELAESTGSGSPSSTLSCDETDYLVDRARHPAASAQDFIFIKD
EPVDDELGLHGLSDDFTLFEDNKQPAQHDFIADLAHYESSVSN
LFGGLE

FIG. 27A

MPVDSSHKTASPLPPRKRAKTEEEKEQRRVERILRNRRAA
HASREKKRRHVEFLENHVVDLESALQESAKATNKLKEIQDIIV
SRLEALGGTVSDLDLTVPEVDFPKSSDLEPMSDLSTSSKSEKAS
TSTRRSLTEDLDEDDVAEYDDEEEDEELPRKMKVLNDKNKSTS
IKQEKLNELPSPLSSDFSDVDEEKSTLTHLKLQQQQQPVDNY
VSTPLSLPEDSVDFINPGNLKIESDENFLLSSNTLQIKHENDTD
YITTAPSGSINDFFNSYDISESNRLHHPAAPFTANAFDLNDFVF
FQE

FIG. 27B gtaaagcacgagaacttcaagaccgttctcagtctggcttctgtaagcgaaaccgagccttcgccgacgacgccgctg
cccagggctcttcttgggcctctccctacgagctggactcttcttctatccagttcaaggacggccagctgcacggcacc
atcctgaagtctgtgtctcccaacgagaaggtgaagctgcccctggtggtgtcttcctggagtctggcgccgctcgagt
ggtggtggacgaggagaagcgaatgaacggcgacatccagctgcgacacgactctaaggcccgaaaggagcgata
caacgaggccgagaagtgggtgctggtcggcggcctggagctgtctaagaccgccaccctgcgacccgagaccga
gtctggcttcacccgagtgctgtacggccccgacaaccagttcgaggccgtgatccgacacgcccccttctctgccgac
ttcaagcgagatggccagacccacgtgcagctgaacaacaaggcctacctgaacatggagcactggcgacccaagg
tggaggtggagggcgagggtgagcagcagacccaggaggacgagtctacctggtgggacgagtctttcggcggca
acaccgacaccaagccccgaggccccgagtctgtgggcctggacatcaccttccccggctacaagcacgtgttcggc
atccccgagcacgccgactccctgtctctgaaggagacccgaggcggcgagggcaaccacgaggagccctaccga
atgtacaacgccgacgtgttcgagtacgagctgtcctctcccatgaccctgtacggcgccatccccttcatgcaggccca
ccgaaaggactctaccgtgggcgtgttctggctgaacgccgccgagacctgggtggacatcgtgaagtctacctcttct
cccaaccccctggccctgggcgtggggagccaccaccgacacccagtctcactggttctctgagtctggccagctggac
gtgttcgtgttcctggggccccacccccaggagatttctaagacctacggcgagctgaccggctacacccagctgcccc
agcactcgccattgcctaccaccagtgtcgatggaactacatcaccgacgaggacgtgaaggaggtggaccgaaact
tgacaagtaccagatccccacgacgtgatctggctggacatcgagtacaccgacgaccgaaagtacttcacctggg
accccctgtctttccccgaccccatctctatggaggagcagctggacgagtctgagcgaaagctggtcgtgatcatcga
ccccacatcaagaaccaggacaagtactctatcgtgcaggagatgaagtctaaggacctggccaccaagaacaagg
acggcgagatttacgacggctggtgttggccccggctcttctcactggatcgacaccttcaaccccgctgccatcaagtg
gtgggtgtctctgttcaagttcgacaagttcaaggcaccctgtctaacgtgttcatctggaacgacatgaacgagccctc
tgtgttcaacggccccgagaccaccatgcccaaggacaaactgcaccacggcaactgggagcaccgagacatccac
aacgtgcacggcatcaccctggtgaacgccacctacgacgccctgctggagcgaaagaagggcgagatccgacgac
ccttcatcctgacccgatcttactacgccggtgcccagcgaatgtctgccatgtggaccggcgacaaccaggccacctg
ggagcacctggccgcctctatccccatggtgctgaacaacggaatcgccggcttccccttcgccggtgccgacgtggg
cggcttcttccagaaccctctaaggagctgctgacccgatggtatcaggccggcatcggtatccttcttccgagccca
cgcccacatcgacacccgacgacgagagccctacctgatcgccgagccccaccgatctatcatctctcaggccatccg
actgcgataccagctgctgccgctggtacaccgccttccacgaggcctctgtgaacggcatgcccatcgtgcgacc
ccagtactacgccacccctgggacgaggccggcttcgccatcgacgaccagctgtacctgggctctaccggcctgct
ggccaagcccgtggtgtctgaggaggccaccaccgccgacatctacctggctgacgacgagaagtactacga

FIG. 36A ctacttcgactacaccgtgtaccagggcgctggcaagcgacacaccgtgcccgctcccatggagaccgtgccctg
ctgatgcagggcggccacgtgatccccgaaaggaccgaccccgacgatcttctgccctgatgcgatgggacccct
acaccctggtggtggtgctggacaagaacggccaggccgacggctctctgtacgtggacgacggcgagaccttcga
ctacgagcgaggcgcctacatccatcgacgattccgattccaggagtctgccctggtctccgaggacgtgggcacca
agggccccaagaccgccgagtacctcaagaccatggccaacgtgcgagtggagcgagtggtggtcgtggaccccc
ccaaggagtggcagggcaagaccctctgtgaccgtgatcgaggacggcgcctctgccgcctctaccgcctccatgca
gtaccactctcagcccgacggcaaggccgcctacgccgtggtgaagaaccccaacgtgggcatcggcaagacctg
gcgaatcgagttctaatagcctag

FIG. 36B agcgctggcgacgcctcttctcgaccccgaggcgtgggccccgagttcgccaagttctacaaggacaccaccacc
ttcacctgtatctctcaccccgccatccagattcccttctctgccgtgaacgacgactactgtgactgtcccgacggct
ctgacgagcccggcacctctgcctgtgcctttctgtctcgaaactctgccctgaccccggtgagcgaccggatct
gacgacctggagctgacctctgccctgcccggcttctactgtaagaacaagggccacaagcccggctacgtgccc
ttccagcgagttaacgatggcatctgtgactacgagctgtgttgtgacggatcggatgagtgggctcgacccggcg
gaaccaagtgtgaggacaagtgtaaggagatcggcaaggagtggcgaaagaaggaggagaagcgacagaagt
ctatgaccgccgctctgaagaagaagaaggacctgctggtcgaggccggacgacagcagaaggaggtcgagga
caacatcaagcgactggaggtggagatccaggcccaggagctgaaggtcaacgacctgcaggccgagctggag
gaggtggagcagcaggaggcctctaaggtcgtcaagggcaagaccgccggcaaggtgaacgtgctggctggcc
tcgccaagtctcgagtggaggagctgcgaaacgccctgatggacgtgcgaaaggagcgagatgacacccgagc
ccgagttaaggaactcgaagagatcctgtctaagttcaaggtggagtacaaccccaacttcaacgacgagggcgtg
aagcgagccgtgcgatcttgggaggactacgccgccaagggcaccctggaggcgccgtgaacaacgccag
gaccgagacctggacgagatcgccaagcccgacgacgagaaggccggcatcaactggagcagtgggagaac
gaggaggacggctgtgaggctggcctggtgtaccagctggccgcctacctgccccccctctctggtggagttcatcg
agggcaaggtgctgttcgtgcgaggcctgctggaggacaacggcatcctgccaaggccgccgagacctctacc
tctgagtctaaggtggtgtctgaggcccgagaggccgtgaagtctgccgagaaggagctgggcgacaagcagaa
gcagctgaaggaccacaagtctgacctggagaccgactacggcgtgggctctatcttccgagccctgaagggcgt
gtgtatctctaaggactctggcgagtacaccctacgagcactgttttctggaccagaccaagcagatccccaagaagg
gcggaggctctacccgaatgggcaagtacaccggcatcggctctgtgtctgtggacgtgctgaacgaggccggc
gagatcgtgcctgaggatcgagtgaccctgcagtacgccaacggccagggctgttggaacggacccgcccgatc
taccaccgtgatcctgacctgtggcgaggaggacgccatcctgaaggtggccgaggacgagaagtgtgtgtactc
tatgcacgtgacctctcccgccgtgtgtccggccggtgacgagggcgccaccgcccccaaccgaaaggacgagc
tgtaatagccta gagctcagcgctaccaagcgaggctctcccaaccccacccgagccgccgctgtgaaggccgccttccagacc
tcttggaacgcctaccaccacttcgccttcccccacgacgacctgcaccccgtgtctaactcgttcgacgacgag
cgaaacggctggggctcttctgccatcgacggcctggacaccgccatcctgatgggcgacgccgacatcgtga
acaccatcctgcagtacgtgccccagatcaacttcaccaccaccgccgtggccaaccagggcatctctgtgttcg
agaccaacatccgatacctgggcggcctgctgtctgcctacgacctgctgcgaggccccttctcttctctggcca
ccaaccagaccctggtgaactctctgctgcgacaggcccagaccctggccaacggcctgaaggtggcttttacc
acccctctggcgtgccccgaccccaccgtgttcttcaaccccaccgtgcgacgatctggcgcctcttctaacaac
gtggccgagatcggctctctggtgctggagtggacccgactgtctgacctgaccggcaaccccagtacgccc
agctggcccagaagggcgagtcttacctgctgaacccaaggtgctctcccgaggcctggcccggactgatcg
gcacttcgtgtctacctcaacggcaccttccaggactcttccggctcttggtctggcctgatggactcttctacg
agtacctgatcaagatgtacctgtacgaccccgtggccttcgcccactacaaggaccgatgggtgctggccgcc
gactctaccatcgcccacctggcctctcacccctctacccgaaaggacctgaccttcctgtcctcttacaacggcc
agtctacctctcccaactctggacacctggcttccttcgccggtggcaacttcatcctgggcggcatcctgctgaa
cgagcagaagtacatcgacttcggcatcaagctggcctcttcctacttcgccacctacaaccagaccgcctctgg
catcggccccgagggcttcgcctggtggactctgtgaccggcgctggcggctctccccctcttctcagtctgg
cttctactcttctgccggcttctgggtgaccgcccctactacatcctgcgacccgagaccctggagtctctgtact
acgcctaccgagtgaccggcgactctaagtggcaggacctggcctgggaggccttctctgccatcgaggacgc
ctgtcgagccggctctgcctactcttctatcaacgacgtgacccaggccaacggtggcggagcctctgacgaca
tggagtctttctggttcgccgaggccctgaagtacgcctacctgatcttcgccgaggaatctgacGtgcaggtgc
aggccaacggcggcaacaagttcgtgttcaacaccgagcccaccccttctctatccgatcttcttctcgacgag
gcggccacctggcccatgacgagctgtaatagcctaggtacc

FIG. 42 cggcggactgcgtccgaaccagctccagcagcgttttttccgggccattgagccgactgcgacccgccaacgtgtct
tggcccacgcactcatgtcatgttggtgttgggaggccactttttaagtagcacaaggcacctagctcgcagcaaggtgt
ccgaaccaaagaagcggctgcagtgtgtgcaaacgcggcggaaacggcgggaaaaagccacgggggcacgaatt
gaggcacgccctcgaatttgagacgagtcacggccccattcgccgcgcaatggctcgccaacgcccggtcttttgca
ccacatcaggttaccccaagccaaacctttgtgttaaaaagcttaacatattataccgaacgtaggtttgggcgggcttgc
tccgtctgtccaaggcaacatttatataagggtctgcatcgccggctcaattgaatctttttcttcttctcttctctatattcatt
cttgaattaaacacacatcaaca

FIG. 43 cttatctggggcagtgaagtatatgttatggtaatagttacgagttagttgaacttatagatagactggactatacggctatc
ggtccaaattagaaagaacgtcaatggctctctgggcggaattcgtataacttcgtatagcaggagttatccgaagcgat
aattaccctgttatccctagcttatcgatacgcgtgcatgctgaggtgtctcacaagtgccgtgcagtcccgcccccactt
gcttctctttgtgtgtagtgtacgtacattatcgagaccgttgttcccgcccacctcgatccggcatgctgaggtgtctcaca
agtgccgtgcagtcccgcccccacttgcttctctttgtgtgtagtgtacgtacattatcgagaccgttgttcccgcccacctc
gatccggcatgctgaggtgtctcacaagtgccgtgcagtcccgcccccacttgcttctctttgtgtgtagtgtacgtacatt
atcgagaccgttgttcccgcccacctcgatccggcatgctgaggtgtctcacaagtgccgtgcagtcccgcccccactt
gcttctctttgtgtgtagtgtacgtacattatcgagaccgttgttcccgcccacctcgatccggcatgcactgatcacgggc
aaaagtgcgtatatatacaagagcgtttgccagccacagatttcactccacacaccacatcacacatacaaccacacac
atccacgtgggaacccgaaactaaggatccatgaagctttccaccatcctcttcacagcctgcgctaccctggccgctac
caagcgaggctctcccaaccccacccgagccgccgctgtgaaggccgccttccagacctcttggaacgcctaccacc
acttcgccttcccccacgacgacctgcaccccgtgtctaactcgttcgacgacgagcgaaacggctgggggctcttctgc
catcgacggcctggacaccgccatcctgatgggcgacgccgacatcgtgaacaccatcctgcagtacgtgccccaga
tcaacttcaccaccacgccgtggccaaccagggcatctctgtgttcgagaccaacatccgataccttgggcggcctgct
gtctgcctacgacctgctgcgaggcccctctcttctctggccaccaaccagaccctggtgaactctctgctgcgacagg
cccagaccctggccaacggcctgaaggtggcttttaccaccccctctggcgtgcccgaccccaccgtgttcttcaacc
caccgtgcgacgatctggcgcctcttctaacaacgtggccgagatcggctctctggtgctggagtggacccgactgtct
gacctgaccggcaaccccagtacgcccagctggcccagaagggcgagtcttacctgctgaaccccaagggctctcc
cgaggcctggcccggactgatcggcaccttcgtgtctacctctaacggcaccttccaggactcttccggctcttggtctg
gctgatggactctttctacgagtacctgatcaagatgtacctgtacgaccccgtggccttcgcccactacaaggaccga
tgggtgctggccgccgactctaccatcgcccacctggcctctcaccccctctaccgaaaggacctgaccttcctgtcctc
ttacaacggccagtctacctctcccaactctggacacctggcttccttcgccggtggcaacttcatcctgggcggcatcct
gctgaacgagcagaagtacatcgacttcggcatcaagctggcctcttcctacttcgccacctacaaccagaccgcctct
ggcatcggccccgagggcttcgcctgggtggactctgtgaccggcgctgcggctctccccctcttctcagtctggct
tctactcttctgccggcttctggtgaccgccccctactacatcctgcgacccgagaccctggagtctctgtactacgcct
accgagtgaccggcgactctaagtggcaggacctggcctgggaggcctctctgccatcgaggacgcctgtcgagcc
ggctctgcctacctctatcaacgacgtgacccaggccaacggtggcggagcctctgacgacatggagtctttctggtt
cgccgaggccctgaagtacgcctacctgatcttcgccgaggaatctgacgtgcaggtgcaggccaacggcggcaaca
agttcgtgttcaacaccgaggcccaccccttctctatccgatcttcttctcgacgaggcggccacctggcccatgacgag
ctgtaatagcctagggtgtctgtggtatctaagctatttatcactctttacaacttctacctcaactatctactttaataaatgaa
tatcgttt

FIG. 44A attctctatgattactgtatatgcgttcctctaagacaaatcgaattccatgtgtaacactcgctctggagagttagtcatccga
cagggtaactctaatctcccaacaccttattaactctgcgtaactgtaactcttcttgccacgtcgatcttactcaattttcctgct
catcatctgctggattgttgtctatcgtctggctctaatacatttattgtttattgcccaaacaacttcattgcacgtaagtgaatt
gttttataacagcgttcgccaattgctgcgccatcgtcgtccggctgtcctaccgttagggtagtgtgtctcacactaccgag
gttactagagttgggaaagcgatactgcctcggacacaccacctggtcttacgactgcagagagaatcggcgttacctcct
cacaaagccctcagtgcggccgccggggtgggcgaagaactccagcatgagatccccgcgctggaggatcatccag
ccggcgtcccggaaaacgattccgaagcccaacctttcatagaaggcggcggtggaatcgaaatctcgtgatggcaggt
tgggcgtcgcttggtcggtcatttcgaaccccagagtcccgctcagaagaactcgtcaagaaggcgatagaaggcgatg
cgctgcgaatcgggagcggcgataccgtaaagcacgaggaagcggtcagcccattcgccgccaagctcttcagcaata
tcacgggtagccaacgctatgtcctgatagcggtccgccacacccagccggccacagtcgatgaatccagaaaagcgg
ccattttccaccatgatattcggcaagcaggcatcgccatgggtcacgacgagatcctcgccgtcgggcatgcgcgctt
gagcctggcgaacagttcggctggcgcgagcccctgatgctcttcgtccagatcatcctgatcgacaagaccggcttcca
tccgagtacgtgctcgctcgatgcgatgtttcgcttggtggtcgaatgggcaggtagccggatcaagcgtatgcagccgc
cgcattgcatcagccatgatggatactttctcggcaggagcaaggtgagatgacaggagatcctgccccggcacttcgcc
caatagcagccagtcccttcccgcttcagtgacaacgtcgagcacagctgcgcaaggaacgcccgtcgtggccagcca
cgatagccgcgctgcctcgtcctgcagttcattcagggcaccggacaggtcggtcttgacaaaaagaaccgggcgccc
tgcgctgacagccggaacacggcggcatcagagcagccgattgtctgttgtgcccagtcatagccgaatagcctctcca
cccaagcggccggagaacctgcgtgcaatccatcttgttcaatcatgcgaaacgatcctcatcctgtctcttgatcagatctt
gatccctgcgccatcagatccttggcggcaagaaagccatccagtttactttgcagggcttcccaaccttaccagagggc
gccccagctggcaattccggttcgcttgctgtccataaaaccgcccagtctagctatcgccatgtaagcccactgcaagct
acctgctttctctttgcgcttgcgttttcccttgtccagatagcccagtagctgacattcatccggggtcagcaccgtttctgcg
gactggctttctacgtgttccgcttcctttagcagcccttgcgccctgagtgcttgcggcagcgtgaagctagcttatgcggt
gtgaaataccgcacagatgcgtaaggagaaaataccgcatcaggcgctcttccgcttcctcgctcactgactcgctgcgct
cggtcgttcggctgcggcgagcggtatcagctcactcaaaggcggtaatacggttatccacagaatcaggggataacgc
aggaaagaacatgtgagcaaaaggccagcaaaaggccaggaaccgtaaaaaggccgcgttgctggcgtttttccatag
gctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcc
cttcgggaagcgtggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggtaagacacga
cttatcgccactggcagcagccactggtaacaggattagcagagcgaggtatgtaggcggtgctacagagttcttgaagt
ggtggcctaactacggctacactagaaggacagtatttggtatctgcgctctgctgaagc cagttaccttcggaaaaagagttggtagctcttgatccggcaaacaaaccaccgctggtagcggcggtttt
tgtttgcaagcagcagattacgcgcagaaaaaaaggatctcaagaagatcctttgatcttttcttactgaacg
gtgatccccaccggaattgcggccgctgtcgggaaccgcgttcaggtggaacaggacacctcccttgcac
ttcttggtatatcagtataggctgatgtattcatagtggggttttcataataaaatttactaacggcaggcaacatt
cactcggcttaaacgcaaaacggaccgtcttgatatcttctgacgcattgaccaccgagaaatagtgttagtt
accgggtgagttattgttcttctacacaggcgacgcccatcgtctagagttgatgtactaactcagatttcact
acctaccctatccctggtacgcacaaagcactttgctagatagagtcgacaaaggcgggcccccctcga
gattaccctgttatccctacataacttcgtatagcatacattatacgaagttattctgaattccgagaaacacaa
caacatgccccattggacagaccatgcggatacacaggttgtgcagtaccatacatactcgatcagacagg
tcgtctgaccatcatacaagctgaacagcgctccatacttgcacgctctctatatacacagttaaattacatat
ccatagtctaacctctaacagttaatcttctggtaagcctcccagccagccttctggtatcgcttggcctcctc
aataggatctcggttctggccgtacagacctcggccgacaattatgatatccgttccggtagacatgacatc
ctcaacagttcggtactgctgtccgagagcgtctcccttgtcgtcaagacccaccccggggggtcagaataa
gccagtcctcagagtcgcccttaggtcggtctgggcaatgaagccaaccacaaactcggggtcggatcg
ggcaagctcaatggtctgcttggagtactcgccagtggccagagagcccttgcaagacagctcggccag
catgagcagacctctggccagcttctcgttgggagaggggactaggaactccttgtactgggagttctcgta
gtcagagacgtcctccttcttctgttcagagacagtttcctcggcaccagctcgcaggccagcaatgattcc
ggttccgggtacaccgtgggcgttggtgatatcggaccactcggcgattcggtgacaccggtactggtgct
tgacagtgttgccaatatctgcgaactttctgtcctcgaacaggaagaaaccgtgcttaagagcaagttcctt
gaggggagcacagtgccggcgtaggtgaagtcgtcaatgatgtcgatatgggtcttgatcatgcacacat
aaggtccgaccttatcggcaagctcaatgagctccttggtggtggtaacatccagagaagcacacaggttg
gttttcttggctgccacgagcttgagcactcgagcggcaaaggcggacttgtggacgttagctcgagcttc
gtaggagggcatttggtggtgaagaggagactgaaataaatttagtctgcagaacttttatcggaac

FIG. 44C tagcaggagttatccgaagcgataattaccctgttatccctagcttatcgatacggcggactgcgtccgaaccagctcca
gcagcgttttttccgggccattgagccgactgcgaccccgccaacgtgtcttggcccacgcactcatgtcatgttggtgtt
gggaggccactttttaagtagcacaaggcacctagctcgcagcaaggtgtccgaaccaaagaagcggctgcagtggt
gcaaacggggcggaaacggcgggaaaaagccacgggggcacgaattgaggcacgccctcgaatttgagacgagt
cacggccccattcgcccgcgcaatggctcgccaacgcccggtcttttgcaccacatcaggttaccccaagccaaacctt
tgtgttaaaaagcttaacatattataccgaacgtaggtttgggcgggcttgctccgtctgtccaaggcaacatttatataag
ggtctgcatcgccggctcaattgaatcttttttcttcttctcttctctatattcattcttgaattaaacacacatcaacaggatcc
atgaagctttccaccatcctcttcacagcctgcgctacccctggccgctaccaagcgaggctctcccaaccccacccgag
ccgccgctgtgaaggccgccttccagacctcttggaacgcctaccaccacttcgccttcccccacgacgacctgcacc
ccgtgtctaactcgttcgacgacgagcgaaacggctggggctcttctgccatcgacggcctggacaccgccatcctgat
gggcgacgccgacatcgtgaacaccatcctgcagtacgtgccccagatcaacttcaccaccaccgccgtggccaacc
agggcatctctgtgttcgagaccaacatccgatacctgggcggcctgctgtctgcctacgacctgctgcgaggcccctt
ctcttctctggccaccaaccagaccctggtgaactctctgctgcgacaggcccagaccctggccaacggcctgaaggt
ggcttttaccaccccctctggcgtgcccgaccccacggtgttcttcaaccccacgtgcgacgatctggcgcctcttcta
acaacgtggccgagatcggctctctggtgctggagtggacccgactgtctgacctgaccggcaaccccagtacgcc
cagctggcccagaagggcgagtcttacctgctgaaccccaaggggctctcccgaggcctggcccggactgatcggca
ccttcgtgtctacctctaacggcaccttccaggactcttccggctcttggtctggcctgatggactctttctacgagtacctg
atcaagatgtacctgtacgaccccgtggccttcgcccactacaaggaccgatgggtgctggccgccgactctaccatc
gccaccctggcctctcacccctctacccgaaaggacctgaccttcctgtctcttacaacggccagtctacctctcccaa
ctctggacacctggcttccttcgccggtggcaacttcatcctgggcggcatcctgctgaacgagcagaagtacatcgac
ttcggcatcaagctggcctcttcctacttcgccacctacaaccagaccgcctctggcatcggccccgagggcttcgcct
gggtggactctgtgaccggcgctggcggctctcccccctcttctcagtctggcttctactcttctgccggcttctgggtga
ccgcccctactacatcctgcgacccgagaccctggagtctctgtactacgcctaccgagtgaccggcgactctaagtg
gcaggacctggcctgggaggccttctctgccatcgaggacgcctgtcgagccggctctgcctactcttctatcaacgac
gtgacccaggccaacggtggcggagcctctgacgacatggagtctttctggttcgccgaggccctgaagtacgcctac
ctgatcttcgccgaggaatctgacgtgcaggtgcaggccaacggcgcggcaacaagtcgtgttcaacaccgaggccca
ccccttctctatccgatcttcttctcgacgaggcggccacctggcccatgacgagctgtaatagcctaggggtgtctgtggt
atctaagctatttatcactcttacaacttctacctcaactatctactttaataaatgaatatcgttattctctatgattactgtata
tgcgttcctctaagacaaatcgaattccatgtgtaacactcgctctggagagttagtcatccgacaggggtaactctaatctc
ccaacaccttattaactctgcgtaactgtaactcttcttgccacgtcgatcttactcaattttcctgctcatcatctgctggatg
ttgtctatcgtctggct

FIG. 45A ctaatacatttattgtttattgcccaaacaactttcattgcacgtaagtgaattgttttataacagcgttcgccaattgctgcgc
catcgtcgtccggctgtcctaccgttagggtagtgtgtctcacactaccgaggttactagagttgggaaagcgatactgc
ctcggacacaccacctggtcttacgactgcagagagaatcggcgttaccttcctcacaaagccctcagtgcggccgcc
cggggtgggcgaagaactccagcatgagatcccgcgctgaggatcatccagccggcgtcccggaaaacgattc
cgaagcccaacctttcatagaaggcggcggtggaatcgaaatctcgtgatggcaggttgggcgtcgcttggtcggtca
tttcgaaccccagagtcccgctcagaagaactcgtcaagaaggcgatagaaggcgatcgctgcgaatcgggagcg
gcgataccgtaaagcacgaggaagcggtcagcccattcgccgccaagctcttcagcaatatcacgggtagccaacg
ctatgtcctgatagcggtccgccacacccagccggccacagtcgatgaatccagaaaagcggccattttccaccatga
tattcggcaagcaggcatcgccatgggtcacgacgagatcctcgccgtcgggcatgcgcgccttgagcctggcgaac
agttcggctggcgcgagcccctgatgctcttcgtccagatcatcctgatcgacaagaccggcttccatccgagtacgtg
ctcgctcgatgcgatgtttcgcttggtggtcgaatgggcaggtagccggatcaagcgtatgcagccgccgcattgcatc
agccatgatggatactttctcggcaggagcaaggtgagatgacaggagatcctgccccggcacttcgcccaatagca
gccagtcccttcccgcttcagtgacaacgtcgagcacagctgcgcaaggaacgcccgtcgtggccagccacgatag
ccgcgctgcctcgtcctgcagttcattcagggcaccggacaggtcggtcttgacaaaaagaaccgggcgcccctgcg
ctgacagccggaacacggcggcatcagagcagccgattgtctgttgtgcccagtcatagccgaatagcctctccacc
aagcggccggagaacctgcgtgcaatccatcttgttcaatcatgcgaaacgatcctcatcctgtctcttgatcagatcttg
atccctgcgccatcagatccttggcggcaagaaagccatccagtttactttgcagggcttcccaaccttaccagaggg
cgccccagctggcaattccggttcgcttgctgtccataaaaccgcccagtctagctatcgccatgtaagcccactgcaa
gctacctgcttctctttgcgcttgcgttttcccttgtccagatagcccagtagctgacattcatccggggtcagcaccgttt
ctgcggactggctttctacgtgttccgcttcctttagcagcccttgcgccctgagtgcttgcggcagcgtgaagctagctt
atgcggtgtgaaataccgcacagatgcgtaaggagaaaataccgcatcaggcgctcttccgcttcctcgctcactgact
cgctgcgctcggtcgttcggctgcggcgagcggtatcagctcactcaaaggcggtaatacggttatccacagaatcag
gggataacgcaggaaagaacatgtgagcaaaaggccagcaaaaggccaggaaccgtaaaaaggccgcgttgctg
gcgtttttccataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttaccggat
acctgtccgcctttctcccttcgggaagcgtggcgctttctcatagctcacgctgtaggtatctcagttcggtgtaggtcgt
tcgctccaagctgggctgtgtgcacgaaccccccgttcagcccgaccgctgcgccttatccggtaactatcgtcttgag
tccaacccggtaagacacgacttatcgccactggcagcagccactggtaacaggattagcagagcgaggtatgtagg
cggtgctacagagttcttgaagtggtggcctaactacggctacactagaaggacagtatttggtatctgcgctctgctga
agccagttaccttcggaaaaagagttggtagctcttgatccggcaaacaaaccaccgctggtagcggcggttttttgttt
gcaagcagcagattacgcgcagaaaa

FIG. 45B aaaggatctcaagaagatcctttgatcttttcttactgaacggtgatccccaccggaattgcggccgctgtcgg
gaaccgcgttcaggtggaacaggacacctcccttgcacttcttggtatatcagtataggctgatgtattcatag
tggggttttcataataaatttactaacggcaggcaacattcactcggcttaaacgcaaaacggaccgtcttga
tatcttctgacgcattgaccaccgagaaatagtgttagttaccgggtgagttattgttcttctacacaggcgacg
cccatcgtctagagttgatgtactaactcagatttcactacctaccctatcctggtacgcacaaagcactttgc
tagatagagtcgacaaaggcgggccccccctcgagattaccctgttatccctacataacttcgtatagcatac
attatacgaagttatctgaattccgcccagagagccattgacgttctttctaatttggaccgatagccgtatagt
ccagtctatctataagttcaactaactcgtaactattaccataacatatacttcactgccccagataaggttccga
taaaaagttctgcagactaaatttatttcagtctcctcttcaccaccaaaatgccctcctacgaagctcgagcta
acgtccacaagtccgcctttgccgctcgagtgctcaagctcgtggcagccaagaaaaccaacctgtgtgctt
ctctggatgttaccaccaccaaggagctcattgagcttgccgataaggtcggaccttatgtgtgcatgatcaa
gacccatatcgacatcattgacgacttcacctacgccggcactgtgctcccctcaaggaacttgctcttaag
cacggtttcttcctgttcgaggacagaaagttcgcagatattggcaacactgtcaagcaccagtaccggtgtc
accgaatcgccgagtggtccgatatcaccaacgcccacggtgtacccggaaccggaatcattgctggcct
gcgagctggtgccgaggaaactgtctctgaacagaagaaggaggacgtctctgactacgagaactcccag
tacaaggagttcctagtccctctcccaacgagaagctggccagaggtctgctcatgctggccgagctgtct
tgcaagggctctctggccactggcgagtactccaagcagaccattgagcttgcccgatccgaccccgagttt
gtggttggcttcattgcccagaaccgacctaagggcgactctgaggactggcttattctgacccccggggtg
ggtcttgacgacaaggggagacgctctcggacagcagtaccgaactgttgaggatgtcatgtctaccggaac
ggatatcataattgtcggccgaggtctgtacggccagaaccgagatcctattgaggaggccaagcgatacc
agaaggctggctgggaggcttaccagaagattaactgttagagggttagactatggatatgtaatttaactgtgt
atatagagagcgtgcaagtatggagcgctgttcagcttgtatgatggtcagacgacctgtctgatcgagtatg
tatggtactgcacaacctgtgtatccgcatggtctgtccaatgggcatgttgttgtgtttctcggaattcgtata
acttcgta caaggggtaggcgaatggtacgattccgccaagtgagactggcgatcgggagaaggggttggtggtcatggggata
gaatttgtacaagtggaaaaaccactacgagtagcggatttgataccacaagtagcagagatatacagcaatggtggg
agtgcaagtatcggaatgtactgtacctcctgtactcgtactcgtacggcactcgtagaaacggggcaatacgggggga
gaagcgatcgcccgtctgttcaatcgccacaagtccgagtaatgctcgagtatcgaagtcttgtacctccctgtcaatca
tggcaccactggtcttgactgtctattcatactggacaagcgccagagttagctagcgaattcgccctcggacatcac
cccatacgacggacacacatgcccgacaaacagcctctcttatgtagctgaaagtatattgaatgtgaacgtgtacaat
atcaggtaccagcgggaggttacggccaaggtgataccggaataaccctggcttggagatggtcggtccattgtactg
aagtgtccgtgtcgtttccgtcactgccccaattggacatgtttgtttttccgatcttcgggcgccctctccttgtctccttgt
ctgtctcctggactgttgctaccccatttctttggcctccattggttcctcccgtctttcacgtcgtctatggttgcatggttt
cccttatacttttccccacagtcacatgttatggaggggtctagatggacatggtgcaaggcccgcagggttgattcgac
gcttttccgcgaaaaaaacaagtccaaataccccgtttattctccctcggctctcggtatttcacatgaaaactataacct
agactacacgggcaaccttaaccccagagtatacttatataccaaaggggatgggtcctcaaaaatcacacaagcaacg
gatccatgaagctttccaccatcctcttcacagcctgcgctaccctggccgctaccaagcgaggctctcccaacccca
cccgagccgccgctgtgaaggccgccttccagacctcttggaacgcctaccaccactcgccttcccccacgacgac
ctgcaccccgtgtctaactcgttcgacgacgagcgaaacggctgtgggctcttctgccatcgacggcctggacaccgc
catcctgatgggcgacgccgacatcgtgaacaccatcctgcagtacgtgccccagatcaacttcaccaccaccgccg
tggccaaccagggcatctctgtgttcgagaccaacatccgatacctggccggcctgctgtctgcctacgacctgctgc
gaggccccttctcttctctggccaccaaccagaccctggtgaactctctgctgcgacaggcccagaccctggccaac
ggcctgaaggtggcttttaccacccccctctggcgtgcccgaccccaccgtgttcttcaaccccaccgtgcgacgatct
ggcgcctcttctaacaacgtggccgagatcggctctctggtgctggagtggacccgactgtctgacctgaccggcaa
cccccagtacgcccagctggcccagaagggcgagtcttacctgctgaaccccaagggctctcccgaggcctggccc
ggactgatcggcaccttcgtgtctcacctctaacggcaccttccaggactcttccggctcttggtctggcctgatggactct
ttctacgagtacctgatcaagatgtacctgtacgaccccgtggccttcgcccactacaaggacgatggtgctggcc
gccgactctaccatcgcccacctggcctctcacccctctacccgaaaggacctgaccttcctgtcctcttacaacggcc
agtctacctctcccaactctggacacctggcttccttcgccggtggcaacttcatcctgggcggcatcctgctgaacga
gcagaagtacatcgacttcggcatcaagctggcctcttcctacttcgccacctacaaccagaccgcctctggcatcgg
ccccgagggcttcgcctggtggactctgtgaccggcgctggcggctctcccccctcttctcagtctggcttctactctt
ctgccggcttctgggtgaccgcccctactacatcctgcgacccgagaccctggagtctctgtactacgctaccgag
tgaccggcgactctaagtggcaggacctggcctggggaggccttctctgccatcgaggacgcctgtcgagccggctct
gcctactcttctatcaacgacgtgacccaggccaacggtggccggagcctctgacgacatggagtctttctggttcgcc
gaggccctgaagtacgcctacctgatcttcgccgag

FIG. 46A gaatctgacgtgcaggtgcaggccaacggcggcaacaagttcgtgttcaacaccgaggcccaccccttctctatc
cgatcttcttctcgacgaggcggccacctggcccatgacgagctgtaatagcctagggtgtctgtggtatctaagct
attatcactctttacaacttctacctcaactatctactttaataaatgaatatcgtttattctctatgattactgtatatgcgtt
cctctaagacaaatcgaattccatgtgtaacactcgctctggagagttagtcatccgacagggtaactctaatctccc
aacaccttattaatctgcgtaactgtaactcttcttgccacgtcgatcttactcaattttcctgctcatcatctgctggatt
gttgtctatcgtctggctctaatacattattgtttattgcccaaacaactttcattgcacgtaagtgaattgttttataaca
gcgttcgccaattgctgcgccatcgtcgtccggctgtcctaccgttaggggtagtgtgtctcacactaccgaggttact
agagttgggaaagcgatactgcctcggacacaccacctggtcttacgactgcagagagaatcggcgttacctcct
cacaaagccctcagtgcggccgcccggggtgggcgaagaactccagcatgagatccccgcgctggaggatcat
ccagccggcgtccggaaaacgattccgaagcccaaccttcatagaaggcggcggtggaatcgaaatctcgtg
atggcaggtgggcgtcgcttggtcggtcatttcgaaccccagagtcccgctcagaagaactcgtcaagaaggcg
atagaaggcgatgcgctgcgaatcgggagcggcgataccgtaaagcacgaggaagcggtcagcccattcgcc
gccaagctcttcagcaatatcacgggtagccaacgctatgtcctgatagcggtccgccacacccagccggccaca
gtcgatgaatccagaaaagcggccattttccaccatgatattcggcaagcaggcatcgccatgggtcacgacgag
atcctcgccgtcgggcatgcgcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcga
atgggcaggtagccggatcaagcgtatgcagccgccgcattgcatcagccatgatggatactttctcggcaggag
caaggtgagatgacaggagatcctgccccggcacttcgcccaatagcagccagtcccttcccgcttcagtgacaa
cgtcgagcacagctgcgcaaggaacgcccgtcgtggccagccacgatagccgcgctgcctcgtcctgcagttca
ttcagggcaccggacaggtcggtcttgacaaaaagaaccgggcgcccctgcgctgacagccggaacacggcg
gcatcagagcagccgattgtctgttgtgcccagtcatagccgaatagcctctccacccaagcggccggagaacct
gcgtgcaatccatcttgttcaatcatgcgaaacgatcctcatcctgtctcttgatcagatcttgatcccctgcgccatca
gatccttggcggcaagaaagccatccagtttactttgcagggcttcccaaccttaccagagggcgccccagctgg
caattccggttcgcttgctgtccataaaaccgcccagtctagctatcgccatgtaagcccactgcaagctacctgctt
tctctttgccgcttgcgttttcccttgtccagatagcccagtagctgacattcatccggggtcagcaccgtttctgcgga
ctggctttctacgtgttccgcttcctttagcagcccttgcgccctgagtgcttgcggcagcgtgaagctagcttatgcg
gtgtgaaataccgcacagatgcgtaaggagaaaataccgcatcaggcgctcttccgcttcctcgctcactgactcg
ctgcgctcggtcgttcggctgcggcgagcggtatcagctcactcaaaggcggtaatacggttatccacagaatca
ggggataacgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcagaggtggcgaaac
ccgacaggactataaag

FIG. 46B ataccaggcgtttcccctggaagctccctcgtgcgctctcctgttccgaccctgccgcttaccggatacctgtccgcc
tttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccg
gtaagacacgacttatcgccactggcagcagccactggtaacaggattagcagagcgaggtatgtaggcggtgcta
cagagttcttgaagtggtggcctaactacggctacactagaaggacagtatttggtatctgcgctctgctgaagccagtt
accttcggaaaagagttggtagctcttgatccggcaaacaaaccaccgctggtagcggcggttttttgtttgcaagca
gcagattacgcgcagaaaaaaggatctcaagaagatcctttgatcttttcttactgaacggtgatccccaccggaatt
gcggccgctgtcgggaaccgcgttcaggtggaacaggacacctccctgcacttcttggtatatcagtataggctgat
gtattcatagtggggttttttcataataaatttactaacggcaggcaacattcactcggcttaaacgcaaaacggaccgtct
tgatatcttctgacgcattgaccaccgagaaatagtgttagttaccggggtgagttattgttcttctacacaggcgacgcc
atcgtctagagttgatgtactaactcagatttcactacctaccctatccctggtacgcacaaagcactttgctagatagag
tcgacaaaggcgggccccccctcgagattaccctgttatccctacataacttcgtatagcatacattatacgaagttatc
tgaattccgcccagagagccattgacgttctttctaatttggaccgatagccgtatagtccagtctatctataagttcaact
aactcgtaactattaccataacatatacttcactgccccagataaggttccgataaaaagttctgcagactaaatttattc
agtctcctcttcaccaccaaaatgccctcctacgaagctcgagctaacgtccacaagtccgcctttgccgctcgagtgc
tcaagctcgtggcagccaagaaaaccaacctgtgtgcttctctggatgttaccaccaccaaggagctcattgagcttgc
cgataaggtcggaccttatgtgtgcatgatcaagacccatatcgacatcattgacgacttcacctacgccggcactgtg
ctcccccctcaaggaacttgctcttaagcacggtttcttcctgttcgaggacagaaagttcgcagatattggcaacactgt
caagcaccagtaccggtgtcaccgaatcgccgagtggtccgatatcaccaacgcccacggtgtacccggaaccgg
aatcattgctggcctgcgagctggtgccgaggaaactgtctctgaacagaagaaggaggacgtctctgactacgaga
actcccagtacaaggagttcctagtcccctctcccaacgagaagctggccagaggtctgctcatgctggccgagctgt
cttgcaagggctctctggccactggcgagtactccaagcagaccattgagcttgcccgatccgaccccgagtttgtgg
ttggcttcattgcccagaaccgacctaagggcgactctgaggactggcttatctgaccccgggggtgggtcttgacg
acaagggagacgctctcggacagcagtaccgaactgttgaggatgtcatgtctaccggaacggatatcataattgtcg
gccgaggtctgtacggccagaaccgagatcctattgaggaggccaagcgataccagaaggctggctgggaggctt
accagaagattaactgttagaggttagactatggatatgtaatttaactgtgtatatagagagcgtgcaagtatggagcg
ctgttcagcttgtatgatggtcagacgaccctgtctgatcgagtatgtatggtactgcacaacctgtgtatccgcatggtct
gtccaatggggcatgttgttgtgtttctcggaattcgtataacttcgtatagcaggagttatccgaagcgataattaccctg
ttatccctagcttatcgattcccacaagacgaacaagtgataggccgagagccgaggacgaggtggagtgca

FIG. 46C taattaccctgttatccctagcttatcgatagagaccgggttggcggcgtatttgtgtcccaaaaaacagccccaattgcc
ccaattgaccccaaattgacccagtagcgggcccaaccccggcgagagccccttcaccccacatatcaaacctcccc
cggttcccacacttgccgttaagggcgtagggtactgcagtctggaatctacgcttgttcagactttgtactagtttctttgt
ctggccatccgggtaaacccatgccggacgcaaaatagactactgaaaattttttttgctttgtggttgggactttagccaag
ggtataaaagaccaccgtccccgaattacctttcctcttcttttctctctctccttgtcaactcacacccgaaggatccatga
agctttccaccatcctcttcacagcctgcgctaccctggccgctaccaagcgaggctctcccaaccccacccgagccg
ccgctgtgaaggccgccttccagacctcttggaacgcctaccaccacttcgccttccccacgacgacctgcaccccgt
gtctaactcgttcgacgacgagcgaaacggctggggctcttctgccatcgacggcctggacaccgccatcctgatggg
cgacgccgacatcgtgaacaccatcctgcagtacgtgccccagatcaacttcaccaccaccgccgtggccaaccagg
gcatctctgtgttcgagaccaacatccgatacctgggcggcctgctgtctgcctacgacctgctgcgaggcccccttctctt
ctctggccaccaaccagaccctggtgaactctctgctgcgacaggcccagaccctggccaacggcctgaaggtggct
tttaccacccctctggcgtgcccgaccccaccgtgttcttcaaccccaccgtgcgacgatctggcgcctcttctaacaa
cgtggccgagatcggctctctggtgctggagtggacccgactgtctgacctgacggcaacccccagtacgcccagc
tggcccagaagggcgagtcttacctgctgaaccccaaggggctctcccgaggcctggcccggactgatcggcaccttc
gtgtctacctctaacggcaccttccaggactcttccggctcttggtctggcctgatggactctttctacgagtacctgatca
agatgtacctgtacgaccccgtggccttcgcccactacaaggaccgatgggtgctggccgccgactctaccatcgccc
acctggcctctcaccccctctacccgaaaggacctgaccttcctgtcctcttacaacggccagtctacctctcccaactctg
gacacctggccttccttcgccggtggcaacttcatcctggccggcatcctgctgaacgagcagaagtacatcgacttcgg
catcaagctggcctcttcctacttcgccacctacaaccagaccgcctctggcatcggccccgagggcttcgcctgggtg
gactctgtgaccggcgctggcggctctccccccctcttctcagtctggcttctactcttctgccggcttctgggtgaccgcc
ccctactacatcctgcgacccgagaccctggagtctctgtactacgcctaccgagtgaccggcgactctaagtggcag
gacctggcctgggaggccttctctgccatcgaggacgcctgtcgagccggctctgcctactcttctatcaacgacgtga
cccaggccaacggtggcggagcctctgacgacatggagtctttctggttcgccgaggcccctgaagtacgcctacctga
tcttcgccgaggaatctgacgtgcaggtgcaggccaacggcggcaacaagttcgtgttcaacaccgaggcccacccc
ttctctatccgatcttcttctcgacgaggcggccacctggcccatgacgagctgtaatagcctaggggtgtctgtggtatcta
agctatttatcactctttacaactctacctcaactatctacttttaataaatgaatatcgtttattctctatgattactgtatatgcgt
tcctctaagacaaatcgaattccatgtgtaacactcgctctggagagttagtcatccgacagggtaactctaatctcccaa
caccttattaactctgcgtaactgtaactcttcttgccacgtcgatcttactcaatttcctgctcatcatctgctggattgttgt
ctatcgtctggctctaatacatttattgtttattgcccaaacaactttcattgcacgtaagtgaattgttttataacagcgttcgc
caattgctgcgccatcgtcgtccggctgtcctaccgttagggtagtgtgtctcacactaccgaggttactagagttgggaa
agcgatactgcctcgg

FIG. 47A acacaccacctggtcttacgactgcagagagaatcggcgttacctcctcacaaagccctcagtgcggccgcccggggt
gggcgaagaactccagcatgagatccccgcgctggaggatcatccagccggcgtcccggaaaacgattccgaagcc
caaccttcatagaaggcggcggtggaatcgaaatctcgtgatggcaggttgggcgtcgcttggtcggtcatttcgaacc
ccagagtcccgctcagaagaactcgtcaagaaggcgatagaaggcgatgcgctgcgaatcgggagcggcgataccg
taaagcacgaggaagcggtcagcccatcgccgccaagctcttcagcaatatcacgggtagccaacgctatgtcctgat
agcggtccgccacacccagccggccacagtcgatgaatccagaaaagcggccattttccaccatgatattcggcaagc
aggcatcgccatgggtcacgacgagatcctcgccgtcgggcatgcgcgccttgagcctggcgaacagttcggctggc
gcgagcccctgatgctcttcgtccagatcatcctgatcgacaagaccggcttccatccgagtacgtgctcgctcgatgcg
atgtttcgcttggtggtcgaatgggcaggtagccggatcaagcgtatgcagccgccgcattgcatcagccatgatggata
ctttctcggcaggagcaaggtgagatgacaggagatcctgccccggcacttcgcccaatagcagccagtcccttccgc
ttcagtgacaacgtcgagcacagctgcgcaaggaacgcccgtcgtggccagccacgatagccgcgctgcctcgtcctg
cagttcattcagggcaccggacaggtcggtcttgacaaaagaaccggggcgcccctgcgctgacagccggaacacgg
cggcatcagagcagccgattgtctgttgtgcccagtcatagccgaatagcctctccacccaagcggccggagaacctgc
gtgcaatccatcttgttcaatcatgcgaaacgatcctcatcctgtctcttgatcagatcttgatccctgcgccatcagatcct
tggcggcaagaaagccatccagtttactttgcagggcttcccaaccttaccagagggcgccccagctggcaattccggtt
cgcttgctgtccataaaaccgcccagtctagctatcgccatgtaagcccactgcaagctacctgctttctcttgcgcttgcg
ttttcccttgtccagatagcccagtagctgacattcatccgggggtcagcaccgtttctgcggactggctttctacgtgttccg
cttcctttagcagcccttgcgccctgagtgcttgcggcagcgtgaagctagcttatgcggtgtgaaataccgcacagatg
cgtaaggagaaaataccgcatcaggcgctcttccgcttcctcgctcactgactcgctgcgctcggtcgttcggctgcggc
gagcggtatcagctcactcaaaggcggtaatacggttatccacagaatcaggggataacgcaggaaagaacatgtgag
caaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccctg
gaagctccctcgtgcgctctcctgttccgaccctgccgcttaccggatacctgtccgcctttctcccttcgggaagcgtgg
cgctttctcatagctcacgctgtaggtatctcagttcggtgtaggtcgttcgctccaagctgggctgtgtgcacgaacccccc
cgttcagcccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtggcctaacta
cggctacactagaaggacagtatttggtatctgcgctctgctgaagccagttaccttcggaaaaagagttggtagctcttg
atccggcaaacaaaccaccgctggtagcggcggtttttttgtttgcaagcagcagattacgcgcagaaaaaaggatctc
aagaagatcctttgatcttttctactgaacggtgatccccaccggaattgcggccgctgtcgggaaccgcgttcaggtgg
aacaggacacctcccttgcacttcttggtatatcagtataggctgatgtattcatagtggggttttttcataataaatttact

FIG. 47B aacggcaggcaacattcactcggcttaaacgcaaaacggaccgtcttgatatcttctgacgcattgaccaccgaga
aatagtgttagttaccgggtgagttattgttcttctacacaggcgacgcccatcgtctagagttgatgtactaactcag
atttcactacctaccctatccctggtacgcacaaagcacttttgctagatagagtcgacaaaggcgggcccccctc
gagattaccctgttatccctacataacttcgtatagcatacattatacgaagttattctgaattccgagaaacacaacaa
catgccccattggacagaccatgcggatacacaggttgtgcagtaccatacatactcgatcagacaggtcgtctga
ccatcatacaagctgaacagcgctccatacttgcacgtctctatatacacagttaaattacatatccatagtctaacct
ctaacagttaatcttctggtaagcctcccagccagccttctggtatcgcttggcctcctcaataggatctcggttctgg
ccgtacagacctggccgacaattatgatatccgttccggtagacatgacatcctcaacagttcggtactgctgtcc
gagagcgtctcccttgtcgtcaagacccaccccgggggtcagaataagccagtcctcagagtcgcccttaggtcg
gttctgggcaatgaagccaaccacaaactcggggtcggatcgggcaagctcaatggtctgcttggagtactcgcc
agtggccagagagcccttgcaagacagctcggccagcatgagcagacctctggccagcttctcgttgggagagg
ggactaggaactccttgtactgggagttctcgtagtcagagacgtcctccttcttctgttcagagacagtttcctcggc
accagctcgcaggccagcaatgattccggttccgggtacaccgtgggcgttggtgatatcggaccactcggcgat
tcggtgacaccggtactggtgctgacagtgttgccaatatctgcgaactttctgtcctcgaacaggaagaaaccgt
gcttaagagcaagtccttgagggggagcacagtgccggcgtaggtgaagtcgtcaatgatgtcgatatgggtctt
gatcatgcacacataaggtccgaccttatcgcaagctcaatgagctccttggtggtggtaacatccagagaagca
cacaggttggttttcttggctgccacgagcttgagcactcgagcggcaaaggcggacttgtggacgttagctcgag
cttcgtaggagggcattttggtggtgaagaggagactgaaataaatttagtctgcagaacttttttatcggaaccttatc
tggggcagtgaagtatatgttatggtaatagttacgagttagttaacttatagatagactggactatacggctatcgg
tccaaattagaaagaacgtcaatggctctctgggcggaattcgtataacttcgtatagcaggagttatccgaagcga

FIG. 47C gagctcagcgctcgaccctgtatccccaagtctttcggctactcttctgtggtgtgtgtgtgtaacgccacctactgtgact
cgttcgacccccccaccttcccgccctgggcaccttctctcgatacgagtctacccgatctggccgacgaatggagct
gtctatgggccccatccaggccaaccacaccggcaccggcctgctgctgaccctgcagcccgagcagaagttccaga
aggtcaagggcttcggcggagccatgaccgacgccgctgccctgaacatcctggccctgtctcccccgctcagaac
ctgctcctgaagtcttacttctctgaggagggcatcggctacaacatcatccgagtgcctatggcctcttgtgacttctctat
ccgaacctacacctacgccgacaccccgacgacttccagctgcacaactctccctgcccgaggaggacaccaagct
gaagatcccctgatccaccgagccctgcagctggccagcgacccgtgtctctgctggcctctccctggacctctccc
acctggctcaagaccaacggcgccgtgaacggcaagggctctctgaagggccagcccggcgacatctaccaccaga
cctggccccgatacttcgtgaagttcctggacgcctacgccgagcacaagctgcagttctgggccgtgaccgccgaga
acgagccctctgctgactgctgtccggctaccccttccagtgtctgggcttcacccccgagcaccagcgagacttcatc
gccgagacctgggacccaccctggccaactctacccaccacaacgtgcgactgctgatgctggacgaccagcgact
gctgctgccccactgggccaaggtggtgctgaccgaccccgaggccgccaagtacgtccacggcatcgctgtccatt
ggtatctggactttctggctcccgccaaggccacccctgggcgagacccaccgactgttccccaacaccatgctgttcgc
ctctgaggcttgtgtgggctctaagttctgggagcagtctgtgcgactgggctcttgggaccgaggcatgcagtactctc
actctatcatcaccaacctgctgtaccacgtggtgggctggaccgactggaacctggccctgaaccccgagggcggac
ccaactgggtgcgaaacttcgtggactctcccatcatcgtggacatcaccaaggacaccttctacaagcagcccatgttc
taccacctgggccacttctctaagttcatccccgagggctctcagcgagtgggcctggtggccctctcagaagaacgacc
tggacgccgtggccctgatgcaccccgacggctctgccgtggtggtggtcctgaaccgatcttctaaggacgtgcccct
gaccatcaaggaccccgccgtgggcttcctggagaccatctctcccggctactctatccacacctacctgtggcgacga
cagtaatagcctaggggtacc

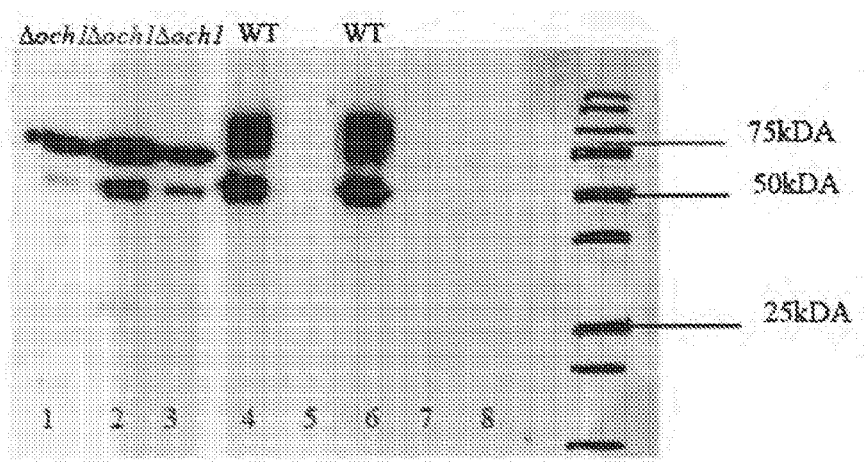

FIG. 51

```
gctccccccgactgatctgtgactctcgagtgctggaacgatacctgctggaagccaaggaagccgag
aacatcaccaccggctgtgccgagcactgttctctgaacgagaacattaccgtgcccgacaccaaggtg
aacttctacgcctggaagcgaatggaggtggggccagcaggccgtggaggtgtggcagggactggctct
gctgtctgaggccgtgctgcgaggacaggctctcctggtgaactcttctcagccctgggagcccctgcag
ctgcacgtggacaaggccgtgtctggcctgcgatctctgaccaccctgctgcgagccctcggtgctcaga
aggaagccatctctccccccgacgccgcctctgctgccccctgcgaaccatcaccgccgacaccttccg
aaagctgttccgagtgtactctaacttcctgcgaggcaagctgaagctgtacaccggcgaggcttgtcg
aaccggcgaccga
```

FIG. 52 ctggacaacggcctggcccgaaccccaccatgggctggctgcactgggagcgattcatgtgtaacct
ggactgtcaggaagagcccgactcttgtatctctgagaagctgttcatggaaatggccgagctgatggt
gtctgagggctggaaggacgccggctacgagtacctgtgtatcgacgactgttggatggccccccagc
gagactctgagggccgactccaggccgaccccagcgattccccacggcatccgacagctcgcca
actacgtgcactctaaggggctgaagctgggcatctacgccgacgtgggcaacaagacctgtgccgg
cttccccggctctttcggctactacgacatcgacgcccagaccttcgccgactggggcgtggacctgct
gaagttcgacggctgttactgtgactctctcgagaacctggccgacggctacaagcacatgtctctggcc
ctgaaccgaaccggccgatctatcgtgtactcttgtgagtggccccctgtacatgtggcccttccagaagc
ccaactacaccgagatccgacagtactgtaaccactggcgaaacttcgccgacatcgacgactcgtgg
aagtctatcaagtctattctggactggacctctttcaaccaggagcgaatcgtcgacgtcgccggacccg
gcggatggaacgaccccgacatgctggtgatcggcaacttcggcctgtcttggaaccagcaggtgacc
cagatggccctgtgggctatcatggctgccccctgttcatgtctaacgacctgcgacacatctctccc
aggccaaggccctgctccaggacaaggacgtgatcgccatcaaccaggaccccctgggcaagcagg
gctaccagctccgacagggcgacaacttcgaggtgtgggagcgaccccctgtctggcctggcctgggc
cgtggccatgatcaaccgacaggagatcggcggaccccgatcttacaccatcgccgtggcctccctgg
gaaagggcgtggcctgtaaccccgccgtttcatcacccagctcctgcccgtgaagcgaaagctggga
ttctacgagtggacctctcgactgcgatctcacatcaaccccaccggcaccgtgctgctccagctcgag
aacaccatgcagatgtctctgaaggacctgctg

FIG. 53

SEQUENCE LISTING

```
<160> NUMBER OF SEQ ID NOS: 75

<210> SEQ ID NO 1
<211> LENGTH: 358
<212> TYPE: DNA
<213> ORGANISM: Yarrowia lipolytica
```

<400> SEQUENCE: 1

```
ggtctcgcca gcgcgcccac cctcttcaac cacgataatg agaccgtcgt ccccgactct      60
cctattgtga agaccgagga agtcgactct acaaactttc tcctccacac ggagtcctcc     120
tcccccccg aactagctga gagcactggc tcaggctcgc catcgtcgac tctgtcctgc      180
gacgaaactg attatcttgt ggaccgggcg cgtcatccag cagcgtcggc acaagatttc     240
wttttcatca aggacgagcc cgttgacgac gagcttggac tgcatggact gtcggatgac     300
ttcaccctgt tgaagacaa caagcagcct gcccagcacg actttattgc tgatctag       358
```

<210> SEQ ID NO 2
<211> LENGTH: 915
<212> TYPE: DNA
<213> ORGANISM: Pichia pastoris

<400> SEQUENCE: 2

```
atgcccgtag attcttctca taagacagct agcccacttc cacctcgtaa aagagcaaag      60
acggaagaag aaaaggagca gcgtcgagtg gaacgtatcc tacgtaatag agagcggcc     120
catgcttcca gagagaagaa acgaagacac gttgaatttc tggaaaaacca cgtcgtcgac    180
ctggaatctg cacttcaaga atcagccaaa gccactaaca agttgaaaga atacaagat     240
atcattgttt caaggttgga agccttaggt ggtaccgtct cagatttgga tttaacagtt    300
ccggaagtcg atttccccaa atcttctgat ttggaaccca tgtctgatct ctcaacttct    360
tcgaaatcgg agaaagcatc tacatccact cgcagatctt tgactgagga tctggacgaa    420
gatgacgtcg ctgaatatga cgacgaagaa gaggacgaag agttacccag gaaaatgaaa    480
gtcttaaacg acaaaaacaa gagcacatct atcaagcagg agaagttgaa tgaacttcca    540
tctcctttgt catccgattt ttcagacgta gatgaagaaa agtcaactct cacacattta    600
aagttgcaac agcaacaaca caaccagta gacaattatg tttctactcc tttgagtctt    660
ccggaggatt cagttgattt tattaaccca ggtaacttaa aaatagagtc cgatgagaac    720
ttcttgttga gttcaaatac tttacaaata aaacacgaaa atgacaccga ctacattact    780
acagctccat caggttccat caatgatttt tttaattctt atgacattag cgagtcgaat    840
cggttgcatc atccagcagc accatttacc gctaatgcat ttgattaaa tgactttgta    900
ttcttccagg aatag                                                     915
```

<210> SEQ ID NO 3
<211> LENGTH: 305
<212> TYPE: PRT
<213> ORGANISM: Yarrowia lipolytica

<400> SEQUENCE: 3

```
Met Ser Ile Lys Arg Glu Glu Ser Phe Thr Pro Thr Pro Glu Asp Leu
 1               5                  10                  15

Gly Ser Pro Leu Thr Ala Asp Ser Pro Gly Ser Pro Glu Ser Gly Asp
                20                  25                  30

Lys Arg Lys Lys Asp Leu Thr Leu Pro Leu Pro Ala Gly Ala Leu Pro
             35                  40                  45

Pro Arg Lys Arg Ala Lys Thr Glu Asn Glu Lys Glu Gln Arg Arg Ile
         50                  55                  60

Glu Arg Ile Met Arg Asn Arg Gln Ala Ala His Ala Ser Arg Glu Lys
 65                  70                  75                  80

Lys Arg Arg His Leu Glu Asp Leu Glu Lys Lys Cys Ser Glu Leu Ser
                 85                  90                  95
```

-continued

```
Ser Glu Asn Asn Asp Leu His His Gln Val Thr Glu Ser Lys Lys Thr
                100                 105                 110

Asn Met His Leu Met Glu Gln His Tyr Ser Leu Val Ala Lys Leu Gln
            115                 120                 125

Gln Leu Ser Ser Leu Val Asn Met Ala Lys Ser Ser Gly Ala Leu Ala
    130                 135                 140

Gly Val Asp Val Pro Asp Met Ser Asp Val Ser Met Ala Pro Lys Leu
145                 150                 155                 160

Glu Met Pro Thr Ala Ala Pro Ser Gln Pro Met Gly Leu Ala Ser Ala
                165                 170                 175

Pro Thr Leu Phe Asn His Asp Asn Glu Thr Val Val Pro Asp Ser Pro
            180                 185                 190

Ile Val Lys Thr Glu Glu Val Asp Ser Thr Asn Phe Leu Leu His Thr
    195                 200                 205

Glu Ser Ser Ser Pro Pro Glu Leu Ala Glu Ser Thr Gly Ser Gly Ser
210                 215                 220

Pro Ser Ser Thr Leu Ser Cys Asp Glu Thr Asp Tyr Leu Val Asp Arg
225                 230                 235                 240

Ala Arg His Pro Ala Ala Ser Ala Gln Asp Phe Ile Phe Ile Lys Asp
                245                 250                 255

Glu Pro Val Asp Asp Glu Leu Gly Leu His Gly Leu Ser Asp Asp Phe
            260                 265                 270

Thr Leu Phe Glu Asp Asn Lys Gln Pro Ala Gln His Asp Phe Ile Ala
    275                 280                 285

Asp Leu Ala His Tyr Glu Ser Ser Val Ser Asn Leu Phe Gly Gly Leu
290                 295                 300

Glu
305

<210> SEQ ID NO 4
<211> LENGTH: 304
<212> TYPE: PRT
<213> ORGANISM: Pichia pastoris

<400> SEQUENCE: 4

Met Pro Val Asp Ser Ser His Lys Thr Ala Ser Pro Leu Pro Pro Arg
1               5                   10                  15

Lys Arg Ala Lys Thr Glu Glu Glu Lys Glu Gln Arg Arg Val Glu Arg
            20                  25                  30

Ile Leu Arg Asn Arg Arg Ala Ala His Ala Ser Arg Glu Lys Lys Arg
        35                  40                  45

Arg His Val Glu Phe Leu Glu Asn His Val Val Asp Leu Glu Ser Ala
    50                  55                  60

Leu Gln Glu Ser Ala Lys Ala Thr Asn Lys Leu Lys Glu Ile Gln Asp
65                  70                  75                  80

Ile Ile Val Ser Arg Leu Glu Ala Leu Gly Gly Thr Val Ser Asp Leu
                85                  90                  95

Asp Leu Thr Val Pro Glu Val Asp Phe Pro Lys Ser Ser Asp Leu Glu
            100                 105                 110

Pro Met Ser Asp Leu Ser Thr Ser Ser Lys Ser Glu Lys Ala Ser Thr
        115                 120                 125

Ser Thr Arg Arg Ser Leu Thr Glu Asp Leu Asp Glu Asp Asp Val Ala
    130                 135                 140

Glu Tyr Asp Asp Glu Glu Glu Asp Glu Glu Leu Pro Arg Lys Met Lys
145                 150                 155                 160
```

```
Val Leu Asn Asp Lys Asn Lys Ser Thr Ser Ile Lys Gln Glu Lys Leu
            165                 170                 175

Asn Glu Leu Pro Ser Pro Leu Ser Ser Asp Phe Ser Asp Val Asp Glu
        180                 185                 190

Glu Lys Ser Thr Leu Thr His Leu Lys Leu Gln Gln Gln Gln Gln Gln
    195                 200                 205

Pro Val Asp Asn Tyr Val Ser Thr Pro Leu Ser Leu Pro Glu Asp Ser
    210                 215                 220

Val Asp Phe Ile Asn Pro Gly Asn Leu Lys Ile Glu Ser Asp Glu Asn
225                 230                 235                 240

Phe Leu Leu Ser Ser Asn Thr Leu Gln Ile Lys His Glu Asn Asp Thr
                245                 250                 255

Asp Tyr Ile Thr Thr Ala Pro Ser Gly Ser Ile Asn Asp Phe Phe Asn
            260                 265                 270

Ser Tyr Asp Ile Ser Glu Ser Asn Arg Leu His His Pro Ala Ala Pro
        275                 280                 285

Phe Thr Ala Asn Ala Phe Asp Leu Asn Asp Phe Val Phe Phe Gln Glu
    290                 295                 300
```

<210> SEQ ID NO 5
<211> LENGTH: 387
<212> TYPE: DNA
<213> ORGANISM: Yarrowia lipolytica

<400> SEQUENCE: 5

```
ggtctcgcca gcgcgcccac cctcttcaac cacgataatg agaccgtcgt ccccgactct     60
cctattgtga agaccgagga agtcgactct acaaactttc tcctccacac ggagtcctcc    120
tcccccccg aactagctga gagcactggc tcaggctcgc catcgtcgac tctgtcctgc    180
gacgaaactg attatcttgt ggaccgggcg cgtcatccag cagtgatgac tgtcgcaact    240
actgaccagc agcgtcggca caagatttca ttttcatcaa ggacgagccc gttgacgacg    300
agcttggact gcatggactg tcggatgact tcaccctgtt tgaagacaac aagcagcctg    360
cccagcacga cttttattgct gatctag                                       387
```

<210> SEQ ID NO 6
<211> LENGTH: 1237
<212> TYPE: DNA
<213> ORGANISM: Pichia pastoris

<400> SEQUENCE: 6

```
atgcccgtag attcttctca taagacagct agcccacttc cacctcgtaa aagagcaaag     60
acggaagaag aaaaggagca gcgtcgagtg gaacgtatcc tacgtaatag agagcggcc    120
catgcttcca gagagaagaa acgaagacac gttgaatttc tggaaaacca cgtcgtcgac    180
ctggaatctg cacttcaaga atcagccaaa gccactaaca agttgaaaga atacaagat    240
atcattgttt caaggttgga agccttaggt ggtaccgtct cagatttgga tttaacagtt    300
ccggaagtcg atttccccaa atcttctgat ttggaaccca tgtctgatct ctcaacttct    360
tcgaaatcgg agaaagcatc tacatccact cgcagatctt tgactgagga tctggacgaa    420
gatgacgtcg ctgaatatga cgacgaagaa gaggacgaag agttacccag gaaaatgaaa    480
gtcttaaacg acaaaaacaa gagcacatct atcaagcagg agaagttgaa tgaacttcca    540
tctcctttgt catccgattt ttcagacgta gatgaagaaa agtcaactct cacacattta    600
aagttgcaac agcaacaaca caaccagta gacaattatg tttctactcc tttgagtctt    660
ccggaggatt cagttgattt tattaaccca ggtaacttaa aaatagagtc cgatgagaac    720
```

| | |
|---|---|
| ttcttgttga gttcaaatac tttacaaata aaacacgaaa atgacaccga ctacattact | 780 |
| acagctccat caggttccat caatgatttt tttaattctt atgacattag cgagtcgaat | 840 |
| cggttgcatc atccagcagt gatgacggat tcatctttac acattacagc aggctccatc | 900 |
| ggcttttcct ctttgattgg ggggggggaa agttctgtag cagggaggcg cagttcagtt | 960 |
| ggcacatatc agttgacatg catagcgatc aggtgattgc tcttgttaac tggtatgcca | 1020 |
| agtcaaccgt tttcggcgta cctactactc tactttaact cttgaattga gatgaaacaa | 1080 |
| tcgcccttgt tcgagacgcg tagttaattt aagatgaatc aatttgcaac aaaagaacaa | 1140 |
| acgaaaaaga taacagcaaa cttaagtttc gtggtctgca gcaccattta ccgctaatgc | 1200 |
| atttgattta aatgactttg tattcttcca ggaatag | 1237 |

<210> SEQ ID NO 7
<211> LENGTH: 2810
<212> TYPE: DNA
<213> ORGANISM: Artificial Sequence
<220> FEATURE:
<223> OTHER INFORMATION: Synthetically generated oligonucleotide

<400> SEQUENCE: 7

| | |
|---|---|
| gtaaagcacg agaacttcaa gacctgttct cagtctggct tctgtaagcg aaaccgagcc | 60 |
| ttcgccgacg acgccgctgc ccagggctct tctgggcct ctccctacga gctggactct | 120 |
| tcttctatcc agttcaagga cggccagctg cacggcacca tcctgaagtc tgtgtctccc | 180 |
| aacgagaagg tgaagctgcc cctggtggtg tctttcctgg agtctggcgc cgctcgagtg | 240 |
| gtggtggacg aggagaagcg aatgaacggc gacatccagc tgcgacacga ctctaaggcc | 300 |
| cgaaaggagc gatacaacga ggccgagaag tgggtgctgg tcgcggcct ggagctgtct | 360 |
| aagaccgcca ccctgcgacc cgagaccgag tctggcttca cccgagtgct gtacggcccc | 420 |
| gacaaccagt tcgaggccgt gatccgacac gccccctttct ctgccgactt caagcgagat | 480 |
| ggccagaccc acgtgcagct gaacaacaag ggctacctga acatggagca ctggcgaccc | 540 |
| aaggtggagg tggagggcga gggtgagcag cagacccagg aggacgagtc tacctggtgg | 600 |
| gacgagtctt tcggcggcaa caccgacacc aagccccgag gccccgagtc tgtgggcctg | 660 |
| gacatcacct tccccggcta caagcacgtg ttcggcatcc ccgagcacgc cgactccctg | 720 |
| tctctgaagg agacccgagg cggcgagggc aaccacgagg agccctaccg aatgtacaac | 780 |
| gccgacgtgt tcgagtacga gctgtcctct cccatgaccc tgtacggcgc catcccccttc | 840 |
| atgcaggccc accgaaagga ctctaccgtg ggcgtgttct ggctgaacgc cgccgagacc | 900 |
| tgggtggaca tcgtgaagtc tacctcttct cccaaccccc tggccctggg cgtgggagcc | 960 |
| accaccgaca cccagtctca ctggttctct gagtctggcc agctggacgt gttcgtgttc | 1020 |
| ctgggcccca ccccccagga gatttctaag acctacggcg agctgaccgg ctacacccag | 1080 |
| ctgccccagc acttcgccat tgcctaccac cagtgtcgat ggaactacat caccgacgag | 1140 |
| gacgtgaagg aggtggaccg aaaacttcgac aagtaccaga tccccctacga cgtgatctgg | 1200 |
| ctggacatcg agtacaccga cgaccgaaag tacttcacct gggacccccct gtcttttccc | 1260 |
| gaccccatct ctatggagga gcagctggac gagtctgagc gaaagctggt cgtgatcatc | 1320 |
| gacccccaca tcaagaacca ggacaagtac tctatcgtgc aggagatgaa gtctaaggac | 1380 |
| ctggccacca gaacaaggga cggcgagatt tacgacggct ggtgttggcc cggctcttct | 1440 |
| cactggatcg acaccttcaa ccccgctgcc atcaagtggg ggtgtctct gttcaagttc | 1500 |
| gacaagttca agggcaccct gtctaacgtg ttcatctgga acgacatgaa cgagccctct | 1560 |

| | |
|---|---|
| gtgttcaacg gccccgagac caccatgccc aaggacaacc tgcaccacgg caactgggag | 1620 |
| caccgagaca tccacaacgt gcacggcatc accctggtga acgccaccta cgacgccctg | 1680 |
| ctggagcgaa agaagggcga gatccgacga cccttcatcc tgacccgatc ttactacgcc | 1740 |
| ggtgcccagc gaatgtctgc catgtggacc ggcgacaacc aggccacctg ggagcacctg | 1800 |
| gccgcctcta tccccatggt gctgaacaac ggaatcgccg gcttccccttcgccggtgcc | 1860 |
| gacgtgggcg gcttcttcca gaacccctct aaggagctgc tgacccgatg gtatcaggcc | 1920 |
| ggcatctggt atcctttctt ccgagcccac gcccacatcg acacccgacg acgagagccc | 1980 |
| tacctgatcg cccgagcccca ccgatctatc atctctcagg ccatccgact gcgataccag | 2040 |
| ctgctgcccg cctggtacac cgccttccac gaggcctctg tgaacggcat gcccatcgtg | 2100 |
| cgaccccagt actacgccca ccctgggac gaggccggct tcgccatcga cgaccagctg | 2160 |
| tacctgggct ctaccggcct gctggccaag cccgtggtgt ctgaggaggc caccaccgcc | 2220 |
| gacatctacc tggctgacga cgagaagtac tacgactact cgactacac cgtgtaccag | 2280 |
| ggcgctggca agcgacacac cgtgcccgct cccatggaga ccgtgcccct gctgatgcag | 2340 |
| ggcggccacg tgatccccccg aaaggaccga ccccgacgat cttctgccct gatgcgatgg | 2400 |
| gaccccctaca ccctggtggt ggtgctggac aagaacggcc aggccgacgg ctctctgtac | 2460 |
| gtggacgacg cgagaccttt cgactacgag cgaggcgcct acatccatcg acgattccga | 2520 |
| ttccaggagt ctgccctggt ctccgaggac gtgggcacca agggcccaa gaccgccgag | 2580 |
| tacctcaaga ccatggccaa cgtgcgagtg gagcgagtgg tggtcgtgga ccccccaag | 2640 |
| gagtggcagg gcaagacctc tgtgaccgtg atcgaggacg gcgcctctgc cgcctctacc | 2700 |
| gcctccatgc agtaccactc tcagcccgac ggcaaggccg cctacgccgt ggtgaagaac | 2760 |
| cccaacgtgg gcatcggcaa gacctggcga atcgagttct aatagcctag | 2810 |

<210> SEQ ID NO 8
<211> LENGTH: 1651
<212> TYPE: DNA
<213> ORGANISM: Artificial Sequence
<220> FEATURE:
<223> OTHER INFORMATION: Synthetically generated oligonucleotide

<400> SEQUENCE: 8

| | |
|---|---|
| agcgctggcg acgcctcttc tcgaccccga ggcgtgggcc ccgagttcgc caagttctac | 60 |
| aaggacacca ccaccttcac ctgtatctct caccccgcca tccagattcc cttctctgcc | 120 |
| gtgaacgacg actactgtga ctgtcccgac ggctctgacg agcccggcac ctctgcctgt | 180 |
| gcctttctgt ctcgaaactc tgccctgacc ccggtgagc gacccggatc tgacgacctg | 240 |
| gagctgacct ctgccctgcc cggcttctac tgtaagaaca agggccacaa gcccggctac | 300 |
| gtgcccttcc agcgagttaa cgatggcatc tgtgactacg agctgtgttg tgacggatcg | 360 |
| gatgagtggg ctcgacccgg cggaaccaag tgtgaggaca agtgtaagga gatcggcaag | 420 |
| gagtggcgaa agaaggagga gaagcgacag aagtctatga ccgccgctct gaagaagaag | 480 |
| aaggacctgc tggtcgaggc cggacgacag cagaaggagg tcgaggacaa catcaagcga | 540 |
| ctggaggtgg agatccaggc ccaggagctg aaggtcaacg acctgcaggc cgagctggag | 600 |
| gaggtggagc agcaggaggc ctctaaggtc gtcaagggca agaccgccgg caaggtgaac | 660 |
| gtgctggctg gcctcgccaa gtctcgagtg gaggagctgc gaaacgccct gatggacgtg | 720 |
| cgaaaggagc gagatgacac ccgagcccga gttaaggaac tcgaagagat cctgtctaag | 780 |
| ttcaaggtgg agtacaaccc caacttcaac gacgagggcg tgaagcgagc cgtgcgatct | 840 |

```
tgggaggact acgccgccaa gggcaccctg gagggcgccg tgaacaacgc ccaggaccga      900
gacctggacg agatcgccaa gcccgacgac gagaaggccg gcatcaactg ggagcagtgg      960
gagaacgagg aggacggctg tgaggctggc ctggtgtacc agctggccgc ctacctgccc     1020
ccctctctgg tggagttcat cgagggcaag gtgctgttcg tgcgaggcct gctggaggac     1080
aacggcatcc tgcccaaggc cgccgagacc tctacctctg agtctaaggt ggtgtctgag     1140
gcccgagagg ccgtgaagtc tgccgagaag gagctgggcg acaagcagaa gcagctgaag     1200
gaccacaagt ctgacctgga gaccgactac ggcgtgggct ctatcttccg agccctgaag     1260
ggcgtgtgta tctctaagga ctctggcgag tacacctacg agcactgttt tctggaccag     1320
accaagcaga tccccaagaa gggcggaggc tctacccgaa tgggcaagta caccggcatc     1380
ggctctgtgt ctgtggacgt gctgaacgag gccggcgaga tcgtgcctga ggatcgagtg     1440
accctgcagt acgccaacgg ccagggctgt tggaacggac ccgcccgatc taccaccgtg     1500
atcctgacct gtggcgagga ggacgccatc ctgaaggtgg ccgaggacga gaagtgtgtg     1560
tactctatgc acgtgacctc tcccgccgtg tgtcccggcg gtgacgaggg cgccaccgcc     1620
cccaaccgaa aggacgagct gtaatagcct a                                   1651
```

<210> SEQ ID NO 9
<211> LENGTH: 1534
<212> TYPE: DNA
<213> ORGANISM: Artificial Sequence
<220> FEATURE:
<223> OTHER INFORMATION: Synthetically generated oligonucleotide

<400> SEQUENCE: 9

```
gagctcagcg ctaccaagcg aggctctccc aaccccaccc gagccgccgc tgtgaaggcc       60
gccttccaga cctcttggaa cgcctaccac cacttcgcct ccccacga cgacctgcac       120 cccgtgtcta actcgttcga cgacgagcga aacggctggg gctcttctgc catcgacggc      180
ctggacaccg ccatcctgat gggcgacgcc gacatcgtga acaccatcct gcagtacgtg      240
ccccagatca acttcaccac caccgccgtg gccaaccagg gcatctctgt gttcgagacc      300
aacatccgat acctgggcgg cctgctgtct gcctacgacc tgctgcgagg ccccttctct      360
tctctggcca ccaaccagac cctggtgaac tctctgctgc acaggccca gaccctggcc      420 aacggcctga aggtggcttt taccaccccc tctggcgtgc ccgaccccac cgtgttcttc      480
aaccccaccg tgcgacgatc tggcgcctct tctaacaacg tggccgagat cggctctctg      540
gtgctggagt ggacccgact gtctgacctg accggcaacc ccagtacgc ccagctggcc      600 cagaagggcg agtcttacct gctgaacccc aagggctctc ccgaggcctg gccggactg      660 atcggcacct tcgtgtctac ctctaacggc accttccagg actcttccgg ctcttggtct      720
ggcctgatgg actcttttcta cgagtacctg atcaagatgt acctgtacga ccccgtggcc      780
ttcgcccact acaaggaccg atgggtgctg gccgccgact ctaccatcgc ccacctggcc      840
tctcacccct ctacccgaaa ggacctgacc ttcctgtcct cttacaacgg ccagtctacc      900
tctcccaact ctggacacct ggcttccttc gccggtggca acttcatcct gggcggcatc      960
ctgctgaacg agcagaagta catcgacttc ggcatcaagc tggcctcttc ctacttcgcc     1020
acctacaaac agaccgcctc tggcatcggc cccgagggct ccgcctggt ggactctgtg     1080 accggcgctg gcggctctcc cccctcttct cagtctggct ctactcttc tgccggcttc     1140 tgggtgaccg cccctacta catcctgcga ccgagaccc tggagtctct gtactacgcc     1200
taccgagtga ccggcgactc taagtggcag gacctggcct gggaggcctt ctctgccatc     1260
```

```
gaggacgcct gtcgagccgg ctctgcctac tcttctatca acgacgtgac ccaggccaac    1320
ggtggcggag cctctgacga catggagtct ttctggttcg ccgaggccct gaagtacgcc    1380
tacctgatct tcgccgagga atctgacgtg caggtgcagg ccaacggcgg caacaagttc    1440
gtgttcaaca ccgaggccca ccccttctct atccgatctt cttctcgacg aggcggccac    1500
ctggcccatg acgagctgta atagcctagg tacc                                1534

<210> SEQ ID NO 10
<211> LENGTH: 500
<212> TYPE: DNA
<213> ORGANISM: Artificial Sequence
<220> FEATURE:
<223> OTHER INFORMATION: Exemplary nucleotide sequence for the GAP
      promoter of Yarrowia lipolytica

<400> SEQUENCE: 10
cggcggactg cgtccgaacc agctccagca gcgttttttc cgggccattg agccgactgc      60
gaccccgcca acgtgtcttg gcccacgcac tcatgtcatg ttggtgttgg gaggccactt     120
tttaagtagc acaaggcacc tagctcgcag caaggtgtcc gaaccaaaga agcggctgca     180
gtggtgcaaa cggggcggaa acggcgggaa aaagccacgg gggcacgaat tgaggcacgc     240
cctcgaattt gagacgagtc acggcccccat tcgcccgcgc aatggctcgc caacgcccgg     300
tcttttgcac cacatcaggt tacccccaagc caaaccttgt tgttaaaaag cttaacatat     360
tataccgaac gtaggtttgg gcgggcttgc tccgtctgtc caaggcaaca tttatataag     420
ggtctgcatc gccggctcaa ttgaatcttt tttcttcttc tcttctctat attcattctt     480
gaattaaaca cacatcaaca                                                 500

<210> SEQ ID NO 11
<211> LENGTH: 6549
<212> TYPE: DNA
<213> ORGANISM: Artificial Sequence
<220> FEATURE:
<223> OTHER INFORMATION: Exemplary motif

<400> SEQUENCE: 11
cttatctggg gcagtgaagt atatgttatg gtaatagtta cgagttagtt gaacttatag      60
atagactgga ctatacggct atcggtccaa attagaaaga acgtcaatgg ctctctgggc     120
ggaattcgta aacttcgta tagcaggagt tatccgaagc gataattacc ctgttatccc      180
tagcttatcg atacgcgtgc atgctgaggt gtctcacaag tgccgtgcag tcccgccccc     240
acttgcttct ctttgtgtgt agtgtacgta cattatcgag accgttgttc ccgcccacct     300
cgatccggca tgctgaggtg tctcacaagt gccgtgcagt cccgccccca cttgcttctc     360
tttgtgtgta gtgtacgtac attatcgaga ccgttgttcc cgcccacctc gatccggcat     420
gctgaggtgt ctcacaagtg ccgtgcagtc ccgccccac ttgcttctct ttgtgtgtag     480
tgtacgtaca ttatcgagac cgttgttccc gcccacctcg atccggcatg ctgaggtgtc     540
tcacaagtgc cgtgcagtcc cgcccccact tgcttctctt tgtgtgtagt gtacgtacat     600
tatcgagacc gttgttcccg cccacctcga tccggcatgc actgatcacg ggcaaaagtg     660
cgtatatata caagagcgtt tgccagccac agatttcac tccacacacc acatcacaca     720
tacaaccaca cacatccacg tgggaacccg aaactaagga tccatgaagc tttccaccat     780
cctcttcaca gcctgcgcta ccctggccgc taccaagcga ggctctccca accccacccg     840
agccgccgct gtgaaggccg ccttccagac ctcttggaac gcctaccacc acttcgcctt     900
```

```
cccccacgac gacctgcacc ccgtgtctaa ctcgttcgac gacgagcgaa acggctgggg    960
ctcttctgcc atcgacggcc tggacaccgc catcctgatg ggcgacgccg acatcgtgaa   1020
caccatcctg cagtacgtgc cccagatcaa cttcaccacc accgccgtgg ccaaccaggg   1080
catctctgtg ttcgagacca acatccgata cctgggcggc ctgctgtctg cctacgacct   1140
gctgcgaggc cccttctctt ctctggccac caaccagacc ctggtgaact ctctgctgcg   1200
acaggcccag accctggcca acggcctgaa ggtggctttt accacccct ctggcgtgcc    1260
cgaccccacc gtgttcttca accccaccgt gcgacgatct ggcgcctctt ctaacaacgt   1320
ggccgagatc ggctctctgg tgctggagtg gacccgactg tctgacctga ccggcaaccc   1380
ccagtacgcc cagctggccc agaagggcga gtcttacctg ctgaaccccca agggctctcc   1440
cgaggcctgg cccggactga tcggcacctt cgtgtctacc tctaacggca ccttccagga   1500
ctcttccggc tcttggtctg gcctgatgga ctctttctac gagtacctga tcaagatgta   1560
cctgtacgac cccgtggcct cgcccacta caaggaccga tgggtgctgg ccgccgactc   1620
taccatcgcc cacctggcct ctcacccctc tacccgaaag gacctgacct tcctgtcctc   1680
ttacaacggc cagtctacct ctcccaactc tggacacctg gcttccttcg ccggtggcaa   1740
cttcatcctg ggcggcatcc tgctgaacga gcagaagtac atcgacttcg gcatcaagct   1800
ggcctcttcc tacttcgcca cctacaacca gaccgcctct ggcatcggcc ccagggctt    1860
cgcctgggtg gactctgtga ccggcgctgg cggctctccc ccctcttctc agtctggctt   1920
ctactcttct gccggcttct gggtgaccgc cccctactac atcctgcgac ccagagccct   1980
ggagtctctg tactacgcct accgagtgac cggcgactct aagtggcagg acctggcctg   2040
ggaggccttc tctgccatcg aggacgcctg tcgagccggc tctgcctact cttctatcaa   2100
cgacgtgacc caggccaacg tggcggagc ctctgacgac atggagtctt tctggttcgc    2160
cgaggccctg aagtacgcct acctgatctt cgccgaggaa tctgacgtgc aggtgcaggc   2220
caacggcggc aacaagttcg tgttcaacac cgaggcccac cccttctcta tccgatcttc   2280
ttctcgacga ggcggccacc tggcccatga cgagctgtaa tagcctaggg tgtctgtggt   2340
atctaagcta tttatcactc tttacaactt ctacctcaac tatctacttt aataaatgaa   2400
tatcgtttat tctctatgat tactgtatat gcgttcctct aagacaaatc gaattccatg   2460
tgtaacactc gctctggaga gttagtcatc gacagggta actctaatct cccaacacct    2520
tattaactct gcgtaactgt aactcttctt gccacgtcga tcttactcaa ttttcctgct   2580
catcatctgc tggattgttg tctatcgtct ggctctaata catttattgt ttattgccca   2640
aacaactttc attgcacgta agtgaattgt tttataacag cgttcgccaa ttgctgcgcc   2700
atcgtcgtcc ggctgtccta ccgttagggt agtgtgtctc acactaccga ggttactaga   2760
gttgggaaag cgatactgcc tcggacacac cacctggtct tacgactgca gagagaatcg   2820
gcgttacctc ctcacaaagc cctcagtgcg gccgcccggg gtgggcgaag aactccagca   2880
tgagatcccc gcgctggagg atcatccagc cggcgtcccg gaaaacgatt ccgaagccca   2940
accttccata gaaggcggcg gtggaatcga aatctcgtga tggcaggttg ggcgtcgctt   3000
ggtcggtcat ttcgaacccc agagtcccgc tcagaagaac tcgtcaagaa ggcgatagaa   3060
ggcgatgcgc tgcgaatcgg gagcggcgat accgtaaagc acgaggaagc ggtcagccca   3120
ttcgccgcca agctcttcag caatatcacg ggtagccaac gctatgtcct gatagcggtc   3180
cgccacaccc agccgccac agtcgatgaa tccagaaaag cggccatttt ccaccatgat    3240
attcggcaag caggcatcgc catgggtcac gacgagatcc tcgccgtcgg gcatgcgcgc   3300
```

```
cttgagcctg gcgaacagtt cggctggcgc gagcccctga tgctcttcgt ccagatcatc    3360
ctgatcgaca agaccggctt ccatccgagt acgtgctcgc tcgatgcgat gtttcgcttg    3420
gtggtcgaat gggcaggtag ccggatcaag cgtatgcagc cgccgcattg catcagccat    3480
gatggatact ttctcggcag gagcaaggtg agatgacagg agatcctgcc ccggcacttc    3540
gcccaatagc agccagtccc ttcccgcttc agtgacaacg tcgagcacag ctgcgcaagg    3600
aacgcccgtc gtggccagcc acgatagccg cgctgcctcg tcctgcagtt cattcagggc    3660
accggacagg tcggtcttga caaaaagaac cgggcgcccc tgcgctgaca gccggaacac    3720
ggcggcatca gagcagccga ttgtctgttg tgcccagtca tagccgaata gcctctccac    3780
ccaagcggcc ggagaacctg cgtgcaatcc atcttgttca atcatgcgaa acgatcctca    3840
tcctgtctct tgatcagatc ttgatcccct gcgccatcag atccttggcg gcaagaaagc    3900
catccagttt actttgcagg gcttcccaac cttaccagag ggcgcccag ctggcaattc     3960 cggttcgctt gctgtccata aaaccgccca gtctagctat cgccatgtaa gcccactgca    4020
agctacctgc tttctctttg cgcttgcgtt ttcccttgtc cagatagccc agtagctgac    4080
attcatccgg ggtcagcacc gtttctgcgg actggctttc tacgtgttcc gcttcctta    4140 gcagcccttg cgccctgagt gcttgcggca gcgtgaagct agcttatgcg gtgtgaaata    4200
ccgcacagat gcgtaaggag aaaataccgc atcaggcgct cttccgcttc ctcgctcact    4260
gactcgctgc gctcggtcgt tcggctgcgg cgagcggtat cagctcactc aaaggcggta    4320
atacggttat ccacagaatc aggggataac gcaggaaaga acatgtgagc aaaaggccag    4380
caaaaggcca ggaaccgtaa aaaggccgcg ttgctggcgt ttttccatag gctccgcccc    4440
cctgacgagc atcacaaaaa tcgacgctca agtcagaggt ggcgaaaccc gacaggacta    4500
taaagatacc aggcgtttcc ccctggaagc tccctcgtgc gctctcctgt tccgaccctg    4560
ccgcttaccg gatacctgtc cgcctttctc ccttcgggaa gcgtggcgct ttctcatagc    4620
tcacgctgta ggtatctcag ttcggtgtag gtcgttcgct ccaagctggg ctgtgtgcac    4680
gaaccccccg ttcagcccga ccgctgcgcc ttatccggta actatcgtct tgagtccaac    4740
ccggtaagac acgacttatc gccactggca gcagccactg gtaacaggat tagcagagcg    4800
aggtatgtag gcggtgctac agagttcttg aagtggtggc ctaactacgg ctacactaga    4860
aggacagtat ttggtatctg cgctctgctg aagccagtta ccttcggaaa aagagttggt    4920
agctcttgat ccggcaaaca aaccaccgct ggtagcggcg ttttttgtt tgcaagcagc     4980 agattacgcg cagaaaaaaa ggatctcaag aagatccttt gatcttttct tactgaacgg    5040
tgatccccac cggaattgcg gccgctgtcg ggaaccgcgt tcaggtggaa caggacacct    5100
cccttgcact tcttggtata tcagtatagg ctgatgtatt catagtgggg ttttcataa     5160 taaatttact aacggcaggc aacattcact cggcttaaac gcaaaacgga ccgtcttgat    5220
atcttctgac gcattgacca ccgagaaata gtgttagtta ccgggtgagt tattgttctt    5280
ctacacaggc gacgcccatc gtctagagtt gatgtactaa ctcagatttc actacctacc    5340
ctatccctgg tacgcacaaa gcactttgct agatagagtc gacaaaggcg gcccccccct    5400
cgagattacc ctgttatccc tacataactt cgtatagcat acattatacg aagttattct    5460
gaattccgag aaacacaaca acatgcccca ttggacagac catgcggata cacaggttgt    5520
gcagtaccat acatactcga tcagacaggt cgtctgacca tcatacaagc tgaacagcgc    5580
tccatacttg cacgctctct atatacacag ttaaattaca tatccatagt ctaacctcta    5640
acagttaatc ttctggtaag cctcccagcc agccttctgg tatcgcttgg cctcctcaat    5700
```

```
aggatctcgg ttctggccgt acagacctcg gccgacaatt atgatatccg ttccggtaga    5760
catgacatcc tcaacagttc ggtactgctg tccgagagcg tctcccttgt cgtcaagacc    5820
caccccgggg gtcagaataa gccagtcctc agagtcgccc ttaggtcggt tctgggcaat    5880
gaagccaacc acaaactcgg ggtcggatcg ggcaagctca atggtctgct ggagtactc     5940
gccagtggcc agagagccct tgcaagacag ctcggccagc atgagcagac ctctggccag    6000
cttctcgttg ggagaggga ctaggaactc cttgtactgg gagttctcgt agtcagagac     6060
gtcctccttc ttctgttcag agacagtttc ctcggcacca gctcgcaggc cagcaatgat    6120
tccggttccg ggtacaccgt gggcgttggt gatatcggac cactcggcga ttcggtgaca    6180
ccggtactgg tgcttgacag tgttgccaat atctgcgaac tttctgtcct cgaacaggaa    6240
gaaaccgtgc ttaagagcaa gttccttgag ggggagcaca gtgccggcgt aggtgaagtc    6300
gtcaatgatg tcgatatggg tcttgatcat gcacacataa ggtccgacct tatcggcaag    6360
ctcaatgagc tccttggtgg tggtaacatc cagagaagca cacaggttgg ttttcttggc    6420
tgccacgagc ttgagcactc gagcggcaaa ggcggacttg tggacgttag ctcgagcttc    6480
gtaggagggc attttggtgg tgaagaggag actgaaataa atttagtctg cagaactttt    6540
tatcggaac                                                            6549

<210> SEQ ID NO 12
<211> LENGTH: 6485
<212> TYPE: DNA
<213> ORGANISM: Artificial Sequence
<220> FEATURE:
<223> OTHER INFORMATION: Exemplary motif

<400> SEQUENCE: 12
tagcaggagt tatccgaagc gataattacc ctgttatccc tagcttatcg atacggcgga      60
ctgcgtccga accagctcca gcagcgtttt ttccgggcca ttgagccgac tgcgaccccg     120
ccaacgtgtc ttggcccacg cactcatgtc atgttggtgt tgggaggcca cttttttaagt   180
agcacaaggc acctagctcg cagcaaggtg tccgaaccaa agaagcggct gcagtggtgc     240
aaacggggcg gaaacggcgg gaaaaagcca cgggggcacg aattgaggca cgccctcgaa     300
tttgagacga gtcacggccc cattcgcccg cgcaatggct cgccaacgcc cggtcttttg    360
caccacatca ggttaccccca agccaaacct ttgtgttaaaa agcttaaaca tattataccg    420
aacgtaggtt tgggcgggct tgctccgtct gtccaaggca acatttatat aagggtctgc     480
atcgccggct caattgaatc tttttttcttc ttctcttctc tatattcatt cttgaattaa    540
acacacatca acaggatcca tgaagctttc caccatcctc ttcacagcct gcgctaccct    600
ggccgctacc aagcgaggct ctcccaaccc cacccgagcc gccgctgtga aggccgcctt    660
ccagacctct tggaacgcct accaccactt cgccttcccc cacgacgacc tgcaccccgt    720
gtctaactcg ttcgacgacg agcgaaacgg ctggggctct tctgccatcg acggcctgga    780
caccgccatc ctgatgggcg acgccgacat cgtgaacacc atcctgcagt acgtgcccca    840
gatcaacttc accaccaccg ccgtggccaa ccagggcatc tctgtgttcg agaccaacat    900
ccgatacctg gccggcctgc tgtctgccta cgacctgctg cgaggcccct tctcttctct    960
ggccaccaac cagaccctgg tgaactctct gctgcgacag gcccagaccc tggccaacgg   1020
cctgaaggtg gcttttacca ccccctctgg cgtgcccgac ccaccgtgt tcttcaaccc    1080
caccgtgcga cgatcggcg cctcttctaa caacgtggcc gagatcggct ctctggtgct   1140
ggagtggacc cgactgtctg acctgaccgg caaccccca tacgcccagc tggcccagaa   1200
```

```
gggcgagtct tacctgctga accccaaggg ctctcccgag gcctggcccg gactgatcgg    1260
caccttcgtg tctacctcta acggcacctt ccaggactct tccggctctt ggtctggcct    1320
gatggactct ttctacgagt acctgatcaa gatgtacctg tacgaccccg tggccttcgc    1380
ccactacaag gaccgatggg tgctggccgc cgactctacc atcgcccacc tggcctctca    1440
cccctctacc cgaaaggacc tgaccttcct gtcctcttac aacggccagt ctacctctcc    1500
caactctgga cacctggctt ccttcgccgg tggcaacttc atcctgggcg catcctgct     1560
gaacgagcag aagtacatcg acttcggcat caagctggcc tcttcctact cgccaccta    1620
caaccagacc gcctctggca tcggccccga gggcttcgcc tgggtggact ctgtgaccgg    1680
cgctggcggc tctccccccct cttctcagtc tggcttctac tcttctgccg gcttctgggt    1740
gaccgccccc tactacatcc tgcgacccga gaccctggag tctctgtact acgcctaccg    1800
agtgaccggc gactctaagt ggcaggacct ggcctgggag gccttctctg ccatcgagga    1860
cgcctgtcga gccggctctg cctactcttc tatcaacgac gtgacccagg ccaacggtgg    1920
cggagcctct gacgacatgg agtctttctg gttcgccgag gccctgaagt acgcctacct    1980
gatcttcgcc gaggaatctg acgtgcaggt gcaggccaac ggcggcaaca agttcgtgtt    2040
caacaccgag gcccacccct ctctatccg atcttcttct cgacgaggcg ccacctggc     2100
ccatgacgag ctgtaatagc ctagggtgtc tgtggtatct aagctattta tcactcttta    2160
caacttctac ctcaactatc tactttaata atgaatatc gtttattctc tatgattact     2220
gtatatgcgt tcctctaaga caaatcgaat tccatgtgta acactcgctc tggagagtta    2280
gtcatccgac agggtaactc taatctccca acaccttatt aactctgcgt aactgtaact    2340
cttcttgcca cgtcgatctt actcaatttt cctgctcatc atctgctgga ttgttgtcta    2400
tcgtctggct ctaatacatt tattgtttat tgcccaaaca actttcattg cacgtaagtg    2460
aattgtttta taacagcgtt cgccaattgc tgcgccatcg tcgtccggct gtcctaccgt    2520
tagggtagtg tgtctcacac taccgaggtt actagagttg ggaaagcgat actgcctcgg    2580
acacaccacc tggtcttacg actgcagaga gaatcggcgt tacctcctca caaagccctc    2640
agtgcggccg cccggggtgg gcgaagaact ccagcatgag atccccgcgc tggaggatca    2700
tccagccggc gtcccggaaa acgattccga agcccaacct ttcatagaag gcggcggtgg    2760
aatcgaaatc tcgtgatggc aggttgggcg tcgcttggtc ggtcatttcg aaccccagag    2820
tcccgctcag aagaactcgt caagaaggcg atagaaggcg atgcgctgcg aatcgggagc    2880
ggcgataccg taaagcacga ggaagcggtc agcccattcg ccgccaagct cttcagcaat    2940
atcacgggta gccaacgcta tgtcctgata gcggtccgcc acacccagcc ggccacagtc    3000
gatgaatcca gaaaagcggc catttccac catgatattc ggcaagcagg catcgccatg    3060
ggtcacgacg agatcctcgc cgtcgggcat gcgcgccttg agcctggcga acagttcggc    3120
tggcgcgagc cctgatgct cttcgtccag atcatcctga tcgacaagac cggcttccat    3180
ccgagtacgt gctcgctcga tgcgatgttt cgcttggtgg tcgaatgggc aggtagccgg    3240
atcaagcgta tgcagccgcc gcattgcatc agccatgatg atactttct cggcaggagc     3300
aaggtgagat gacaggagat cctgccccgg cacttcgccc aatagcagcc agtcccttcc    3360
cgcttcagtg acaacgtcga gcacagctgc gcaaggaacg cccgtcgtgg ccagccacga    3420
tagccgcgct gcctcgtcct gcagttcatt cagggcaccg gacaggtcgg tcttgacaaa    3480
aagaaccggg cgcccctgcg ctgacagccg gaacacggcg gcatcagagc agccgattgt    3540
ctgttgtgcc cagtcatagc cgaatagcct ctccacccaa gcggccggag aacctgcgtg    3600
```

```
caatccatct tgttcaatca tgcgaaacga tcctcatcct gtctcttgat cagatcttga    3660
tcccctgcgc catcagatcc ttggcggcaa gaaagccatc cagtttactt tgcagggctt    3720 cccaaccta ccagagggcg ccccagctgg caattccggt tcgcttgctg tccataaaac    3780
cgcccagtct agctatcgcc atgtaagccc actgcaagct acctgctttc tctttgcgct    3840
tgcgttttcc cttgtccaga tagcccagta gctgacattc atccggggtc agcaccgttt    3900
ctgcggactg gctttctacg tgttccgctt cctttagcag cccttgcgcc ctgagtgctt    3960
gcggcagcgt gaagctagct tatgcggtgt gaaataccgc acagatgcgt aaggagaaaa    4020
taccgcatca ggcgctcttc cgcttcctcg ctcactgact cgctgcgctc ggtcgttcgg    4080
ctgcggcgag cggtatcagc tcactcaaag gcggtaatac ggttatccac agaatcaggg    4140
gataacgcag gaaagaacat gtgagcaaaa ggccagcaaa aggccaggaa ccgtaaaaag    4200
gccgcgttgc tggcgttttt ccataggctc cgcccccctg acgagcatca caaaaatcga    4260
cgctcaagtc agaggtggcg aaacccgaca ggactataaa gataccaggc gtttccccct    4320
ggaagctccc tcgtgcgctc tcctgttccg accctgccgc ttaccggata cctgtccgcc    4380
tttctccctt cgggaagcgt ggcgctttct catagctcac gctgtaggta tctcagttcg    4440
gtgtaggtcg ttcgctccaa gctgggctgt gtgcacgaac cccccgttca gcccgaccgc    4500
tgcgccttat ccggtaacta tcgtcttgag tccaacccgg taagacacga cttatcgcca    4560
ctggcagcag ccactggtaa caggattagc agagcgaggt atgtaggcgg tgctacagag    4620
ttcttgaagt ggtggcctaa ctacggctac actagaagga cagtatttgg tatctgcgct    4680
ctgctgaagc cagttacctt cggaaaaaga gttggtagct cttgatccgg caaacaaacc    4740
accgctggta gcggcggttt tttgtttgca agcagcagat tacgcgcaga aaaaaggat    4800 ctcaagaaga tcctttgatc ttttctact gaacggtgat ccccaccgga attgcggccg    4860
ctgtcgggaa ccgcgttcag gtggaacagg acacctccct tgcacttctt ggtatatcag    4920
tataggctga tgtattcata gtggggtttt tcataataaa tttactaacg gcaggcaaca    4980
ttcactcggc ttaaacgcaa aacggaccgt cttgatatct tctgacgcat tgaccaccga    5040
gaaatagtgt tagttaccgg gtgagttatt gttcttctac acaggcgacg cccatcgtct    5100
agagttgatg tactaactca gatttcacta cctaccctat ccctggtacg cacaaagcac    5160
tttgctagat agagtcgaca aaggcgggcc ccccctcgag attaccctgt tatccctaca    5220
taacttcgta tagcatacat tatacgaagt tattctgaat tccgcccaga gagccattga    5280
cgttctttct aattggacc gatagccgta tagtccagtc tatctataag ttcaactaac    5340
tcgtaactat taccataaca tatacttcac tgccccagat aaggttccga taaaaagttc    5400
tgcagactaa atttatttca gtctcctctt caccaccaaa atgccctcct acgaagctcg    5460
agctaacgtc cacaagtccg cctttgccgc tcgagtgctc aagctcgtgg cagccaagaa    5520
aaccaacctg tgtgcttctc tggatgttac caccaccaag gagctcattg agcttgccga    5580
taaggtcgga ccttatgtgt gcatgatcaa gacccatatc gacatcattg acgacttcac    5640
ctacgccggc actgtgctcc ccctcaagga acttgctctt aagcacggtt tcttcctgtt    5700
cgaggacaga aagttcgcag atattggcaa cactgtcaag caccagtacc ggtgtcaccg    5760
aatcgccgag tggtccgata tcaccaacgc ccacggtgta cccggaaccg gaatcattgc    5820
tggcctgcga gctggtgccg aggaaactgt ctctgaacag aagaaggagg acgtctctga    5880
ctacgagaac tccagtaca aggagttcct agtcccctct cccaacgaga agctggccag    5940
aggtctgctc atgctggccg agctgtcttg caagggctct ctggccactg gcgagtactc    6000
```

-continued

```
caagcagacc attgagcttg cccgatccga ccccgagttt gtggttggct tcattgccca      6060
gaaccgacct aagggcgact ctgaggactg gcttattctg acccccgggg tgggtcttga      6120
cgacaaggga gacgctctcg gacagcagta ccgaactgtt gaggatgtca tgtctaccgg      6180
aacggatatc ataattgtcg gccgaggtct gtacggccag aaccgagatc ctattgagga      6240
ggccaagcga taccagaagg ctggctggga ggcttaccag aagattaact gttagaggtt      6300
agactatgga tatgtaattt aactgtgtat atagagagcg tgcaagtatg gagcgctgtt      6360
cagcttgtat gatggtcaga cgacctgtct gatcgagtat gtatggtact gcacaacctg      6420
tgtatccgca tggtctgtcc aatgggggcat gttgttgtgt ttctcggaat tcgtataact      6480
tcgta                                                                  6485

<210> SEQ ID NO 13
<211> LENGTH: 6996
<212> TYPE: DNA
<213> ORGANISM: Artificial Sequence
<220> FEATURE:
<223> OTHER INFORMATION: Exemplary motif

<400> SEQUENCE: 13 caagggtag gcgaatggta cgattccgcc aagtgagact ggcgatcggg agaagggttg         60
gtggtcatgg gggatagaat ttgtacaagt ggaaaaacca ctacgagtag cggatttgat       120
accacaagta gcagagatat acagcaatgg tgggagtgca agtatcggaa tgtactgtac       180
ctcctgtact cgtactcgta cggcactcgt agaaacgggg caatacgggg gagaagcgat       240
cgcccgtctg ttcaatcgcc acaagtccga gtaatgctcg agtatcgaag tcttgtacct       300
ccctgtcaat catggcacca ctggtcttga cttgtctatt catactggac aagcgccaga       360
gttagctagc gaatttcgcc ctcggacatc accccatacg acggacacac atgcccgaca       420
aacagcctct cttattgtag ctgaaagtat attgaatgtg aacgtgtaca atatcaggta       480
ccagcgggag gttacggcca aggtgatacc ggaataaccc tggcttggag atggtcggtc       540
cattgtactg aagtgtccgt gtcgtttccg tcactgcccc aattggacat gtttgttttt       600
ccgatctttc gggcgccctc tccttgtctc cttgtctgtc tcctggactg ttgctacccc       660
atttctttgg cctccattgg ttcctccccg tctttcacgt cgtctatggt tgcatggttt       720
cccttatact tttcccccaca gtcacatgtt atggagggggt ctagatggac atggtgcaag       780
gcccgcaggg ttgattcgac gcttttccgc gaaaaaaaca agtccaaata ccccgcgttta       840 ttctccctcg gctctcggta tttcacatga aaactataac ctagactaca cgggcaacct       900 taacccccaga gtatacttat ataccaaagg gatgggtcct caaaaatcac acaagcaacg       960
gatccatgaa gctttccacc atcctcttca gcctgcgc tacccggcc gctaccaagc      1020 gaggctctcc caaccccacc cgagccgccg ctgtgaaggc cgccttccag acctcttgga      1080
acgcctacca ccacttcgcc ttcccccacg acgacctgca ccccgtgtct aactcgttcg      1140
acgacgagcg aaacggctgg ggctcttctg ccatcgacgg cctggacacc gccatcctga      1200
tgggcgacgc cgacatcgtg aacaccatcc tgcagtacgt gccccagatc aacttcacca      1260
ccaccgccgt ggccaaccag ggcatctctg tgttcgagac caacatccga tacctgggcg      1320
gcctgctgtc tgcctacgac ctgctgcgag gccccttctc ttctctggcc accaaccaga      1380
ccctggtgaa ctctctgctg cgacaggccc agaccctggc caacggcctg aaggtggctt      1440
ttaccacccc ctctggcgtg cccgacccca ccgtgttctt caaccccacc gtgcgacgat      1500
ctggcgcctc ttctaacaac gtggccgaga tcggctctct ggtgctggag tggaccccgac      1560
```

```
tgtctgacct gaccggcaac ccccagtacg cccagctggc ccagaagggc gagtcttacc    1620
tgctgaaccc caagggctct cccgaggcct ggcccggact gatcggcacc ttcgtgtcta    1680
cctctaacgg caccttccag gactcttccg gctcttggtc tggcctgatg gactctttct    1740
acgagtacct gatcaagatg tacctgtacg acccgtggc cttcgcccac acaaggacc     1800 gatgggtgct ggccgccgac tctaccatcg cccacctggc ctctcacccc tctacccgaa    1860
aggacctgac cttcctgtcc tcttacaacg gccagtctac ctctcccaac tctggacacc    1920
tggcttcctt cgccggtggc aacttcatcc tgggcggcat cctgctgaac gagcagaagt    1980
acatcgactt cggcatcaag ctggcctctt cctacttcgc cacctacaac cagaccgcct    2040
ctggcatcgg ccccgagggc ttcgcctggg tggactctgt gaccggcgct ggcggctctc    2100 cccctcttc tcagtctggc ttctactctt ctgccggctt ctgggtgacc gcccctact     2160 acatcctgcg acccgagacc ctggagtctc tgtactacgc ctaccgagtg accggcgact    2220
ctaagtggca ggacctggcc tgggaggcct tctctgccat cgaggacgcc tgtcgagccg    2280
gctctgccta ctcttctatc aacgacgtga cccaggccaa cggtggcgga gcctctgacg    2340
acatggagtc tttctggttc gccgaggccc tgaagtacgc ctacctgatc ttcgccgagg    2400
aatctgacgt gcaggtgcag gccaacggcg gcaacaagtt cgtgttcaac accgaggccc    2460
accccttctc tatccgatct tcttctcgac gaggcggcca cctggcccat gacgagctgt    2520
aatagcctag ggtgtctgtg gtatctaagc tatttatcac tctttacaac ttctacctca    2580
actatctact ttaataaatg aatatcgttt attctctatg attactgtat atgcgttcct    2640
ctaagacaaa tcgaattcca tgtgtaacac tcgctctgga gagttagtca tccgacaggg    2700
taactctaat ctcccaacac cttattaact ctgcgtaact gtaactcttc ttgccacgtc    2760
gatcttactc aattttcctg ctcatcatct gctggattgt tgtctatcgt ctggctctaa    2820
tacatttatt gtttattgcc caaacaactt tcattgcacg taagtgaatt gttttataac    2880
agcgttcgcc aattgctgcg ccatcgtcgt ccggctgtcc taccgttagg gtagtgtgtc    2940
tcacactacc gaggttacta gagttgggaa agcgatactg cctcggacac accacctggt    3000
cttacgactg cagagagaat cggcgttacc tcctcacaaa gccctcagtg cggccgcccg    3060
gggtgggcga agaactccag catgagatcc ccgcgctgga ggatcatcca gccggcgtcc    3120
cggaaaacga ttccgaagcc caacctttca tagaaggcgg cggtggaatc gaatctcgt    3180 gatggcaggt tgggcgtcgc ttggtcggtc atttcgaacc ccagagtccc gctcagaaga    3240
actcgtcaag aaggcgatag aaggcgatgc gctgcgaatc gggagcggcg ataccgtaaa    3300
gcacgaggaa gcggtcagcc cattcgccgc caagctcttc agcaatatca cgggtagcca    3360
acgctatgtc ctgatagcgg tccgccacac ccagccggcc acagtcgatg aatccagaaa    3420
agcggccatt ttccaccatg atattcggca agcaggcatc gccatgggtc acgacgagat    3480
cctcgccgtc gggcatgcgc gccttgagcc tggcgaacag ttcggctggc gcgagcccct    3540
gatgctcttc gtccagatca tcctgatcga caagaccggc ttccatccga gtacgtgctc    3600
gctcgatgcg atgtttcgct tggtggtcga atgggcaggt agccggatca agcgtatgca    3660
gccgccgcat tgcatcagcc atgatggata cttttctcggc aggagcaagg tgagatgaca    3720
ggagatcctg ccccggcact tcgcccaata gcagccagtc ccttcccgct tcagtgacaa    3780
cgtcgagcac agctgcgcaa ggaacgcccg tcgtggccag ccacgatagc cgcgctgcct    3840
cgtcctgcag ttcattcagg gcaccggaca ggtcggtctt gacaaaaaga accgggcgcc    3900
cctgcgctga cagccggaac acggcggcat cagagcagcc gattgtctgt tgtgcccagt    3960
```

```
catagccgaa tagcctctcc acccaagcgg ccggagaacc tgcgtgcaat ccatcttgtt    4020
caatcatgcg aaacgatcct catcctgtct cttgatcaga tcttgatccc ctgcgccatc    4080
agatccttgg cggcaagaaa gccatccagt ttactttgca gggcttccca accttaccag    4140
agggcgcccc agctggcaat tccggttcgc ttgctgtcca taaaaccgcc cagtctagct    4200
atcgccatgt aagcccactg caagctacct gctttctctt tgcgcttgcg ttttcccttg    4260
tccagatagc ccagtagctg acattcatcc ggggtcagca ccgtttctgc ggactggctt    4320
tctacgtgtt ccgcttcctt tagcagccct tgcgccctga gtgcttgcgg cagcgtgaag    4380
ctagcttatg cggtgtgaaa taccgcacag atgcgtaagg agaaaatacc gcatcaggcg    4440
ctcttccgct tcctcgctca ctgactcgct gcgctcggtc gttcggctgc ggcgagcggt    4500
atcagctcac tcaaaggcgg taatacggtt atccacagaa tcaggggata acgcaggaaa    4560
gaacatgtga gcaaaaggcc agcaaaaggc caggaaccgt aaaaaggccg cgttgctggc    4620
gtttttccat aggctccgcc cccctgacga gcatcacaaa aatcgacgct caagtcagag    4680
gtggcgaaac ccgacaggac tataaagata ccaggcgttt ccccctggaa gctccctcgt    4740
gcgctctcct gttccgaccc tgccgcttac cggatacctg tccgcctttc tcccttcggg    4800
aagcgtggcg ctttctcata gctcacgctg taggtatctc agttcggtgt aggtcgttcg    4860
ctccaagctg ggctgtgtgc acgaaccccc cgttcagccc gaccgctgcg ccttatccgg    4920
taactatcgt cttgagtcca acccggtaag acacgactta tcgccactgg cagcagccac    4980
tggtaacagg attagcagag cgaggtatgt aggcggtgct acagagttct tgaagtggtg    5040
gcctaactac ggctacacta aggacagta tttggtatc tgcgctctgc tgaagccagt    5100
taccttcgga aaagagttg gtagctcttg atccggcaaa caaaccaccg ctggtagcgg    5160
cggttttttg tttgcaagca gcagattacg cgcagaaaaa aaggatctca agaagatcct    5220
ttgatctttt cttactgaac ggtgatcccc accggaattg cggccgctgt cgggaaccgc    5280
gttcaggtgg aacaggacac ctcccttgca cttcttggta tatcagtata ggctgatgta    5340
ttcatagtgg ggttttttcat aataaattta ctaacggcag gcaacattca ctcggcttaa    5400
acgcaaaacg gaccgtcttg atatcttctg acgcattgac caccgagaaa tagtgttagt    5460
taccgggtga gttattgttc ttctacacag gcgacgccca tcgtctagag ttgatgtact    5520
aactcagatt tcactaccta ccctatccct ggtacgcaca aagcactttg ctagatagag    5580
tcgacaaagg cgggcccccc ctcgagatta ccctgttatc cctacataac ttcgtatagc    5640
atacattata cgaagttatt ctgaattccg cccagagagc cattgacgtt ctttctaatt    5700
tggaccgata gccgtatagt ccagtctatc tataagttca actaactcgt aactattacc    5760
ataacatata cttcactgcc ccagataagg ttccgataaa aagttctgca gactaaattt    5820
atttcagtct cctcttcacc accaaaatgc cctcctacga agctcgagct aacgtccaca    5880
agtccgcctt tgccgctcga gtgctcaagc tcgtggcagc caagaaaacc aacctgtgtg    5940
cttctctgga tgttaccacc accaaggagc tcattgagct tgccgataag gtcggacctt    6000
atgtgtgcat gatcaagacc catatcgaca tcattgacga cttcacctac gccggcactg    6060 tgctcccct caaggaactt gctcttaagc acggtttctt cctgttcgag gacagaaagt    6120
tcgcagatat tggcaacact gtcaagcacc agtaccggtg tcaccgaatc gccgagtggt    6180
ccgatatcac caacgcccac ggtgtacccg gaaccggaat cattgctggc ctgcgagctg    6240
gtgccgagga aactgtctct gaacagaaga aggaggacgt ctctgactac gagaactccc    6300
agtacaagga gttcctagtc ccctctccca acgagaagct ggccagaggt ctgctcatgc    6360
```

-continued

```
tggccgagct gtcttgcaag ggctctctgg ccactggcga gtactccaag cagaccattg    6420
agcttgcccg atccgacccc gagtttgtgg ttggcttcat tgcccagaac cgacctaagg    6480
gcgactctga ggactggctt attctgaccc ccggggtggg tcttgacgac aagggagacg    6540
ctctcggaca gcagtaccga actgttgagg atgtcatgtc taccggaacg gatatcataa    6600
ttgtcggccg aggtctgtac ggccagaacc gagatcctat tgaggaggcc aagcgatacc    6660
agaaggctgg ctgggaggct taccagaaga ttaactgtta gaggttagac tatggatatg    6720
taatttaact gtgtatatag agagcgtgca agtatggagc gctgttcagc ttgtatgatg    6780
gtcagacgac ctgtctgatc gagtatgtat ggtactgcac aacctgtgta tccgcatggt    6840
ctgtccaatg ggcatgttg ttgtgtttct cggaattcgt ataacttcgt atagcaggag     6900
ttatccgaag cgataattac cctgttatcc ctagcttatc gattcccaca agacgaacaa    6960
gtgataggcc gagagccgag gacgaggtgg agtgca                              6996
```

<210> SEQ ID NO 14
<211> LENGTH: 7195
<212> TYPE: DNA
<213> ORGANISM: Artificial Sequence
<220> FEATURE:
<223> OTHER INFORMATION: Exemplary motif

<400> SEQUENCE: 14

```
taattaccct gttatcccta gcttatcgat agagaccggg ttggcggcgt atttgtgtcc      60
caaaaaacag ccccaattgc cccaattgac cccaaattga cccagtagcg ggcccaaccc     120
cggcgagagc ccccttcacc ccacatatca aacctccccc ggttcccaca cttgccgtta     180
agggcgtagg gtactgcagt ctggaatcta cgcttgttca gactttgtac tagtttcttt     240
gtctggccat ccgggtaacc catgccggac gcaaaataga ctactgaaaa ttttttttgct    300 ttgtggttgg gactttagcc aagggtataa aagaccaccg tccccgaatt acctttcctc     360 ttctttttctc tctctccttg tcaactcaca cccgaaggat ccatgaagct ttccaccatc    420
ctcttcacag cctgcgctac cctggccgct accaagcgag gctctcccaa ccccacccga     480
gccgccgctg tgaaggccgc cttccagacc tcttggaacg cctaccacca cttcgccttc    540
ccccacgacg acctgcaccc cgtgtctaac tcgttcgacg acgagcgaaa cggctggggc    600
tcttctgcca tcgacggcct ggacaccgcc atcctgatgg gcgacgccga catcgtgaac    660
accatcctgc agtacgtgcc ccagatcaac ttcaccacca ccgccgtggc caaccagggc    720
atctctgtgt tcgagaccaa catccgatac ctgggcggcc tgctgtctgc ctacgacctg    780
ctgcgaggcc ccttctcttc tctggccacc aaccagaccc tggtgaactc tctgctgcga    840
caggcccaga ccctggccaa cggcctgaag gtggcttttta ccacccctc tggcgtgccc    900 gaccccaccg tgttcttcaa ccccaccgtg cgacgatctg cgcctcttc taacaacgtg    960 gccgagatcg gctctctggt gctggagtgg acccgactgt ctgacctgac cggcaacccc    1020
cagtacgccc agctggccca gaagggcgag tcttacctgc tgaaccccaa gggctctccc    1080
gaggcctggc ccggactgat cggcaccttc gtgtctacct ctaacggcac cttccaggac    1140
tcttccggct cttggtctgg cctgatggac tcttctactg agtacctgat caagatgtac    1200
ctgtacgacc ccgtggcctt cgcccactac aaggaccgat gggtgctggc cgccgactct    1260
accatcgccc acctggcctc tcaccctct acccgaaagg acctgacctt cctgtcctct    1320
tacaacggcc agtctacctc tcccaactct ggacacctgg cttccttcgc cggtggcaac    1380
ttcatcctgg gcggcatcct gctgaacgag cagaagtaca tcgacttcgg catcaagctg    1440
```

```
gcctcttcct acttcgccac ctacaaccag accgcctctg gcatcggccc cgagggcttc    1500
gcctgggtgg actctgtgac cggcgctggc ggctctcccc cctcttctca gtctggcttc    1560
tactcttctg ccggcttctg ggtgaccgcc ccctactaca tcctgcgacc cgagaccctg    1620
gagtctctgt actacgccta ccgagtgacc ggcgactcta gtggcagga cctggcctgg    1680 gaggccttct ctgccatcga ggacgcctgt cgagccggct ctgcctactc ttctatcaac    1740
gacgtgaccc aggccaacgg tggcggagcc tctgacgaca tggagtcttt ctggttcgcc    1800
gaggccctga agtacgccta cctgatcttc gccgaggaat ctgacgtgca ggtgcaggcc    1860
aacggcggca acaagttcgt gttcaacacc gaggcccacc ccttctctat ccgatcttct    1920
tctcgacgag gcggccacct ggcccatgac gagctgtaat agcctagggt gtctgtggta    1980
tctaagctat ttatcactct ttacaacttc tacctcaact atctacttta ataaatgaat    2040
atcgtttatt ctctatgatt actgtatatg cgttcctcta agacaaatcg aattccatgt    2100
gtaacactcg ctctggagag ttagtcatcc gacagggtaa ctctaatctc caacaccttt    2160
attaactctg cgtaactgta actcttcttg ccacgtcgat cttactcaat tttcctgctc    2220
atcatctgct ggattgttgt ctatcgtctg gctctaatac atttattgtt tattgcccaa    2280
acaactttca ttgcacgtaa gtgaattgtt ttataacagc gttcgccaat tgctgcgcca    2340
tcgtcgtccg gctgtcctac cgttagggta gtgtgtctca cactaccgag gttactagag    2400
ttgggaaagc gatactgcct cggacacacc acctggtctt acgactgcag agagaatcgg    2460
cgttacctcc tcacaaagcc ctcagtgcgg ccgcccgggg tgggcgaaga actccagcat    2520
gagatccccg cgctggagga tcatccagcc ggcgtcccgg aaaacgattc cgaagcccaa    2580
cctttcatag aaggcggcgg tggaatcgaa atctcgtgat ggcaggttgg gcgtcgcttg    2640
gtcggtcatt tcgaacccca gagtcccgct cagaagaact cgtcaagaag gcgatagaag    2700
gcgatgcgct gcgaatcggg agcggcgata ccgtaaagca cgaggaagcg gtcagcccat    2760
tcgccgccaa gctcttcagc aatatcacgg gtagccaacg ctatgtcctg atagcggtcc    2820
gccacaccca gccggccaca gtcgatgaat ccagaaaagc ggccattttc caccatgata    2880
ttcggcaagc aggcatcgcc atgggtcacg acgagatcct cgccgtcggg catgcgcgcc    2940
ttgagcctgg cgaacagttc ggctggcgcg agcccctgat gctcttcgtc cagatcatcc    3000
tgatcgacaa gaccggcttc catccgagta cgtgctcgct cgatgcgatg tttcgcttgg    3060
tggtcgaatg ggcaggtagc cggatcaagc gtatgcagcc gccgcattgc atcagccatg    3120
atggatactt tctcggcagg agcaaggtga gatgacagga tcctgcccc ggcacttcg    3180 cccaatagca gccagtccct tcccgcttca gtgacaacgt cgagcacagc tgcgcaagga    3240
acgcccgtcg tggccagcca cgatagccgc gctgcctcgt cctgcagttc attcagggca    3300
ccggacaggt cggtcttgac aaaaagaacc gggcgcccct gcgctgacag ccggaacacg    3360
gcggcatcag agcagccgat tgtctgttgt gcccagtcat agccgaatag cctctccacc    3420
caagcggccg gagaacctgc gtgcaatcca tcttgttcaa tcatgcgaaa cgatcctcat    3480
cctgtctctt gatcagatct tgatcccctg cgccatcaga tccttggcgg caagaaagcc    3540
atccagttta ctttgcaggg cttcccaacc ttaccagagg gcgccccagc tggcaattcc    3600
ggttcgcttg ctgtccataa aaccgcccag tctagctatc gccatgtaag cccactgcaa    3660
gctacctgct ttctctttgc gcttgcgttt tcccttgtcc agatagccca gtagctgaca    3720
ttcatccggg gtcagcaccg tttctgcgga ctggctttct acgtgttccg cttcctttag    3780
cagcccttgc gccctgagtg cttgcggcag cgtgaagcta gcttatgcgg tgtgaaatac    3840
```

```
cgcacagatg cgtaaggaga aaataccgca tcaggcgctc ttccgcttcc tcgctcactg    3900
actcgctgcg ctcggtcgtt cggctgcggc gagcggtatc agctcactca aaggcggtaa    3960
tacggttatc cacagaatca ggggataacg caggaaagaa catgtgagca aaaggccagc    4020
aaaaggccag gaaccgtaaa aaggccgcgt tgctggcgtt tttccatagg ctccgccccc    4080
ctgacgagca tcacaaaaat cgacgctcaa gtcagaggtg gcgaaacccg acaggactat    4140
aaagatacca ggcgtttccc cctggaagct ccctcgtgcg ctctcctgtt ccgaccctgc    4200
cgcttaccgg atacctgtcc gcctttctcc cttcgggaag cgtggcgctt tctcatagct    4260
cacgctgtag gtatctcagt tcggtgtagg tcgttcgctc caagctgggc tgtgtgcacg    4320
aaccccccgt tcagcccgac cgctgcgcct tatccggtaa ctatcgtctt gagtccaacc    4380
cggtaagaca cgacttatcg ccactggcag cagccactgg taacaggatt agcagagcga    4440
ggtatgtagg cggtgctaca gagttcttga agtggtggcc taactacggc tacactagaa    4500
ggacagtatt tggtatctgc gctctgctga agccagttac cttcggaaaa agagttggta    4560
gctcttgatc cggcaaacaa accaccgctg gtagcggcgg ttttttgttt gcaagcagca    4620
gattacgcgc agaaaaaaag gatctcaaga agatcctttg atcttttctt actgaacggt    4680
gatccccacc ggaattgcgg ccgctgtcgg gaaccgcgtt caggtggaac aggacacctc    4740
ccttgcactt cttggtatat cagtataggc tgatgtattc atagtggggt ttttcataat    4800
aaatttacta cacaccacct ggtcttacga ctgcagagag aatcggcgtt acctcctcac    4860
aaagccctca gtgcggccgc ccggggtggg cgaagaactc cagcatgaga tccccgcgct    4920
ggaggatcat ccagccggcg tcccggaaaa cgattccgaa gcccaacctt tcatagaagg    4980
cggcggtgga atcgaaatct cgtgatggca ggttgggcgt cgcttggtcg gtcatttcga    5040
accccagagt cccgctcaga agaactcgtc aagaaggcga tagaaggcga tgcgctgcga    5100
atcgggagcg gcgataccgt aaagcacgag gaagcggtca gcccattcgc cgccaagctc    5160
ttcagcaata tcacgggtag ccaacgctat gtcctgatag cggtccgcca cacccagccg    5220
gccacagtcg atgaatccag aaaagcggcc attttccacc atgatattcg gcaagcaggc    5280
atcgccatgg gtcacgacga gatcctcgcc gtcgggcatg cgcgccttga gcctggcgaa    5340
cagttcggct ggcgcgagcc cctgatgctc ttcgtccaga tcatcctgat cgacaagacc    5400
ggcttccatc cgagtacgtg ctcgctcgat gcgatgtttc gcttggtggt cgaatgggca    5460
ggtagccgga tcaagcgtat gcagccgccg cattgcatca gccatgatgg atactttctc    5520
ggcaggagca aggtgagatg acaggagatc ctgccccggc acttcgccca atagcagcca    5580
gtcccttccc gcttcagtga acaacgtcgag cacagctgcg caaggaacgc ccgtcgtggc    5640
cagccacgat agccgcgctg cctcgtcctg cagttcattc agggcaccgg acaggtcggt    5700
cttgacaaaa agaaccgggc gcccctgcgc tgacagccgg aacacggcgg catcagagca    5760
gccgattgtc tgttgtgccc agtcatagcc gaatagcctc tccacccaag cggccggaga    5820
acctgcgtgc aatccatctt gttcaatcat gcgaaacgat cctcatcctg tctcttgatc    5880
agatcttgat cccctgcgcc atcagatcct ggcggcaag aaagccatcc agtttacttt    5940
gcagggcttc ccaaccttac cagagggcgc cccagctggc aattccggtt cgcttgctgt    6000
ccataaaacc gcccagtcta gctatcgcca tgtaagccca ctgcaagcta cctgctttct    6060
ctttgcgctt gcgttttccc ttgtccagat agcccagtag ctgacattca tccggggtca    6120
gcaccgtttc tgcggactgg ctttctacgt gttccgcttc ctttagcagc ccttgcgccc    6180
tgagtgcttg cggcagcgtg aagctagctt atgcggtgtg aaataccgca cagatgcgta    6240
```

-continued

| | |
|---|---|
| aggagaaaat accgcatcag gcgctcttcc gcttcctcgc tcactgactc gctgcgctcg | 6300 |
| gtcgttcggc tgcggcgagc ggtatcagct cactcaaagg cggtaatacg gttatccaca | 6360 |
| gaatcagggg ataacgcagg aaagaacatg tgagcaaaag gccagcaaaa ggccaggaac | 6420 |
| cgtaaaaagg ccgcgttgct ggcgtttttc cataggctcc gcccccctga cgagcatcac | 6480 |
| aaaaatcgac gctcaagtca gaggtggcga aacccgacag gactataaag ataccaggcg | 6540 |
| tttccccctg gaagctccct cgtgcgctct cctgttccga ccctgccgct taccggatac | 6600 |
| ctgtccgcct ttctcccttc gggaagcgtg gcgctttctc atagctcacg ctgtaggtat | 6660 |
| ctcagttcgg tgtaggtcgt tcgctccaag ctgggctgtg tgcacgaacc ccccgttcag | 6720 |
| cccgaccgct gcgccttatc cggtaactat cgtcttgagt ccaacccggt aagacacgac | 6780 |
| ttatcgccac tggcagcagc cactggtaac aggattagca gagcgaggta tgtaggcggt | 6840 |
| gctacagagt tcttgaagtg gtggcctaac tacggctaca ctagaaggac agtatttggt | 6900 |
| atctgcgctc tgctgaagcc agttaccttc ggaaaaagag ttggtagctc ttgatccggc | 6960 |
| aaacaaacca ccgctggtag cggcggtttt ttgtttgcaa gcagcagatt acgcgcagaa | 7020 |
| aaaaaggatc tcaagaagat cctttgatct tttcttactg aacggtgatc cccaccggaa | 7080 |
| ttgcggccgc tgtcgggaac cgcgttcagg tggaacagga cacctcccct tgcacttcttg | 7140 |
| gtatatcagt ataggctgat gtattcatag tggggttttt cataataaat ttact | 7195 |

<210> SEQ ID NO 15
<211> LENGTH: 1518
<212> TYPE: DNA
<213> ORGANISM: Artificial Sequence
<220> FEATURE:
<223> OTHER INFORMATION: Synthetically generated oligonucleotide

<400> SEQUENCE: 15

| | |
|---|---|
| gagctcagcg ctcgaccctg tatcccccaag tctttcggct actcttctgt ggtgtgtgtg | 60 |
| tgtaacgcca cctactgtga ctcgttcgac ccccccacct tccccgccct gggcaccttc | 120 |
| tctcgatacg agtctacccg atctggccga cgaatggagc tgtctatggg ccccatccag | 180 |
| gccaaccaca ccggcaccgg cctgctgctg accctgcagc ccgagcagaa gttccagaag | 240 |
| gtcaagggct tcggcggagc catgaccgac gccgctgccc tgaacatcct ggccctgtct | 300 |
| ccccccgctc agaacctgct cctgaagtct tacttctctg aggagggcat cggctacaac | 360 |
| atcatccgag tgcctatggc ctcttgtgac ttctctatcc gaacctacac ctacgccgac | 420 |
| accccccgacg acttccagct gcacaacttc tccctgcccg aggaggacac caagctgaag | 480 |
| atcccccctga tccaccgagc cctgcagctg gccagcgac ccgtgtctct gctggcctct | 540 |
| ccctggacct ctcccacctg gctcaagacc aacggcgccg tgaacggcaa gggctctctg | 600 |
| aagggccagc ccggcgacat ctaccaccag acctgggccc gatacttcgt gaagttcctg | 660 |
| gacgcctacg ccgagcacaa gctgcagttc tgggccgtga ccgccgagaa cgagccctct | 720 |
| gctggactgc tgtccggcta ccccttccag tgtctgggct tcacccccga gcaccagcga | 780 |
| gacttcatcg cccgagacct gggacccacc tggccaact ctaccaccaa caacgtgcga | 840 |
| ctgctgatgc tggacgacca gcgactgctg ctgccccact gggccaaggt ggtgctgacc | 900 |
| gaccccgagg ccgccaagta cgtccacggc atcgctgtcc attggtatct ggactttctg | 960 |
| gctcccgcca aggccaccct gggcgagacc caccgactgt tccccaacac catgctgttc | 1020 |
| gcctctgagg cttgtgtggg ctctaagttc tgggagcagt ctgtgcgact gggctcttgg | 1080 |
| gaccgaggca tgcagtactc tcactctatc atcaccaacc tgctgtacca cgtggtgggc | 1140 |

```
tggaccgact ggaacctggc cctgaacccc gagggcggac ccaactgggt gcgaaacttc    1200
gtggactctc ccatcatcgt ggacatcacc aaggacacct tctacaagca gcccatgttc    1260
taccacctgg gccacttctc taagttcatc cccgagggct ctcagcgagt gggcctggtg    1320
gcctctcaga agaacgacct ggacgccgtg gccctgatgc accccgacgg ctctgccgtg    1380
gtggtggtcc tgaaccgatc ttctaaggac gtgcccctga ccatcaagga ccccgccgtg    1440
ggcttcctgg agaccatctc tcccggctac tctatcccac cctacctgtg cgacgacag     1500 taatagccta ggggtacc                                                  1518

<210> SEQ ID NO 16
<211> LENGTH: 498
<212> TYPE: DNA
<213> ORGANISM: Artificial Sequence
<220> FEATURE:
<223> OTHER INFORMATION: Synthetically generated oligonucleotide

<400> SEQUENCE: 16
gctccccccc gactgatctg tgactctcga gtgctggaac gatacctgct ggaagccaag     60
gaagccgaga acatcaccac cggctgtgcc gagcactgtt ctctgaacga gaacattacc    120
gtgcccgaca ccaaggtgaa cttctacgcc tggaagcgaa tggaggtggg ccagcaggcc    180
gtggaggtgt ggcagggact ggctctgctg tctgaggccg tgctgcgagg acaggctctc    240
ctggtgaact cttctcagcc ctgggagccc ctgcagctgc acgtggacaa ggccgtgtct    300
ggcctgcgat ctctgaccac cctgctgcga gccctcggtg ctcagaagga agccatctct    360 cccccgacg ccgcctctgc tgccccctg cgaaccatca ccgccgacac cttccgaaag    420
ctgttccgag tgtactctaa cttcctgcga ggcaagctga agctgtacac cggcgaggct    480
tgtcgaaccg gcgaccga                                                  498

<210> SEQ ID NO 17
<211> LENGTH: 1194
<212> TYPE: DNA
<213> ORGANISM: Artificial Sequence
<220> FEATURE:
<223> OTHER INFORMATION: Synthetically generated oligonucleotide

<400> SEQUENCE: 17
ctggacaacg gcctggcccg aaccccccacc atgggctggc tgcactggga gcgattcatg     60
tgtaacctgg actgtcagga agagcccgac tcttgtatct ctgagaagct gttcatggaa    120
atggccgagc tgatggtgtc tgagggctgg aaggacgccg gctacgagta cctgtgtatc    180
gacgactgtt ggatggcccc ccagcgagac tctgagggcc gactccaggc cgacccccag    240
cgattccccc acggcatccg acagctcgcc aactacgtgc actctaaggg cctgaagctg    300
ggcatctacg ccgacgtggg caacaagacc tgtgccggct tccccggctc tttcggctac    360
tacgacatcg acgcccagac cttcgccgac tggggcgtgg acctgctgaa gttcgacggc    420
tgttactgtg actctctcga gaacctggcc gacggctaca gcacatgtc tctggccctg    480 aaccgaaccg gccgatctat cgtgtactct tgtgagtggc cctgtacat gtggcccttc    540 cagaagccca actacaccga gatccgacag tactgtaacc actggcgaaa cttcgccgac    600
atcgacgact cgtggaagtc tatcaagtct attctggact ggacctcttt caaccaggag    660
cgaatcgtcg acgtcgccgg accggcggga tggaacgacc ccgacatgct ggtgatcggc    720
aacttcggcc tgtcttggaa ccagcaggtg acccagatgg ccctgtgggc tatcatggct    780 gccccccctgt tcatgtctaa cgacctgcga cacatctctc cccaggccaa ggccctgctc    840
```

-continued

```
caggacaagg acgtgatcgc catcaaccag gacccctgg gcaagcaggg ctaccagctc      900
cgacagggcg acaacttcga ggtgtgggag cgacccctgt ctggcctggc ctgggccgtg      960
gccatgatca accgacagga gatcggcgga ccccgatctt acaccatcgc cgtggcctcc     1020
ctgggaaagg gcgtggcctg taaccccgcc tgtttcatca cccagctcct gcccgtgaag     1080
cgaaagctgg gattctacga gtggacctct cgactgcgat ctcacatcaa ccccaccggc     1140
accgtgctgc tccagctcga gaacaccatg cagatgtctc tgaaggacct gctg           1194
```

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
tcgctatcac gtctctagc                                                    19

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
tctctgtata cttgtatgta ctg                                               23

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
ctagggataa cagggtaatg gtgtgacgaa gtatcgag                               38

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
cattaccctg ttatccctag cgagatcatg gactgg                                 36

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
gacgcggccg catgagcttc aacattccca aaac                                   34

<210> SEQ ID NO 23
<211> LENGTH: 49
<212> TYPE: DNA
<213> ORGANISM: Artificial Sequence
<220> FEATURE:
<223> OTHER INFORMATION: Primer

```
<400> SEQUENCE: 23
ctagggataa cagggtaata caaaattcag aaataaaaat actttacag          49

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
cattaccctg ttatccctaa gtaacatgag tgctatgag                     39

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
cgcttaatta aatgcatgga ggtattgctg                               30

<210> SEQ ID NO 26
<211> LENGTH: 46
<212> TYPE: DNA
<213> ORGANISM: Artificial Sequence
<220> FEATURE:
<223> OTHER INFORMATION: Primer

<400> SEQUENCE: 26
ggtgcttcga ctatcagttt cggaggattg ggtgattctt tttatg             46

<210> SEQ ID NO 27
<211> LENGTH: 46
<212> TYPE: DNA
<213> ORGANISM: Artificial Sequence
<220> FEATURE:
<223> OTHER INFORMATION: Primer

<400> SEQUENCE: 27
cataaaaaga atcacccaat cctccgaaac tgatagtcga agcacc             46

<210> SEQ ID NO 28
<211> LENGTH: 32
<212> TYPE: DNA
<213> ORGANISM: Artificial Sequence
<220> FEATURE:
<223> OTHER INFORMATION: Primer

<400> SEQUENCE: 28
tgagcggccg cttttctact tcagagctgg ag                            32

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
ggcttaatta attggtagtg atataatgta acgc                          34

<210> SEQ ID NO 30
<211> LENGTH: 39
<212> TYPE: DNA
```

```
<213> ORGANISM: Artificial Sequence
<220> FEATURE:
<223> OTHER INFORMATION: Primer

<400> SEQUENCE: 30
tagggataac agggtaatca cgacacatac tcattcaag                    39

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
attaccctgt tatccctaga aggagatgta gcgtaag                      37

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tgataaatag cttagatacc acag                                    24

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
acatacaacc acacacatc                                          19

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
ggcggatcca tggtgctgca cccgtttc                                28

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35
ggccctaggc tactcaaact cctcgcgaat c                            31

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
ggtctcgcca gcgcgcccac cctcttc                                 27
```

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ctagatcagc aataaagtcg tgctgggc                                    28

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
ggatccatgt ctatcaagcg agaagagtcc                                  30

<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39
cctaggctag atcagcaata aagtcgtgct gggc                             34

<210> SEQ ID NO 40
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 40
cgactatccg gttcggatca ttgggtgatt cttttatga g                      41

<210> SEQ ID NO 41
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 41
ctcataaaaa gaatcaccca atgatccgaa ccggatagtc g                     41

<210> SEQ ID NO 42
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 42
cgactatccg gttcggatca ggtggtgatt cttttatga g                      41

<210> SEQ ID NO 43
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 43
ctcataaaaa gaatcaccac ctgatccgaa ccggatagtc g                                41

<210> SEQ ID NO 44
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 44
ggtgcttcga ctatcagttt cggaggattg ggtgattctt tttatg                          46

<210> SEQ ID NO 45
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 45
cataaaaaga atcacccaat cctccgaaac tgatagtcga agcacc                          46

<210> SEQ ID NO 46
<211> LENGTH: 38
<212> TYPE: DNA
<213> ORGANISM: Artificial Sequence
<220> FEATURE:
<223> OTHER INFORMATION: Synthetically generated oligonucleotide

<400> SEQUENCE: 46
cccgatatcg gatccatgaa gaactctgtc ggtatttc                                   38

<210> SEQ ID NO 47
<211> LENGTH: 70
<212> TYPE: DNA
<213> ORGANISM: Artificial Sequence
<220> FEATURE:
<223> OTHER INFORMATION: Synthetically generated oligonucleotide

<400> SEQUENCE: 47
gggaagctta acgcggttcc agcgggtccg gatacggcac cggcgcaccc aacgaccaac           60
ctgtggtcag                                                                  70

<210> SEQ ID NO 48
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 48
cagtgcggcc gcactccctc ttttcactca ctattg                                     36

<210> SEQ ID NO 49
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 49
cattaccctg ttatccctac gctcagatcc aattgttttg gtggtc                          46

<210> SEQ ID NO 50

```
<211> LENGTH: 53
<212> TYPE: DNA
<213> ORGANISM: Artificial Sequence
<220> FEATURE:
<223> OTHER INFORMATION: Synthetically generated oligonucleotide

<400> SEQUENCE: 50
gtagggataa cagggtaatg ctctcaagga cggaccagat gagactgtta tcg         53

<210> SEQ ID NO 51
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 51
gactttaatt aaaccctatg tggcacctca acccacatct cccgtc                 46

<210> SEQ ID NO 52
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 52
cagtggatcc atgaactctc ctattttcac taccg                             35

<210> SEQ ID NO 53
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 53
gactcctagg aagcttccag gttacaagtt gttac                             35

<210> SEQ ID NO 54
<211> LENGTH: 73
<212> TYPE: DNA
<213> ORGANISM: Artificial Sequence
<220> FEATURE:
<223> OTHER INFORMATION: Primer

<400> SEQUENCE: 54
cctaggtcac tccaatcccc caaacaggtt gctgacgctc gactcatagt gagctagatc  60
agcaataaag tcg                                                     73

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
ggatccatgt ctatcaagcg agaagagtcc                                   30

<210> SEQ ID NO 56
<211> LENGTH: 25
<212> TYPE: DNA
<213> ORGANISM: Artificial Sequence
<220> FEATURE:
<223> OTHER INFORMATION: Primer
```

```
<400> SEQUENCE: 56
gaattcatgc ccgtagattc ttctc                                            25

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
gagtcttccg gaggattcag                                                  20

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
cctggaagaa tacaaagtc                                                   19

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
cctaggctat tcctggaaga atacaaagtc                                       30

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
ggtattgctg agcgtatgca aa                                               22

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ccaccgatcc atacggagta ct                                               22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
cgacctggaa tctgcacttc aa                                               22

<210> SEQ ID NO 63
<211> LENGTH: 22
<212> TYPE: DNA
```

<213> ORGANISM: Artificial Sequence
<220> FEATURE:
<223> OTHER INFORMATION: Primer

<400> SEQUENCE: 63
cggtaccacc taaggcttcc aa        22

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
ccagccaact gtgttgattc aa        22

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
ggagctggtg gaataccagt ca        22

<210> SEQ ID NO 66
<211> LENGTH: 57
<212> TYPE: DNA
<213> ORGANISM: Artificial Sequence
<220> FEATURE:
<223> OTHER INFORMATION: Primer

<400> SEQUENCE: 66
gatccatgaa gctttccacc atcctcttca cagcctgcgc taccctggcc gcggtac        57

<210> SEQ ID NO 67
<211> LENGTH: 65
<212> TYPE: DNA
<213> ORGANISM: Artificial Sequence
<220> FEATURE:
<223> OTHER INFORMATION: Primer

<400> SEQUENCE: 67
gtaccggccg gccgcttctg gagaactgcg gcctcagaag gagtgatggg ggaagggagg        60
gcggc        65

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
ggcagcgcta caaaacgtgg atctcccaac        30

<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69

```
ggccctaggt tacaactcgt cgtgagcaag                                     30

<210> SEQ ID NO 70
<211> LENGTH: 17
<212> TYPE: DNA
<213> ORGANISM: Pichia pastoris

<400> SEQUENCE: 70
atccagcagt gatgacg                                                   17

<210> SEQ ID NO 71
<211> LENGTH: 17
<212> TYPE: DNA
<213> ORGANISM: Saccharomyces cerevisiae

<400> SEQUENCE: 71
atccagccgt gattacg                                                   17

<210> SEQ ID NO 72
<211> LENGTH: 15
<212> TYPE: DNA
<213> ORGANISM: Pichia pastoris

<400> SEQUENCE: 72
ggtctgcagc accat                                                     15

<210> SEQ ID NO 73
<211> LENGTH: 15
<212> TYPE: DNA
<213> ORGANISM: Saccharomyces cerevisiae

<400> SEQUENCE: 73
tgtccgaagc gcagt                                                     15

<210> SEQ ID NO 74
<211> LENGTH: 18
<212> TYPE: PRT
<213> ORGANISM: Pichia pastoris

<400> SEQUENCE: 74

Ala Pro Phe Thr Ala Asn Ala Phe Asp Leu Asn Asp Phe Val Phe Phe
1               5                   10                  15

Gln Glu

<210> SEQ ID NO 75
<211> LENGTH: 18
<212> TYPE: PRT
<213> ORGANISM: Saccharomyces cerevisiae

<400> SEQUENCE: 75

Glu Ala Gln Ser Gly Leu Asn Ser Phe Glu Leu Asn Asp Phe Phe Ile
1               5                   10                  15

Thr Ser
```

YARROWIA LIPOLYTICA AND PICHIA PASTORIS HAC1 NUCLEIC ACIDS

TECHNICAL FIELD

The invention relates to methods of obtaining glycosylated molecules, particularly protein and lipid molecules.

BACKGROUND

High performance expression systems are required to produce most biopharmaceuticals (e.g., recombinant proteins) currently under development. The biological activity of many of these biopharmaceuticals is dependent on their modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

SUMMARY

The present invention is based, at least in part, on: (a) the discovery that single gene deletion (Outer CHain elongation (OCH1) deletion) in Yarrowia lypolitica cells resulted in the substantially homogeneous production of glycosylated proteins having α-1,2-linked mannose residues on a $Man_5GlcNAc_2$ (structural formula IV; FIG. 1) backbone; (b) the discovery that overexpression of an engineered alpha-1,2-mannosidase targeted to the ER of Yarrowia lipolytica cells (both with AND without OCH1 deletion) resulted in the substantially homogenous production of glycosylated proteins carrying the $Man_5GlcNAc_2$ N-glycan structure (structural formula IV; FIG. 1); (c) the discovery that inactivating the Asparagine Linked Glycosylation 3 (ALG3) enzyme activity in Yarrowia lipolytica cells results in highly increased levels of glucosylated glycans; and (d) the discovery that overexpression of a wild-type form of a Yarrowia lipolytica gene (MNN4) in Yarrowia lipolytica results in hyperphosphorylation of α-1,2-linked mannose residues. Thus, the genetically engineered cells (e.g., Yarrowia lipolytica, Arxula adeninivorans, or other related species dimorphic yeast cells) can be used in methods to produce target molecules having an altered N-glycosylation form as compared to the N-glycosylation form of the target molecules produced in non-genetically engineered cells of the same species. As administration of N-glycosylated target molecules (e.g., N-glycosylated proteins) to patients having a metabolic disorder (e.g., a lysosomal storage disorder) has been shown to ameliorate the symptoms of the disorder, the methods and cells described are useful for the preparation of N-glycosylated target molecules for the treatment of, inter alia, metabolic disorders such as lysosomal storage disorders.

The present invention is also based, at least in part, on the discovery of the spliced form of the Yarrowia lipolytica and Pichia pastoris HAC1 gene. The protein encoded by the HAC1 gene, Hac1p, is a transcriptional activator that activates transcription of several target genes by binding to a DNA sequence motif termed the Unfolded Protein Response (UPR) element. Among the Hac1p target genes are those that encode chaperones, foldases, and proteins which are responsible for lipid- and inositol metabolism. As the spliced form Hac1p is a more potent transcriptional activator than the form encoded by the unspliced HAC1 mRNA, overexpression of the spliced form of Hac1p transcription factor can lead to an increased expression of native and heterologeous proteins as well as an increase in ER membrane. Thus, the spliced form of Hac1p can be used to increase the production of membrane and secreted proteins in a variety of eukaryotic cells (e.g., fungal cells (e.g., Yarrowia lipolytica or any other yeast cells described herein), plant cells, or animal cells (e.g., mammalian cells such as human cells) by simultaneous activation of the UPR and expression of target molecules.

The present invention is further based on the discovery of a mutant form of the MNS1 mannosidase capable of converting $Man_8GlcNAc_2$ (structural formula I; FIG. 4) structures to $Man_5GlcNAc_2$ (structural formula IV; FIG. 4), $Man_6GlcNAc_2$ (structural formula V; FIG. 4) and $Man_7GlcNAc_2$ (structural formula VI; FIG. 4) when expressed in Yarrowia lipolytica. Thus, genetically engineered eukaryotic cells (e.g., fungal cells (e.g., Yarrowia lipolytica or any other yeast cells described herein), plant cells, or animal cells (e.g., mammalian cells such as human cells)) expressing mutant forms of mannosidase such as MNS1 can be used in methods to produce target molecules having an altered N-glycosylation form as compared to the N-glycosylation form of the target molecules produced in non-genetically engineered cells of the same species. Therefore, the cells and methods described are useful for the preparation of N-glycosylated target molecules for the treatment of, inter alia, metabolic disorders such as lysosomal storage disorders (see below).

In one aspect, the disclosure features a method of producing an altered N-glycosylation form of a target protein. The method includes the step of introducing into a cell a nucleic acid encoding a target protein, wherein the cell produces the target protein in an altered N-glycosylation form and wherein the cell is a Yarrowia lipolytica or an Arxula adeninivorans cell (or a related species dimorphic yeast cell) genetically engineered to contain at least one modified N-glycosylation activity. The method can also include the step of providing the Yarrowia lipolytica or an Arxula adeninivorans cell (or related species dimorphic yeast cell) genetically engineered to contain at least one modified N-glycosylation activity. The method can also include the step of isolating the altered N-glycosylation form of the target protein.

In some embodiments, the target protein can be an endogenous protein or an exogenous protein. The target protein can be a mammalian protein such as a human protein. The target protein can be, for example, a pathogen protein, a lysosomal protein, a growth factor, a cytokine, a chemokine, an antibody or antigen-binding fragment thereof, or a fusion protein. The fusion protein can be, for example, a fusion of a pathogen protein, a lysosomal protein, a growth factor, a cytokine, or a chemokine with an antibody or an antigen-binding fragment thereof. The target protein can be, for example, one associated with a lysosomal storage disorder (LSD). The target protein can be, for example, glucocerebrosidase, galactocerebrosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphinogmyelinase, thioesterase, cathepsin K, or lipoprotein lipase.

In some embodiments, the altered N-glycosylation form can contain one or more N-glycan structures such as, e.g., $Man_5GlcNAc_2$, $Man_8GlcNAc_2$, $Man_9GlcNAc_2$, $Man_3GlcNAc_2$, $Glc_1Man_5GlcNAc_2$, $Glc_2Man_5GlcNAc_2$. In some embodiments, the altered glycosylation can be, for example, $Man_5GlcNAc_2$, $Man_8GlcNAc_2$, $Man_9GlcNAc_2$, $Man_3GlcNAc_2$, $Glc_1Man_5GlcNAc_2$, $Glc_2Man_5GlcNAc_2$.

In some embodiments, the altered N-glycosylation form of the target protein can be homogenous or substantially homogenous. For example, the fraction of altered target molecules that contain the altered glycosylation can be at least about 20%, at least about 30%, at least about 40%, at least about 45%, at least about 50%, at least about 55%, at least about 60%, at least about 65%, at least about 70%, at least about 75%, at least about 80%, at least about 85%, at least about 90%, or at least about 95% or more.

In some embodiments, the cell can be genetically engineered to be deficient in at least one N-glycosylation activity. The N-glycosylation activity can be, for example, ALG3 activity, OCH1 activity, MNS1 activity, or MNN9 activity.

In some embodiments, at least one modification can be: (a) deletion of a gene encoding a protein having the N-glycosylation activity; (b) expression of a mutant form of a protein having the N-glycosylation activity; (c) introduction or expression of an RNA molecule that interferes with the functional expression of a protein having the N-glycosylation activity; (d) expression of a protein having N-glycosylation activity (such as ALG6 or an alpha-mannosidase (e.g., an alpha-mannosidase targeted to the endoplasmic reticulum). The expressed protein can be a protein encoded by an exogenous nucleic acid in the cell. The expressed protein can be an alpha-mannosidase with a pH optimum below 7.5 (e.g., a pH optimum below 5.1). The protein having N-glycosylation activity can be an exogenous protein. The protein having N-glycosylation activity can be a mammalian protein (such as a human protein) or a lower eukaryotic (e.g., a fungus, a protozoan, or a trypanosome) protein. The lower eukaryote can be selected from the group consisting of *Typanosoma brucei*, *Trichoderma harzianum*, an *Aspergillus*, and any other lower eukaryote described herein.

In some embodiments, the N-glycosylation activity can be a glucosyltransferase activity. In some embodiments, the protein having N-glycosylation activity is ALG6 or an alpha-mannosidase. The alpha-mannosidase can be targeted to the endoplasmic reticulum. For example, the protein having N-glycosylation activity can be a fusion protein comprising an alpha-mannosidase polypeptide and an HDEL endoplasmic reticulum retention peptide.

In some embodiments, the protein having N-glycosylation activity can be a protein that is capable of removing glucose residues from $Man_5GlcNAc_2$. For example, the protein having N-glycosylation activity can be a protein having α-1,3-glucosidase activity such as, but not limited to, a glucosidase II (e.g., one or both of the alpha and beta subunit of a glucosidase II) or a mutanase.

In some embodiments, the cell can be genetically engineered to comprise at least two modified N-glycosylation activities such as any of the modified N-glycosylation activities described herein. The at least two modified N-glycosylation activities can comprise, e.g., a deficiency in an ALG3 activity and an elevated level of an ALG6 activity.

In some embodiments, the cell can be genetically engineered to comprise at least three modified N-glycosylation activities such as any of the modified N-glycosylation activities described herein. The at least three modified N-glycosylation activities can comprise, e.g., a deficiency in an ALG3 activity; an elevated level of an ALG6 activity; and an elevated level of a a glucosidase II activity.

In some embodiments, the cell is not genetically engineered to be deficient in an OCH1 activity.

In some embodiments, modification can comprise expression of a protein or biologically active variant thereof capable of effecting mannosyl phosphorylation of the target protein. The protein or biologically active variant thereof capable of effecting mannosyl phosphorylation can be MNN4, PNO1, or MNN6. In some embodiments, at least about 30% of the mannosyl residues of a glycoprotein can be phosphorylated.

In some embodiments, the method can further include additional processing of the glycoprotein. The additional processing can occur in vitro or in vivo. The additional processing can comprise addition of a heterologous moiety to the modified glycoprotein. The heterologous moiety can be a polymer or a carrier. The additional processing can comprise enzymatic or chemical treatment of the altered N-glycosylation form of the target protein. For example, the additional processing can comprise treatment of the altered N-glycosylation form of the target protein with a mannosidase, a mannanase, a phosphodiesterase, a glucosidase, or a glycosyltransferase. The additional processing can include treatment of the altered N-glycosylation form of the target protein with hydrofluoric acid. The additional processing can include phosphorylation of the altered N-glycosylation form of the target protein.

In another aspect, the disclosure provides a method of producing an altered N-glycosylation form of a target protein. The method includes the steps of: providing a eukaryotic cell (e.g., a fungal cell, a plant cell, or an animal cell) genetically engineered to comprise at least one modified N-glycosylation activity; and introducing into the cell a nucleic acid encoding a target protein, wherein the cell produces the target protein in an altered N-glycosylation form.

In another aspect, the disclosure features a method of producing an altered N-glycosylation form of a target protein, The method includes the step of contacting a target protein with a cell lysate prepared from a *Yarrowia lipolytica* or an *Arxula adeninivorans* cell genetically engineered to comprise at least one modified N-glycosylation activity, wherein the contacting of the target protein with the cell lysate results in an altered N-glycosylation form of the target protein.

In yet another aspect, the disclosure features a method of producing an altered N-glycosylation form of a target protein, which method includes the step of contacting a target protein with one or more proteins having N-glycosylation activity, wherein the one or more proteins having N-glycosylation activity are obtained from a *Yarrowia lipolytica* or an *Arxula adeninivorans* cell genetically engineered to comprise at least one modified N-glycosylation activity and wherein contacting the target molecule with the one or more proteins having N-glycosylation activity results in an altered N-glycosylation form of the target protein.

In another aspect, the disclosure provides an isolated protein having altered N-glycosylation, wherein the protein is produced by any of the methods described above.

In yet another aspect, the disclosure provides an isolated *Yarrowia lipolytica* or *Arxula adeninivorans* cell (or other related species dimorphic yeast cell) genetically engineered to comprise at least one modified N-glycosylation activity. The N-glycosylation activity can be, for example, ALG3 activity, OCH1 activity, MNS1 activity, or MNN9 activity. The modification can be any of those described herein. For example, the modification can include: (a) deletion of a gene encoding a protein having the N-glycosylation activity, (b) expression of a mutant form of a protein having the N-glycosylation activity, (c) introduction or expression of an RNA molecule that interferes with the functional expression of a protein having the N-glycosylation activity, or (d) expression of a protein having N-glycosylation activity. The protein having N-glycosylation activity can be, for example, ALG6. The protein having N-glycosylation activity can be a mammalian protein such as a human protein. The modification can also include expression of a protein (e.g., MNN4 or PNO1) or biologically active variant thereof capable of promoting mannosyl phosphorylation of the modified glycoprotein.

In another aspect, the disclosure provides a method of treating a disorder treatable by administration of a protein having altered N-glycosylation. The method includes the steps of administering to a subject a protein obtained by any of the methods described above, wherein the subject is one having, or suspected of having, a disease treatable by administration of a protein having altered N-glycosylation. The method can also include the steps of (a) providing a subject and/or (b) determining whether the subject has a disease treatable by administration of a protein having altered N-glycosylation. The subject can be mammal such as a human. The disorder can be, for example, a cancer, an immunological disorder (e.g., an inflammatory condition) or a metabolic disorder. The metabolic disorder can be any of those described herein, e.g., a lysosomal storage disorder (LSD) such as Gaucher disease, Tay-Sachs disease, Pompe disease, Niemann-Pick disease, or Fabry disease. The protein can be one associated with an LSD, e.g., the protein can be, for example, glucocerebrosidase, alpha-galactosidase. The protein can be, for example, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartyl-glucosaminidase, iduronate-2-sulfatase, alpha-glu-cosaminide-N-acetyltransferase, beta-D-glucoronidase, hyaluronidase, alpha-L-mannosidase, alpha-neurominidase, phosphotransferase, acid lipase, acid ceramidase, sphingomyelinase, thioesterase, cathepsin K, or lipoprotein lipase.

In another aspect, the disclosure provides a substantially pure culture of *Yarrowia lipolytica* or *Arxula adeninivorans* cells (or other related species dimorphic yeast cells), a substantial number of which being genetically engineered to comprise at least one modified N-glycosylation activity (such as any of the modifications described herein). The culture of cells can contain one or more subpopulations of cells, each subpopulation comprising a different modified glycosylation activity.

In yet another aspect, the disclosure provides: (a) an isolated nucleotide sequence comprising SEQ ID NO:1 or SEQ ID NO:2; (b) an isolated nucleotide sequence comprising a sequence that is at least 80% identical to SEQ ID NO:1 or SEQ ID NO:2; or (c) a polypeptide encoded by the isolated nucleotide sequence of (a) or (b). In some embodiments, the isolated nucleic acid sequence is SEQ ID NO:1 or SEQ ID NO:2.

In another aspect, the disclosure features an isolated nucleic acid containing: (a) a nucleotide sequence that hybridizes under highly stringent conditions to the complement of SEQ ID NO:1 or SEQ ID NO:2; or (b) the complement of the nucleotide sequence.

In yet another aspect, the disclosure provides: (a) an isolated nucleotide sequence comprising (or consisting of) any of the nucleic acid sequences depicted herein; (b) an isolated nucleotide sequence comprising a sequence that is at least 80% identical to any of the nucleic acid sequences depicted herein; or (c) a polypeptide encoded by the isolated nucleotide sequence of (a) or (b). In some embodiments, the isolated nucleic acid sequence is any of the nucleic acid sequences depicted herein.

In another aspect, the disclosure features an isolated nucleic acid containing: (a) a nucleotide sequence that hybridizes under highly stringent conditions to the complement of any of the nucleic acid sequences depicted herein; or (b) the complement of the nucleotide sequence.

In yet another aspect, the disclosure provides: (a) a vector comprising any of the nucleic acid sequences described above or (b) a cultured cell containing the vector of (a). The vector can be an expression vector. The nucleic acid sequence in the vector can be operably linked to expression control sequence.

In another aspect, the disclosure provides a method for producing a protein. The method includes the step of culturing any of the cells described above under conditions permitting the expression of the polypeptide. The method can also include the step of after culturing the cell, isolating the polypeptide from the cell or the medium in which the cell was cultured. The cell can be, e.g., a cultured cell containing a vector comprising any of the nucleic acid sequences described above.

The target molecules (e.g., target proteins), proteins having N-glycosylation activity, and altered N-glycosylation molecules described herein (collectively referred to as "molecules of the invention") can, but need not, be isolated. The term "isolated" as applied to any of the molecules of the invention described herein refers to a molecule, or a fragment thereof, that has been separated or purified from components (e.g., proteins or other naturally-occurring biological or organic molecules) which naturally accompany it. It is understood that recombinant molecules (e.g., recombinant proteins) will always be "isolated." Typically, a molecule of the invention is isolated when it constitutes at least 60%, by weight, of the total molecules of the same type in a preparation, e.g., 60% of the total molecules of the same type in a sample. For example, an altered glycosylation protein is isolated when it constitutes at least 60%, by weight, of the total protein in a preparation or sample. In some embodiments, a molecule of the invention in the preparation consists of at least 75%, at least 90%, or at least 99%, by weight, of the total molecules of the same type in a preparation.

As used herein, an "altered N-glycosylation form" of a target molecule is an N-glycosylation form of a target molecule produced by a genetically engineered host cell (e.g., *Yarrowia lipolytica* cell, *Arxula adeninivorans* cell, or a cell of another related dimorphic yeast cell species) that differs from the N-glycosylation form of the target molecule produced in a non-genetically engineered cell of the same species as the genetically engineered cell. Thus, an altered glycosylation form of a target molecule can be, for example, a form of the target molecule that is not N-glycosylated. Moreover, an altered glycosylation form of a target molecule can be, e.g., a form of the target molecule that has altered phosphorylation of one or more N-linked glycans.

As used herein, the term "other related dimorphic yeast cell species" refers to yeasts related to *Yarrowia lipolytica* and *Arxula adeninivorans* that belong to the family *Dipodascaceae* such as *Arxula*, *Dipodascus* (e.g. *D. albidus*, *D. ingens*, or *D. specifer*), Galactomyces (e.g. *G. reesii* or *G. geotrichum*), *Sporopachyderma*, *Stephanoascus* (e.g., *S. ciferii*), *Wickerhamiella*, and *Zygoascus*. Specifically, yeasts in the clade *Metchnikowia* (e.g., *M. pulcherrima* or *M. agaves*) and *Stephanoascus* (to which *Y. lipolytica* is assigned by analysis of the D1/D2 domain of the 26S-rDNA sequences of species such as Arxula (e.g. *A. adeninivorans* or *A. terrestris*)) and some *Candida* species (e.g., *C. apicola* but not *C. albicans*, *C. maltosa*, or *C. tropicalis*).

"Polypeptide" and "protein" are used interchangeably and mean any peptide-linked chain of amino acids, regardless of length or post-translational modification.

The disclosure also provides (i) biologically active variants and (ii) biologically active fragments or biologically active variants thereof, of the wild-type, full-length, mature "target proteins" or "proteins having N-glycosylation activity" described herein. Biologically active variants of full-length, mature, wild-type proteins or fragments of the proteins can contain additions, deletions, or substitutions. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (a) full-length, wild-type, mature polypeptides or fragments thereof containing at least five amino acids; and (b) internal or terminal (C or N) irrelevant or heterologous amino acid sequences. In the context of such fusion proteins, the term "heterologous amino acid sequences" refers to an amino acid sequence other than (a). A fusion protein containing a peptide described herein and a heterologous amino acid sequence thus does not correspond in sequence to all or part of a naturally occurring protein. A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response (e.g., for antibody generation; see below) or endoplasmic reticulum or Golgi apparatus retention signals. Heterologous sequences can be of varying length and in some cases can be a longer sequences than the full-length target proteins to which the heterologous sequences are attached.

A "fragment" as used herein, refers to a segment of the polypeptide that is shorter than a full-length, immature protein. Fragments of a protein can have terminal (carboxy or amino-terminal) and/or internal deletions. Generally, fragments of a protein will be at least four (e.g., at least five, at least six, at least seven, at least eight, at least nine, at least 10, at least 12, at least 15, at least 18, at least 25, at least 30, at least 35, at least 40, at least 50, at least 60, at least 65, at least 70, at least 75, at least 80, at least 85, at least 90, or at least 100 or more) amino acids in length.

Biologically active fragments or biologically active variants of the target proteins or proteins having N-glycosylation activity have at least 25% (e.g., at least: 30%; 40%; 50%; 60%; 70%; 75%; 80%; 85%; 90%; 95%; 97%; 98%; 99%; 99.5%, or 100% or even greater) of the activity of the wild-type, full-length, mature protein. In the case of a target protein, the relevant activity is the ability of the target protein to undergo altered N-glycosylation in a genetically engineered cell. In the case of a protein having N-glycosylation activity, the relevant activity is N-glycosylation activity.

Depending on their intended use, the proteins, biologically active fragments, or biologically active variants thereof can be of any species, such as, e.g., fungus (including yeast), nematode, insect, plant, bird, reptile, or mammal (e.g., a mouse, rat, rabbit, hamster, gerbil, dog, cat, goat, pig, cow, horse, whale, monkey, or human). In some embodiments, biologically active fragments or biologically active variants include immunogenic and antigenic fragments of the proteins. An immunogenic fragment is one that has at least 25% (e.g., at least: 30%; 40%; 50%; 60%; 70%; 75%; 80%; 85%; 90%; 95%; 97%; 98%; 99%; 99.5%, or 100% or even more) of the ability of the relevant full-length, immature protein to stimulate an immune response (e.g., an antibody response or a cellular immune response) in an animal of interest. An antigenic fragment of a protein is one having at least 25% (e.g., at least: 30%; 40%; 50%; 60%; 70%; 75%; 80%; 85%; 90%; 95%; 97%; 98%; 99%; 99.5%, or 100% or even greater) of the ability of the relevant full-length, immature protein to be recognized by an antibody specific for the protein or a T cell specific to the protein.

"N-glycosylation activity" as used herein refers to any activity that is (i) capable of adding N-linked glycans to a target molecule (i.e., an oligosaccharyltransferase activity); (ii) removing N-linked glycans from a target molecule, (iii) modifying one or more N-linked glycans on a target molecule, (iv) modifying dolichol-linked oligosaccharides; or (v) is capable of aiding the activity of the activities under (i-iv). As such, N-glycosylation activity includes, e.g., N-glycosidase activity, glycosidase activity, glycosyltransferase activity, sugar nucleotide synthesis, modification, or transporter activity. Modification of one or more N-linked glycans on a target molecule includes the action of a mannosylphosphoryltransferase activity, a kinase activity, or a phosphatase activity, e.g., a mannosylphosphoryltransferase, a kinase, or a phosphatase activity that alters the phosphorylation state of N-linked glycans on target molecules.

As used herein, to "genetically engineer" a cell or a "genetically engineered cell" and like terminology refers to any artificially created genetic alteration of a cell that results in at least one modified N-glycosylation activity in the cell as compared to a non-genetically engineered cell (e.g., a fungal cell such as *Yarrowia lipolytica* cell, *Arxula adeninivorans* cell, or other related species dimorphic yeast cell, a plant cell, or an animal cell (e.g., a mammalian cell such as a human cell)). Thus, it is understood that artificially created genetic alterations do not include, e.g., spontaneous mutations. Examples of artificial genetic alterations are described below (see "Genetically Engineered Cells").

As used herein, the term "wild-type" as applied to a nucleic acid or polypeptide refers to a nucleic acid or a polypeptide that occurs in, or is produced by, respectively, a biological organism as that biological organism exists in nature.

The term "heterologous" as applied herein to a nucleic acid in a host cell or a polypeptide produced by a host cell refers to any nucleic acid or polypeptide (e.g., an protein having N-glycosylation activity) that is not derived from a cell of the same species as the host cell. Accordingly, as used herein, "homologous" nucleic acids, or proteins, are those that occur in, or are produced by, a cell of the same species as the host cell.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast y.

It will be clear from the above that "exogenous" nucleic acids can be "homologous" or "heterologous" nucleic acids. In contrast, the term "endogenous" as used herein with reference to nucleic acids or genes (or proteins encoded by the nucleic acids or genes) and a particular cell refers to any nucleic acid or gene that does occur in (and can be obtained from) that particular cell as found in nature.

As an illustration of the above concepts, an expression plasmid encoding a *Y. lipolytica* ALG6 protein that is transformed into a *Y. lipolytica* cell is, with respect to that cell, an exogenous nucleic acid. However, the ALG6 protein coding sequence and the ALG6 protein produced by it are homologous with respect to the cell. Similarly, an expression plasmid encoding a Arxula adeninivorans ALG6 protein that is transformed into a *Y. lipolytica* cell is, with respect to that cell, an exogenous nucleic acid. In contrast with the previous example, however, the ALG6 protein coding sequence and the ALG6 protein produced by it are heterologous with respect to the cell.

As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., within an intronic region of a gene or 3' to the coding region of the gene.

As used herein, "operably linked" means incorporated into a genetic construct so that expression control sequences effectively control expression of a coding sequence of interest.

Variants of any of the nucleic acid sequences described herein (e.g., the HAC1 sequences as depicted in SEQ ID NO:1 or SEQ ID NO:2) can have a sequence that is homologous, e.g., a sequence bearing at least about 70% (e.g., at least about 75%, at least about 80%, at least about 85%, at least about 90%, at least about 95%, or at least about 99%) homologous (identical) to the wild-type nucleic acid sequence. Such wild-type sequences can be isolated from nature or can be produced by recombinant or synthetic methods. Thus a wild-type sequence nucleic acid can have the nucleic acid sequence of naturally occurring human nucleic acid sequences, monkey nucleic acid sequences, murine nucleic acid sequences, or any other species that contains a homologue of the wild-type nucleic acid of interest. As used herein, a "homologous" or "homologous nucleic acid sequence" or similar term, refers to sequences characterized by homology at the nucleotide level of at least a specified percentage and is used interchangeably with sequence identity.

Percent homology or identity can be determined by, for example, the Gap program (Wisconsin Sequence Analysis Package, Version 8 for UNIX, Genetics Computer Group, University Research Park, Madison, Wis.), using default settings, which uses the algorithm of Smith and Waterman ((1981) Adv. Appl. Math. 2:482-489). In some embodiments, homology between a probe and target (see below) is between about 50% to about 60%. In some embodiments, homology between a probe and target nucleic acid is between about 55% to 65%, between about 65% to 75%, between about 70% to 80%, between about 75% and 85%, between about 80% and 90%, between about 85% and 95%, or between about 90% and 100%.

The term "probe," as used herein, refers to nucleic acid sequences of variable length. In some embodiments, probes comprise at least 10 and as many as 6,000 nucleotides. In some embodiments probes comprise at least 12, at lease 14, at least 16, at least 18, at least 20, at least 25, at least 50 or at least 75 or 100 contiguous nucleotides. Longer length probes are usually obtained from natural or recombinant sources (as opposed to direct, chemical synthesis), are highly specific to the target sequence, and are much slower to hybridize to the target than longer oligomers. Probes can be single or double stranded nucleic acid molecules.

In some embodiments, a variant nucleic acid described herein can have a sequence comprising one or both strands with partial complementary (e.g., at least 50%, at least 60%, at least 70%, at least 80%, at least 90%, at least 95%, at least 96%, at least 97%, at least 98%, at least 99% complementary) to a region, portion, domain, or segment of the wild-type nucleic acid of interest (e.g., the HAC1 nucleic acid sequences as depicted in SEQ ID NO:1 or SEQ ID NO:2). In some embodiments, a variant nucleic acid sequence of interest can have a sequence comprising one or both strands with full complementary (i.e., 100% complementary) to a region, portion, domain, or segment of the wild-type nucleic acid sequence. Sequence "complementarity" refers to the chemical affinity between specific nitrogenous bases as a result of their hydrogen bonding properties (i.e., the property of two nucleic acid chains having base sequences such that an antiparallel duplex can form where the adenines and uracils (or thymine, in the case of DNA or modified RNA) are apposed to each other, and the guanines and cytosines are apposed to each other). Fully complementary sequences, thus, would be two sequences that have complete one-to-one correspondence (i.e., adenine to uracil/thymidine and guanine to cytosine) of the base sequences when the nucleotide sequences form an antiparallel duplex.

Hybridization can also be used as a measure of homology between two nucleic acid sequences. A nucleic acid sequence described herein, or a fragment or variant thereof, can be used as a hybridization probe according to standard hybridization techniques. The hybridization of a certain probe of interest (e.g., a probe of a HAC1 nucleotide sequence, e.g., the HAC1 nucleotide sequences as depicted in SEQ ID NOS:1 or 2) to DNA or RNA from a test source (e.g., a eukaryotic cell) is an indication of the presence of DNA or RNA (e.g., a HAC1 nucleotide sequence) corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention, e.g., methods of producing altered N-glycosylation molecules, will be apparent from the following detailed description, and from the claims.

BRIEF DESCRIPTION OF THE DRAWINGS

FIGS. 4A and 4B are schematic diagrams depicting the structure of the various N-glycan structures described herein.

FIGS. 5A-5E are schematic diagrams depicting the cloning strategy for OCH1 gene disruption in Yarrowia lipolytica. "PCR" refers to polymerase chain reaction.

FIGS. 12A-12H are schematic diagrams depicting the cloning strategy for an α-galactosidase expression vector.

FIG. 15 is a sequence alignment of an isolated DNA fragment (SEQ ID NO:1) sequence obtained from the unfolded protein response (UPR)-induced strain *Yarrowia lipolytica* with a genomic HAC1 DNA sequence (SEQ ID NO:5). The boxed sequence corresponds to the non-conventionally spliced intron.

FIG. 16 is a series of sequence alignments of the predicted 5' (top) and 3' (bottom) splice sites of *Pichia pastoris* (SEQ ID NOs 70, 72) and Saccharomyces cerevisiae (SEQ ID NOs 71, 73). Nucleotides in bold underlined are present in the loop structure.

FIGS. 17A and 17B are two partial views of a sequence alignment of the HAC1 cDNA obtained from DTT-induced (I) (SEQ ID NO:2) and non-induced (NI) (SEQ ID NO:6) *Pichia pastoris* cultures.

FIG. 18 is a sequence alignment of the 18 amino acid C-terminal regions of *Pichia pastoris* (SEQ ID NO: 74) and *Saccharomyces cerevisiae* (SEQ ID NO:75). Conserved amino acids are in bold and underlined.

FIGS. 27A and 27B are amino acid sequences of HAC1 proteins of *Yarrowia lipolytica* (FIG. 27A; SEQ ID NO:3) and *Pichia pastoris* (FIG. 27B; SEQ ID NO:4).

FIGS. 36A and 36B is the depiction of a nucleotide sequence of a cDNA encoding a mature form of *Aspergillus niger* (lacking signal peptide) glucosidase II α, which is codon-optimized cDNA for expression in *Yarrowia lipolytica*. (SEQ ID NO:7).

FIG. 37 is the depiction of a nucleotide sequence of a cDNA encoding a mature form of *Aspergillus niger* (lacking signal peptide) glucosidase II β, which is codon-optimized cDNA for expression in *Yarrowia lipolytica*. (SEQ ID NO:8).

FIG. 42 is the depiction of a nucleotide sequence of an exemplary cDNA sequence encoding a *Trichoderma reesei* α-1,2 mannosidase, codon optimized for expression in *Yarrowia lipolytica* (SEQ ID NO:9) containing the LIP2 pre signal sequence.

FIG. 43 is the depiction of a nucleotide sequence of an exemplary nucleotide sequence for the GAP promoter of *Yarrowia lipolytica*. (SEQ ID NO:10).

FIGS. 44A-44C are the depiction of a nucleotide sequence of an exemplary nucleic acid sequence (SEQ ID NO:11) for the expression vector pYLHUXdL2preManHDEL, which contains a cDNA sequence encoding a *Trichoderma reesei* α-1,2 mannosidase, codon optimized for expression in *Yarrowia lipolytica* and containing the LIP2 pre signal sequence.

FIGS. 45A-45C are the depiction of a nucleotide sequence of an exemplary nucleic acid sequence (SEQ ID NO:12) for the expression vector pYLGUXdL2preManHDEL, which contains a cDNA sequence encoding a *Trichoderma reesei* α-1,2 mannosidase, codon optimized for expression in *Yarrowia lipolytica* and containing the LIP2 pre signal sequence.

FIGS. 46A-46C are the depiction of a nucleotide sequence of an exemplary nucleic acid sequence (SEQ ID NO:13) for the expression vector pYLPUXdL2preManHDEL, which contains a cDNA sequence encoding a *Trichoderma reesei* α-1,2 mannosidase, codon optimized for expression in *Yarrowia lipolytica* and containing the LIP2 pre signal sequence.

FIGS. 47A-47C are the depiction of a nucleotide sequence of an exemplary nucleic acid sequence (SEQ ID NO:14) for the expression vector pYLTUXdL2preManHDEL, which contains a cDNA sequence encoding a *Trichoderma reesei* α-1,2 mannosidase, codon optimized for expression in *Yarrowia lipolytica* and containing the LIP2 pre signal sequence.

FIG. 50 is an exemplary nucleic acid sequence for human glucocerebrosidase (GLCM, Swiss Prot entry nr: P04062; SEQ ID NO:15), which was chemically synthesized as a codon-optimized cDNA for expression in *Yarrowia lipolytica*.

FIG. 51 is a photograph of an immunoblot depicting the mobility pattern of human glucocerebrosidase expressed in *Yarrowia lipolytica* strains MTLY60 (WT; lanes 4 and 6) and MTLY60Δoch1 (Δoch1; first three lanes). The molecular weight (kDa) of the proteins is depicted, by way of molecular weight markers, at the far right of the immunoblot.

FIG. 52 is an exemplary nucleic acid sequence for human erythropoietin (Epo, Swiss Prot entry nr: P01588; SEQ ID NO:16), which was chemically synthesized as a codon-optimized cDNA for expression in *Yarrowia lipolytica*.

FIG. 53 is an exemplary nucleic acid sequence for human α-galactosidase A (AGAL, Swiss Prot entry nr: P06280; SEQ ID NO:17), which was chemically synthesized as a codon-optimized cDNA for expression in *Yarrowia lipolytica*.

DETAILED DESCRIPTION

Figure 1:
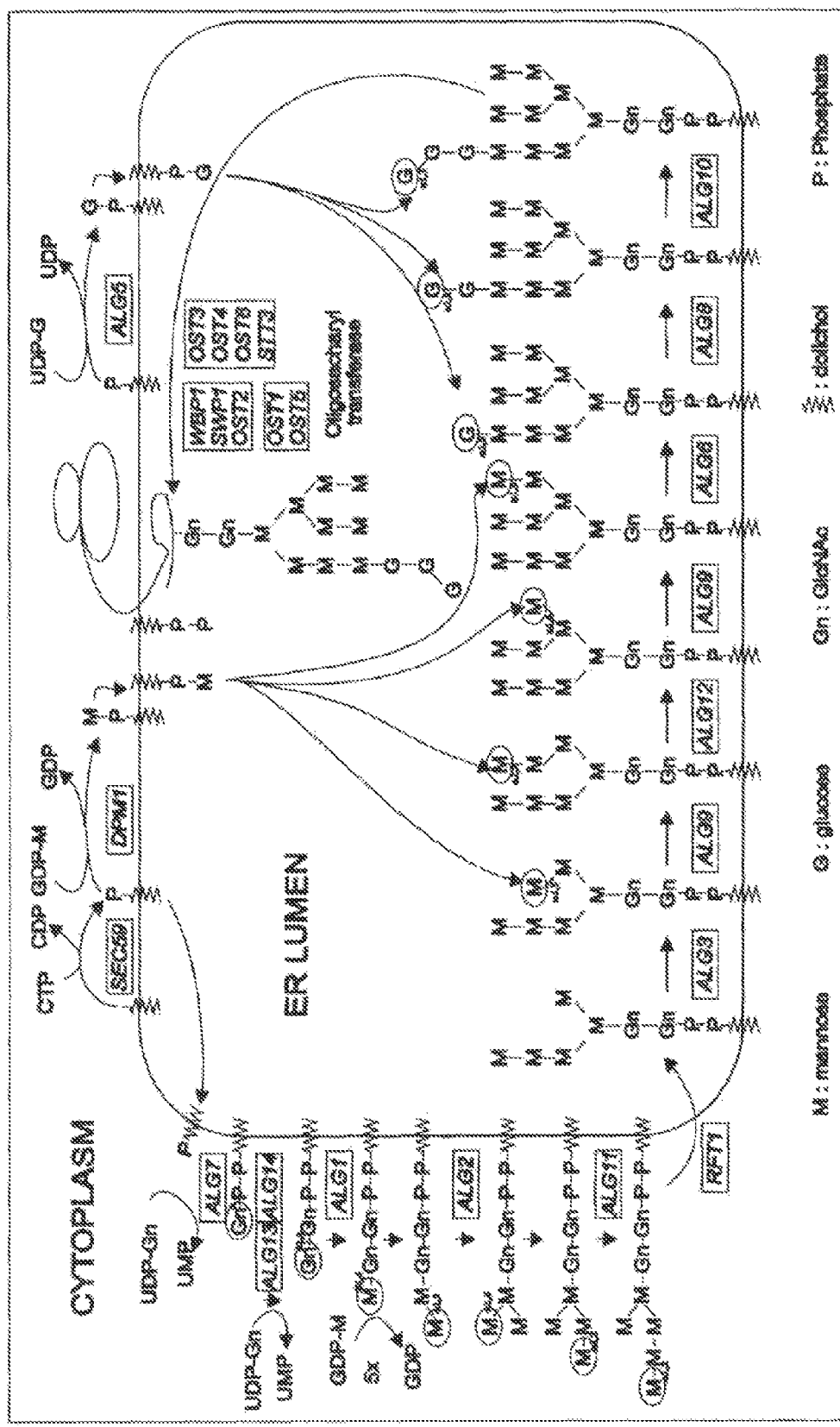
FIG. 1 is a schematic diagram depicting N-glycan precursor synthesis at the yeast endoplasmic reticulum. Genes whose encoded protein has an activity mediating the indicated enzymatic conversions are in shaded boxes (e.g., ALG7; upper left). "UDP" and "UMP" refer to uridine diphosphate and uridine monophosphate, respectively. "GDP" and "GMP" refer to guano sine diphosphate and guanosine monophosphate respectively. "Gn" refers to N-acetylglucosamine. "M" refers to monomeric mannose, G refers to glucose, Pi refers to phosphate

The methods and genetically engineered cells described herein can be used to produce target molecules (e.g., target protein or target dolichol) having an altered N-glycosylation form as compared to the N-glycosylation form of the target molecules produced in non-genetically engineered cells. Administration of glycosylated target molecules (e.g., glycosylated proteins) to patients having metabolic disorders (e.g., lysosomal storage disorders) has been shown to ameliorate the symptoms of the disorders. Thus, the methods and cells described are useful for the preparation of altered N-glycosylated target molecules for, inter alia, the treatment of metabolic disorders such as lysosomal storage disorders. Such altered N-glycosylation molecules are also useful in a wide-variety of other fields, e.g., the food and beverage industries; the pharmaceutical industry (e.g., as vaccines); the agriculture industry; and the chemical industry, to name a few.

Altered N-Glycosylation Molecule

Target molecules, as used herein, refer to any molecules that undergo altered N-glycosylation by one or more N-glycosylation activities from a genetically engineered cell (e.g., a fungal cell such as *Yarrowia lipolytica* or *Arxula adeninivorans* (or other related species dimorphic yeast) cell; a plant cell, or an animal cell). In some embodiments, the target molecules are capable of being trafficked through one or more steps of the *Yarrowia lipolytica* or *Arxula adeninivorans* (or other related species dimorphic yeast) secretory pathway, resulting in their altered N-glycosylation by the host cell machinery. The target molecules can be endogenous or exogenous.

Target proteins, their biologically active fragments, or biologically active variants thereof, can include proteins containing additions, deletions, or substitutions as described above. Suitable target proteins include pathogen proteins (e.g., tetanus toxoid; diptheria toxoid; viral surface proteins (e.g., cytomegalovirus (CMV) glycoproteins B, H and gCIII; human immunodeficiency virus 1 (HIV-1) envelope glycoproteins; Rous sarcoma virus (RSV) envelope glycoproteins; herpes simplex virus (HSV) envelope glycoproteins; Epstein Barr virus (EBV) envelope glycoproteins; varicella-zoster virus (VZV) envelope glycoproteins; human papilloma virus (HPV) envelope glycoproteins; Influenza virus glycoproteins; and Hepatitis family surface antigens), lysosomal proteins (e.g., glucocerebrosidase, cerebrosidase, or galactocerebrosidase), insulin, glucagon, growth factors, cytokines, chemokines, antibodies or fragments thereof, or fusions of any of the proteins to antibodies or fragments of antibodies (e.g., protein-Fc). Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, e.g., interleukins (e.g., IL-1 to IL-33 (e.g., IL-1, IL-2, IL-3, IL-4, IL-5, IL-6, IL-7, IL-8, IL-9, IL-10, IL-12, IL-13, or IL-15)). Chemokines include, e.g., I-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [R. A. Henderson and O. J. Finn, Advances in Immunology, 62, pp. 217-56 (1996)]. In some embodiments, the target protein can be one associated with a lysosomal storage disorder, which target proteins include, e.g., alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphingomyelinase, thioesterase, cathepsin K, and lipoprotein lipase.

Target proteins can also be fusion proteins. Fusions proteins include, e.g., a fusion of (i) any protein described herein or fragment thereof with (ii) an antibody or fragment thereof. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods of the invention.

Target proteins can also be joined to one or more of a polymer, a carrier, an adjuvant, an immunotoxin, or a detectable (e.g., fluorescent, luminescent, or radioactive) moiety. For example, a target protein can be joined to polyethyleneglycol, which polymer moiety can be used, e.g., to increase the molecular weight of small proteins and/or increase circulation residence time.

In some embodiments, the target molecule can be, or contain, dolichol.

Genetically Engineered Cells

Described herein are genetically engineered cells having at least one modified N-glycosylation activity, which cells are useful for the production of one or more target molecules having an altered N-glycosylation form. Cells suitable for genetic engineering include, e.g., fungal cells (e.g., *Yarrowia lipolytica* or any other related dimorphic yeast cells described herein), plant cells, or animal cells (e.g., (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, or transformed cells. The cells can be those in an animal, e.g., a non-human mammal. Such cells, prior to the genetic engineering as specified herein, can be obtained from a variety of commercial sources and research resource facilities, such as, for example, the American Type Culture Collection (Rockville, Md.). Target molecules include proteins such as any of the target proteins described herein (see above). Target molecules also include dolichol.

Genetic engineering of a cell includes genetic modifications such as: (i) deletion of an endogenous gene encoding a protein having N-glycosylation activity; (ii) introduction of a recombinant nucleic acid encoding a mutant form of a protein (e.g., endogenous or exogenous protein) having N-glycosylation activity (i.e., expressing a mutant protein having an N-glycosylation activity); (iii) introduction or expression of an RNA molecule that interferes with the functional expression of a protein having the N-glycosylation activity; (iv) introduction of a recombinant nucleic acid encoding a wild-type (e.g., endogenous or exogenous) protein having N-glycosylation activity (i.e., expressing a protein having an N-glycosylation activity); or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), antisense RNA, or micro RNA (miRNA). It is understood that item (ii) includes, e.g., replacement of an endogenous gene (e.g., by homologous recombination) with a gene encoding a protein having greater N-glycosylation activity relative to the endogenous gene so replaced. Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., site-directed mutagenesis or homologous recombination; see accompanying Examples) or can be introduced randomly (for example, cells can be chemically mutagenized as described in, e.g., Newman and Ferro-Novick (1987) J. Cell Biol. 105(4):1587, the disclosure of which is incorporated herein by reference in its entirety.

The genetic modifications described herein can result in one or more of (i) an increase in one or more N-glycosylation activities in the genetically modified cell, (ii) a decrease in one or more N-glycosylation activities in the genetically modified cell, (iii) a change in the localization or intracellular distribution of one or more N-glycosylation activities in the genetically modified cell, or (iv) a change in the ratio of one or more N-glycosylation activities in the genetically modified cell. It is understood that an increase in the amount of an N-glycosylation activity can be due to overexpression of one or more proteins having N-glycosylation activity, an increase in copy number of an endogenous gene (e.g., gene duplication), or an alteration in the promoter or enhancer of an endogenous gene that stimulates an increase in expression of the protein encoded by the gene. A decrease in one or more N-glycosylation activities can be due to overexpression of a mutant form (e.g., a dominant negative form) of one or more proteins having N-glysosylation altering activities, introduction or expression of one or more interfering RNA molecules that reduce the expression of one or more proteins having an N-glycosylation activity, or deletion of one or more endogenous genes that encode a protein having N-glycosylation activity.

Methods of deleting or disrupting one or more endogenous genes are described in the accompanying Examples. For example, to disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis.

As detailed in the accompanying examples, subsequent to its use in selection, a selectable marker can be removed from the genome of the host cell by, e.g., Cre-loxP systems (see below).

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative.

A recombinant nucleic acid (e.g., one encoding a wild-type or mutant form of a protein having N-glycosylation activity) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in Pichia pastoris. The disclosure of U.S. Pat. No. 4,837,148 is incorporated herein by reference in its entirety.

Integrative vectors are disclosed, e.g., in U.S. Pat. No. 4,882,279 (the disclosure of which is incorporated herein by reference in its entirety). Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., Yarrowia lipolytica, Arxula adeninivorans, or other related dimorphic yeast species) promoter, which enables them to be expressed in yeast. Suitable yeast promoters include, e.g., ADC1, TPI1, ADH2, hp4d, POX, and Gal10 (see, e.g., Guarente et al. (1982) Proc. Natl. Acad. Sci. USA 79(23):7410) promoters. Additional suitable promoters are described in, e.g., Zhu and Zhang (1999) Bioinformatics 15(7-8):608-611 and U.S. Pat. No. 6,265,185, the disclosures of each of which are incorporated herein by reference in their entirety. Where the expression vector is to be introduced into an animal cell, such as a mammalian cell, the expression vector can feature a recombinant nucleic acid under the control of an animal cell promoter suitable for expression in the host cell of interest. Examples of mammalian promoters include, e.g., SV40 or cytomegalovirus (CMV) promoters.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

Genetic engineering of a cell also includes activating an endogenous gene (e.g., a gene encoding a protein having N-glycosylation activity) that is present in the host cell, but is normally not expressed in the cells or is not expressed at significant levels in the cells. For example, a regulatory sequence (e.g., a gene promoter or an enhancer) of an endogenous gene can be modified such that the operably-linked coding sequence exhibits increased expression. Homologous recombination or targeting can be used to replace or disable the regulatory region normally associated with the gene with a regulatory sequence which causes the gene to be expressed at levels higher than evident in the corresponding non-genetically engineered cell, or causes the gene to display a pattern of regulation or induction that is different than evident in the corresponding non-genetically engineered cell. Suitable methods for introducing alterations of a regulatory sequence (e.g., a promoter or enhancer) of a gene are described in, e.g., U.S. Application Publication No. 20030147868, the disclosure of which is incorporated herein by reference in its entirety.

It is understood that other genetically engineered modifications can also be conditional. For example, a gene can be conditionally deleted using, e.g., a site-specific DNA recombinase such as the Cre-loxP system (see, e.g., Gossen et al. (2002) Ann. Rev. Genetics 36:153-173 and U.S. Application Publication No. 20060014264, the disclosures of each of which are incorporated by reference in their entirety).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) Proc. Nat. Acad. Sci. USA 75:1929; Ito et al. (1983) J. Bacteriol. 153:163; U.S. Pat. No. 4,879,231; and Sreekrishna et al. (1987) Gene 59:115, the disclosures of each of which are incorporated herein by reference in their entirety. Electroporation and PEG1000 whole cell transformation procedures may also be used, as described by Cregg and Russel, Methods in Molecular Biology: *Pichia* Protocols, Chapter 3, Humana Press, Totowa, N.J., pp. 27-39 (1998), the disclosure of which is incorporated herein by reference in its entirety. Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated herein by reference in its entirety).

Transformed yeast cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*). The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

Genetic engineering, as described herein, can be used to express (e.g., overexpress), introduce modifications into, or delete any number of genes, e.g., genes encoding proteins having N-glycosylation activity. Such genes include, e.g., ALG7, ALG13, ALG14, ALG1, ALG2, ALG11, RFT1, ALG3, ALG9, ALG12, ALG6, ALG8, ANL1, ALG10, ALG5, OST3, OST4, OST6, STT3, OST1, OST5, WBP1, SWP1, OST2, DPM1, SEC59, OCH1, MNN9, VAN1, MNN8, MNN10, MNN11, HOC1, MNN2, MNN5, MNN6, KTR1, YUR1, MNN4, KRE2, KTR2, KTR3, MNN1, MNS1, MNN4, PNO1, MNN9, glucosidase I, glucosidase II, or endomannosidase. The genes encoding proteins having N-glycosylation activity can be from any species (e.g., lower eukaryotes (e.g., fungus (including yeasts) or trypanosomes), plant, or animal (e.g., insect, bird, reptile, or mammal (e.g., a rodent such as mouse or rat, dog, cat, horse, goat, cow, pig, non-human primate, or human)) containing such genes. Exemplary fungal species from which genes encoding proteins having N-glycosylation activity can be obtained include, without limitation, *Pichia anomala, Pichia bovis, Pichia canadensis, Pichia carsonii, Pichia farinose, Pichia fermentans, Pichia fluxuum, Pichia membranaefaciens, Pichia membranaefaciens, Candida valida, Candida albicans, Candida ascalaphidarum, Candida amphixiae, Candida Antarctica, Candida atlantica, Candida atmosphaerica, Candida blattae, Candida carpophila, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida membranifaciens, Candida milleri, Candida oleophila, Candida oregonensis, Candida parapsilosis, Candida quercitrusa, Candida shehatea, Candida temnochilae, Candida tenuis, Candida tropicalis, Candida tsuchiyae, Candida sinolaborantium, Candida sojae, Candida viswanathii, Candida utilis, Pichia membranaefaciens, Pichia silvestris, Pichia membranaefaciens, Pichia chodati, Pichia membranaefaciens, Pichia menbranaefaciens, Pichia minuscule, Pichia pastoris, Pichia pseudopolymorpha, Pichia quercuum, Pichia robertsii, Pichia saitoi, Pichia silvestrisi, Pichia strasburgensis, Pichia terricola, Pichia vanriji, Pseudozyma Antarctica, Rhodosporidium toruloides, Rhodotorula glutinis, Saccharomyces bayanus, Saccharomyces bayanus, Saccharomyces momdshuricus, Saccharomyces uvarum, Saccharomyces bayanus, Saccharomyces cerevisiae, Saccharomyces bisporus, Saccharomyces chevalieri, Saccharomyces delbrueckii, Saccharomyces exiguous, Saccharomyces fermentati, Saccharomyces fragilis, Saccharomyces marxianus, Saccharomyces mellis, Saccharomyces rosei, Saccharomyces rouxii, Saccharomyces uvarum, Saccharomyces willianus, Saccharomycodes ludwigii, Saccharomycopsis capsularis, Saccharomycopsis fibuligera, Saccharomycopsis fibuligera, Endomyces hordei, Endomycopsis fobuligera. Saturnispora saitoi, Schizosaccharomyces octosporus, Schizosaccharomyces pombe, Schwanniomyces occidentalis, Torulaspora delbrueckii, Torulaspora delbrueckii, Saccharomyces dairensis, Torulaspora delbrueckii, Torulaspora fernentati, Saccharomyces fermentati, Torulaspora delbrueckii, Torulaspora rosei, Saccharomyces rosei, Torulaspora delbrueckii, Saccharomyces rosei, Torulaspora delbrueckii, Saccharomyces delbrueckii, Torulaspora delbrueckii, Saccharomyces delbrueckii, Zygosaccharomyces mongolicus, Dorulaspora globosa, Debaryomyces globosus, Torulopsis globosa, Trichosporon cutaneum, Trigonopsis variabilis, Williopsis californica, Williopsis saturnus, Zygosaccharomyces bisporus, Zygosaccharomyces bisporus, Debaryomyces disporua. Saccharomyces bisporas, Zygosaccharomyces bisporus, Saccharomyces bisporus, Zygosaccharomyces mellis, Zygosaccharomyces priorianus, Zygosaccharomyces rouxiim, Zygosaccharomyces rouxii, Zygosaccharomyces*

*barkeri, Saccharomyces rouxii, Zygosaccharomyces rouxii, Zygosaccharomyces major, Saccharomyces rousii, Pichia anomala, Pichia bovis, Pichia Canadensis, Pichia carsonii, Pichiafarinose, Pichiafermentans, Pichia fluxuum, Pichia membranaefaciens, Pichia pseudopolymorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis, Zygosaccharomyces rouxii,* or any other fungi (e.g., yeast) known in the art or described herein. Exemplary lower eukaryotes also include various species of *Aspergillus* including, but not limited to, *Aspergillus caesiellus, Aspergillus candidus, Aspergillus carneus, Aspergillus clavatus, Aspergillus deflectus, Aspergillus flavus, Aspergillusfumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus,* or *Aspergillus versicolor.* Exemplary protozoal genera from which genes encoding proteins having N-glycosylation activity can be obtained include, without limitation, *Blastocrithidia, Crithidia, Endotrypanum, Herpetomonas, Leishmania, Leptomonas, Phytomonas, Trypanosoma* (e.g., *T. bruceii, T. gambiense, T. rhodesiense,* and *T. cruzi*), and Wallaceina.

It is understood that genetic engineering, as described herein, can be used to express (e.g., overexpress), introduce modifications into, or delete any number of genes (e.g., genes encoding proteins having N-glycosylation activity) and/or any combination of one or more (e.g., two, three, four, five, six, seven, eight, nine, 10, 11, 12, 15, or 20 or more) of any of the genes recited herein.

In some embodiments, the genetically engineered cell lacks the ALG3 (Genbank® Accession Nos: XM_503488, Genolevures Ref: YALI0E03190g) gene or gene product (e.g., mRNA or protein) thereof. In some embodiments, the genetically engineered cell expresses (e.g., overexpresses) the ALG6 (Genbank® Accession Nos: XM_502922, Genolevures Ref: YALI0D17028g) protein. In some embodiments, the genetically engineered cell expresses the MNN4 gene (Genbank® Accession Nos: XM_503217, Genolevures Ref: YALI0D24101g). In some embodiments, the genetically engineered cell lacks the OCH1 and/or MNN9 gene or gene products (e.g., mRNA or protein) thereof. In some embodiments, the genetically engineered cell does not lack the OCH1 gene or a gene product (e.g., mRNA or protein) thereof. In some embodiments, the genetically engineered cell expresses an alpha or beta subunit (or both the alpha and the beta subunit) of a glucosidase II such as the glucosidase II of *Yarrowia lipolytica* or *Trypanosoma brucei.* In some embodiments, the genetically engineered cell expresses a mutantase such as the mutanase of *T. harzianum.* In some embodiments, the genetically engineered cell can have any combination of these modifications.

For example, in some embodiments, the genetically engineered cell can lack the ALG3 (e.g., the ALG3 gene exemplified by Genbank® Accession Nos: XM_503488, Genolevures Ref: YALI0E03190g) gene or gene product (e.g., mRNA or protein) thereof, can overexpress the ALG6 (e.g., the ALG6 as exemplified by Genbank® Accession Nos: XM_502922, Genolevures Ref: YALI0D17028g) protein; can overexpress one or both of the alpha and the beta subunit of a glucosidase II (such as the glucosidase II of *Yarrowia lipolytica, Trypanosoma brucei,* or any other species described herein); can overexpress an alpha-1,2-mannosidase; and overexpress one or more (and any combination) of the following: a glycosidase, a glycosyltransferase, a sugar-nucleotide transporter, a sugar-nucleotide modifying enzyme. In some embodiments, the genetically engineered cell does not lack the OCH1 gene or a gene product (e.g., mRNA or protein) thereof.

In some embodiments, the genetically modified cell can contain a mannosidase activity (e.g., an α-mannosidase activity). The mannosidase activity can be targeted to the endoplasmic reticulum. The mannosidase can have a pH optimum at least below 7.5 (e.g., at least below 7.4, at least below 7.3, at least below 7.2, at least below 7.1, at least below 7.0, at least below 6.9, at least below 6.8, at least 6.7, at least below 6.6, at least below 6.5, at least 6.4, at least below 6.3, at least below 6.2, at least below 6.1, at least below 6.0, at least below 5.9, at least below 5.8, at least below 5.7, at least below 5.6, at least below 5.5, at least below 5.4, at least below 5.3, at least below 5.2, at least below 5.1, at least below 5.0, at least below 4.9, at least below 4.8, or at least below 4.7).

The mannosidase can be MNS1.

For example, the genetically engineered cell can overexpress a mannosidase (e.g., an alpha-1,2-mannosidase or any other mannosidase described herein), but not lack the OCH1 gene or a gene product (e.g., mRNA or protein) thereof. The mannosidase can be a wild-type form of the protein or can be a mutant form such as a fusion protein containing a mannosidase and an HDEL ER-retention amino acid sequence (see Examples). (It is understood that any protein having N-glycosylation activity can be engineered into a fusion protein comprising an HDEL sequence).

In some embodiments, the genetically modified cell can contain an activity capable of promoting mannosyl phosphorylation of the altered N-glycosylation form of the target molecule. For example, a nucleic acid encoding an activity that promotes phosphorylation of N-glycans (e.g. MNN4, MNN6, PNO1) can be introduced in the genetically engineered cell, which cell is capable of increasing phosphorylating the N-glycosylation of the target molecule.

In some embodiments, the genetically modified cell can contain an activity capable of removing mannose residues that cap phosphorylation (e.g., a mannosidase such as the one from Jack Bean) from the altered N-glycosylation molecules.

In some embodiments, the genetically modified cell is capable of removing glucose residues from $Man_5GlcNAc_2$. For example, the genetically modified cell can overexpress a protein having α-1,3-glucosidase activity such as, but not limited to, a mutanase or one or both of the alpha and beta subunit of a glucosidase II (such as the glucosidase II of *Yarrowia lipolytica, Trypanosoma brucei,* or any other fungal species described herein).

In embodiments where a protein having N-glycosylation activity is derived from a cell that is of a different type (e.g., of a different species) than the cell into which the protein is to be expressed, a nucleic acid encoding the protein can be codon-optimized for expression in the particular cell of interest. For example, a nucleic acid encoding a protein having N-glycosylation from *Trypanosoma brucei* can be codon-optimized for expression in a yeast cell such as *Yarrowia lipolytica.* Such codon-optimization can be useful for increasing expression of the protein in the cell of interest. Methods for codon-optimizing a nucleic acid encoding a protein are known in the art and described in, e.g., Gao et al. (Biotechnol. Prog. (2004) 20(2): 443-448), Kotula et al. (Nat. Biotechn. (1991) 9, 1386-1389), and Bennetzen et al. (J. Biol. Chem. (1982) 257(6):2036-3031).

A cell can also be genetically engineered to produce predominantly N-glycans that are intermediates of a mammalian (e.g., human) glycosylation pathway. For example, one or more nucleic acids encoding human proteins having N-glycosylation activity can be introduced into the cell. In some embodiments, human proteins can be introduced into the cell and one or more endogenous yeast proteins having N-glycosylation activity can be suppressed (e.g., deleted or mutated). Techniques for "humanizing" a fungal glycosylation pathway are described in, e.g., Choi et al. (2003) Proc. Natl. Acad. Sci. USA 100(9):5022-5027; Verveken et al. (2004) Appl. Environ. Microb. 70(5):2639-2646; and Gemgross (2004) Nature Biotech. 22(11):1410-1414, the disclosures of each of which are incorporated herein by reference in their entirety.

Where the genetic engineering involves, e.g., changes in the expression of a protein or expression of an exogenous protein (including a mutant form of an endogenous protein), a variety of techniques can be used to determine if the genetically engineered cells express the protein. For example, the presence of mRNA encoding the protein or the protein itself can be detected using, e.g., Northern Blot or RT-PCR analysis or Western Blot analysis, respectively. The intracellular localization of a protein having N-glycosylation activity can be analyzed by using a variety of techniques, including subcellular fractionation and immunofluorescence.

Additional genetic modifications and methods for introducing them into any of the cells described herein can be adapted from the disclosures of, e.g., U.S. Pat. Nos. 7,029,872; 5,272,070; and 6,803,225; and U.S. Application Publication Nos. 20050265988, 20050064539, 20050170452, and 20040018588, the disclosures of each of which are incorporated herein by reference in their entirety.

While the engineering steps performed in dimorphic yeast species to achieve in vivo production of the $Man_5GlcNAc_2$ and $Man_3GlcNAc_2$ can be different from the engineering steps performed in other yeast species, it will be clear to those skilled in the art that the engineering techniques to produce modified glycoproteins (with the $Man_5GlcNAc_2$ and $Man_3GlcNAc_2$ core N-glycan structures) in dimorphic yeasts in vivo can be adapted by routine experimentation from the methods disclosed in, inter alia, U.S. Pat. No. 7,326,681 and U.S. Publication Nos. 20040018590, 20060040353, and 20060286637 (the disclosure of each of which is incorporated by reference in its entirety). The adapted methods can thus be used to achieve production of glycoproteins modified with human-type hybrid and complex N-glycans. These complex N-glycans can have 2 to 5 branches initiated with a GlcNAc residue onto the above-named core glycans, which can be further extended, e.g., with galactose, fucose and sialic acid residues.

In some embodiments, the mutant or wild-type proteins having N-glycosylation activity can be isolated from the genetically engineered cells using standard techniques. For example, following the expression of a mutant or wild-type protein in the genetically engineered cell, the protein can be isolated from the cell itself or from the media in which the cell was cultured. Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

In some embodiments, the isolated proteins having N-glycosylation activity can be frozen, lyophilized, or immobilized and stored under appropriate conditions, which allow the proteins to retain activity.

The disclosure also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Methods of Producing Altered N-Glycosylation Molecules

Described herein are methods of producing an altered N-glycosylation form of a target molecule. The methods generally involve the step of contacting a target molecule with one or more N-glycosylation activities from a genetically engineered cell (e.g., a fungal cell (e.g., *Yarrowia lipolytica, Arxula adeninivorans*, or any other related dimorphic yeast cells described herein), a plant cell, or an animal cell (e.g., nematode, insect, plant, bird, reptile, or mammal (e.g., a mouse, rat, rabbit, hamster, gerbil, dog, cat, goat, pig, cow, horse, whale, monkey, or human)). The methods can be cell-based or non-cell based.

Cell based methods can include the steps of introducing into a cell (e.g., a fungal cell (e.g., *Yarrowia lipolytica, Arxula adeninivorans*, or any other related dimorphic yeast cells described herein), a plant cell, or an animal cell) genetically engineered to have at least one modified N-glycosylation activity a nucleic acid encoding a target molecule subject to N-glycosylation in the cell, wherein the cell produces the target molecule in an altered N-glycosylation form. The target molecule can be, e.g., a protein such as any of the target proteins described herein. In embodiments where the target protein is a lipid, the nucleic acid can be one encoding one or more enzymes which promote the synthesis of the lipid.

The types of modifications produced by the genetic engineering of the cells are described herein (see the accompanying Examples and "Genetically Engineered Cells" above).

Methods for introducing a nucleic acid are known in the art and are described in the accompanying Examples and above.

Introduction or expression of a target molecule (e.g., a target protein) into a genetically engineered cell can result in the trafficking of the target molecule through the endoplasmic reticulum and/or Golgi apparatus of the cell, thereby producing an altered N-glycosylation form of the target molecule.

Figure 4A:
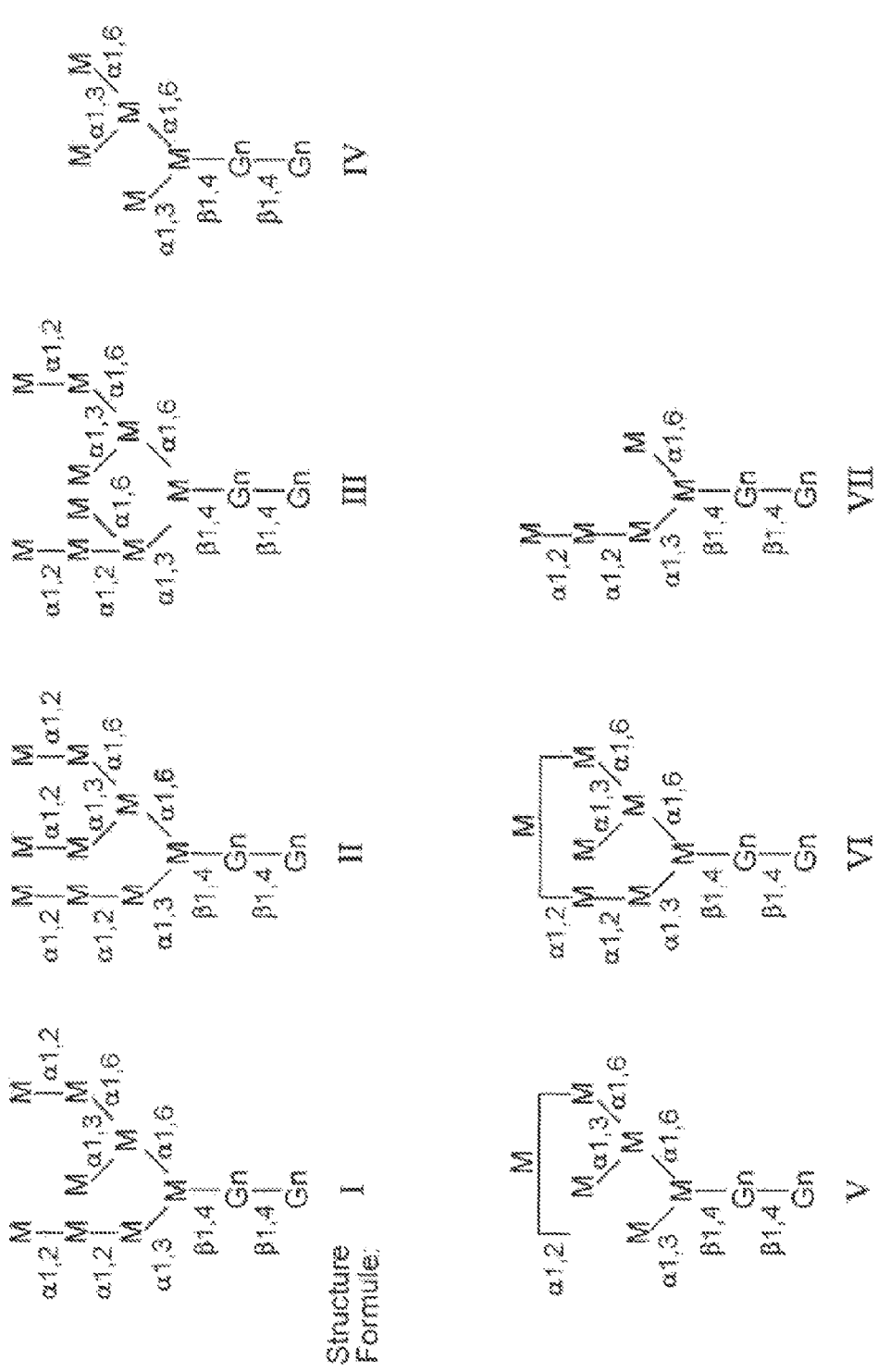
Figure 5B:
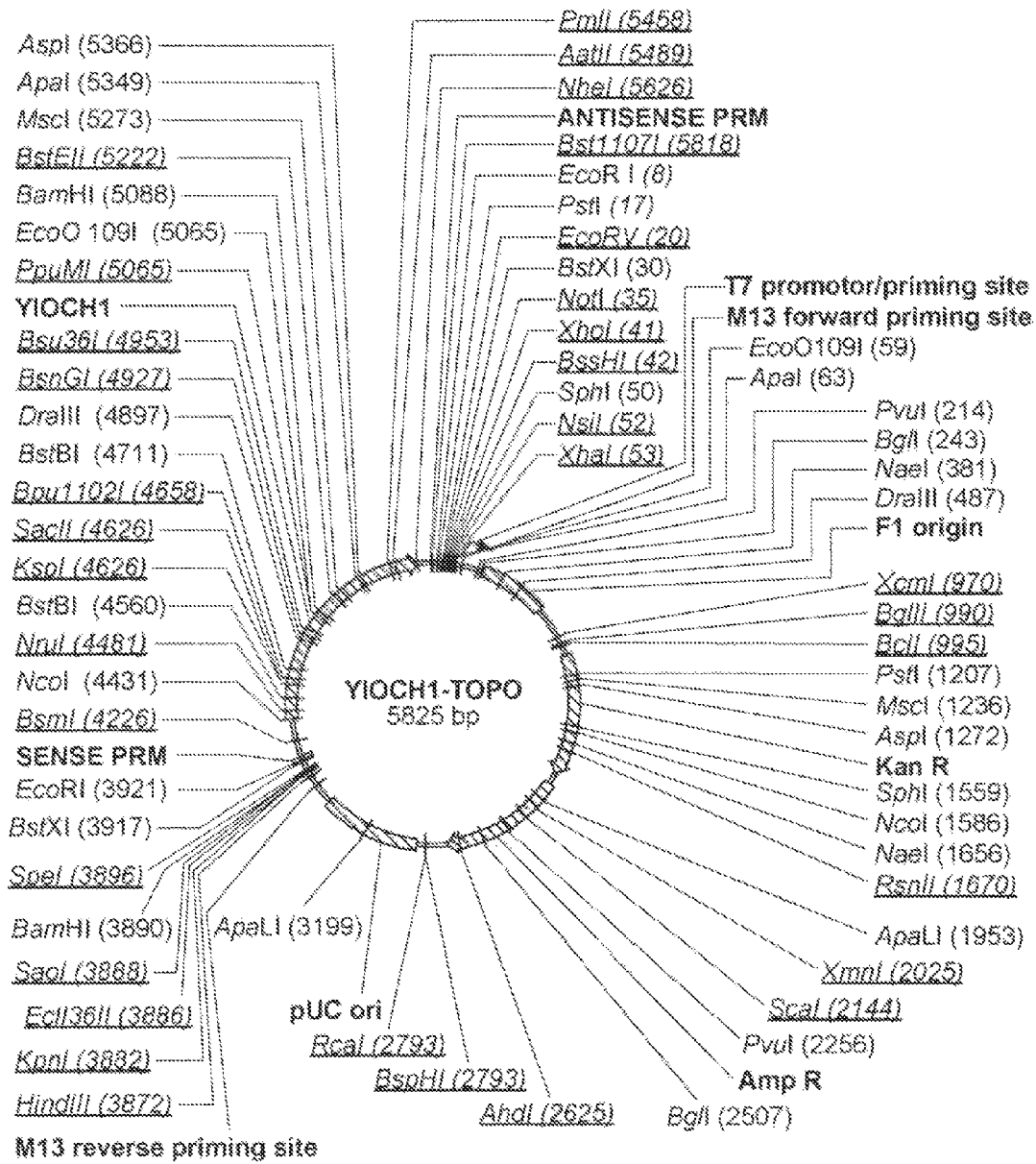
Figure 5C:
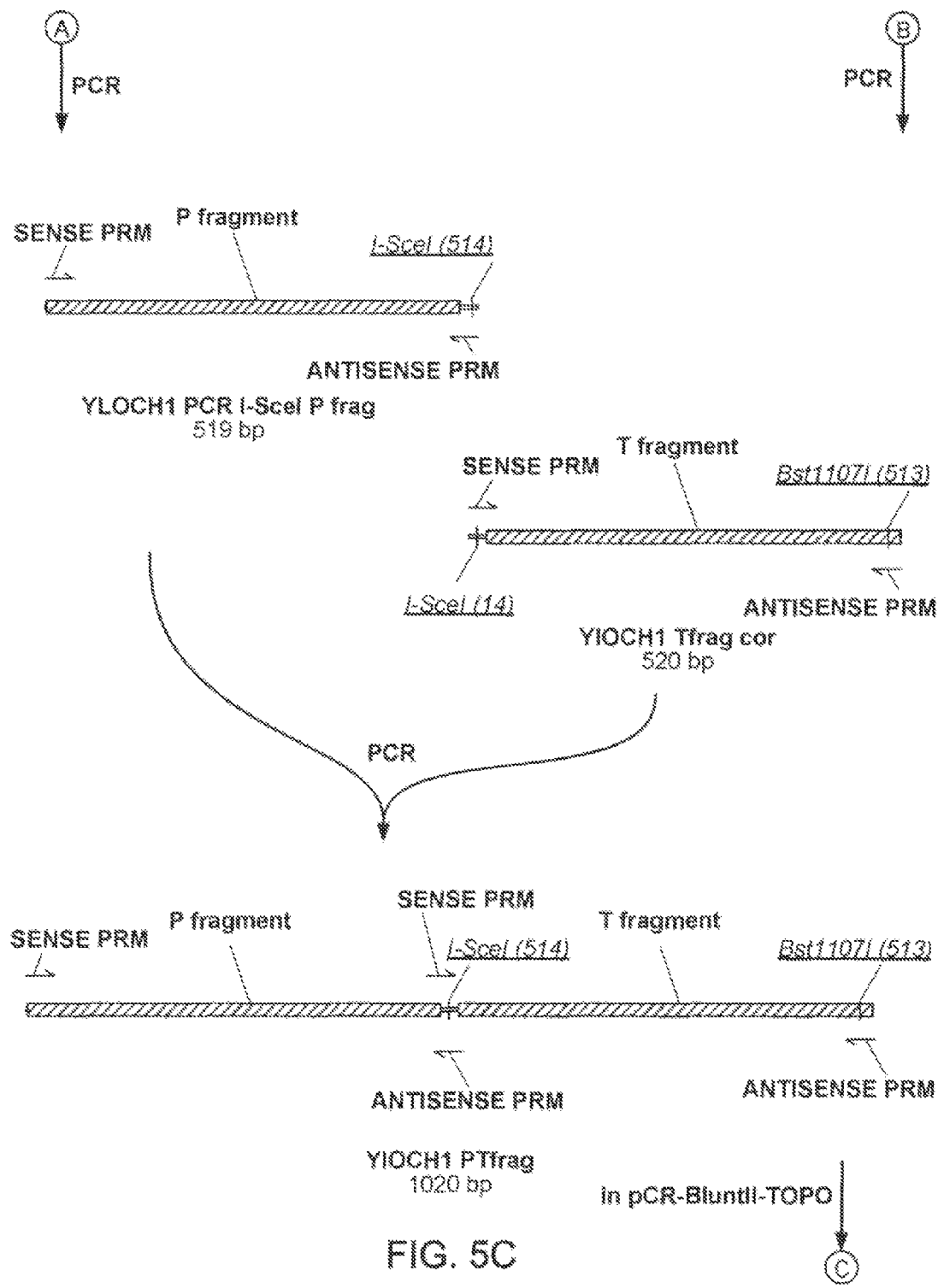
Figure 5D:
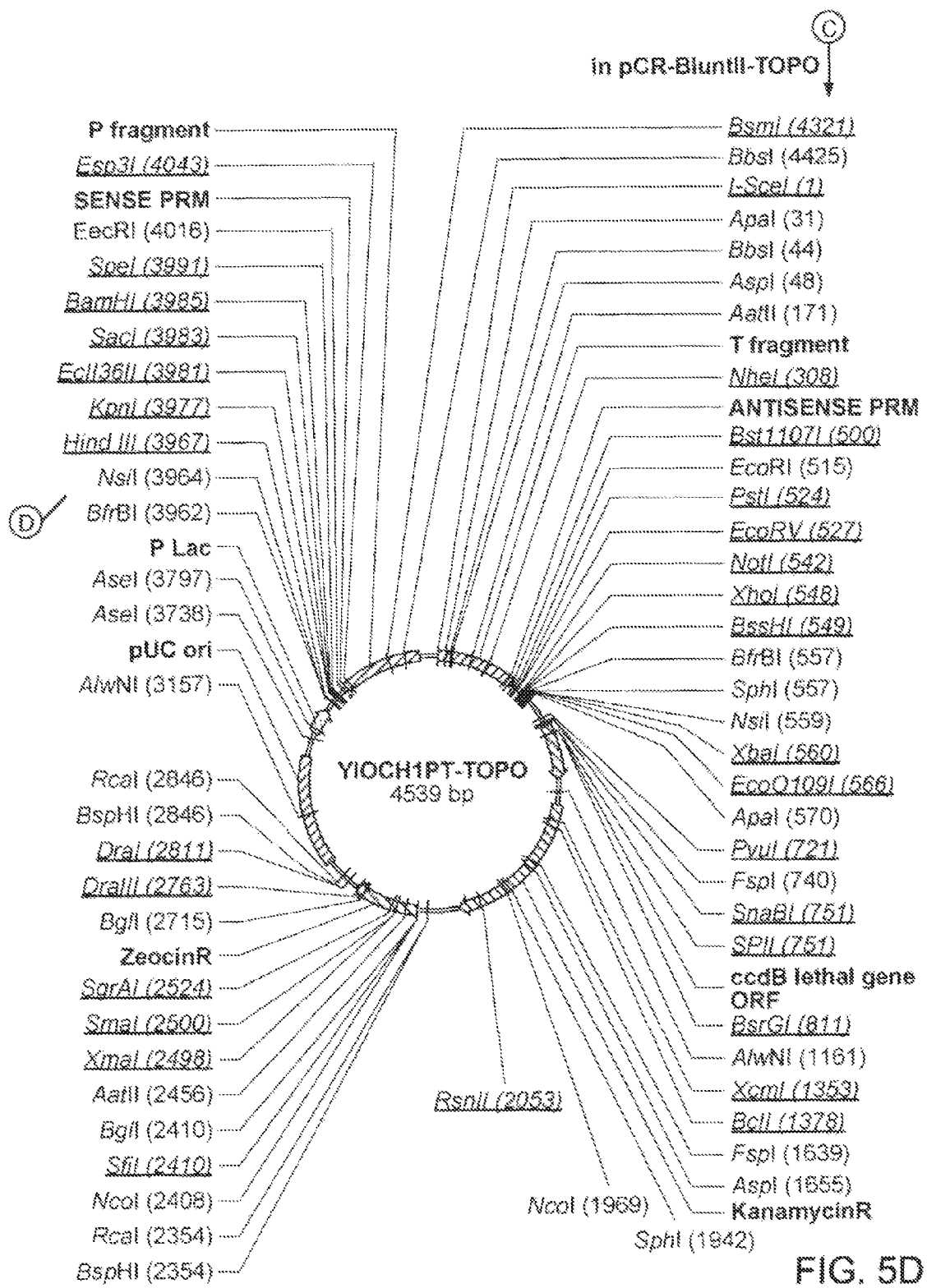
Figure 5E:
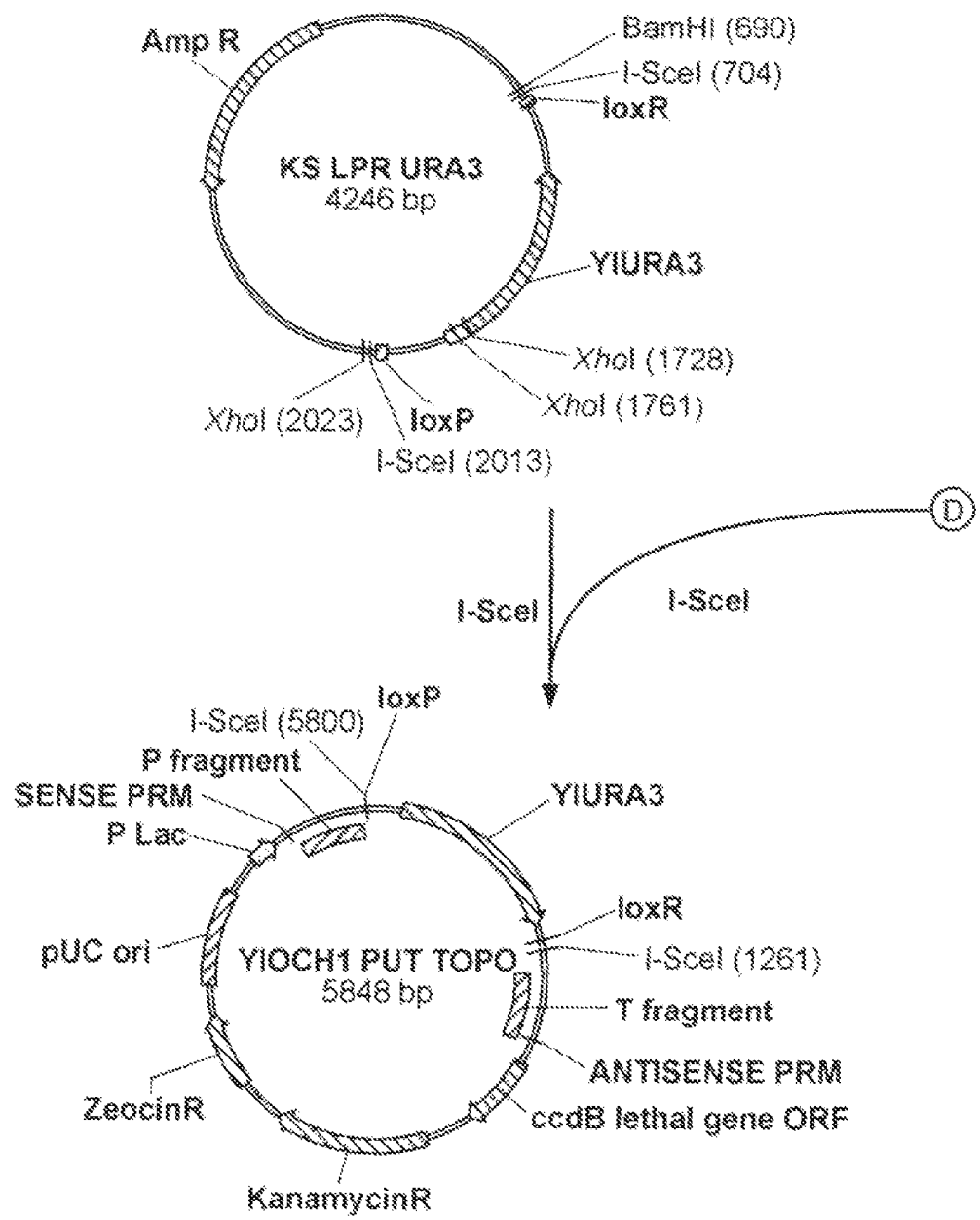

Following the processing of the target molecule (e.g., in the genetically modified cell), the altered N-glycosylation form of the target molecule (e.g., the target protein) can contain one or more N-glycan structures. For example, the altered form of the target molecule can contain one or more specific N-glycan structures such as Man5GlcNAc2 (structural formula I or VII; FIG. 4A), Man8GlcNAc2 (structural formula I; FIG. 4A), Man9GlcNAc2 (structural formula II; FIG. 4A), Man3GlcNAc2 (structural formula XIV; FIG. 4B), Glc1Man5GlcNAc2 (structural formula VIII; FIG. 4B), or Glc2Man5GlcNAc2 (structural formula IX; FIG. 4B) ("Man" is mannose; "Glc" is glucose; and "GlcNAc" is N-acetylglucosamine).

The target molecules having altered N-glycosylation produced from the genetically engineered cells can be homogeneous (i.e., all altered N-glycosylation molecules containing the same specific N-glycan structure) or can be substantially homogeneous. By "substantially homogeneous" is meant that the altered target molecules are at least about 25% (e.g., at least about 27%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or at least about 99%) of the target molecules having altered N-glycosylation produced by the genetically engineered cell.

Where the genetically engineered cell includes one or more N-glycosylation activities that effect the phosphorylation of an N-glycan, an altered N-glycosylation form of a target molecule can have at least about 25% (e.g., at least about 27%, at least about 30%, at least about 35%, at least about 40%, at least about 45%, at least about 50%, at least about 55%, at least about 60%, at least about 65%, at least about 70%, at least about 75%, or at least about 80%) of its mannosyl residues phosphorylated.

Where any of the genetic modifications of the genetically engineered cell are inducible or conditional on the presence of an inducing cue (e.g., a chemical or physical cue), the genetically engineered cell can, optionally, be cultured in the presence of an inducing agent before, during, or subsequent to the introduction of the nucleic acid. For example, following introduction of the nucleic acid encoding a target protein, the cell can be exposed to a chemical inducing agent that is capable of promoting the expression of one or more proteins having N-glycosylation activity. Where multiple inducing cues induce conditional expression of one or more proteins having N-glycosylation activity, a cell can be contacted with multiple inducing agents.

Following processing by one or more N-glycosylation activities, the altered target molecule can be isolated. The altered target molecule can be maintained within the yeast cell and released upon cell lysis or the altered target molecule can be secreted into the culture medium via a mechanism provided by a coding sequence (either native to the exogenous nucleic acid or engineered into the expression vector), which directs secretion of the molecule from the cell. The presence of the altered target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the altered target protein (or the target protein itself).

In some embodiments, the isolated altered target molecules can be frozen, lyophilized, or immobilized and stored under appropriate conditions, e.g., which allow the altered target molecules to retain biological activity.

The altered N-glycosylation form of the target molecule can be further processed in vivo (e.g., in the genetically engineered cell) or can be processed in vitro following isolation from the genetically engineered cell or cell medium. The further processing can include modifications of one or more N-glycan residues of the altered target molecule or modifications to the altered target molecule other than to its N-glycan residues. The additional processing of the altered target molecule can include the addition (covalent or non-covalent joining) of a heterologous moiety such as a polymer or a carrier. The further processing can also involve enzymatic or chemical treatment of the altered target molecule. Enzymatic treatment can involve contacting the altered target molecule with one or more of a glycosidase (e.g., mannosidase or mannanase), a phosphodiesterase, a phospholipase, a glycosyltransferase, or a protease for a time sufficient to induce modification of the altered target molecule. Enzymatic treatment can also involve contacting the altered target molecule with an enzyme capable of removing one or more glucose residues from $Man_5GlcNAc_2$ such as, but not limited to, a mannosidase or one or both of the alpha and beta subunit of a glucosidase II. Chemical treatment can, for example, involve contacting the altered target molecule with an acid such as hydrofluoric acid for a time sufficient to induce modification of the altered target molecule. Hydrofluoric acid treatment under certain conditions specifically removes the mannose residues that are phosphodiester-linked to glycans, while leaving the phosphate on the glycan. An altered target molecule can be further processed by addition or removal of a phosphate group from one or more N-glycans. For example, a altered target molecule can be contacted with a mannosyl kinase or a mannosyl phosphatase.

In some embodiments, any of the altered target molecules described herein, following isolation, can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

It is understood that a target molecule can be, but need not be, processed in a genetically engineered cell. For example, the disclosure also features cell-free methods of producing a target molecule having an altered N-glycosylation form, which methods include the step of contacting a target molecule under N-glycosylation conditions with a cell lysate prepared from a cell (e.g., a fungal cell (e.g., *Yarrowia lipolytica, Arxula adeninivorans*, or any other related dimorphic yeast cells described herein), a plant cell, or an animal cell (e.g., nematode, insect, plant, bird, reptile, or mammal (e.g., a mouse, rat, rabbit, hamster, gerbil, dog, cat, goat, pig, cow, horse, whale, monkey, or human)) genetically engineered to have at least one modified N-glycosylation activity, wherein the contacting of the target molecule to the cell lysate produces an altered N-glycosylation form of the target molecule.

By "N-glycosylation conditions" is meant that a mixture (e.g., of target molecule and cell lysate) is incubated under conditions that allow for altered N-glycosylation (as described above).

Suitable methods for obtaining cell lysates that preserve the activity or integrity of one or more N-glycosylation activities in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Inhibitors can be chosen such that they do not interfere with or only minimally adversely affect the N-glycosylation activity, or activities, of interest. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, J. Chromatogr. A 814:71-81 (1998)).

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) J. Biol. Chem. 266(7):4329-4333; Moreau et al. (1991) J. Biol. Chem. 266(7):4322-4328; Rexach et al. (1991) J. Cell Biol. 114(2):219-229; and Paulik et al. (1999) Arch. Biochem. Biophys. 367(2):265-273; the disclosures of each of which are incorporated herein by reference in their entirety.

The disclosure also provides methods of producing a target molecule having an altered N-glycosylation form that includes the step of contacting a target molecule under N-glycosylation conditions with one or more isolated proteins having N-glycosylation activity, wherein contacting the target molecule with the one or more proteins having N-glycosylation activity produces an altered N-glycosylation form of the target molecule and wherein the one or more proteins having N-glycosylation activity are prepared from a cell (e.g., a fungal cell (e.g., *Yarrowia lipolytica, Arxula adeninivorans*, or any other related dimorphic yeast cells described herein), a plant cell, or an animal cell (e.g., nematode, insect, plant, bird, reptile, or mammal (e.g., a mouse, rat, rabbit, hamster, gerbil, dog, cat, goat, pig, cow, horse, whale, monkey, or human)) genetically engineered to have at least one modified N-glycosylation activity.

One or more proteins having N-glycosylation activity can be purified using standard techniques as described above. A target molecule can be contacted with one or more proteins in a suitable buffer for a time sufficient to induce modification of the target molecule as described in, e.g., Lee and Park (2002) 30(6):716-720 and Fujita and Takegawa (2001) Biochem. Biophys. Res. Commun. 282(3):678-682, the disclosures of which are incorporated herein by reference in their entirety.

In some embodiments, the target molecule can be contacted with just one protein having N-glycosylation activity. In some embodiments, the target molecule can be contacted with more than one protein having N-glycosylation activity. The target molecule can be contacted with more than one protein at the same time or sequentially. Where the target molecule is contacted sequentially to more than one protein having N-glycosylation activity, the target molecule can, but need not, be purified after one or more steps. That is, a target molecule can be contacted with protein activity A, then purified before contacting the molecule to protein activity B, and so on.

It some embodiments of the cell free methods, it can be advantageous to link the target molecule to a solid-phase support prior to contacting the target molecule with one or more N-glycosylation activities. Such linkage can allow for easier purification following the N-glycosylation modifications. Suitable solid-phase supports include, but are not limited to, multi-well assay plates, particles (e.g., magnetic or encoded particles), a column, or a membrane.

Methods for detecting N-glycosylation (e.g., altered N-glycosylation) of a target molecule include DNA sequencer-assisted (DSA), fluorophore-assisted carbohydrate electrophoresis (FACE) (as described in the accompanying Examples) or surface-enhanced laser desorption/ionization time-of-flight mass spectrometry (SELDI-TOF MS) and. For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Optionally, isolated mannoproteins can be further treated with one or more enzymes to confirm their N-glycan status. Exemplary enzymes include, e.g., α-mannosidase or α-1,2 mannosidase, as described in the accompanying Examples. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) Glycobiology 11(4):275-281 and Freire et al. (2006) Bioconjug. Chem. 17(2):559-564, the disclosures of each of which are incorporated herein by reference in their entirety.

Disorders Treatable by Altered N-Glycosylation Molecules

The isolated, altered N-glycosylation molecules (e.g., the altered N-glycosylation proteins or dolichol) described herein can be used to treat a variety of disorders, which disorders are treatable by administration of one or more altered N-glycosylation molecules (e.g., a protein having altered N-glycosylation). Examples of some specific medical conditions that can be treated or prevented by administration of an altered N-glycosylation molecule (e.g., an altered N-glycoprotein or an altered N-glycosylated dolichol) are reviewed in the following sections.

(i) Metabolic Disorders

A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism disorders of mitochondrial function, disorders of peroxisomal function, and lysosomal storage disorders (LSDs).

Examples of metabolic disorders that can be treated through the administration of one or more altered N-glycosylation molecules (or pharmaceutical compositions of the same) described herein can include, e.g., hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypothyroidism, congenital long QT syndrome, tyroxine binding globulin deficiency, familial hypercholesterolemia, familial chylomicronemia, abeta-lipoproteinema, low plasma lipoprotein A levels, hereditary emphysema with liver injury, congenital hypothyroidism, osteogenesis imperfecta, hereditary hypofibrinogenemia, alpha-1antichymotrypsin deficiency, nephrogenic diabetes insipidus, neurohypophyseal diabetes insipidus, adenosine deaminase deficiency, Pelizaeus Merzbacher disease, von Willebrand disease type IIA, combined factors V and VIII deficiency, spondylo-epiphyseal dysplasia tarda, choroideremia, I cell disease, Batten disease, ataxia telangiectasias, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dubin-Johnson syndrome, X-linked hypophosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Hurler disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis (types II, III, and IV), cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infections (e.g., chest infections or pneumonias), kidney impairment, progressive brain damage, seizures, extra thick meconium, coughing, wheezing, excess saliva or mucous production, shortness of breath, abdominal pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, macroglossia, areflexia, lower back pain, sleep apnea, orthopnea, somolence, lordosis, or scoliosis. It is understood that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms such as, but not limited to, temperature intolerance, corneal whirling, pain, skin rashes, nausea, or dirarrhea. A patient with Gaucher syndrome can present with splenomegaly, cirrhosis, convulsions, hypertonia, apnea, osteoporosis, or skin discoloration.

In addition to the administration of one or more altered N-glycosylation molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" (such as one described herein) is a subject that has a predisposition to develop a disorder, i.e., a genetic predisposition to develop metabolic disorder as a result of a mutation in a enzyme such as alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neurominidase, phosphotransferase, acid lipase, acid ceramidase, sphingomyelinase, thioesterase, cathepsin K, or lipoprotein lipase. Clearly, subjects "at risk of developing a metabolic disorder" are not all the subjects within a species of interest.

A subject "suspected of having a disorder" is one having one or more symptoms of a disorder (e.g., a metabolic disorder or any other disorder described herein) such as any of those described herein.

(ii) Cancer

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a subject can also be one "at risk of developing a cancer" when the subject has been exposed to mutagenic or carcinogenic levels of certain compounds (e.g., carcinogenic compounds in cigarette smoke such as Acrolein, Arsenic, Benzene, Benz{a}anthracene, Benzo{a}pyrene, Polonium-210 (Radon), Urethane, or Vinyl Chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like.

In addition to the administration of one or more altered N-glycosylation molecules described herein, a cancer can also be treated by chemotherapeutic agents, ionizing radiation, immunotherapy agents, or hyperthermotherapy agents. Chemotherapeutic agents include, e.g., cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, and methotrexate.

(iii) Inflammatory Disorders

An "inflammatory disorder," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be a response that is inappropriate in magnitude or duration, e.g., anaphylaxis. Thus, the inappropriately targeted response can be due to the presence of a microbial infection (e.g., viral, bacterial, or fungal). Types of inflammatory disorders (e.g., autoimmune disease) can include, but are not limited to, osteoarthritis, rheumatoid arthritis (RA), spondyloarthropathies, POEMS syndrome, Crohn's disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory disorders are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory disorders can also include ulcerative colitis and asthma.

A subject "at risk of developing an inflammatory disorder" refers to a subject with a family history of one or more inflammatory disorders (e.g., a genetic predisposition to one or more inflammatory disorders) or one exposed to one or more inflammation-inducing conditions. For example, a subject can have been exposed to a viral or bacterial superantigen such as, but not limited to, staphylococcal enterotoxins (SEs), a *streptococcus pyogenes* exotoxin (SPE), a *staphylococcus aureus* toxic shock-syndrome toxin (TSST-1), a streptococcal mitogenic exotoxin (SME) and a streptococcal superantigen (SSA). From the above it will be clear that subjects "at risk of developing an inflammatory disorder" are not all the subjects within a species of interest.

A subject "suspected of having an inflammatory disorder" is one who presents with one or more symptoms of an inflammatory disorder. Symptoms of inflammatory disorders are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain.

In addition to the administration of one or more altered N-glycosylation molecules described herein, an inflammatory disorder can also be treated by non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept).

Methods suitable for treating (e.g., preventing or ameliorating one or more symptoms of) any of the disorders described herein using any of the altered N-glycosylation molecules (or pharmaceutical compositions thereof) are set forth in the following section.

Pharmaceutical Compositions and Methods of Treatment

An altered N-glycosylation molecule (e.g., an altered N-glycosylation form of a target molecule such as a target protein) can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing an altered N-glycosylation molecule can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798,113, and 5,800,828, each incorporated herein by reference in their entirety. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984), incorporated herein by reference in its entirety); microencapsulation (see, e.g., U.S. Pat. Nos. 4,352,883; 4,353,888; and 5,084,350, herein incorporated by reference in its entirety); continuous release polymer implants (see, e.g., Sabel, U.S. Pat. No. 4,883,666, incorporated herein by reference in its entirety); macroencapsulation (see, e.g., U.S. Pat. Nos. 5,284,761, 5,158,881, 4,976,859 and 4,968,733 and published PCT patent applications WO92/19195, WO 95/05452, the disclosures of each of which are incorporated herein by reference in their entirety); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

An altered N-glycosylation molecule (e.g., an altered N-glycosylation form of a target molecule such as a target protein) suitable for topical administration can be administered to a mammal (e.g., a human patient) as, e.g., a cream, a spray, a foam, a gel, an ointment, a salve, or a dry rub. A dry rub can be rehydrated at the site of administration. An altered N-glycosylation molecule can also be infused directly into (e.g., soaked into and dried) a bandage, gauze, or patch, which can then be applied topically. Altered N-glycosylation molecules can also be maintained in a semi-liquid, gelled, or fully-liquid state in a bandage, gauze, or patch for topical administration (see, e.g., U.S. Pat. No. 4,307,717, the content of which is incorporated herein by reference in its entirety).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, an altered N-glycosylation molecule can be first administered at different dosing regimens. The unit dose and regimen depend on factors that include, e.g., the species of mammal, its immune status, the body weight of the mammal. Typically, levels of an altered N-glycosylation molecule in a tissue can be monitored using appropriate screening assays as part of a clinical testing procedure, e.g., to determine the efficacy of a given treatment regimen.

The frequency of dosing for an altered N-glycosylation molecule is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such altered N-glycosylation molecules (e.g., an altered N-glycosylation form of target molecules such as target proteins) or pharmaceutical compositions thereof can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the ED50 with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of an altered N-glycosylation molecule is an amount of the molecule that is capable of producing a medically desirable result (e.g., amelioration of one or more symptoms of a metabolic disorder or decreased proliferation of cancer cells) in a treated subject. A therapeutically effective amount of an altered N-glycosylation molecule (i.e., an effective dosage) includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

An altered N-glycosylation molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents are administered at the same time. Alternatively, the altered N-glycosylation molecule (e.g., protein or dolichol) can be administered first in time and the one or more additional agents administered second in time. The one or more additional agents can be administered first in time and the altered N-glycosylation molecule (e.g., protein or dolichol) administered second in time. The altered N-glycosylation molecule can replace or augment a previously or currently administered therapy. For example, upon treating with an altered N-glycosylation molecule of the invention, administration of the one or more additional agents can cease or diminish, e.g., be administered at lower levels. Administration of the previous therapy can also be maintained. In some instances, a previous therapy can be maintained until the level of the altered N-glycosylation molecule (e.g., the dosage or schedule) reaches a level sufficient to provide a therapeutic effect. The two therapies can be administered in combination.

It will be appreciated that in instances where a previous therapy is particularly toxic (e.g., a treatment for a metabolic disorder with significant side-effect profiles), administration of the altered N-glycosylation molecule (e.g., protein or dolichol) can be used to offset and/or lessen the amount of the previously therapy to a level sufficient to give the same or improved therapeutic benefit, but without the toxicity.

In some instances, when the subject is administered an altered N-glycosylation molecule (e.g., protein, dolichol, or a dolichol-linked lipid) or pharmaceutical composition of the invention the first therapy is halted. The subject can be monitored for a first pre-selected result, e.g., an improvement in one or more symptoms of a metabolic disorder such as any of those described herein (e.g., see above). In some cases, where the first pre-selected result is observed, treatment with the altered N-glycosylation molecule (e.g., an altered N-glycosylation protein or an altered N-glycosylation dolichol) is decreased or halted. The subject can then be monitored for a second pre-selected result after treatment with the altered N-glycosylation molecule (e.g., protein or dolichol) is halted, e.g., a worsening of a symptom of a metabolic disorder. When the second pre-selected result is observed, administration of the altered N-glycosylation molecule (e.g., protein or dolichol) to the subject can be reinstated or increased, or administration of the first therapy is reinstated, or the subject is administered both an altered N-glycosylation molecule (e.g., protein, dolichol, or a dolichol-linked lipid) and first therapy, or an increased amount of the altered N-glycosylation molecule (e.g., protein or dolichol) and the first therapeutic regimen.

The altered N-glycosylation molecule (e.g., protein or dolichol) can also be administered with a treatment for one or more symptoms of a disease (e.g., a metabolic disorder). For example, the altered N-glycosylation molecule (e.g., protein, dolichol, or a dolichol-linked lipid) can be co-administered (e.g., at the same time or by any combination regimen described above) with, e.g., a pain medication.

It is understood that in some embodiments, an altered N-glycosylation molecule is one in which the altered glycosylation increases the ability of the molecule to produce a medically relevant product. For example, an altered N-glycosylation molecule can be an enzyme capable of producing a therapeutic product (e.g., a small molecule or therapeutic peptide), which enzyme's activity is increased or optimized by glycosylation. Such products and methods of using the products are within the scope of the present disclosure.

Any of the pharmaceutical compositions described herein can be included in a container, pack, or dispenser together with instructions for administration.

The following are examples of the practice of the invention. They are not to be construed as limiting the scope of the invention in any way.

EXAMPLES

Example 1

Plasmids, Primers and Strains

Table 1 contains a list of all of the plasmids used in the construction of vectors (e.g., expression vectors) and deletion cassettes used in the experiments described herein. The MTLY60 strain of *Yarrowia lipolytica* was used in the experiments.

Table 2 contains a list of primers (the names of the primers) and the utility of the primers used in the following examples.

TABLE 1

| Plasmids: |
| --- |
| JMP62 |
| pYLTsA |
| pYLHmL |
| pYLHmA |
| JMP113 |
| JMP114 |
| pRRQ2 |
| JME 507 |
| JME 509 |
| JME 461 |
| KS-LPR-URA3 |
| KS-LPR-LEU2 |
| Cre ARS68 |
| LEU2 |

TABLE 2

| Primers: | Name: | Use: |
| --- | --- | --- |
| TCGCTATCACGTCTCTAGC (SEQ ID NO: 18) | YIoch1 prom fw | Amplification Yl0CH1 Amplification Yl0CH1 P fragment |
| TCTCTGTATACTTGTATGT ACTG (SEQ ID NO: 19) | YIoch1 ter rev | Amplification Yl0CH1 Amplification Yl0CH1 T fragment |
| CTAGGGATAACAGGGTAA TGGTGTGACGAAGTATCG AG (SEQ ID NO: 20) | YIOCH1 Pfrag rev | Amplification P fragment incl I-Sce I site |
| CATTACCCTGTTATCCCTA GCGAGATCATGGACTGG (SEQ ID NO: 21) | YIOCH1 Tfrag fw | Amplification T fragment incl I-Sce I site |
| GACGCGGCCGCATGAGCT TCAACATTCCCAAAAC (SEQ ID NO: 22) | YIMNS1 ORF + Ter (Pfrag) S | Amplification of YIMNS1 P frag. (ORF + terminator) |
| CTAGGGATAACAGGGTAA TACAAAATTCAGAAATAA AAATACTTTACAG (SEQ ID NO: 23) | YIMNS1 ORF + Ter (Pfrag) AS | Amplification of YIMNS1 P frag. (ORF + termin.) + I-SceI |
| CATTACCCTGTTATCCCTA AGTAACATGAGTGCTATG AG (SEQ ID NO: 24) | YIMNS1 Tfrag S | Amplification of YIMNS1 T frag. (downstream terminator.) + I-SceI |
| CGCTTAATTAAATGCATGG AGGTATTGCTG (SEQ ID NO: 25) | YIMNS1 Tfrag AS | Amplification of YIMINS1 T frag. (downstream terminator.) |
| GGTGCTTCGACTATCAGTT TCGGAGGATTGGGTGATTC TTTTTATG (SEQ ID NO: 26) | ScMNS1 mut 269-273 S | ScMNS1 mutation primer to shift to mam. Golgi type mannase => proof of concept in Sc |
| CATAAAAAGAATCACCCA ATCCTCCGAAACTGATAGT CGAAGCACC (SEQ ID NO: 27) | ScMNS1 mut 269-273 AS | YIMNS1 mutation primer to shift to mam. Golgi type mannase => proof of concept in Sc |
| TGAGCGGCCGCTTTTCTAC TTCAGAGCTGGAG (SEQ ID NO: 28) | YIMNN9 P fw | YIMNN9 KO primer |

TABLE 2-continued

| Primers: | Name: | Use: |
|---|---|---|
| GGCTTAATTAATTGGTAGT GATATAATGTAACGC (SEQ ID NO: 29) | YlMNN9 T rv | YlMNN9 KO primer |
| TAGGGATAACAGGGTAAT CACGACACATACTCATTCA AG (SEQ ID NO: 30) | YlMNN9 P rv | YlMNN9 KO primer |
| ATTACCCTGTTATCCCTAG AAGGAGATGTAGCGTAAG (SEQ ID NO: 31) | YlMNN9 T fw | YlMNN9 KO primer |
| TGATAAATAGCTTAGATAC CACAG (SEQ ID NO: 32) | LIP2 rv | Reverse primer used for sequencing |
| ACATACAACCACACACAT C (SEQ ID NO: 33) | 5' hp4d | Forward primer used for sequencing |
| GGCGGATCCATGGTGCTGC ACCCGTTTC (SEQ ID NO: 34) | YlMNN4 BamHI fw | Forward primer for amplification of YlMNN4 |
| GGCCCTAGGCTACTCAAAC TCCTCGCGAATC (SEQ ID NO: 35) | YlMNN4 AvrII rv | Reverse primer for amplification of YlMNN4 |
| GGTCTCGCCAGCGCGCCCA CCCTCTTC (SEQ ID NO: 36) | HAC1FW06-003 | Forward primer region around HAC1 splice site |
| CTAGATCAGCAATAAAGT CGTGCTGGGC (SEQ ID NO: 37) | HAC1Rv06-001 | Reverse primer region around HAC1 splice site |
| GGATCCATGTCTATCAAGC GAGAAGAG TCC (SEQ ID NO: 38) | HAC1Fw06-002 | Amplification of HAC1 gene includes start codon and BamHI restriction site |
| CCTAGGCTAGATCAGCAAT AAAGTCGTGCTGGGC (SEQ ID NO: 39) | HAC1RV06-006 | Amplification of HAC1 gene includes stop codon and AvrII restriction site |

Example 2

Yarrowia lipolytica OCH1 and MNN9 Disruption

A strategy to knock out both OCH1 (GenBank® Accession No: AJ563920) and MNN9 (GenBank® Accession No: AF441127) genes in Yarrowia lipolytica was set up as described in Fickers et al. ((2003) J Microbiol Methods. 55(3):727-37) for the LIP2 gene. The gene construction strategy that was followed for the OCH1 gene is depicted in FIGS. 5A-5E.

The OCH1 KO fragment was isolated from the plasmid YlOCH1 PUT TOPO by restriction digest and by PCR and was transformed to Yarrowia lipolytica strain MTLY60. 20 uracil prototrophic strains were obtained and screened by PCR on genomoic DNA (gDNA) using primers Yloch1 prom fw (SEQ ID NO:18) and Yloch1 ter rev (SEQ ID NO:19) to analyse the genomic integration of the plasmid. A fragment of the correct size (i.e., 2618 bp vs. 1894 bp in the wild type) was amplified in 2 of the 20 clones tested. Several clones contained a random integrated copy of the construct and therefore both fragments were amplified.

To remove the URA3 gene, the two positive clones were transformed with the episomal plasmid pRRQ2 that contains an expression cassette for the Cre recombinase. Removal of the URA3 gene was screened for by PCR on gDNA using primers Yloch1 prom fw and Yloch1 ter rev (see above). The 2328 bp fragment (incl. URA3) was absent from, and a 1075 bp (excl. URA3) fragment of 1075 bp was present in, the positive clones.

A Southern blot analysis was performed on the 2 positive clones to check whether aberrant DNA integration had occurred. Genomic DNA (gDNA) was double digested with EcoRV/HindIII, subjected to agarose-gel electrophoresis, and transferred to nitrocellulose membrane. The membrane was probed with a 500 bp SpeI/I-SceI fragment from plasmid YlOCH1 PT TOPO. A fragment of 1456 bp was present in Δoch1 PUT, whereas a fragment of 2066 bp in Δoch1 PT and a fragment of 2893 bp in the wild type strain was present.

Figure 6A:
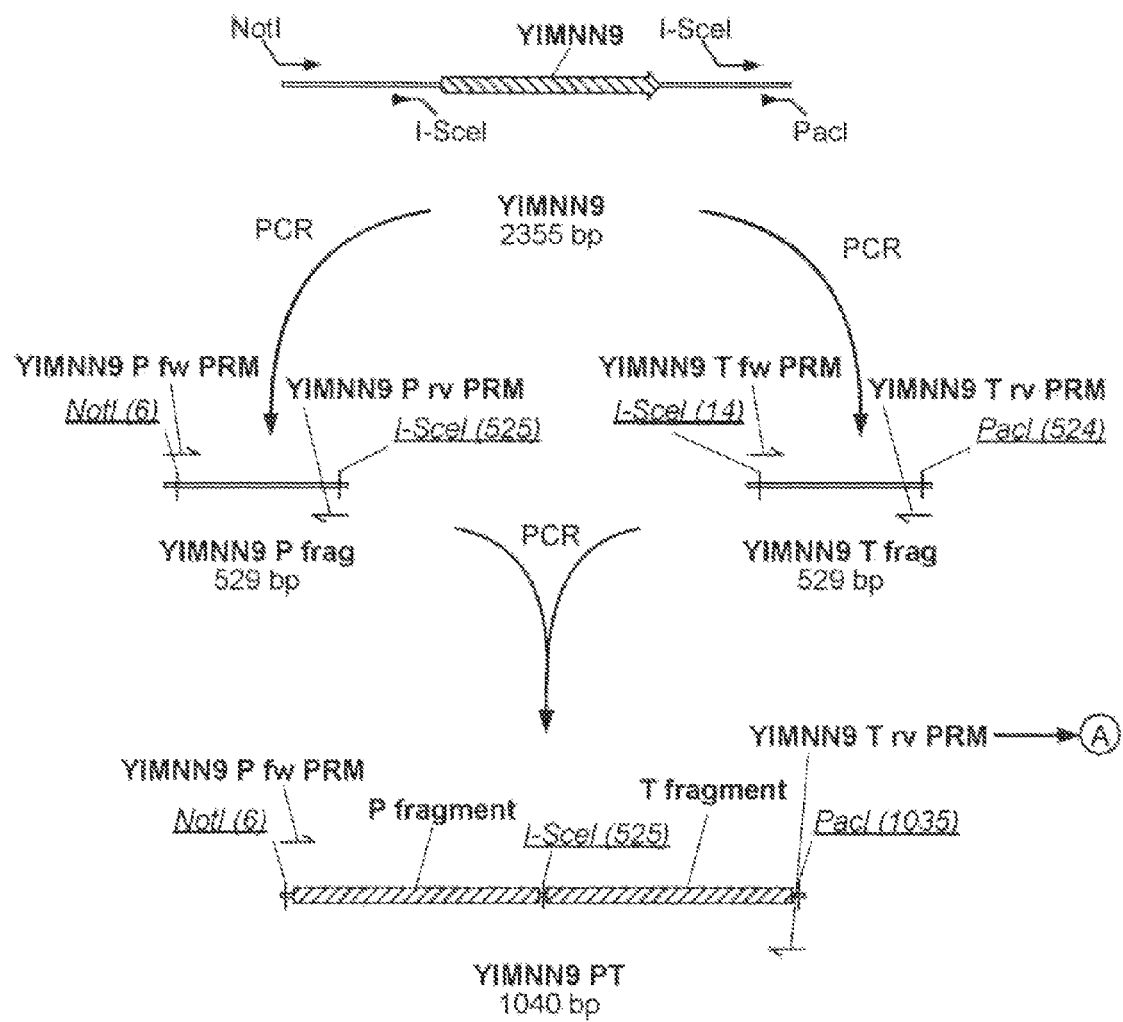
FIGS. 6A and 6B are schematic diagrams depicting the cloning strategy for MNN9 gene disruption fragment. "PCR" refers to polymerase chain reaction.
Figure 6B:
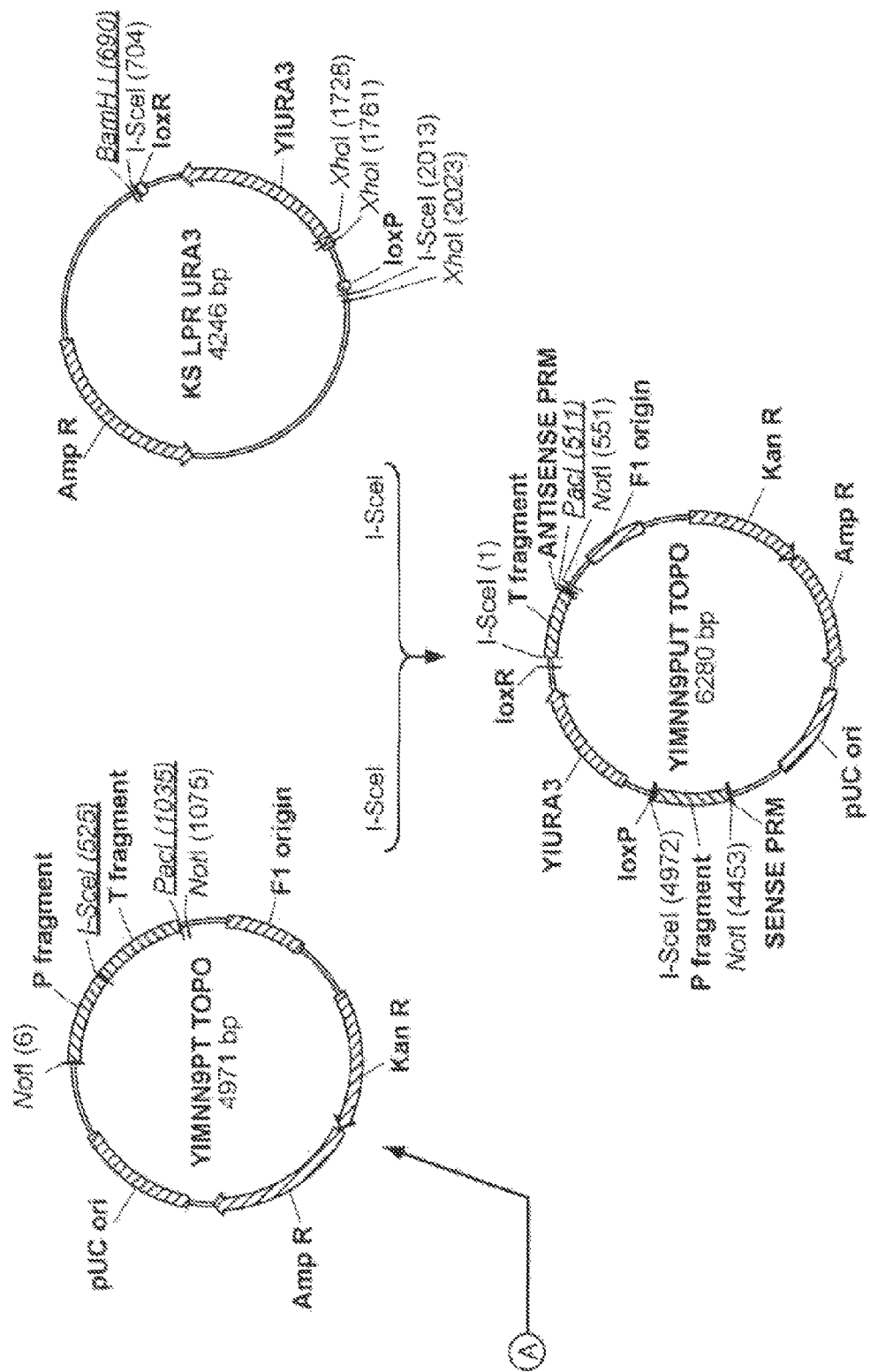

A construction strategy to inactivate MNN9 was set up and is depicted in FIGS. 6A and 6B.

The disruption fragment was cut out of plasmid YlMNN9PUT TOPO by a NotI/PacI double digest and transformed to MTLY60 and Δoch1 PT clone 9. Several URA3 positive clones were obtained for both strains and they were screened for correct integration of the construct by PCR on gDNA after single clones were isolated. A fragment of 2349 bp was amplified in the disruptant strains, whereas in the non-transformants, a fragment of 2056 bp was amplified using primers YlMNN9 P fw and YlMNN9 T rv. (Table 2).

Figure 7:
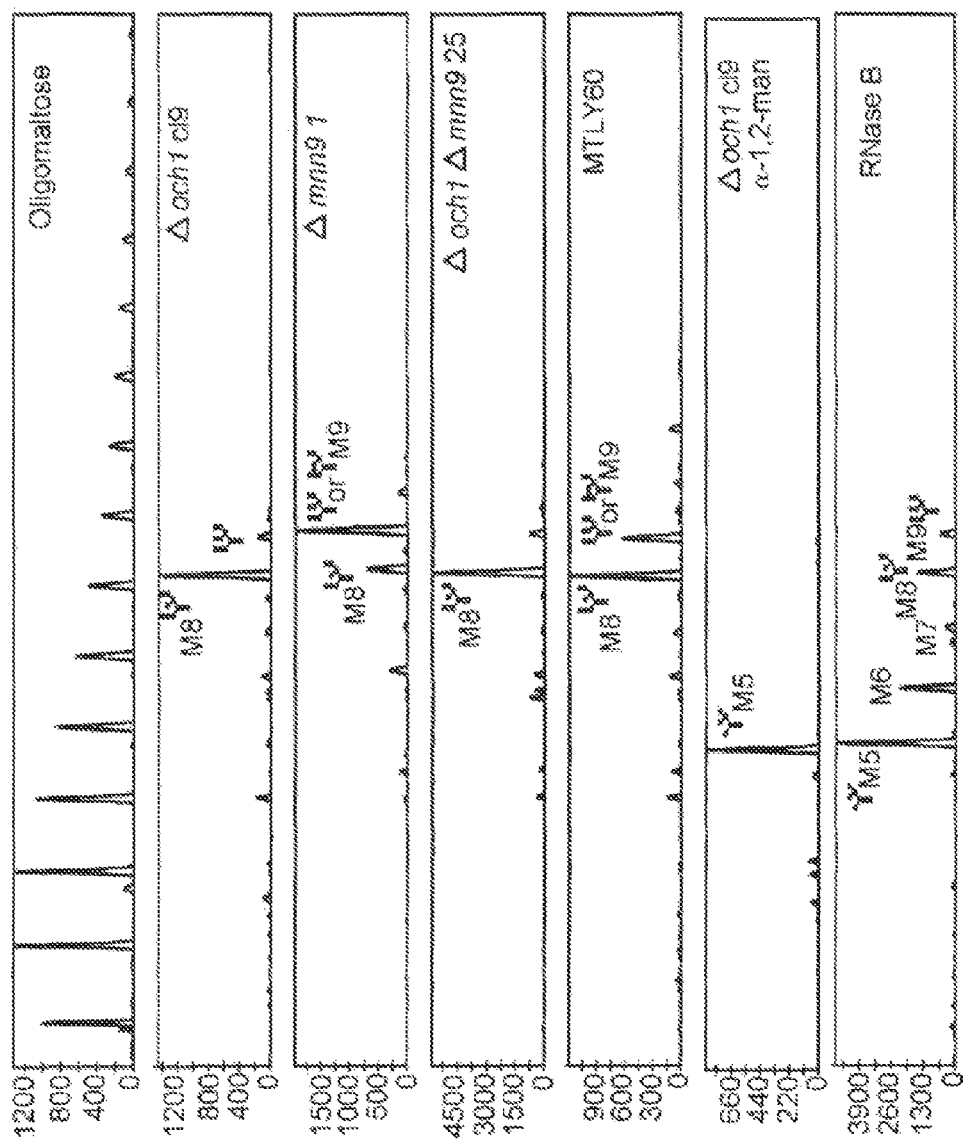
FIG. 7 is a series of electroferograms depicting N-glycan analysis of mannoproteins obtained from wild-type Yarrowia lipolytica cells or glycosylation mutant (e.g., Δoch1 cl9, Δmnn9 1 and Δoch1 Δmnn9) cells and MTLY60 strain cells. In some cases, the N-glycans were further treated with α-1,2 mannosidase. Analysis was performed using DNA sequencer-assisted, fluorophore-assisted carbohydrate electrophoresis (DSA-FACE). "M5," "M6," "M7," "M8," and "M9," refer to the number of mannose residues conjugated to the base N-acetylglucosamine structure. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.
Figure 8A:
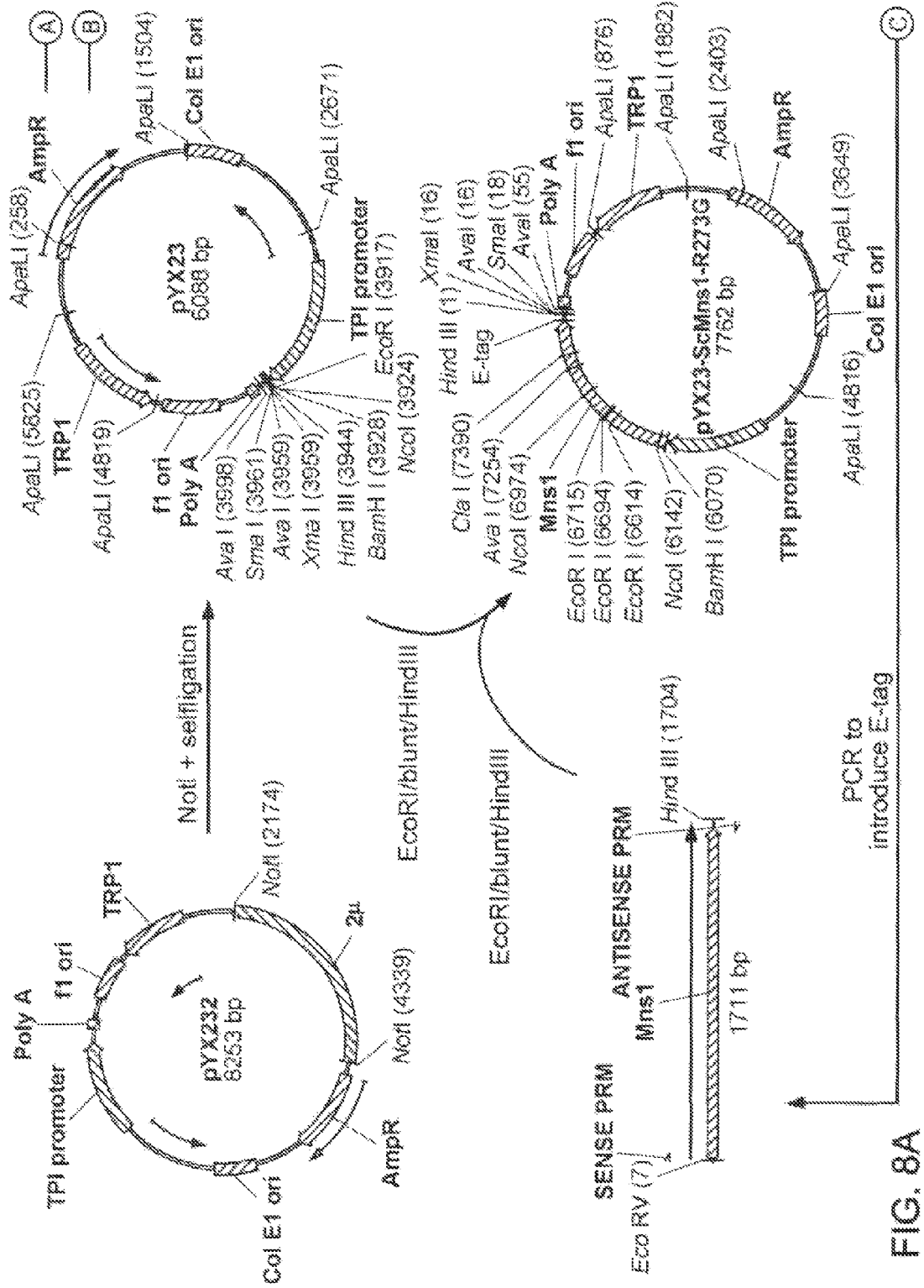
FIGS. 8A-8E are schematic diagrams depicting the cloning strategy for S. cerevisiae MNS1 expression vector. "PCR" refers to polymerase chain reaction.
Figure 8B:
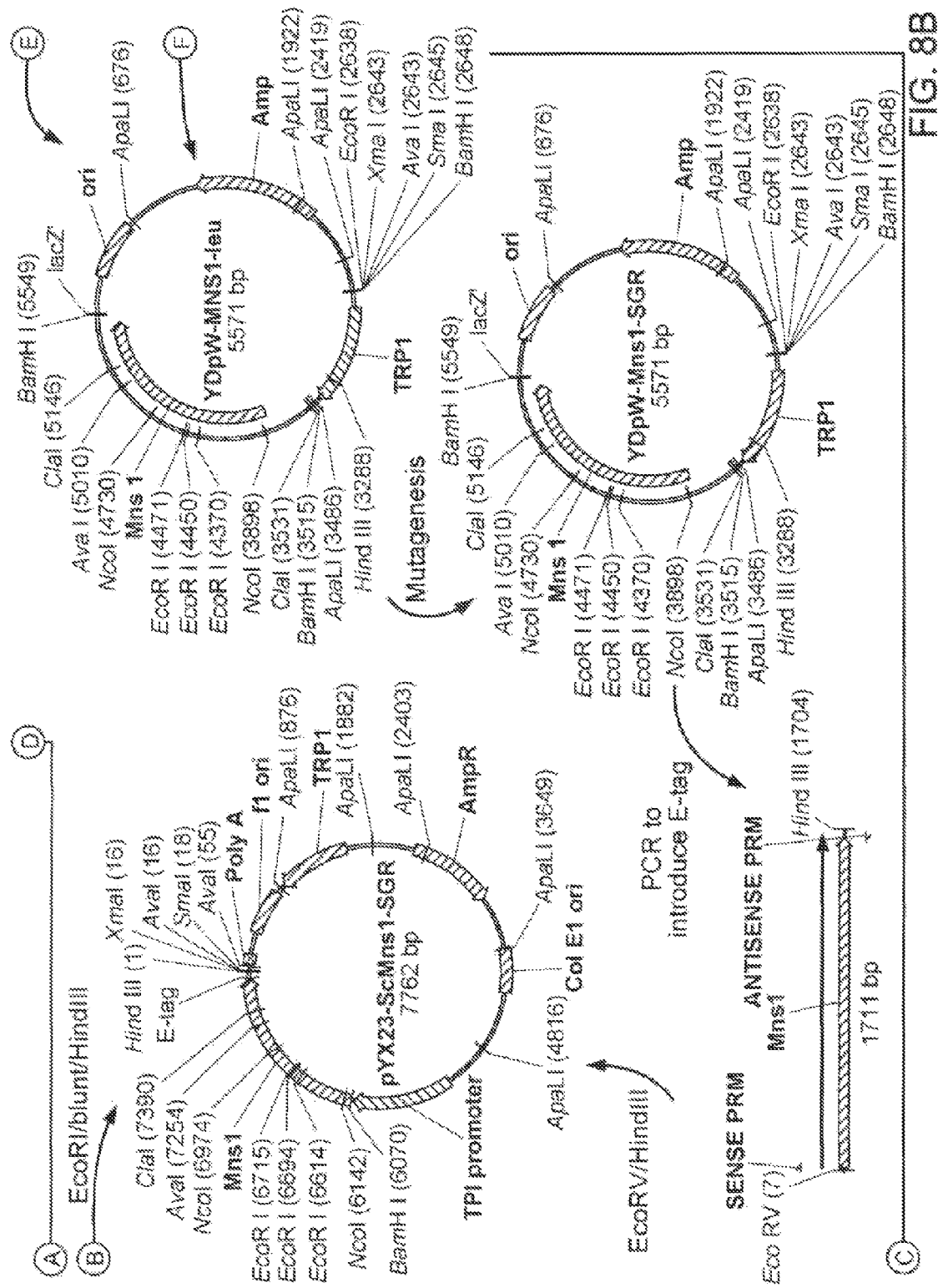
Figure 8C:
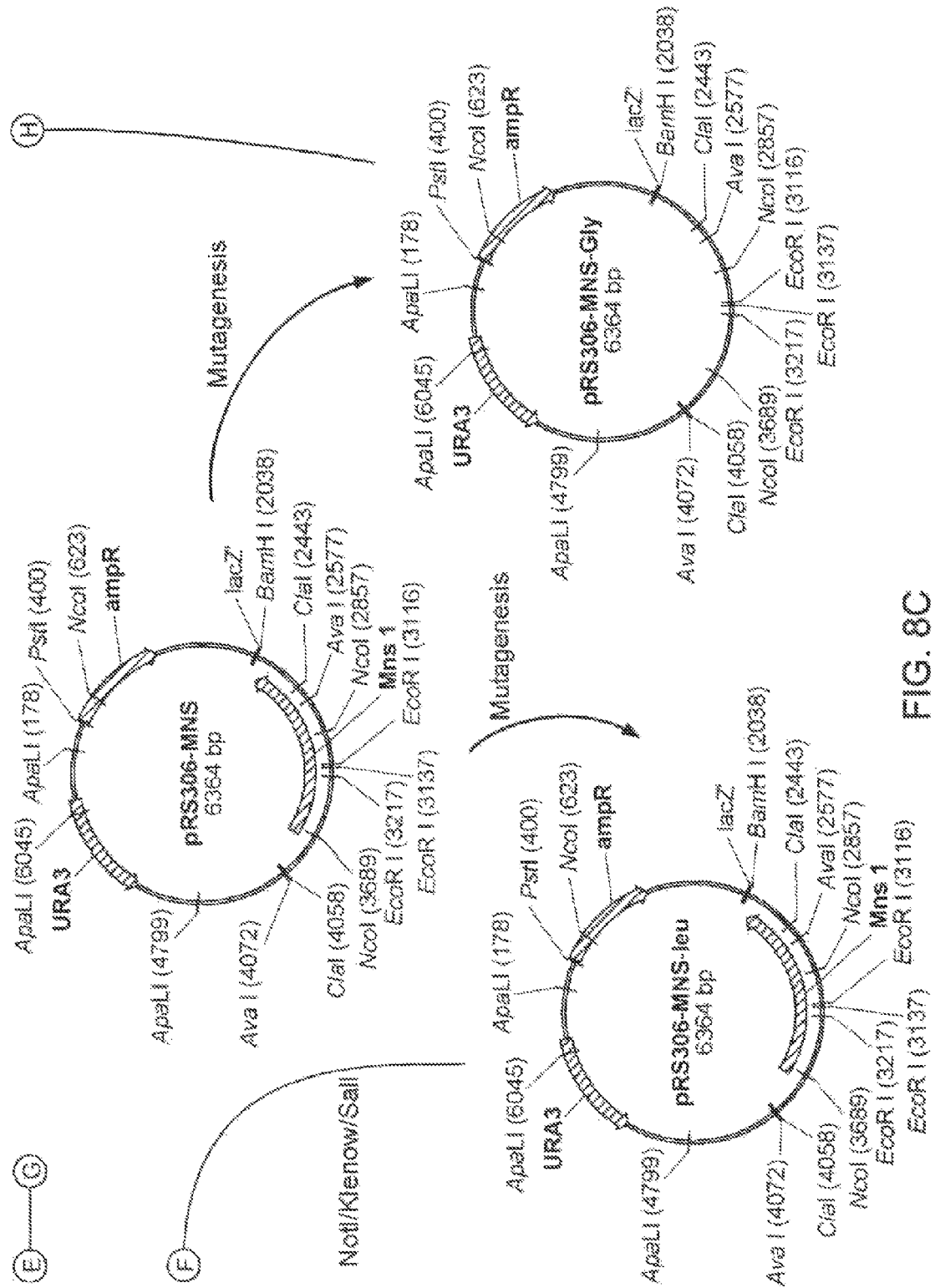
Figure 8D:
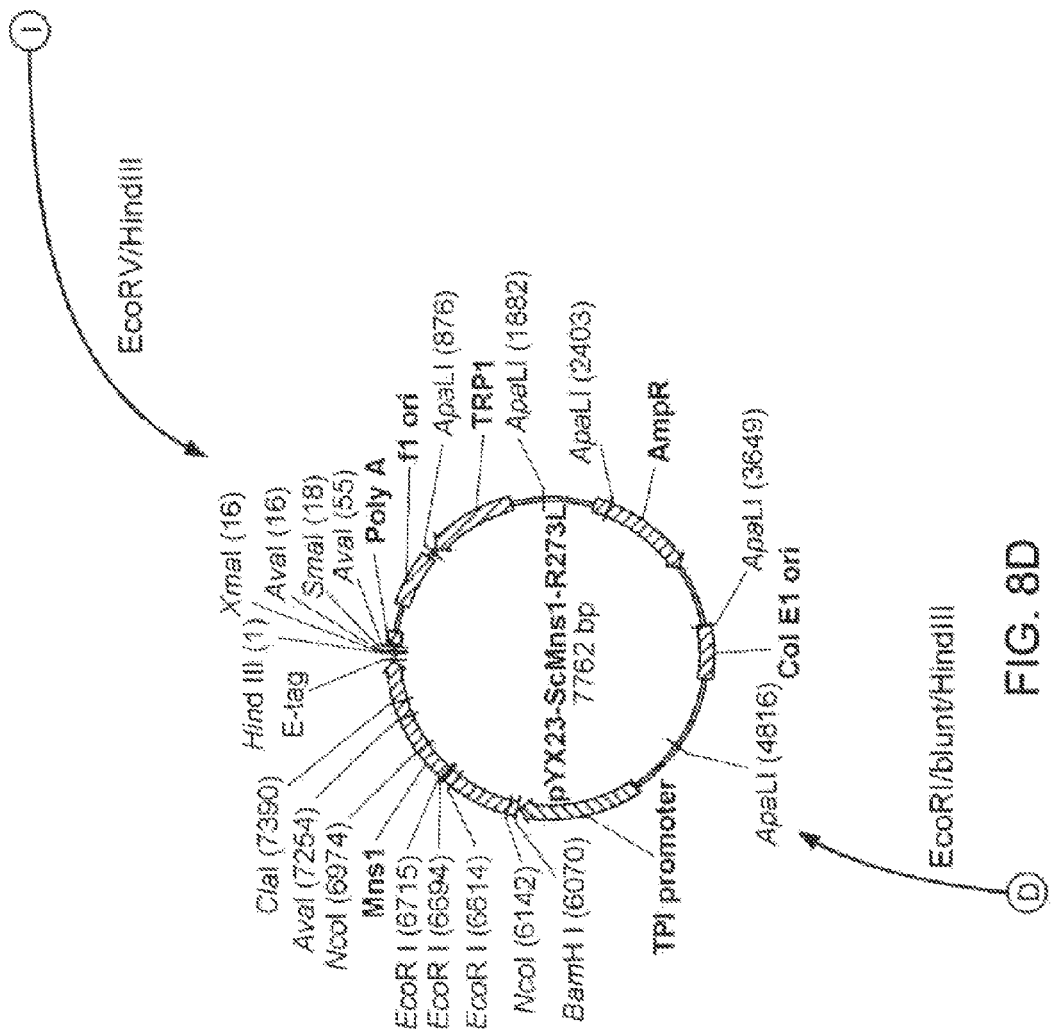
Figure 8E:
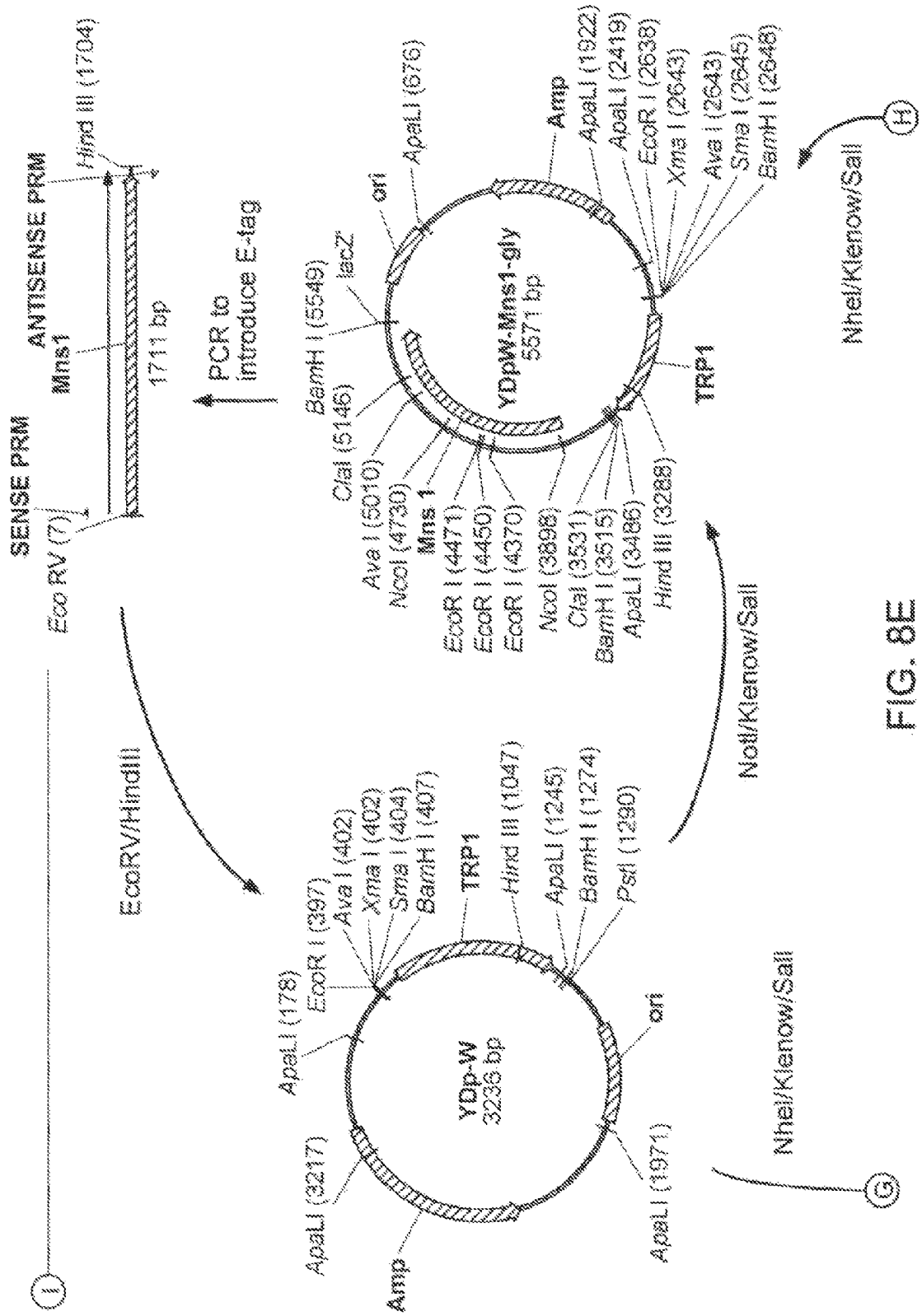

To analyze the N-glycan structures that were synthesized by the mutant strains, DSA-FACE was performed on glycans derived from mannoproteins (FIG. 7). The wild-type (MTLY60) strain has as main core type glycan structures mainly Man$_8$GlcNAc$_2$ (structural formula I; FIG. 4A) and a substantial amount of Man$_9$GlcNAc$_2$ (structural formula II; FIG. 4A) the latter most probably containing an additional mannose as a result of Och1p activity. Furthermore, some larger structures can be seen. The Δoch1 strain has mainly Man$_8$GlcNAc$_2$ (structure formula I) and a small portion of Man$_9$GlcNAc$_2$ (structural formula II; FIG. 4A), both of which are sensitive to α-1,2-mannosidase treatment (indicated Δoch1 α-1,2-man) resulting in trimming to Man$_5$GlcNAc$_2$ (structural formula IV; FIG. 4A). The Δmnn9 strain accumulates more Man$_9$GlcNAc$_2$ (structural formula II; FIG. 4A) than the Δoch1 strain, which indicates that Mnn9p is involved in the elongation of the glycan structure subsequent to Och1p activity. The double mutant Δoch1 Δmnn9 displays a glycosylation phenotype that resembles the one from the Δoch1 strain.

Example 3

Mutagenesis of MNS1

Figure 2:
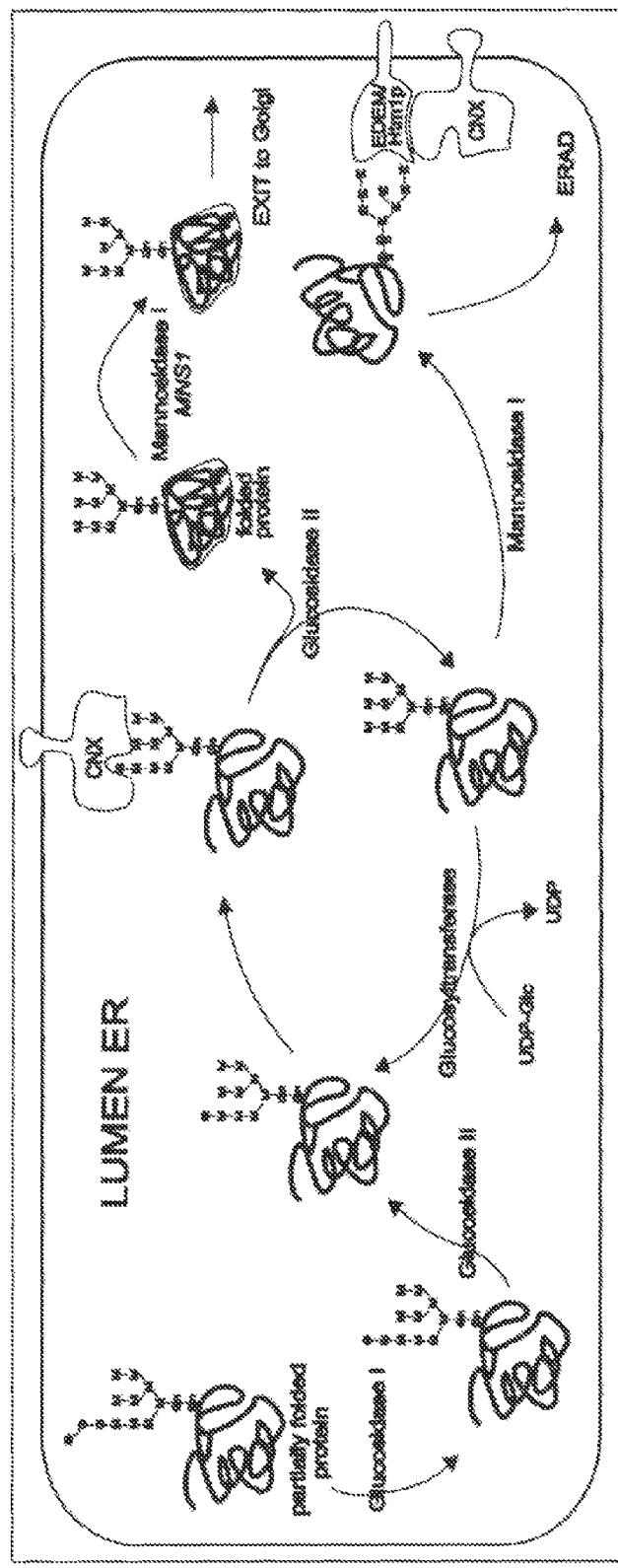
FIG. 2 is a schematic diagram depicting N-glycan processing in the yeast endoplasmic reticulum.
Figure 3:
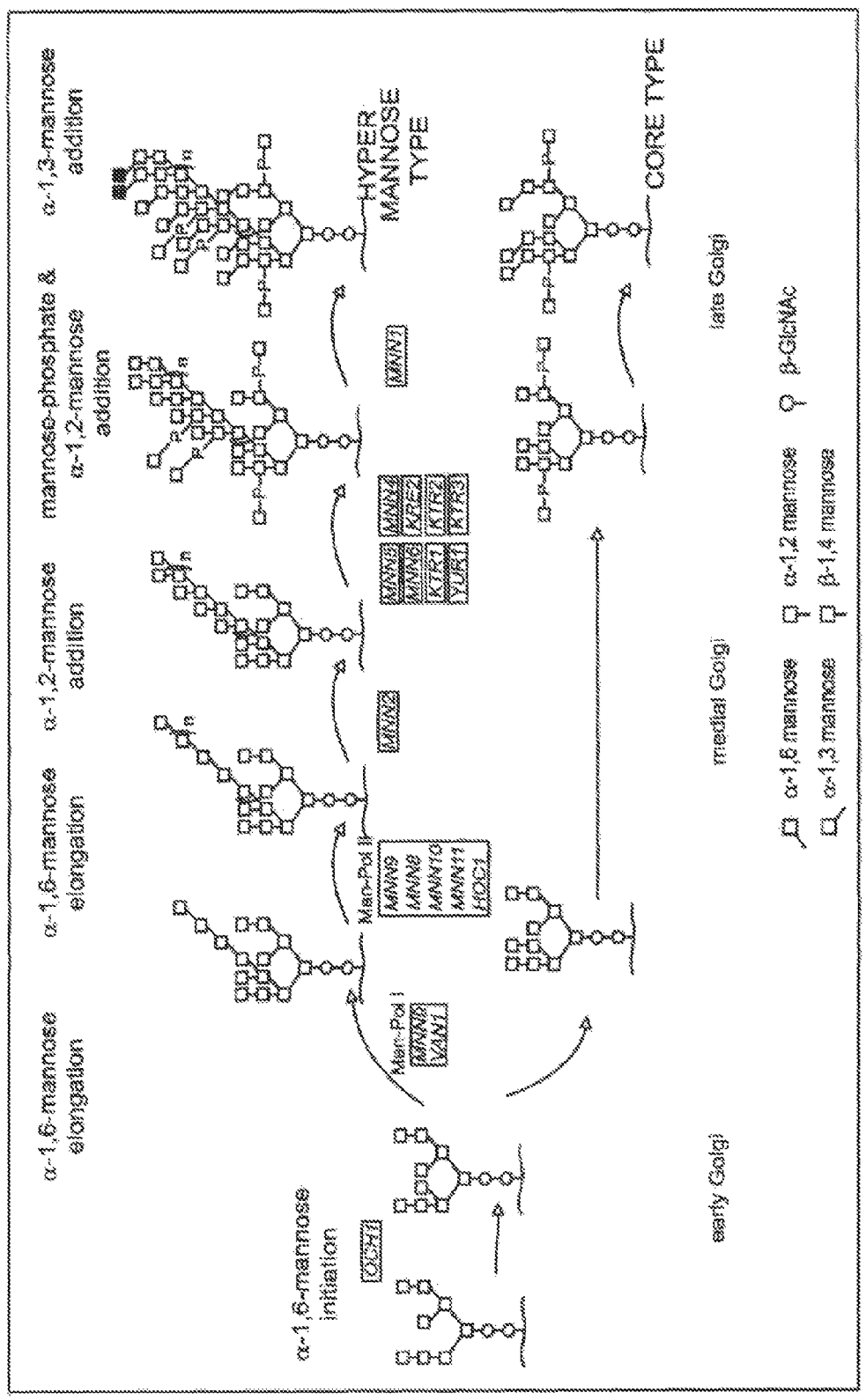
FIG. 3 is a schematic diagram depicting N-glycan processing in the S. cerevisiae Golgi apparatus. Genes whose encoded protein has an activity mediating the indicated enzymatic conversions are in shaded boxes (e.g., OCH1; middle left).

MNS1 (ER α-1,2-mannosidase) is involved in the trimming of the Man$_9$GlcNAc$_2$ to Man$_8$GlcNAc$_2$ and has a strict substrate specificity in the sense that it is only able to trim the α-1,2-mannose that is linked to the α-1,3-mannose of the central arm (FIG. 2). To determine where the MNS1 gene could be mutagenized in order to shift its substrate specificity towards a Golgi type α-1,2-mannosidase, the primary sequences of several ER type mannosidases were compared with Golgi type mannosidases. One region that is different between the two classes was identified. In addition, an oligosaccharide that was crystallised in the catalytic site of the Golgi type mannosidase into the yeast MNS1 was also analyzed to identify possible interactions between sugar and protein. Surprisingly, the same sites were identified using both methods.

The MNS1 gene from *Saccharomyces cerevisiae* (GenBank® Accession No: Z49631, sgd: YJR131W) was mutated in order to change its substrate specificity. Three mutated versions were made: two with one mutation (R273L and R273G) and one with 3 mutations (R269S/S272G/R273L) in the same region:
A) R273L (arginine 273 to leucine)
B) R273G (arginine 273 to glycine)
C) R269S/S272G/R273L (arginine 269 to serine/serine 272 to glycine/arginine 273 to leucine).
All mutations were made using the Quick Change (Stratagene) mutagenesis kit.
Constructs were made to express the 3 different mutant genes under control of the strong constitutive TPI1 promoter. Oligonucleotides CGACTATCCGGTTCGGATCATTGGGT-GATTCTTTTTATGAG (SEQ ID NO:40) and CTCAT-AAAAAGAATCACCCAATGATCCGAACCGGATAGTCG (SEQ ID NO:41) were used to generate mutant R273L, and oligonucleotides CGACTATCCGGTTCGGATCAGGTG-GTGATTCTTTTTATGAG (SEQ ID NO:42) and CTCAT-AAAAAGAATCACCACCTGATCCGAACCG-GATAGTCG (SEQ ID NO:43) were used to obtain mutant R273G using the wild type gene as a template. Oligonucleotides GGTGCTTCGACTATCAGTTTCGGAGGAT-TGGGTGATTCTTTTTATG (SEQ ID NO:44) and CAT-AAAAAGAATCACCCAATCCTCCGAAACTGATAGTC GAAGCACC (SEQ ID NO:45) were used to obtain mutant R269S/S272G/R273L using mutant R273L as template DNA. Via PCR reaction using oligonucleotides CCCGATATCGGATCCATGAAGAACTCT-GTCGGTATTTC (SEQ ID NO:46) and GGGAAGCT-TAACGCGGTTCCAGCGGCGGGTCCGGATACG-GCACCGGCGCACCCAACGAC CAACCTGTGGTCAG (SEQ ID NO:47) the coding sequence of an E-tag was added at the 3' end of the mutant and the wild type MNS1 open reading frames to allow protein detection after expression. An overview of the construction strategy is presented in FIGS. 8A-8E.

The three constructs, as well as the non-mutated gene (as a negative control), were transformed to *S. cerevisiae* strain XW27 (MATα leu2 ura3 trp1 his3 ade2 lys2 och1::LEU2 mnn1::URA3 mnn6::ADE2) using TRP1 as a selection marker after digestion of the plasmids with XbaI to direct the construct to the TRP1 locus in the *S. cerevisiae* genome. The latter strain is able to synthesize uniform Man$_8$GlcNAc$_2$ (on its glycoproteins. If the mutated enzyme is active this Man$_8$GlcNAc$_2$ (structural formula I; FIG. 4A) should be trimmed to Man$_5$GlcNAc$_2$ (structural formula IV; FIG. 4A), Man$_6$GlcNAc$_2$ (structural formula V; FIG. 4A) and/or Man$_7$GlcNAc$_2$ (structural formula VI; FIG. 4A).

Figure 9:
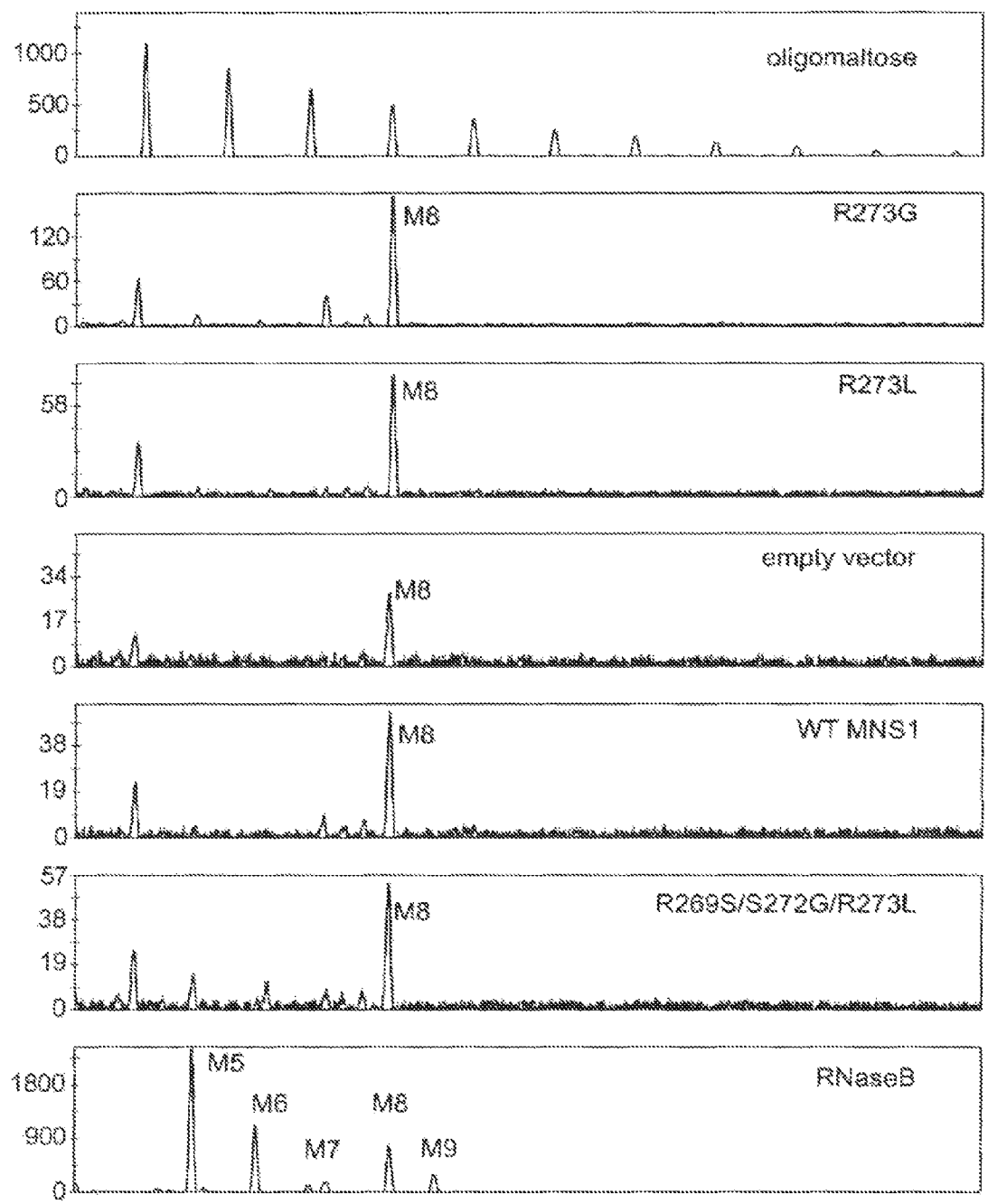
FIG. 9 is a series of electroferograms depicting N-glycan analysis of secreted glycoproteins obtained from MTLY60 cells expressing wild-type (WT) Mns1p or various mutant forms (i.e., R273G, R273L, or R269S/S272G/R273L) of Mns1p as indicated. Analysis was performed using DSA-FACE. "M5," "M6," "M7," "M8," "M9," refers to the number of mannose residues conjugated to the base N-acetylglucosamine structure. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.

Tryptophan prototrophic strains were isolated, grown in liquid SDC-trp medium and mannoproteins were prepared. N-glycans derived from mannoproteins were analysed via DSA-FACE. As can be appreciated from FIG. 9, a small amount of Man$_8$GlcNAc$_2$ (structural formula I; FIG. 4) from the strains that contain the R273G and R269S/S272G/R273L mutations are converted to Man$_5$GlcNAc$_2$ (structural formula IV; FIG. 4A), Man$_6$GlcNAc$_2$ (structural formula V; FIG. 4A) and Man$_7$GlcNAc$_2$ (structural formula VI; FIG. 4A). The expression of the other mutant or the wild type gene cause an altered N-glycosylation phenotype. To evaluate whether all mutants are equally well expressed, a Western blot analysis was performed using an antibody specific for an E-tag (a 13 amino acid epitope added to the MNS1 proteins). All mutant proteins, as well as the wild-type MNS1 protein, were expressed equally well.

Example 4

Increasing Phosphorylation

Expression of *Yarrowia lipolytica* MNN4

To increase the phosphorylation of Man$_8$GlcNAc$_2$, *Yarrowia liplytica* MNN4 (a homologue of the *P. pastoris* PNO1) was overexpressed in *Yarrowia lipolytica* to promote the core type phosphorylation of N-glycans.

Figure 10:
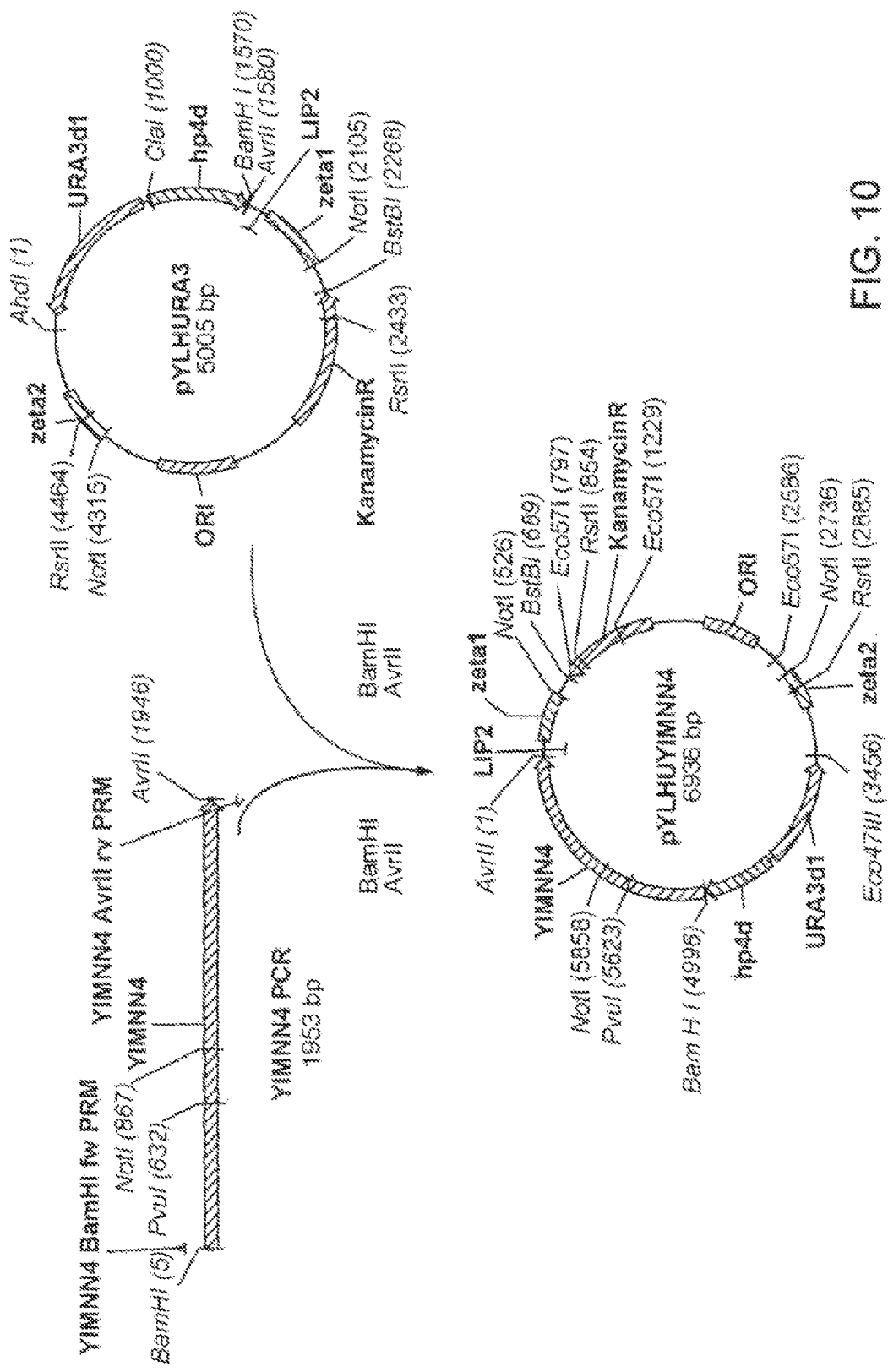
FIG. 10 is a schematic diagram depicting the cloning strategy for an MNN4 expression vector.

The coding sequence of the *Yarrowia lipolytica* MNN4 (XM_503217, YALI0D24101g) gene was amplified using primers GGCGGATCCATGGTGCTGCACCCGTTTC (YlMNN4 BamHI fw; SEQ ID NO:34) and GGCCCTAG-GCTACTCAAACTCCTCGCGAATC (YlMNN4 AvrII rv; SEQ ID NO:35). This open reading frame (ORF) was cloned into the plasmid using BamHI and AvrII sites, which placed the ORF under control of the hp4d promoter of plasmid pYlHURA3 that contains the URA3d1 gene as a selection marker and the zeta sequences for improving random integration (FIG. 10).

Prior to transformation in the MTLY60 Δoch1 strain, the plasmid containing the MNN4 expression cassette was digested either with Eco47III for integration in the URA3 locus, PvuI for integration in the MNN4 locus, or RsrII/BstBI for random integration. Transformants targeted to the URA3 and MNN4 locus were analysed by PCR using a primer in the hp4d promoter and one in the LIP2 terminator. Transformants with random integration of the construct were evaluated by Southern blot analysis.

Figure 11:
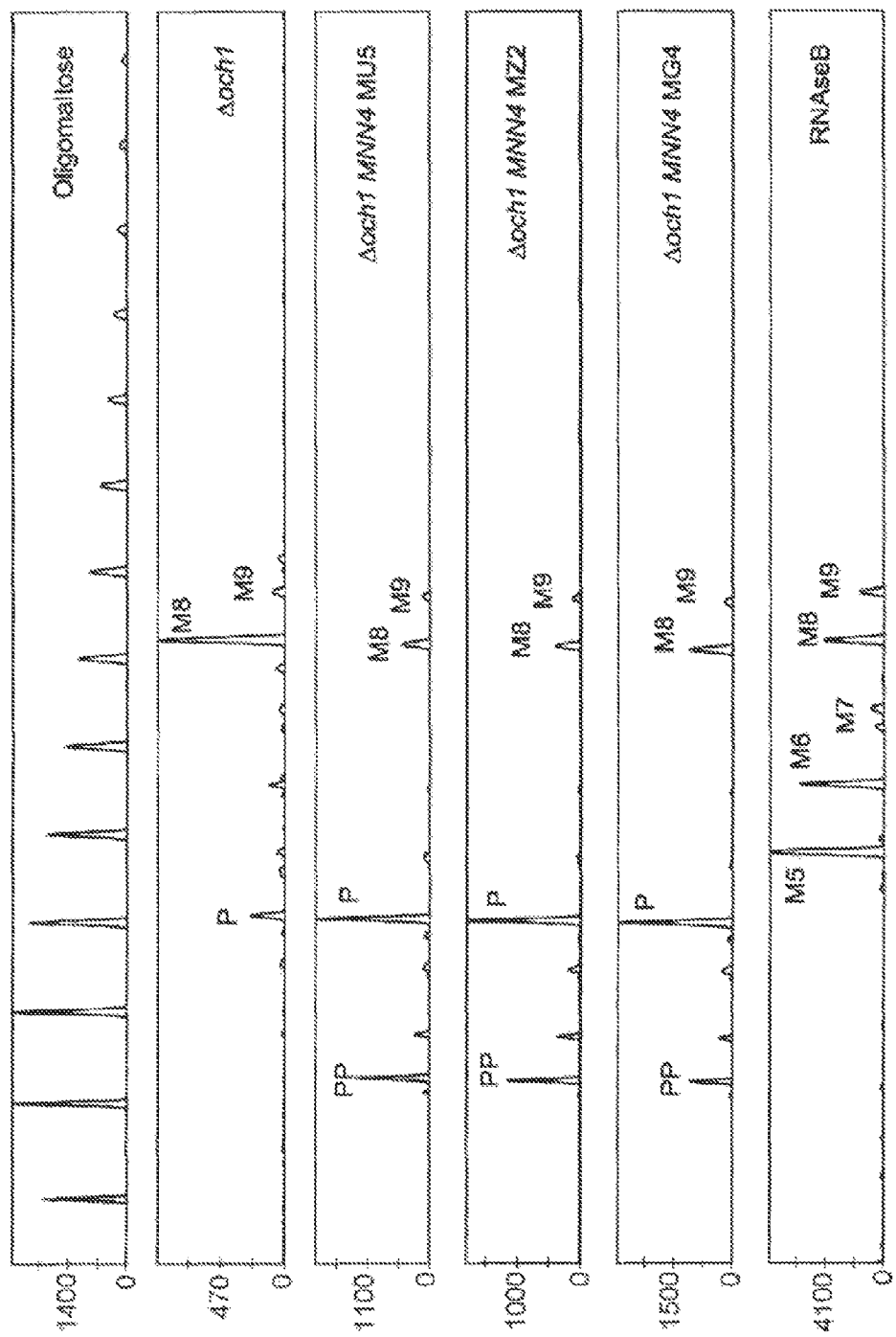
FIG. 11 is a series of electroferograms depicting N-glycan analysis of secreted glycoproteins obtained from wild-type MTLY60 cells or glycosylation mutant cells as indicated. Analysis was performed using DSA-FACE. "M5," "M6," "M7," "M8," "M9," refers to the number of mannose residues conjugated to the chitobiose core structure. "P" refers to mannoproteins containing one phosphate residue and "PP" refers to mannoproteins containing two phosphate residues. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.
Figure 12A:
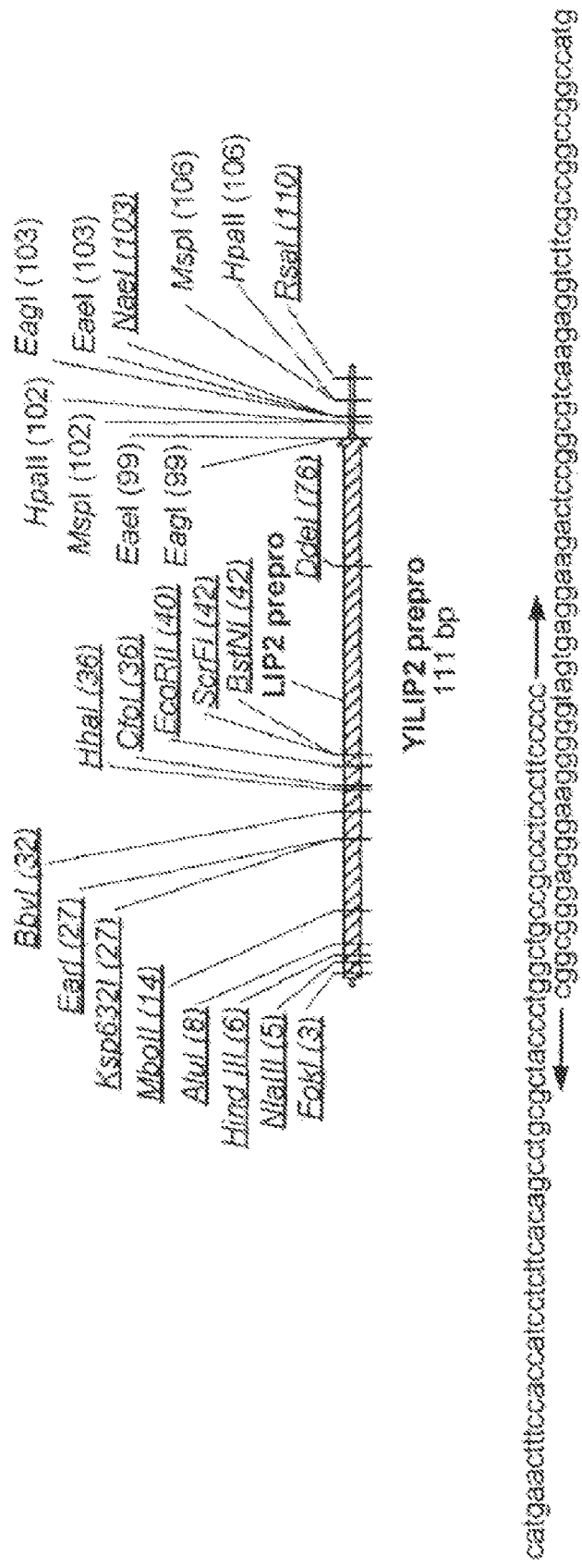
Figure 12B:
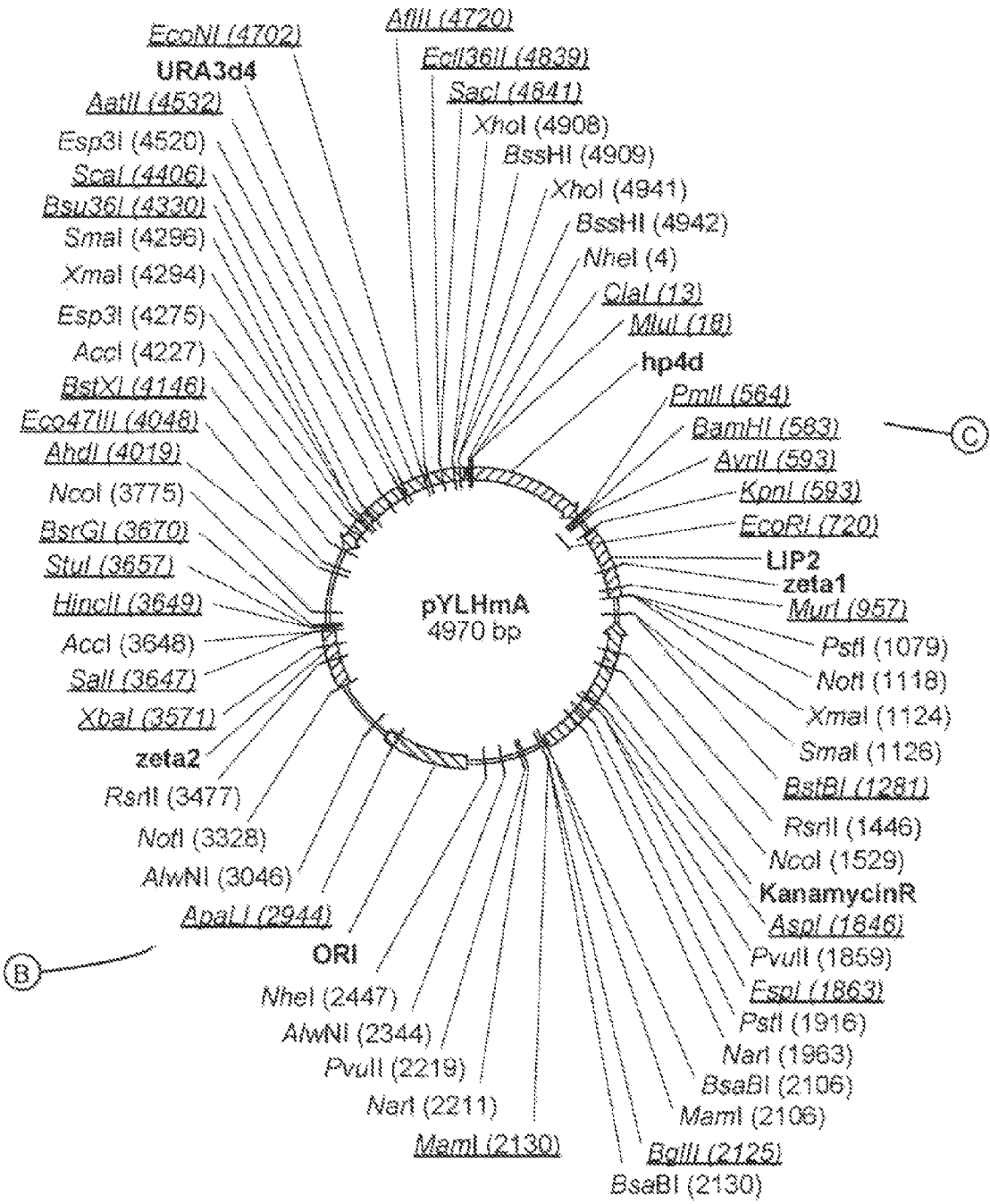
Figure 12C:
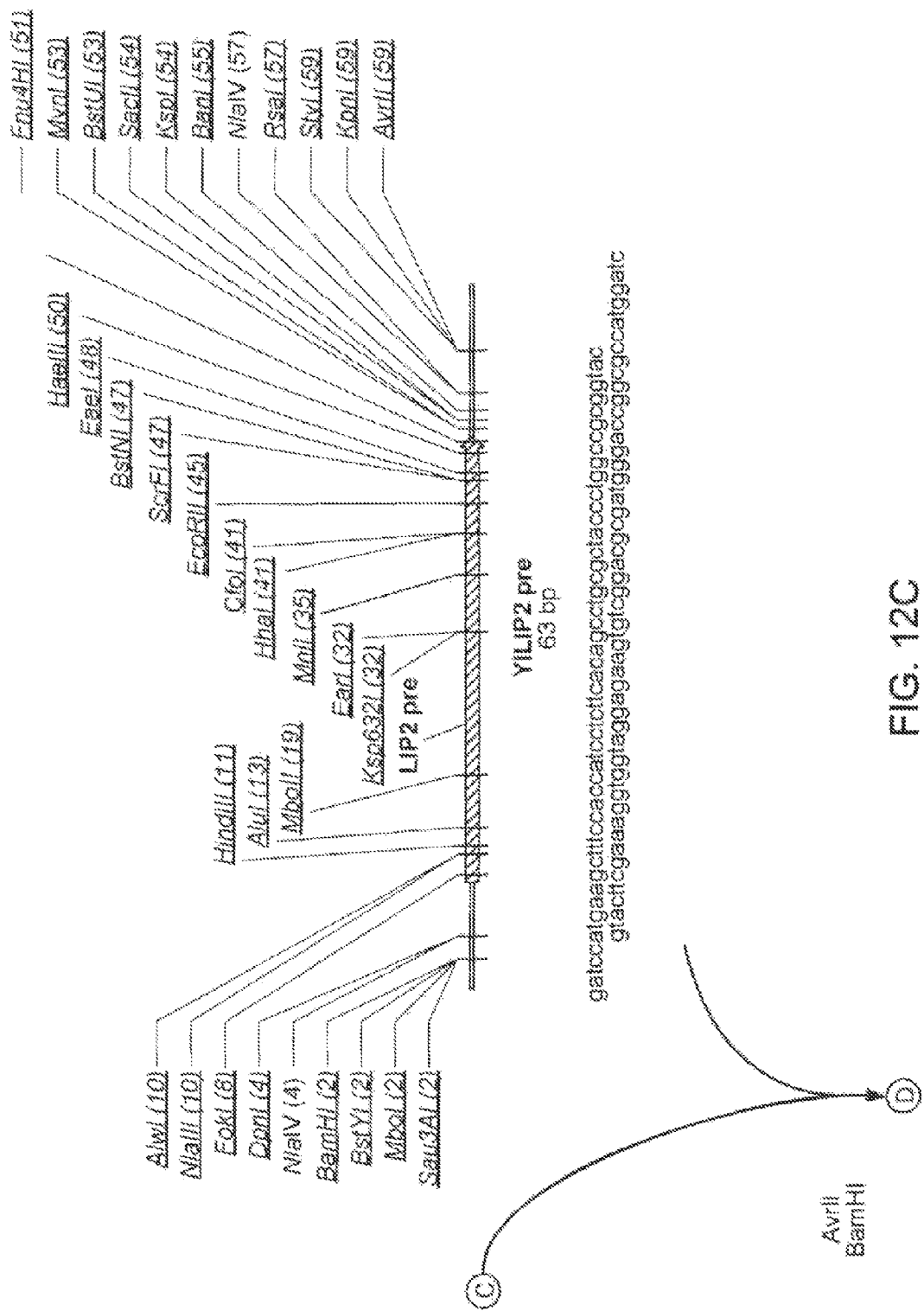
Figure 12D:
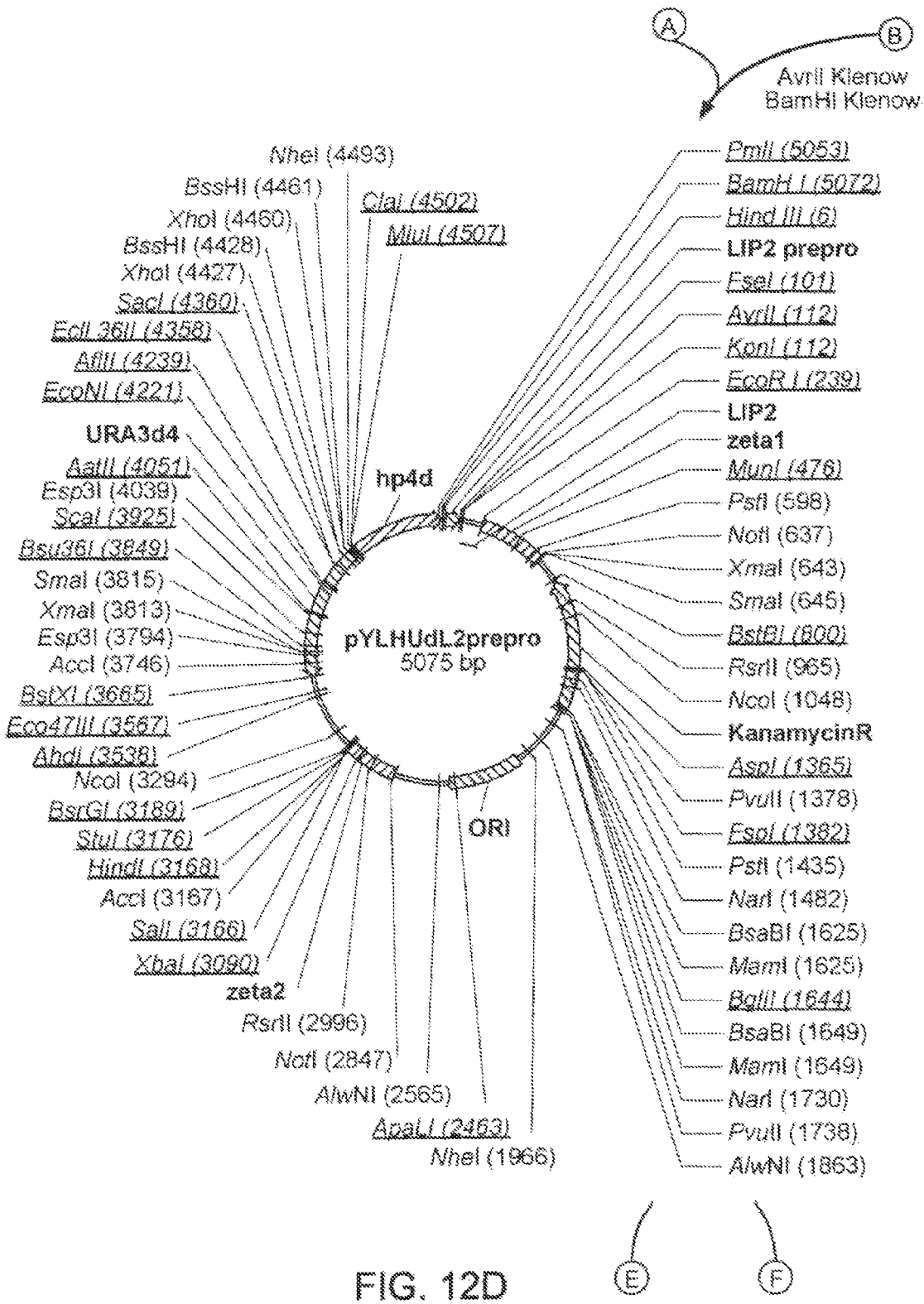
Figure 12E:
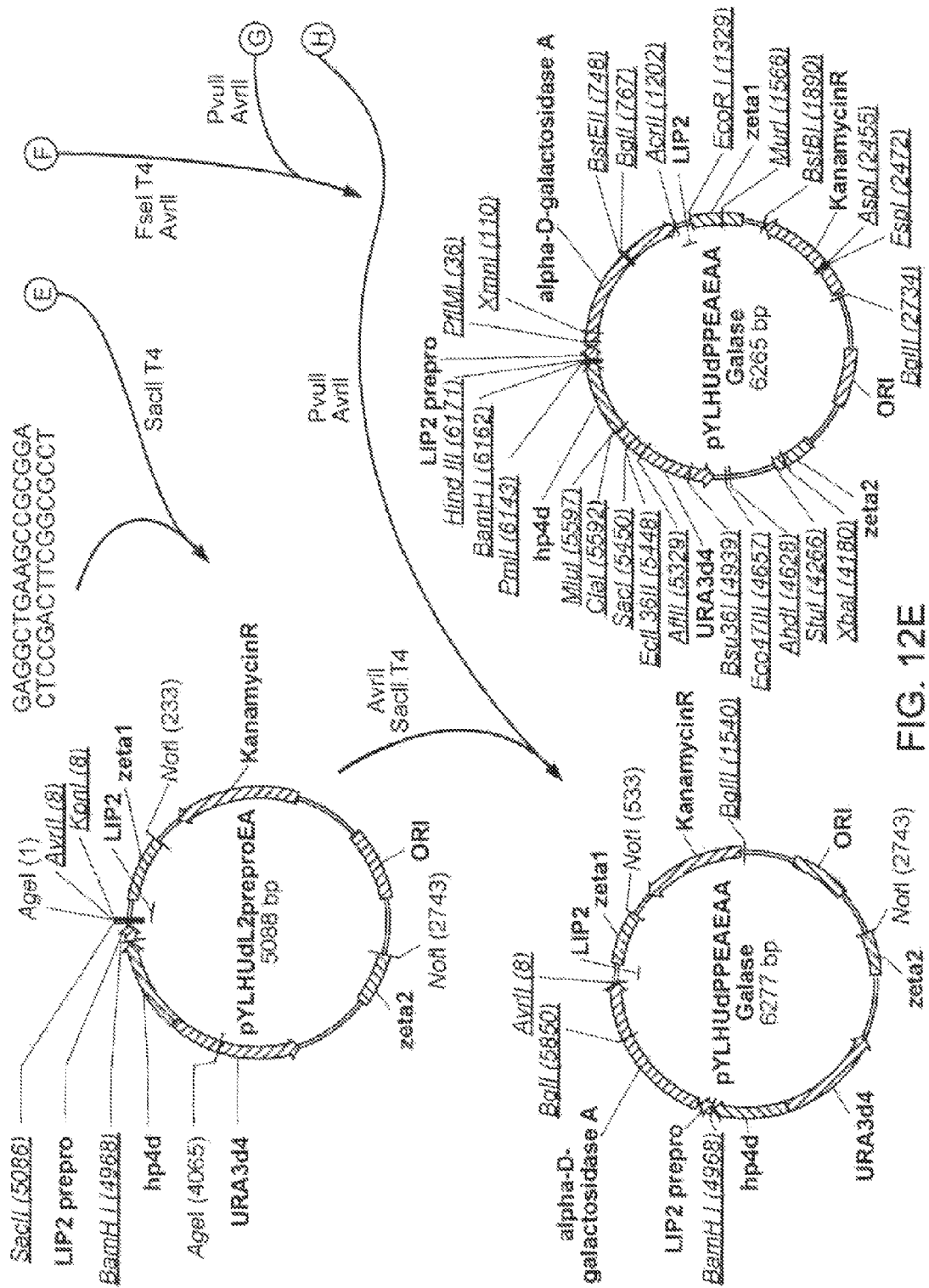
Figure 12G:
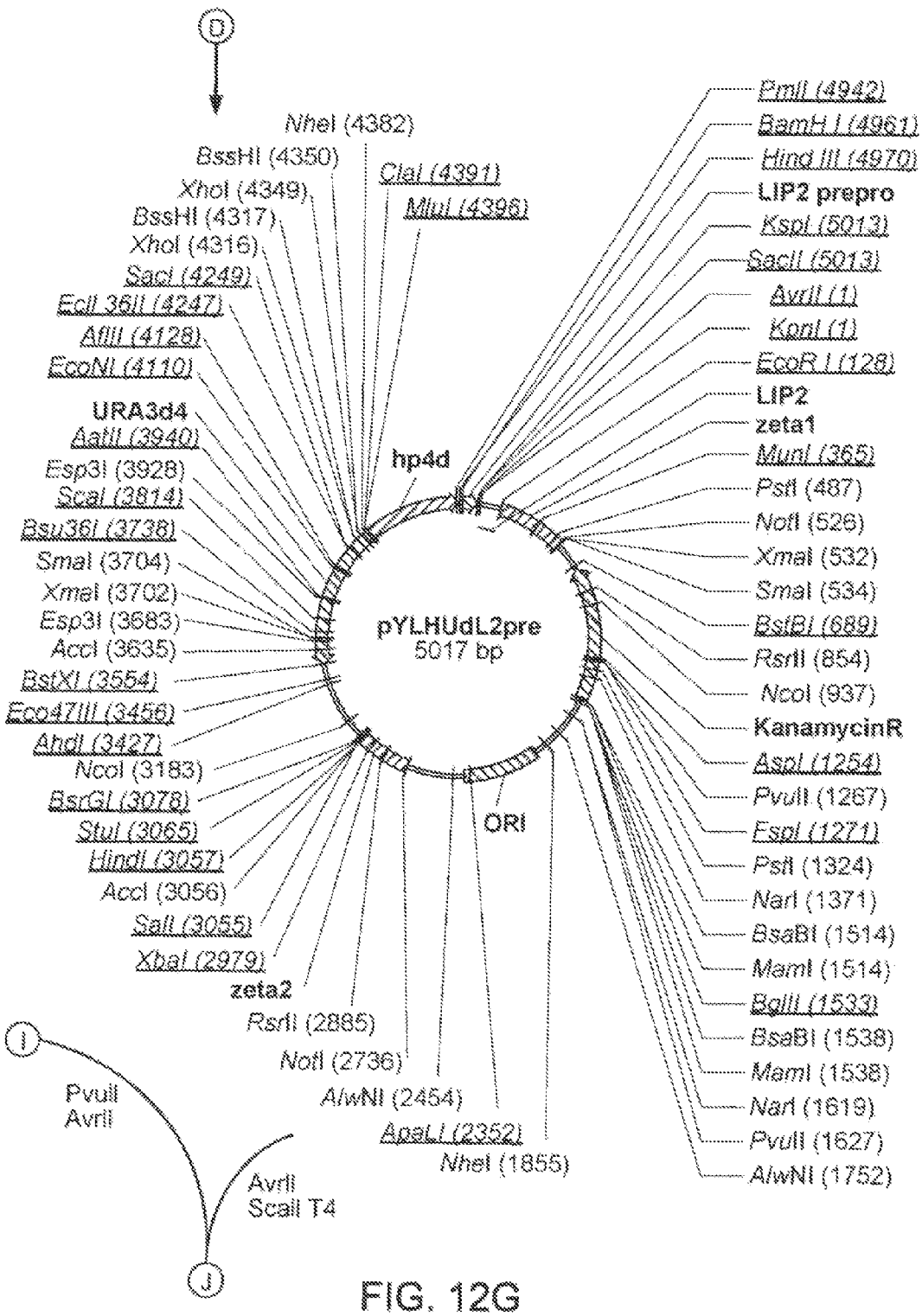
Figure 12H:
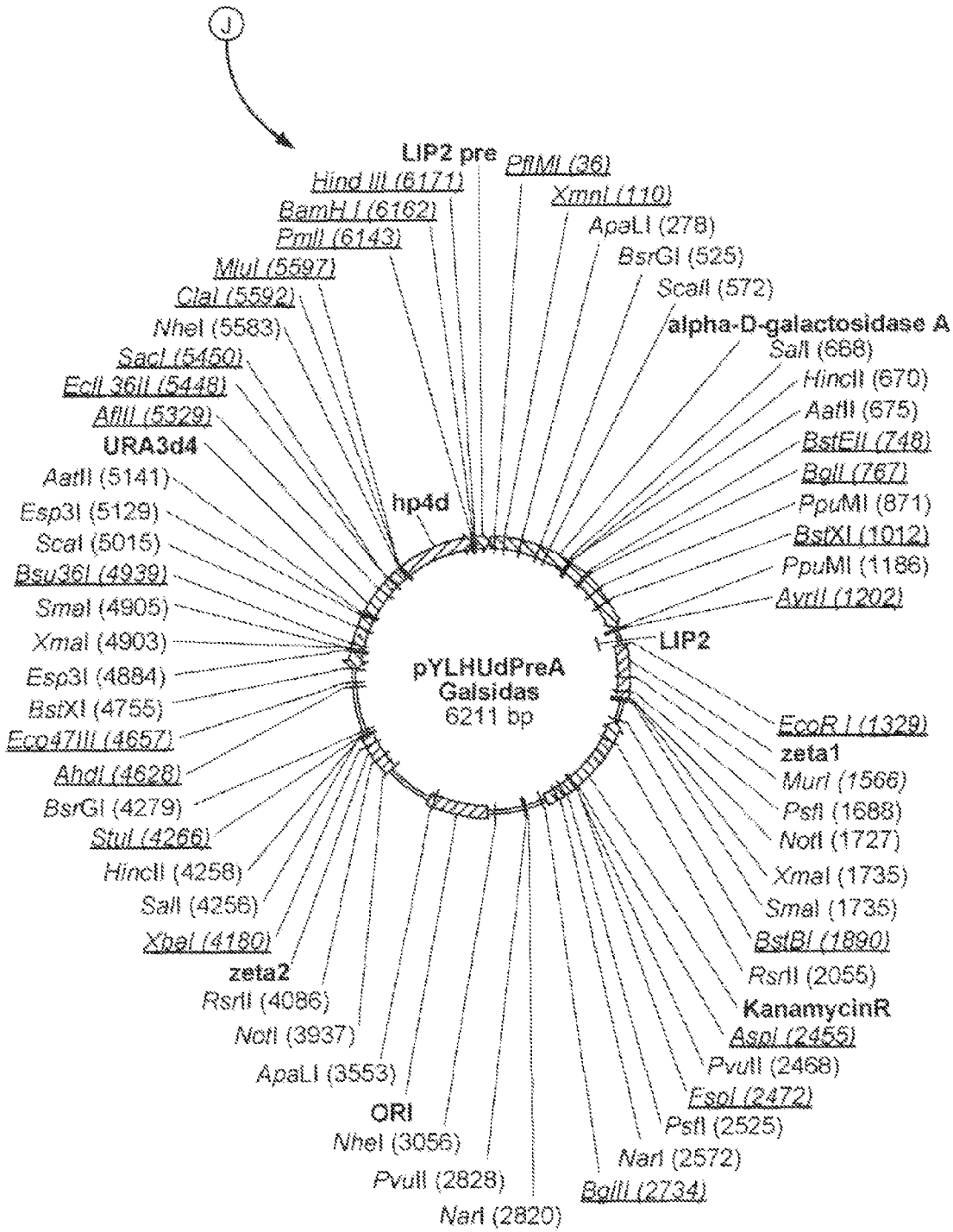

To evaluate whether manno-phosphorylation was increased we analysed N-glycans derived from secreted glycoproteins after 48 hours culture in YPD medium by DSA-FACE capillary electrophoresis (FIG. 11). The amount of $Man_8GlcNAc_2$ (structural formula I) was drastically reduced in favour of two structures that migrate faster (compared to $Man_8GlcNAc_2$ (structural formula I; FIG. 4A)) and that are likely to contain one (P) (structural formula X or XI; FIG. 4B) and two (PP) (structural formula XII; FIG. 4B) phosphate residues, respectively (FIG. 11). Thus, it can be concluded that the random integrated expression cassettes perform better than the cassettes integrated in the URA3 locus or the MNN4 locus, in that order. The MZ2 exhibited the highest level of phosphorylation.

Assuming that both peaks derive from the $Man_8GlcNAc_2$ (structural formula I; FIG. 4A) peak, the amount of $Man_8GlcNAc_2$ converted to phosphorylated glycans was quantitated (Table 3).

TABLE 3

| N-glycan struct. | height | area | % signal | Phosph-Status |
|---|---|---|---|---|
| Strain Δoch1 | | | | |
| M82P (struct. form. XII) | 18 | 302 | 1.02826 | 18.91045* |
| M8P (struct. form. X or XI) | 261 | 5252 | 17.88219 | |
| M8 (struct. form. I) | 928 | 23816 | 81.08955 | 81.08955* |
| | | 29370 | 100 | 100 |
| Strain MU5 | | | | |
| M82P (struct. form. XII) | 1319 | 19736 | 27.16773 | 81.17283* |
| M8P (struct. form. X or XI) | 2025 | 39232 | 54.00509 | |
| M8 (struct. form. I) | 539 | 13677 | 18.82717 | 18.82717* |
| | | 72645 | 100 | 100 |
| Strain MZ2 | | | | |
| M82P (struct. form. XII) | 1182 | 17662 | 27.75299 | 83.11282* |
| M8P (struct. form. X or XI) | 1803 | 35231 | 55.35984 | |
| M8 (struct. form. I) | 419 | 10747 | 16.88718 | 16.88718* |
| | | 63640 | 100 | 100 |

Table 3 Legend:
Height and area refer to the peak height and peak area as determined from electropherograms. "% signal" refers to the proportion of each glycan in the N-glycan mixture. The numbers identified by asterisk depict the proportion of phosphorylated $Man_8Gn_2$ (top) and the proportion of non-phosphorylated $Man_8Gn_2$ (bottom).

These results indicated that more than 80% of $Man_8GlcNAc_2$ (structural formula I; FIG. 4A) that is present in the parent Δoch1 is phosphorylated in the strain that over expresses the YlMNN4 gene.

Example 5

Modifying Glycosylation by Lipid-linked Oligosaccharide Modification in the Endoplasmic Reticulum Materials and Methods Strains, culture conditions and reagents. *Escherichia coli* strains MC1061 or TOP10 or DH5α were used for the amplification of recombinant plasmid DNA and grown in a thermal shaker at 37° C. in Luria-Broth (LB) medium supplemented with 100 μg/ml of carbenicillin or 50 μg/ml of kanamycin depending on the plasmids used.

*Yarrowia lipolytica* MTLY60 (ura3 leu2) strain was used as parent strain. All yeast strains were cultured in a 28° C. incubator. They were grown on YPD medium (2% dextrose, 2% bacto-peptone and 1% yeast extract) or synthetic dextrose complete (SDC) medium (0.17% YNB w/o amino acids and without ammonium sulphate, 1% glucose, 0.5% $NH_4Cl$, 50 mM K/Na phosphate buffer pH 6.8 and 0.077% Complete Supplement Mixture (Qbiogene Inc, Morgan Irvine, Calif.)). For selection of Ura+ and Leu+ transformants 0.077% CSM-ura or CSM-leu was added respectively.

Standard genetic techniques. Transformation competent cells of *Yarrowia lipolytica* were prepared as described in Boisrame et al. (1996) J. Biol. Chem. 271(20):11668-75, the disclosure of which is incorporated herein by reference in its entirety. Genomic DNA from all yeast strains was isolated using a published protocol (Epicenter Kit catologue No. MPY80200; Epicenter Biotechnologies, Madison, Wis.). The protocol involves non-enzymatic cell lysis at 65° C., followed by removal of protein by precipitation and nucleic acid precipitation and resuspension. PCR amplification was performed in a final volume of 50 μl containing 5 μl of 10× buffer (200 mM Tris-HCl pH8.4 and 500 mM KCl), a variable quantity of $MgCl_2$, 2.5 μM dNTP, 50 ng of template, 50 pmol of the proper primers and 2.5 units of either Taq or Pfu DNA polymerase. Cycling conditions used were as follows: denaturation at 94° C. for 10 minutes followed by hot start and 30 cycles of 94° C. for 45 seconds, suitable annealing temperature for 45 seconds and extension at 72° C. for 1 minute per kb followed by 10 min of extension at 72° C. DNA fragments (PCR products or fragments) recovered from gel were purified using NucleoSpin extract II (Macherey-Nagel). DNA sequencing was performed by VIB Genetic Service Facility (Antwerp, Belgium).

Vector Construction.

(i) Knock-out (gene-replacement) of the ALG3 gene. The promoter fragment (P) of the ALG3 gene (GenBank® Accession No: XM_503488, Genolevures: YALI0E03190g) was amplified from genomic DNA of the *Yarrowia lipolytica* MTLY60 strain by PCR with 5'CAGTGCGGCCGCACTC-CCTCTTTTCACTCACTATTG3' (SEQ ID NO:48) and 5'CATTACCCTGTTATCCCTACGCTCA-GATCCAATTGTTTTGGTGGTC3' (SEQ ID NO:49) as the forward and reverse primers, respectively, using Taq polymerase (Invitrogen). The overhanging A nucleotide was removed with T4 DNA polymerase (Fermentas, Ontario, Canada). The terminator fragment (T) of the ALG3 gene was amplified from genomic DNA of the *Yarrowia lipolytica* MTLY60 strain by PCR with 5'GTAGGGATAACAGGG-TAATGCTCTCAAGGACGGACCAGAT-GAGACTGTTATCG3' (SEQ ID NO:50) and 5'GACTT-TAATTAAACCCTATGTGGCACCTCAACCCACATCTC CCGTC3' (SEQ ID NO:51) as the forward and reverse primers, respectively, using the proofreading Pfu DNA polymerase (Fermentas). Because of overlapping primer sequences containing an IsceI restriction site, both fragments could be linked by PCR with the P-forward primer and the T-reverse primer. This co-amplicon was then subcloned in a pCR-2.1 TOPO TA (Invitrogen) vector and the correctness of the co-amplicon's sequence was confirmed by sequencing. The co-amplicon was then cloned using the NotI-PacI sites into an intermediate vector.

(ii) Overexpression of the ALG6 gene. The ALG6 ORF (1725 bp) together with the terminator (415 bp downstream) of the ALG6 gene (GenBank® Accession No: XM_502922, Genolevures: YALI0D17028g) were cloned from genomic DNA of the *Yarrowia lipolytica* MTLY60 strain by PCR with 5'CAGTGGATCCATGAACTCTC- CTATTTTCACTACCG3' (SEQ ID NO:52) and 5'GACTC-CTAGGAAGCTTCCAGGTTACAAGTTGTTAC3' (SEQ ID NO:53) as the forward and reverse primers, respectively, using the proofreading Pfu DNA polymerase (Fermentas). The sequence was cloned in pCR-Blunt II-TOPO (Invitrogen) and the correctness of the ALG6 ORF sequence was confirmed by sequencing (as above). Next, the ALG6 ORF was cloned in a vector (pYLHmA) containing the hp4d promoter via BamHI and AvrII and subsequently cloned in the intermediate vector via the unique restriction sites ClaI and HindIII present in the terminator fragment of ALG3.

(iii) Selection marker cassette. To remove the selectable marker URA3 from the host genomic DNA, the Cre-lox recombination system was used, e.g., as described by Fickers et al. ((2003) J. Microbiol. Methods 55(3):727-737, the disclosure of which is incorporated herein by reference in its entirety). Upon expression of the Cre recombinase from the plasmid pRRQ2 (hp4d-cre, LEU2) (a gift from the Institut National de Recherche Agronomique (INRA)), the marker gets excised by recombination between the two lox sites. In both constructs, with and without the ALG6 overexpression cassette, the URA3 selection marker flanked by lox sites, was inserted in the introduced I-SceI site between P and T fragments of the vector, resulting in a "PUT" construct.

Preparation of mannoproteins. Yeast strains were grown overnight in 10 ml standard YPD medium in 50 ml falcon tubes, rotating at 250 rpm in a 28° C. incubator. The cells were then pelleted by centrifugation at 4000 rpm at 4° C. The supernatants were removed, and the cells were first washed with 2 ml of 0.9% NaCl solution followed by two washes with 2 ml of water and subsequently resuspended in 1.5 ml of 0.02 M sodium citrate pH 7 in a microcentrifuge tube. After autoclaving the tubes for 90 minutes at 121° C., the tubes were vortexed and the cellular debris was pelleted by centrifugation. The supernatants were collected and the mannoproteins were precipitated overnight with 4 volumes of methanol at 4° C. with rotary motion. The precipitate was then obtained by centrifugation of the alcohol precipitated material. The pellets were allowed to dry and dissolved in 50 µl of water.

Sugar analysis. DNA sequencer-assisted (DSA), fluorophore-assisted carbohydrate electrophoresis (FACE) was performed with an ABI 3130 DNA sequencer as described by Callewaert et al. (2001; supra). Briefly, glycoproteins were denatured for 1 hour in RCM buffer (8M urea, 360 mM Tris pH 8.6 and 3.2 mM EDTA) at 50° C. followed by immobilization on a prewetted PVDF membrane of a IP plate containing 15 µl RCM. Prewetting of the membrane was done with 300 µl MeOH, 3 times washed with 300 µl water and 50 µl RCM, followed by vacuum removal. The glycoproteins were reduced for 1 hour with 50 µl 0.1M dithiothreitol and washed 3 times with 300 µl water. A 30 minute incubation in the dark with 50 µl 0.1M iodoacetic acid was used to carboxymethylate the SH groups, followed by 3 washes with 300 µl water. The plates were subsequently incubated for 1 hour with 100 µl 1% polyvinylpyrrolidone 360 to saturate the unoccupied binding sites on the membrane, again followed by 3 washes with 300 µl water. Next, the N-glycans were released by 3 hours treatment with peptide: N-glycosidase F (PNGase F)×U in 50 µl of 10 mM Tris-acetate pH 8.3. N-glycans were recuperated and derivatized with the fluorophore 8-aminopyrene-1,3,6-trisulfonate (APTS) by reductive amination. This was accomplished with an overnight (ON) incubation at 37° C. with 1 µl of 1:1 mixture of 20 mM APTS in 1.2M citric acid and 1M NaCNBH$_3$ in DMSO and quenching by addition of 4 µl water. Excess label was removed by size fractionation on Sephadex G-10 resin. The remaining labeled N-glycans were then concentrated by evaporation. The N-glycans of RNase B and an oligomaltose ladder were included as size markers. Data analysis was performed using Genemapper® software (Applied Biosystems). Glycosidase digests on the labeled sugars were performed ON at 37° C. in 100 mM NH$_4$AC pH5. Additional Jack bean (JB) mannosidase was added after ON digestion and left for another 24 hours at 37° C.

Disruption of the ALG3 Gene in *Yarrowia lipolytica*

Figure 13:
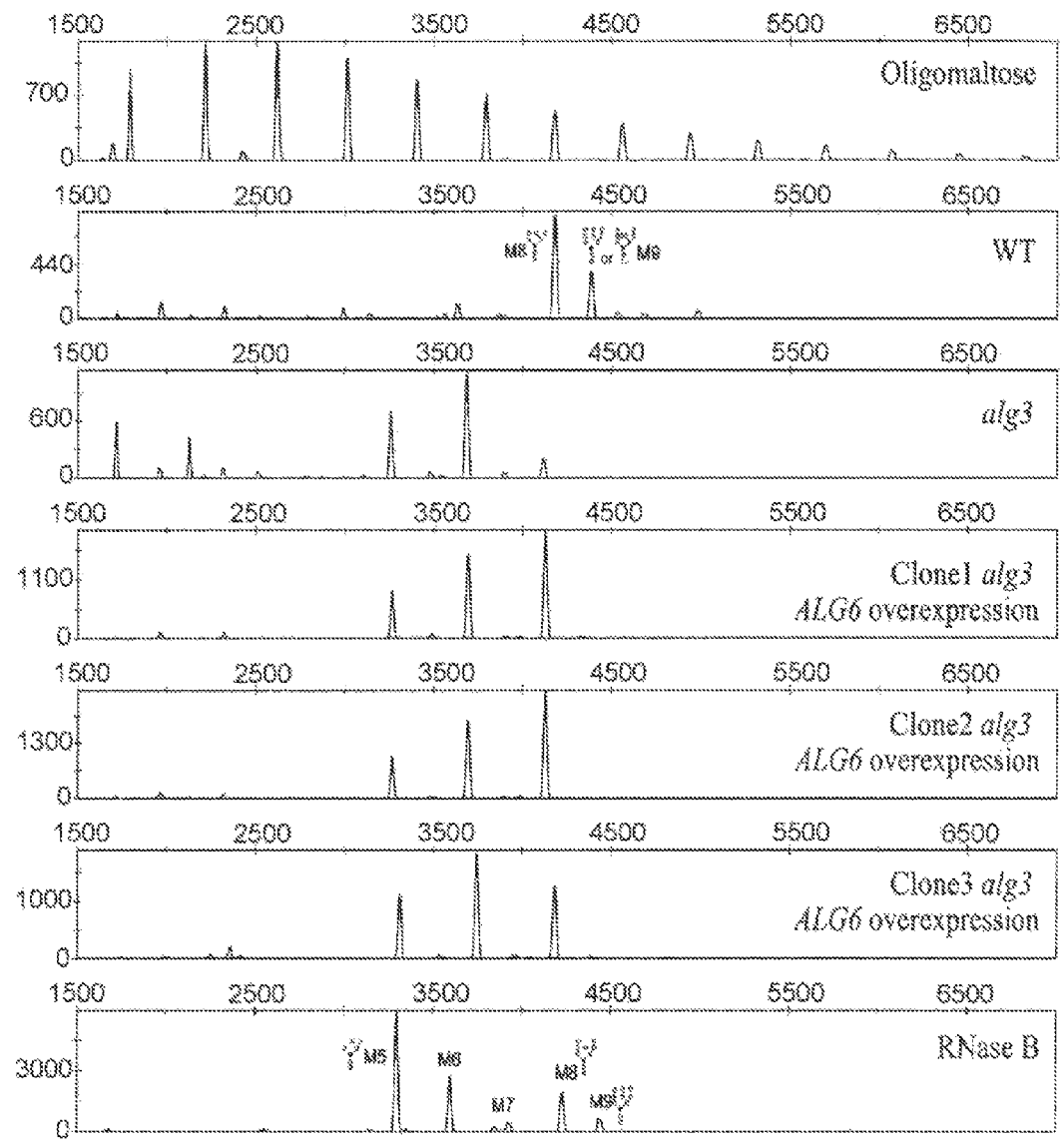
FIG. 13 is a series of electroferograms depicting N-glycan analysis of mannoproteins and phosphomannoproteins obtained from wild-type MTLY60 cells or various clones of glycosylation mutant cells as indicated. "alg3" indicates that the cell is an ALG3 knockout. "ALG6 overexpression" indicates that the protein product of ALG6 is overexpressed in the cell. Analysis was performed using DSA-FACE. "M5," "M6," "M7," "M8," and "M9,"" refer to the number of mannose residues conjugated to the base N-acetylglucosamine structure. The Y-axis represents the relative fluorescence units as an indication of the amount of each of the mannose structures. The X-axis represents the relative mobility of each complex mannose structure through a polyacrylamide gel. The top electroferogram is an analysis of oligomaltose for use as a mobility standard.

To disrupt the ALG3 gene, a vector was generated that includes parts of the promoter and terminator of ALG3 and has a URA3 selection marker cassette and was designated pYLalg3PUT. A NotI and PacI site were integrated to linearize the vector and thereby remove the *E. coli* related DNA elements. Double homologous recombination at the promoter and terminator site was used to replace ALG3 with the URA3 selectable marker, which resulted in an alg3::URA3 mutant strain. The knockout strategy applied was described by Fickers et al. (2003; supra) and makes use of the Cre-lox recombination system, that facilitates efficient marker rescue. Upon integration in the genomic ALG3 contig the Alg3p α-1,6-mannosyltransferase activity should be lost. This was monitored by analyzing the glycosylation pattern of the mannoproteins of several transformants. The N-glycans derived from mannoproteins were analysed by DSA-FACE (capillary electrophoresis) and treated with a selection of exoglycosidases to reveal the structures. Seven out of 24 transformants gave a change in glycosylation profile (three of which are depicted in FIG. 13). In all seven transformants, correct integration of the knockout cassette in the genome could be confirmed by PCR. Three main glycan structures were found by analyzing the profiles: (i) one (structural formula VII; FIG. 4A) that runs at the same size as the Man$_5$GlcNAc$_2$ structure of RNase B (the latter being structural formula IV; FIG. 4A); (ii) one at a distance of one glucose-unit extra; and (iii) one at the distance of two extra glucose-units. (FIG. 13). These results indicate that ALG3 was disrupted in these cells.

Overexpression of α-1,6-mannosyltransferase Alg6p

A strategy was developed in which a constitutively active overexpression cassette for the first glucosyltransferase, i.e., Alg6p, was incorporated into the alg3 gene replacement vector. This vector was designated pYLalg3PUT-ALG6. A NotI/PacI fragment of this vector was transformed into the *Yarrowia lipolytica* MTLY60 strain. In this way, disruption of ALG3 and overexpression of ALG6 under control of the hp4d promoter is achieved. Correct integration in the genome was again confirmed by PCR. DSA-FACE analysis of the N-glycans derived from mannoproteins showed that half of the transformants, i.e., 12 out of 24, exhibited a change in glycosylation pattern comparing to the WT strain. Overexpression of ALG6 led to a mild clonal variation (FIG. 13).

Identification of the N-Glycan Structures

Figure 14:
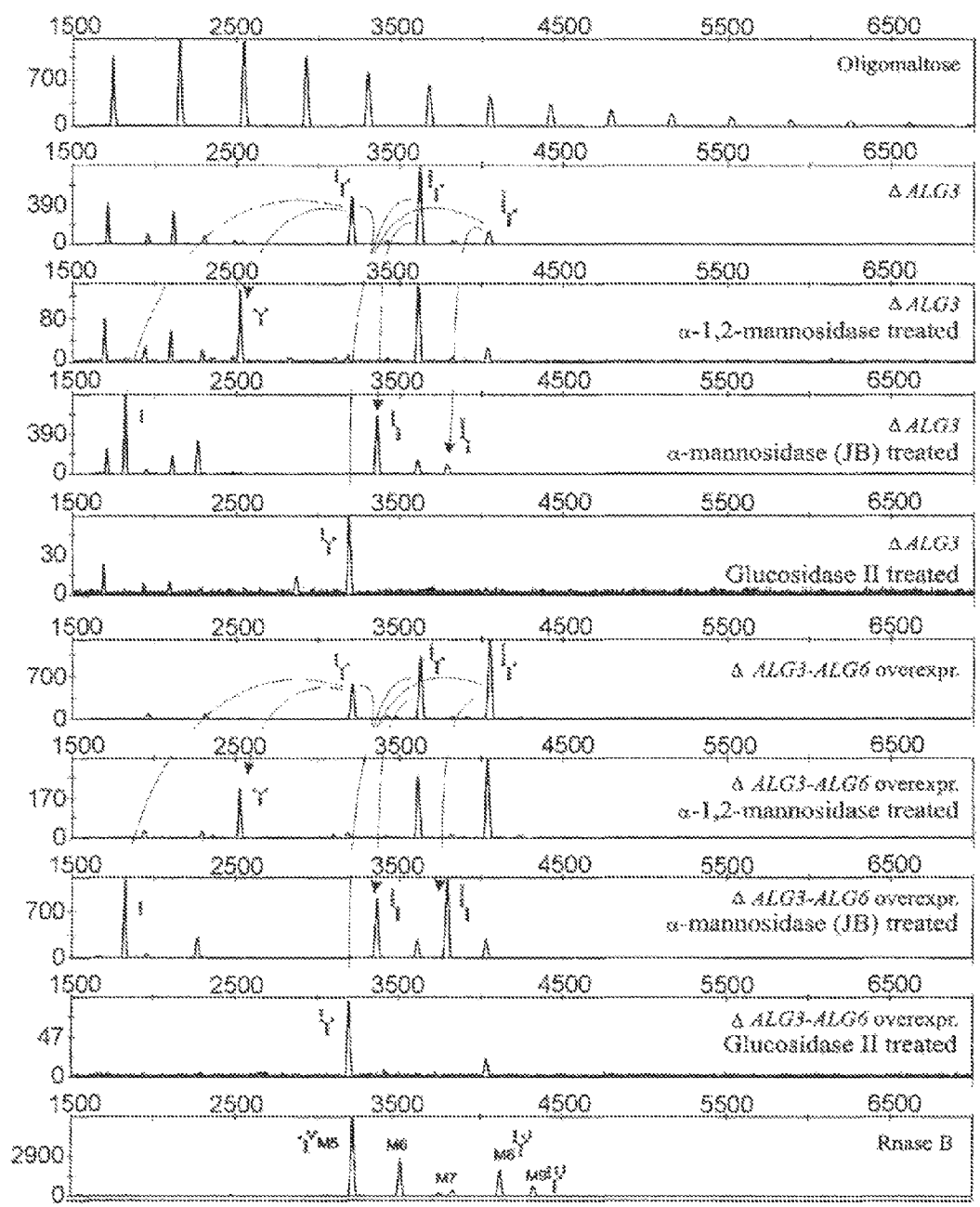
FIG. 14 is a series of electroferograms depicting N-glycan analysis of mannoproteins and phosphomannoproteins obtained from wild-type MTLY60 cells or various clones of glycosylation mutant cells as indicated. "alg3" indicates that the cell is an ALG3 knockout. "ALG6 overexpression" indicates that the protein product of ALG6 is overexpressed in the cell. One peak runs at the same position as $Man_5GlcNAc_2$ of the RNaseB marker and shifts with two glucose-units after α-1,2-mannosidase treatment and with 4 glucose-units after alpha-mannosidase (JB) digest. This fits with a $Man_5GlcNAc_2$ structure as expected. The additional two peaks run at a distance of about one and two glyco-units and are not affected by a-1,2-mannosidase digestion. Both peaks shift one glucose-unit upon a-mannosidase (JB) digestion. Minor shifts are due to the higher salt concentrations of the added enzymes, e.g. JB mannosidase. Analysis was performed using DSA-FACE. "M5," "M6," "M7," "M8," and "M9," refer to the number of mannose residues conjugated to the chitobiose core structure. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.

To further elucidate the nature of the glycan structures from the experiments described above, in vitro digests of glycans derived from the mannoproteins (as above) were performed with a selection of exoglycosidases. The mannoprotein glycans were analyzed with the following enzymes: α-1,2-mannosidase; α-mannosidase (JB) and glucosidase II. Three observed glycan structures represent Man$_5$GlcNAc$_2$ (structural formula VII; FIG. 4A), GlcMan$_5$GlcNAc$_2$ (structural formula VIII; FIG. 4B) and Glc$_2$Man$_5$GlcNAc$_2$ (structural formula IX; FIG. 4A) (FIG. 14). These results indicate that there is very little to no high mannose elongation by α-1,6-mannosyltranferases (e.g., Och1p).

Figure 28:
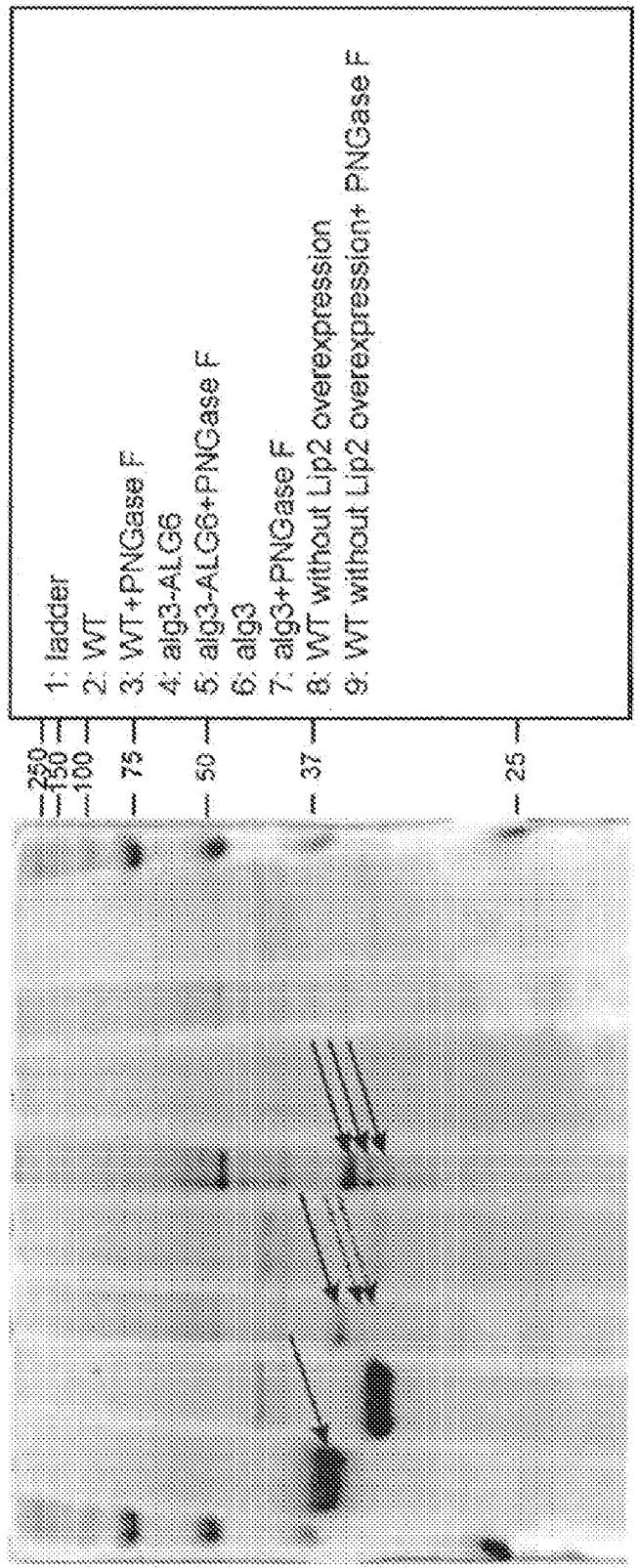
FIG. 28 is a photograph of a Coomassie blue stained polyacrylamide gel depicting the results of Lip2p overexpression in various *Yarrowia lipolytica* cell (MTLY60, MTLY60Δalg3 and MTLY60Δalg3ALG6) cultures. The following samples were resolved in the gel: Lane 1 ("ladder"), a combination of proteins of known molecular weight, Lane 2 ("WT"), Lip2p protein obtained from WT *Yarrowia lipolytica* cells (MTLY60) overexpressing Lip2p; Lane 3 ("WT+PGase F"), Lip2p protein obtained from WT *Yarrowia lipolytica* cells overexpressing Lip2p and treated with PNGase F enzyme; Lane 4 ("alg3-ALG6"), Lip2p protein obtained from *Yarrowia* cells deficient in alg3 and overexpressing both Lip2p and ALG6 (MTLY60Δalg3ALG6); Lane 5 ("alg3–ALG6+ PNGase F"), Lip2p protein obtained from *Yarrowia* cells deficient in alg3 and overexpressing both Lip2p and ALG6 (MTLY60Δalg3ALG6) and treated with PNGase F enzyme; Lane 6 ("alg3"), Lip2p protein obtained from *Yarrowia lipolytica* cells deficient in alg3 and overexpressing Lip2p (MTLY60Δalg3); Lane 7 ("alg3+PNGase F"), Lip2p protein obtained from *Yarrowia lipolytica* cells deficient in alg3 and overexpressing Lip2p (MTLY60Δalg3) treated with PNGase F enzyme; Lane 8 ("WT without Lip2p overexpression"), protein obtained from MTLY60 cells; and Lane 9 ("WT without Lip2p overexpression+PNGase F"), protein obtained from MTLY60 cells and treated with PNGase F enzyme.

To determine if ALG6 overexpression is necessary for promoting N-glycosylation site-occupancy, Lipase 2 (LIP2) from *Yarrowia lipolytica* was expressed in three different strains of *Yarrowia*: MTLY60, MTLY60Δalg3 and MTLY60Δalg3ALG6. A construct for the *Yarrowia lipolytica* LIP2, under control of a TEF constitutive promoter was obtained from INRA. The expression cassette was transformed to the above-mentioned strains and the expression of the protein was verified by subjecting the supernatant prepared from the transformed cells to SDS-PAGE analysis (FIG. 28). The Lip2p protein has 2 glycosylation sites. Lip2p protein derived from the alg3-deficient ("knockout") yeast strain was resolved by SDS-PAGE into three distinct bands that were visualized using Coomassie blue staining of the gel (FIG. 28). To confirm that all three forms of protein in the gel were different glycosylation forms of the Lip2p protein, Lip2p protein obtained from the alg3-deficient ("knockout") yeast strain was subject to treatment with PNGase F (an enzyme that removes oligosaccharide residues from glycoproteins) and then subjected to SDS-PAGE analysis as described above. Treatment of the Lip2p protein with PNGase F resulted in a single band (which had the same molecular weight as non-glycosylated Lip2p) on the gel following Coomassie blue staining and indicated that all three forms of protein previously observed were different glycosylation forms of the same Lip2p molecule. The same is true for the Lip2p derived from the alg3ALG6 strain. However, the amount of protein in a reduced glycosylation form is decreased. Thus, it can be concluded that overexpression of ALG6 can (at least partially) restore N-glycosylation site-occupancy, which is reduced in the alg3 knockout mutant yeast strain.

Removing Capping Glucose Structures

Next, to eliminate mono (structural formula VIII; FIG. 4B) and bi-glucosylated (structural formula IX; FIG. 4B) Man$_5$GlcNAc$_2$ (structural formula VII; FIG. 4A) structures in vivo, cells were genetically engineered to overexpress the α-subunit of the enzyme glucosidase II. The α subunit of glucosidase II of *Yarrowia* (GenBank® Accession No: XM_500574) and the α subunit of glucosidase II *Trypanosoma brucei* (GenBank® Accession No: AJ865333) were independently cloned as two strategies to overexpress the protein. The α subunit of glucosidase II *Trypanosoma brucei* was chosen since its natural substrate is GlcMan$_5$GlcNAc$_2$ (structural formula VIII; FIG. 4B). Both genes were cloned under control of the constitutive hp4d promoter and their plasmids contain the URA3 marker. These constructs were transformed into alg3 mutant yeast strains, both with and without ALG6 overexpression.

Figure 29:
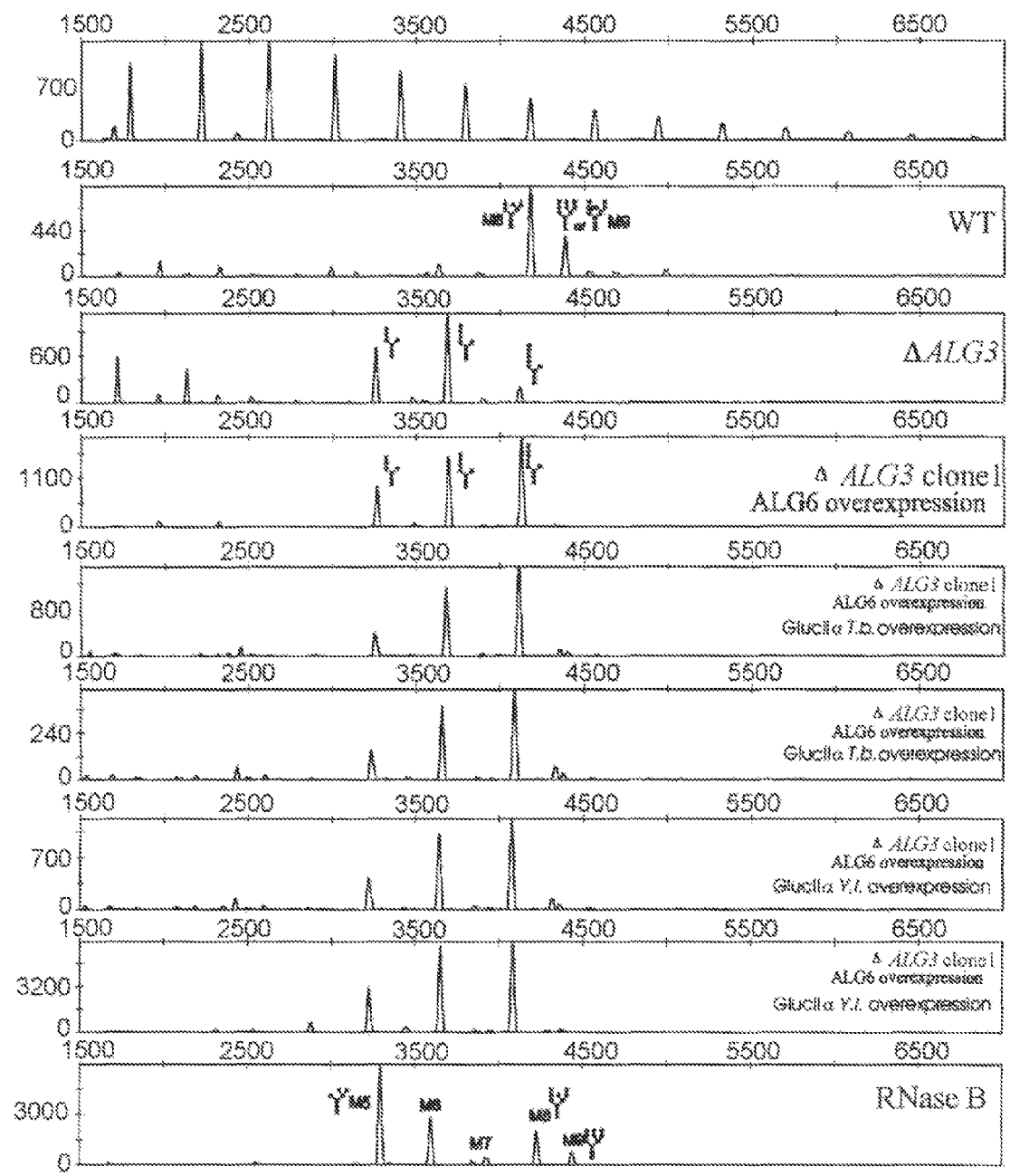
FIG. 29 is a series of electroferograms depicting N-glycan analysis of glycoproteins obtained from various *Yarrowia lipolytica* cells (WT (MTLY60); Δalg3; Δalg3 ALG6 overexpressing; and clones of Δalg3 overexpressing ALG6 along with the alpha subunit of glucosidase II from *Y. lipolytica* (Yl) or *Typanosoma brucei* (Tb)) as indicated. Analysis was performed using DSA-FACE. "M5," "M6," "M7," "M8," and "M9," refer to the number of mannose residues conjugated to the chitobiose core structure. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

Oligosaccharides were prepared from secreted proteins derived from cultured cells containing the constructs and the profile of the oligosaccharides was determined by DSA-FACE analysis. All transformants gave the same DSA-FACE profile, two different clones of each glucosidaseII α are depicted in FIG. 29. From these results it was concluded that the overexpression of either the *Yarrowia* or the *Trypanosoma* glucosidase II α subunit has only a minor effect on the amount of mono (structural formula VIII; FIG. 4B) and bi-glucosylated (structural formula IX; FIG. 4B) Man$_5$GlcNAc$_2$ (structural formula VII; FIG. 4A) structures.

Figure 30:
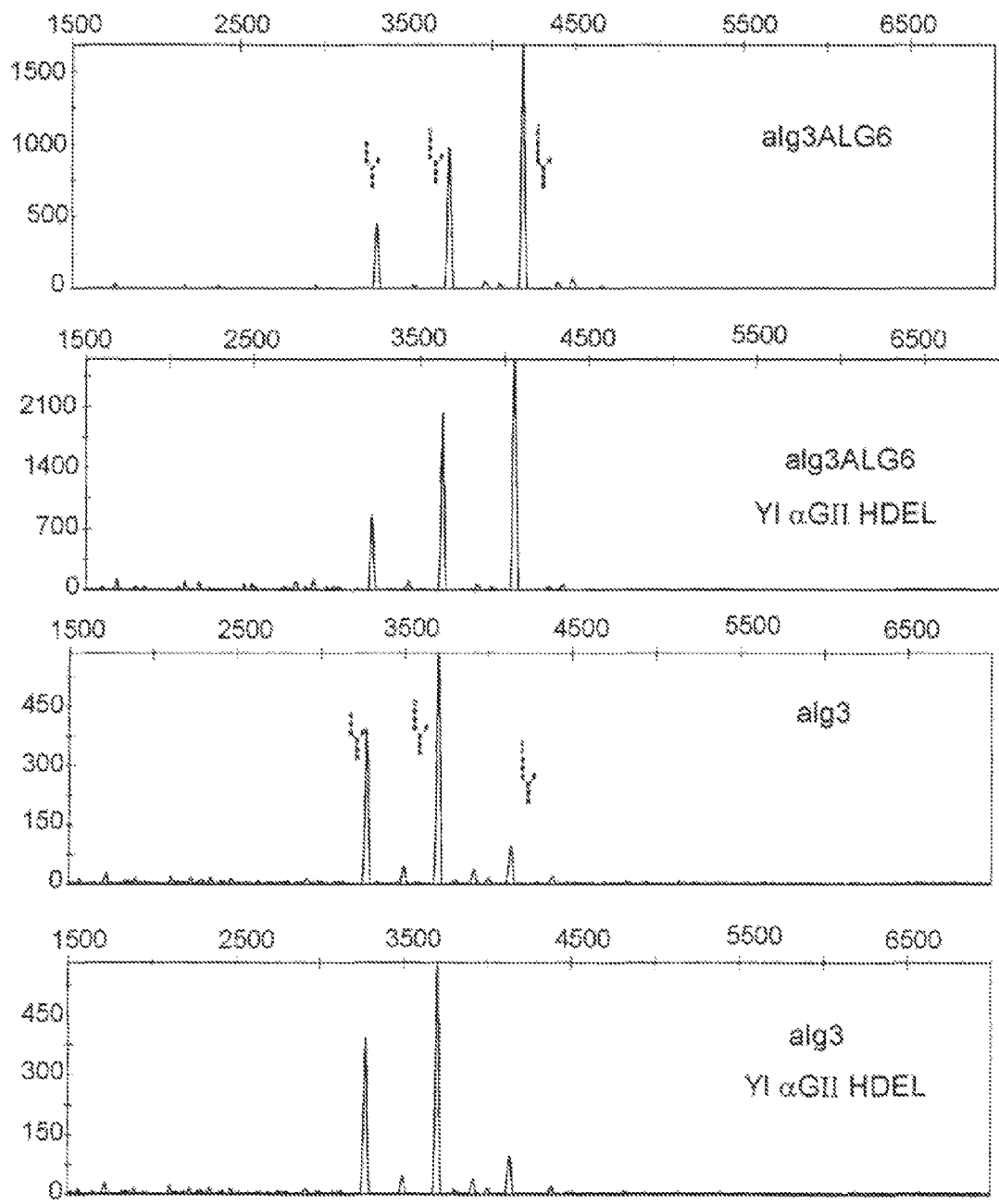
FIG. 30 is a series of electroferograms depicting N-glycan analysis of glycoproteins obtained from various *Yarrowia lipolytica* cells (Δalg3; Δalg3 ALG6 overexpressing; and clones of Δalg3 overexpressing ALG6 along with the alpha subunit of glucosidase II from *Y. lipolytica* (Yl) containing an HDEL sequence as indicated. Analysis was performed using DSA-FACE. The Y-axis represents the relative fluorescence units as an indication of the amount of each of the mannose structures. The X-axis represents the relative mobility of each complex mannose structure through a gel.
Figure 31:
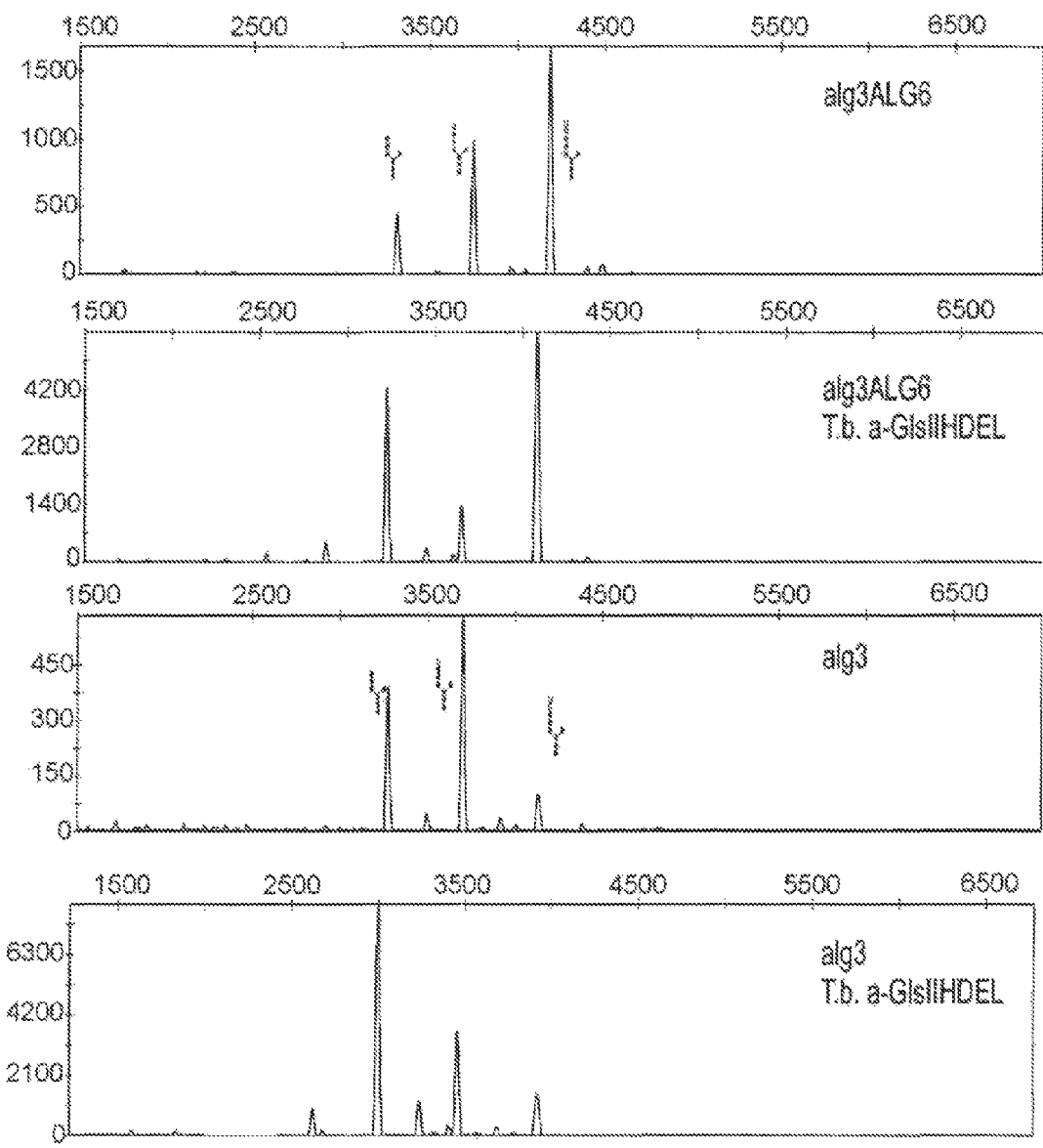
FIG. 31 is a series of electroferograms depicting N-glycan analysis of glycoproteins obtained from various *Yarrowia lipolytica* cells (Δalg3; Δalg3 ALG6 overexpressing; and clones of Δalg3 overexpressing ALG6 along with the alpha subunit of glucosidase II from *Trypanosoma brucei* (Tb) containing an HDEL sequence) as indicated. Analysis was performed using DSA-FACE. The Y-axis represents the relative fluorescence units as an indication of the amount of each of the mannose structures. The X-axis represents the relative mobility of each complex mannose structure through a gel.

Expression of Glucosidase II α-Subunits of *Yarrowia lipolytica* and *Trypanosoma brucei* Tagged with an HDEL Sequence To improve the effect of the expression of *Yarrowia* or the *Trypanosoma glucosidase* II α subunit on removing glucose residues from Man$_5$GlcNAc$_2$ in vivo, a nucleic acid encoding an HDEL tag was added using molecular biology techniques in frame to the 3' end of the nucleic acid encoding each of the two GlsII α enzymes. The HDEL tag was meant to serve as a retrieval mechanism from the Golgi to the ER. Plasmids encoding HDEL-tagged glucosidase II sequences from both *Yarrowia lipolytica* (Y.l.) and *Trypanosoma brucei* (T.b.) under control of the hp4d promoter were transformed to the alg3 KO strain with and without overexpression of the ALG6 gene. As can be seen in FIG. 30, overexpression of the *Yarrowia lipolytica* glucosidase II α subunit had only a minor effect on the amount of glucosylated structures. In contrast, overexpressing the α-Glucosidase II of *Typanosoma brucei* α subunit with an extra HDEL tag leads to a reduction of the mono-glucose peak (see FIG. 31).

Treatment of Glucosylated Glycans with Mutanase

Figure 32:
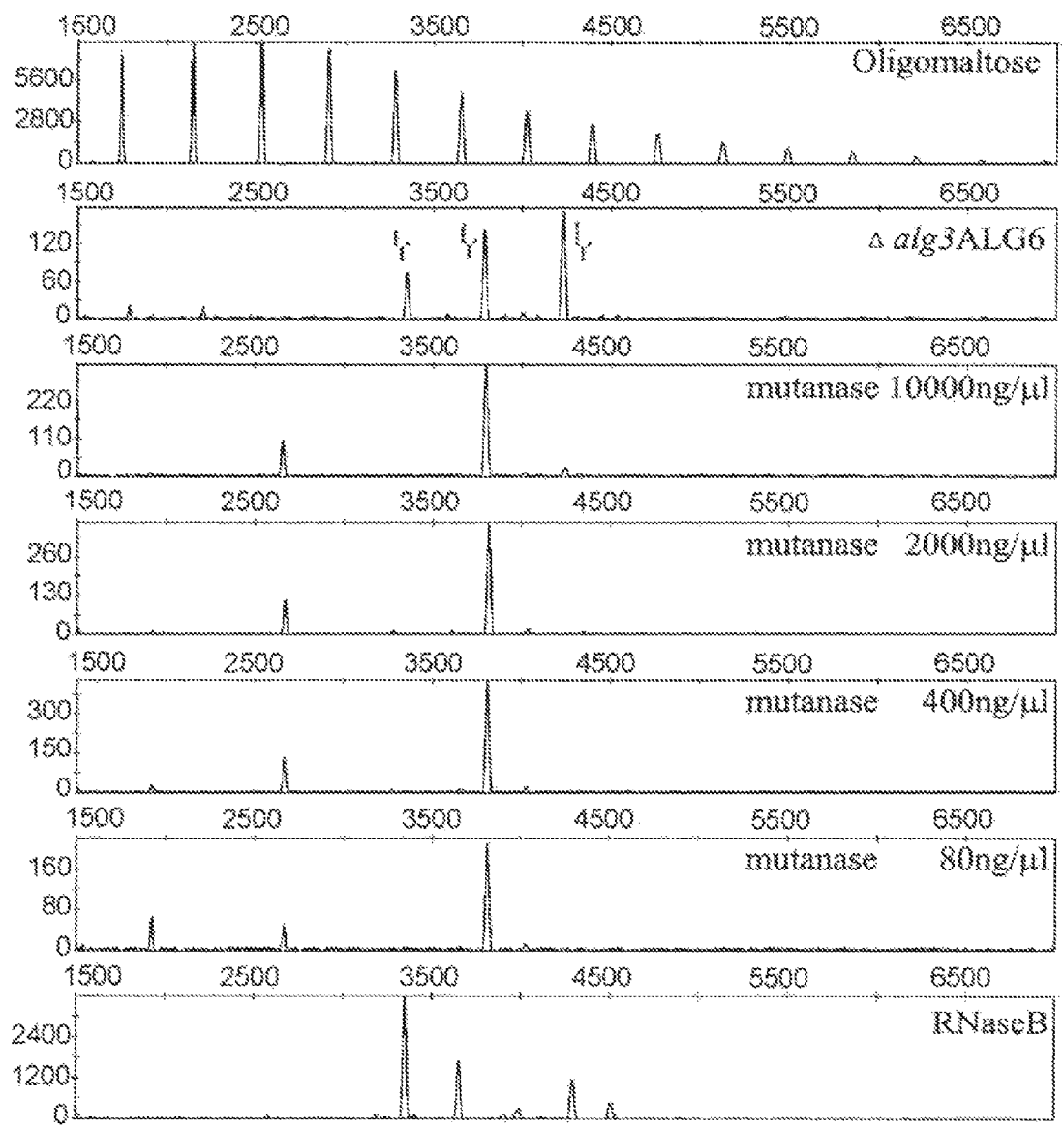
FIG. 32 is a series of electroferograms depicting N-glycan analysis of glycoproteins obtained from alg3ALG6 *Yarrowia lipolytica* cells treated in vitro with different concentrations of mutanase as indicated. Analysis was performed using DSA-FACE. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

The above-described results demonstrate one exemplary means of reducing mono-glucosylated forms of Man$_5$GlcNAc$_2$. To reduce bi-glucosylated forms of Man$_5$GlcNAc$_2$ from glycoproteins, the mutanase of *T. harzianum* was investigated as one potential solution. An enzyme preparation was obtained from Novozymes (Novozyme 234; Bagsvaerd, Denmark) and was used to digest oligosaccharides in vitro. That is, mutanase was added in different concentrations to the oligosaccharides derived from a alg3ALG6 strain (glycans: Man$_5$GlcNAc$_2$, GlcMan$_5$GlcNAc$_2$ and Glc$_2$Man$_5$GlcNAc$_2$). As shown in the DSA-FACE profile of FIG. 32, the bi-glucose peak observed in the oligosaccharides was effectively reduced.

Figure 33:
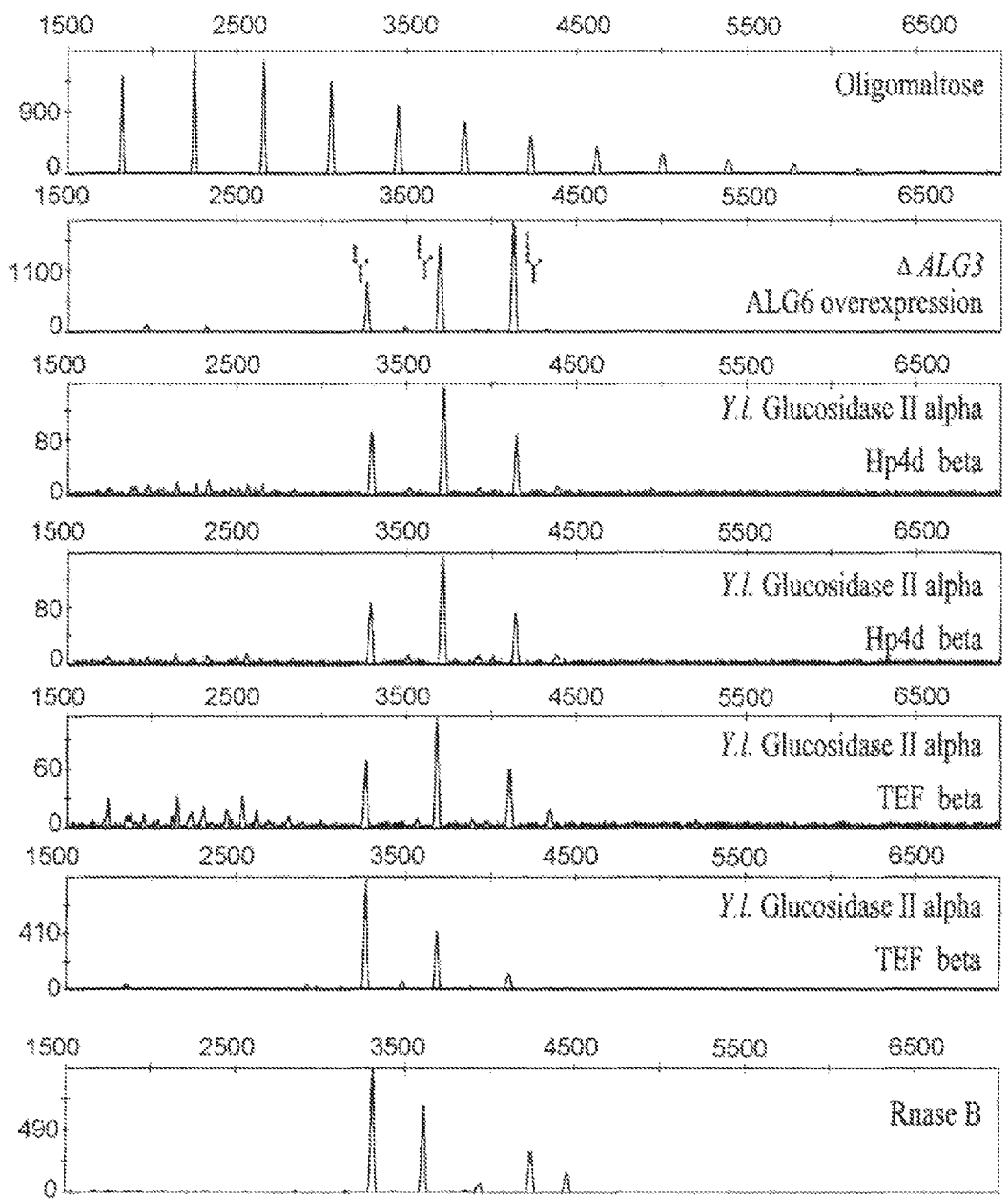
FIG. 33 is a series of electroferograms depicting N-glycan analysis of glycoproteins obtained from various *Yarrowia lipolytica* cells (Δalg3; Δalg3 ALG6 overexpressing; and clones of Δalg3 overexpressing ALG6 along with the alpha subunit of glucosidase II from *Y. lipolytica* (Y.l.) and the beta subunit of glucosidase II from Y.l. expressed under the control of Hp4d or TEF promoters) as indicated. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

Next, the mutanase of *T. harzianum* was overexpressed in vivo. An HDEL-sequence containing mutanase was synthesized as a codon-optimized cDNA for expression in *Yarrowia lipolytica*. The mature protein was cloned in frame with the LIP2 pre signal sequence under control of the TEF1 promoter (FIG. 33). This construct is transformed into alg3 mutant yeast strains, both with and without ALG6 overexpression. Oligosaccharides are prepared from cultured cells containing the construct and the profile of the oligosaccharides is determined by DSA-FACE analysis. It is expected that the DSA-FACE profile will show a reduction in the bi-glucose peak observed in the oligosaccharides. From these results it will be concluded that the overexpression of mutanase in vivo is effective at reducing the bi-glucose peak observed in oligosaccharides as compared to cells not overexpressing the mutanase.

Co-Expression of Yl GlsII α- and β Subunits

It is known that the α- and β-subunits of glucosidase II form a heterodimeric complex whereby the β-subunit is responsible for retrieval of the complex to the ER and is also involved in substrate recognition, whereas the α-subunit contains the catalytic activity. Since the overexpression of only the α-subunit of glucosidase II had a small effect on bi-glucose oligosaccharide structures, the α- and β-subunits were co-expressed.

Figure 34:
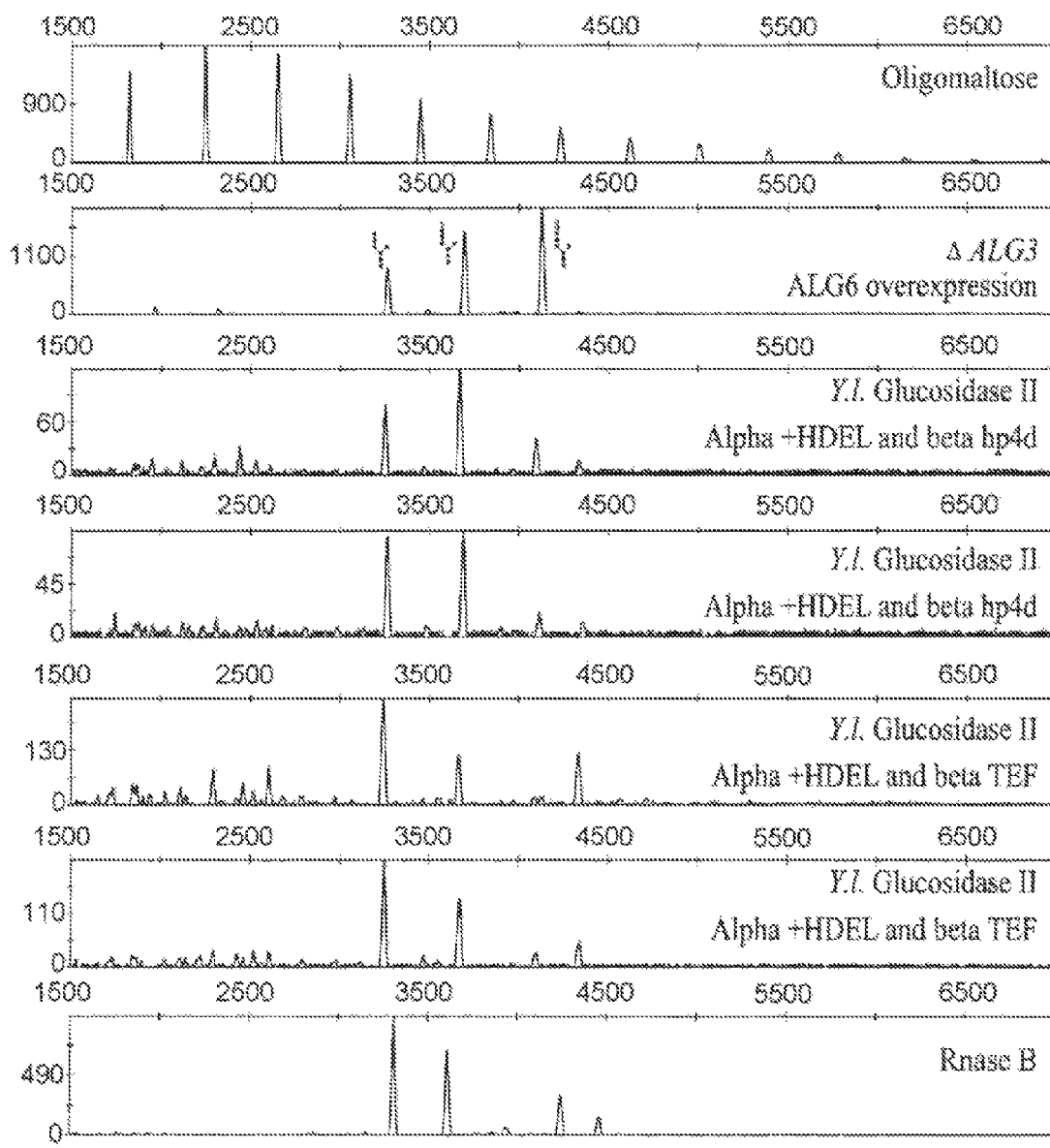
FIG. 34 is a series of electroferograms depicting N-glycan analysis of glycoproteins obtained from various *Yarrowia lipolytica* cells (Δalg3 ALG6 overexpressing; and clones of Δalg3 overexpressing ALG6 along with the HDEL-containing alpha subunit of glucosidase II from *Y. lipolytica* (Y.l.) and the beta subunit of glucosidase II from Y.l. expressed under the control of Hp4d or TEF promoters) as indicated. Analysis was performed using DSA-FACE. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

The open reading frame of the β-subunit (YALI0B03652g) was amplified from genomic DNA that was isolated from the MTLY60 strain using PCR and was cloned under control of the TEF1 and hp4d promoter. The constructs were made with LEU2 as a selection marker and with the glucosidase II β-subunit under control of the TEF1 and the hp4d promoter. These were transformed to the alg3 knockout strains with and without ALG6 overexpression and overexpressing the *Yarrowia lipolytica* Glucosidase II α subunit with and without an HDEL sequence tag. N-glycans were prepared from proteins secreted from the cells and the DSA-FACE profiles of the N-glycans are depicted in FIGS. 33 and 34 (alg3 knockout with overexpression of ALG6). It can be concluded from these profiles that overexpressing the β subunit of glucosidase II from *Yarrowia lipolytica* did have a positive effect on the trimming of the glucosylated sugars. In general, the efficacy of the β subunit of glucosidase II was improved when expressed under the TEF1 promoter. The glucosylated structures were even more reduced when the *Yarrowia lipolytica* glucosidase II α subunit contained an HDEL tag (FIGS. 33 and 34).

Figure 35:
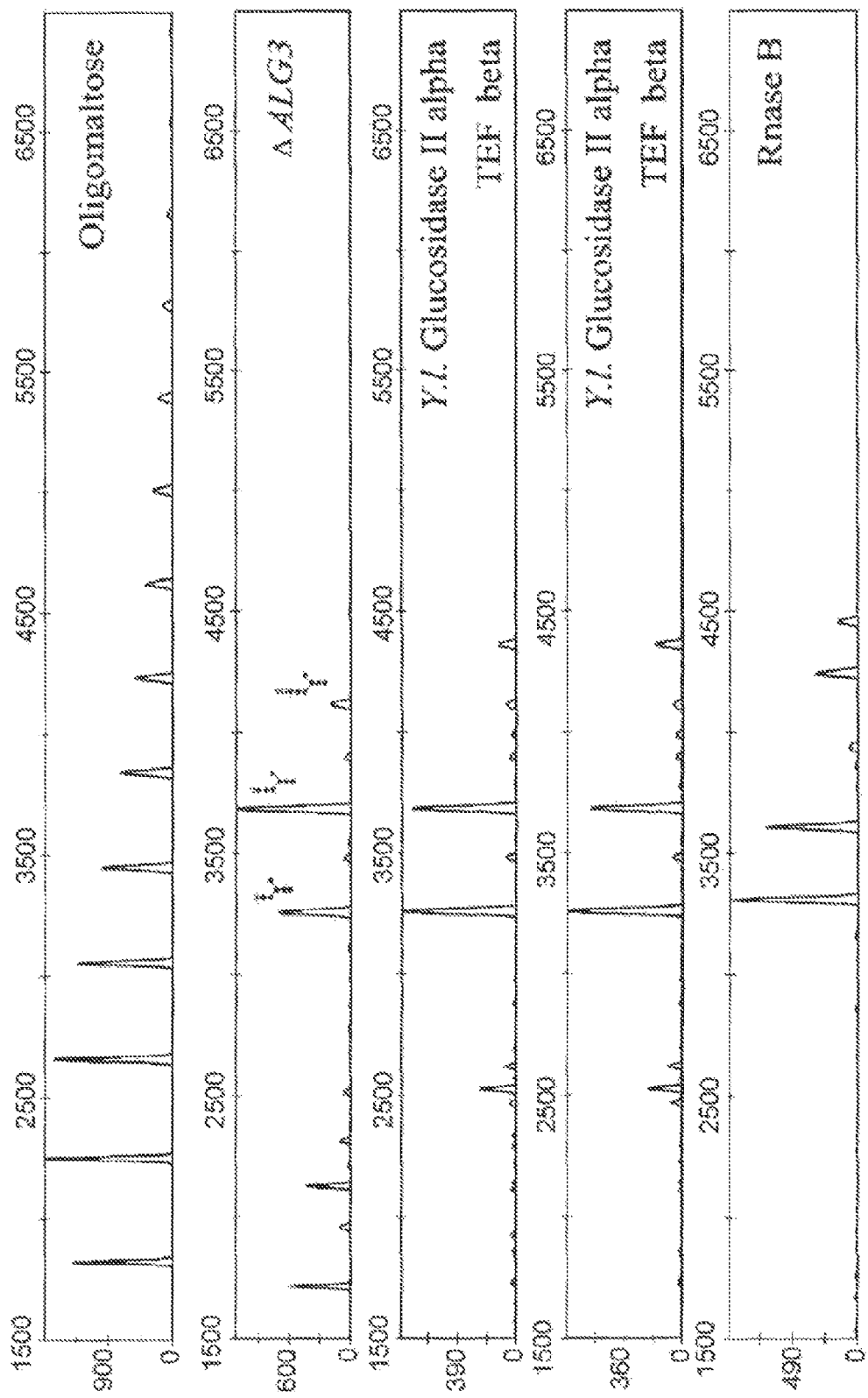
FIG. 35 is a series of electroferograms depicting N-glycan analysis of glycoproteins obtained from various *Yarrowia lipolytica* cells (Δalg3 and clones of Δalg3 overexpressing the alpha subunit of glucosidase II from *Y. lipolytica* (Y.l.) and the beta subunit of glucosidase II from Y.l. expressed under the control of a TEF promoter) as indicated. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

For alg3-deficient cells without ALG6 overexpression, similar results regarding reduction of glucosylated structures were observed for each of the different cell populations (FIG. 35).

Expression of *Aspergillus* GlsII a and b Subunit

Figure 38:
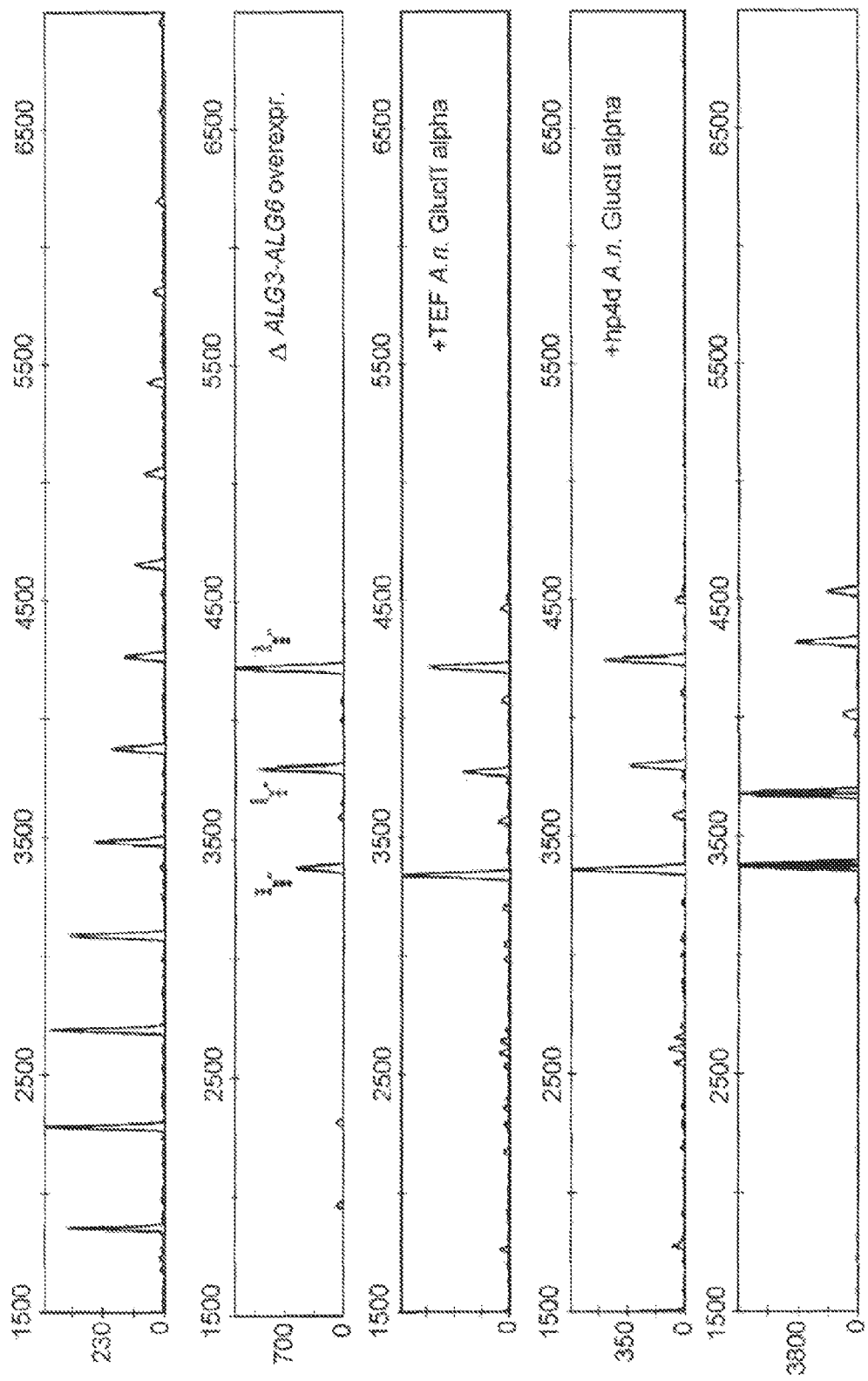
FIG. 38 is a series of electroferograms depicting N-glycan analysis of glycoproteins obtained from various *Yarrowia lipolytica* cells (Δalg3 and ALG6 overexpressing along with the alpha subunit of glucosidase II from *Aspergillus niger* (An) expressed under the control of a TEF or hp4d promoter) as indicated. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard. The bottom electroferogram is an analysis of RNAse B.

In order for the glucose residues to be removed from the glucose bearing structures that occur in alg3-deficient background, the *Aspergillus niger* mature (lacking signal peptide) glucosidase II α and β were synthesized as codon-optimized cDNA for expression in *Yarrowia lipolytica* (α-subunit (SEQ ID NO:7; FIGS. 36A-36B) β-subunit: (SEQ ID NO:8; FIG. 37). *Aspergillus niger* (An) glucosidase α subunit was cloned under control of the constitutive TEF1 and hp4d promoters and had URA3 gene as a selection marker. The expression cassettes (ORFs under control of TEF1 and hp4d) were transformed to *Yarrowia lipolytica* alg3ALG6 strain, Transformant candidates were grown in YPD and glycans from secreted proteins were analysed by DSA-FACE. It can be deduced from FIG. 38 that the two glucosylated structures are less abundant in the transformant strains compared to the non-transformant (alg3ALG6).

To further reduce the glucosylated glycan structures a construct is made with β-subunit of the *Aspergillus niger* glucosidase II under control of TEF1 promoter or hp4d promoter with LEU2 as a selection marker. This construct is transformed to *Yarrowia lipolytica* alg3ALG6 strain expressing the An glucosidase II α-subunit. It is expected that expression of the β-subunit of the *Aspergillus niger* glucosidase II will result in a decrease in glucosylated structures in *Yarrowia lipolytica* cells.

Example 6

Identification of the HAC1 Intron and Cloning and Isolation of the HAC1 Gene

*Y. lipolytica* HAC1 splice site. On the basis of sequence homology between the intronic regions of HAC1 in *Yarrowia lipolytica* and the fungi *Trichoderma reesei* and *Aspergillus nidulans*, a potential splice site of the *Yarrowia lipolytica* HAC1 (Genbank: XM_500811, Genolevures: Yali0B12716g) was identified. The 5' and 3' splice sites were predicted to be localized in a characteristic loop structure and the intron was calculated to be 29 bp long.

Primers were developed around the splice site in order to identify the intron. First strand cDNA was synthesized from the isolated mRNA from an UPR (unfolded protein response) induced (by means of growth in dithiothreitol (DTT)) and non-induced culture (negative control) with gene specific primers. PCR was then performed on first strand using primers HAC1FW06-003 and HAC1Rv06-001. Amplification products were analyzed on a 1.5% agarose gel.

Figure 15:
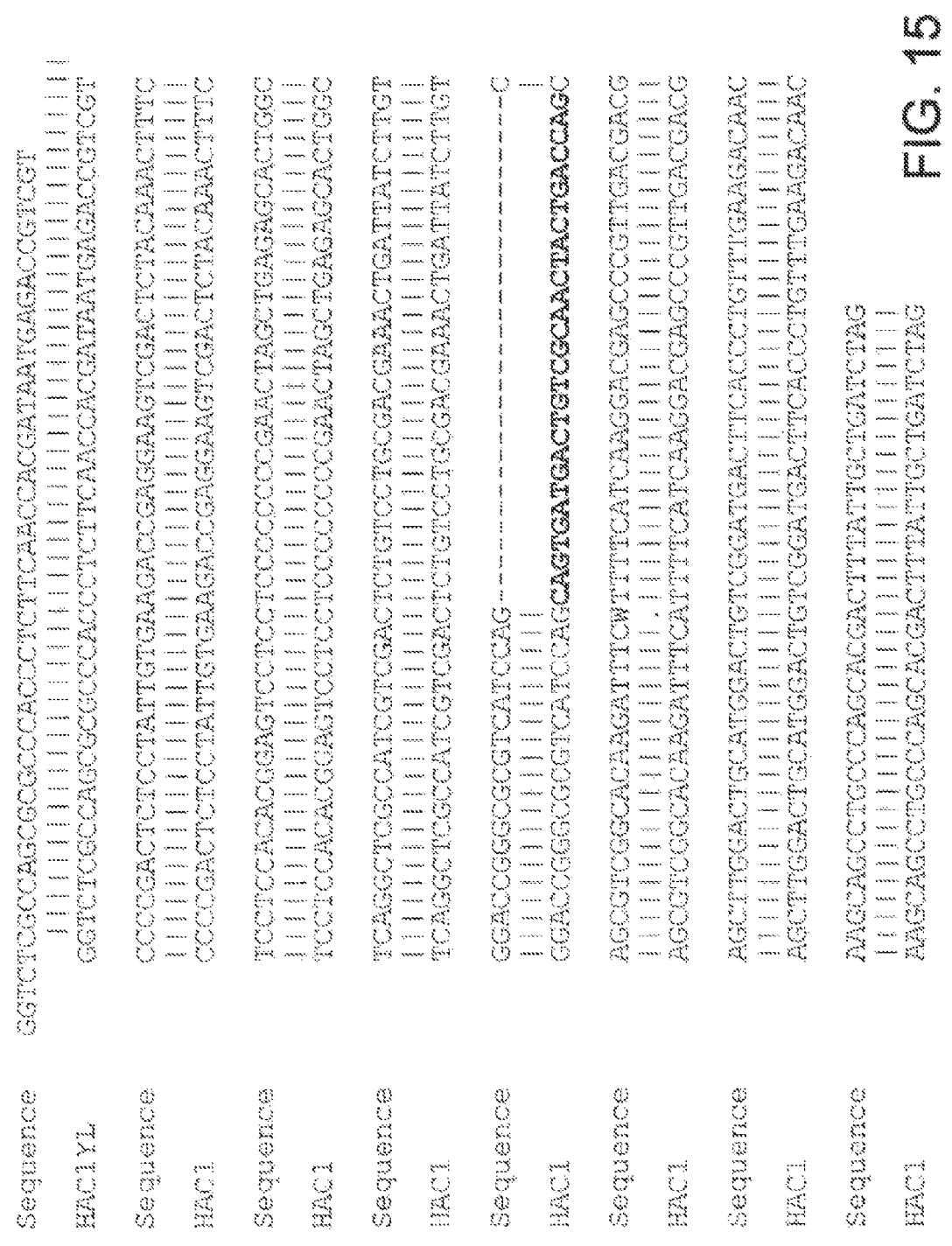

A fragment of +/−400 bp was expected to be amplified for the non-induced cells; a 29 bp smaller fragment was expected to be amplified for the induced cells. Fragments of the correct size were obtained from the non-induced cells and the UPR induced cells. Two more amplification products were obtained for the UPR induced culture. The middle fragment was the same size as the band obtained for the non-induced culture and was interpreted as being unspliced HAC1. The lower, most prominent band was purified from the gel and cloned into a sequencing vector. After sequencing the construct, a sequence alignment was performed in order to identify the splice site (FIG. 15). From the sequence alignment it can be seen that the splice site is located at the position that was predicted from the comparison of the *Yarrowia lipolytica* and the fungal (*Trichoderma reesei* and *Aspergillus nidulans*) HAC1 sequences. The splice site is 29 bp long.

In order to isolate the active full length HAC1 sequence, primers were engineered to have restriction sites suitable for cloning into an expression vector. Primer sequences were as follows: Hac1ylRv07-018: CCTAGGTCACTCCAATC-CCCCAAACAGGTTGCTGACGCTCGACT-CATAGTGAGCTAGATCAGCAATAAAGTCG (SEQ ID NO:54) and HAC1Fw06-002:GGA TCC ATG TCT ATC AAG CGA GAA GAG TCC (SEQ ID NO:55). A 10 ml culture of yeast cells was incubated for 1.5 hours in the presence of 5 mM DTT to induce the UPR response. Following the incubation, RNA was isolated from the DTT-treated cells and first strand cDNA was prepared from the isolated RNA using reverse transcriptase and PCR using the cDNA as a template and the above primers. The PCR-amplified sequence containing the spliced HAC1 was inserted into the pCR-blunt-TOPO cloning vector using standard molecular biology techniques and sequenced.

*Pichia pastoris* HAC1 splice site. On the basis of sequence homology of the intronic regions of the *Pichia pastoris* and *Saccharomyces cerevisiae* HAC1 genes, a potential splice site in the *Pichia pastoris* HAC1 gene was identified (FIG. 16). The 5' and 3'splice sites were predicted to be localized in a characteristic loop structure and the intron was calculated to be 322 bp in length.

Primers (HAC1Fw06-004 and HAC1Rv06-005) were developed around the predicted splice site in order to identify the intron (see Table 4). A fragment of 257 nucleotides was expected to be amplified when the intron is removed and a 579 bp fragment if intron is still present. First strand cDNA was synthesized from the isolated mRNA from an UPR induced and non-induced culture. The UPR was induced by adding 5 mM DTT to a 10 ml culture of exponentially growing cells. The cells were cultured in the presence of DTT for 1.5 hours. The amplification product was analyzed by 1.5% agarose gel electrophoresis. A fragment of approximately 257 bp was obtained from cDNA from both non-induced and induced cells.

TABLE 4

Primers

| Primer code | sequence 5'→3' | Information |
|---|---|---|
| HAC1-KarI | GAATTCATGCCCGTAGATTC TTCTC (SEQ ID NO: 56) | Forward primer Hac1 gene + start codon and EcoRI site |
| HAC1 Fw06-004 | GAGTCTTCCGGAGGATTCAG (SEQ ID NO: 57) | Forward primer Hac1 gene region around 5' splice site |
| HAC1 Rv06-005 | CCTGGAAGAATACAAAGTC (SEQ ID NO: 58) | Reverse primer Hac1 gene near stop codon |
| HAC1 Rv06-009 | CCTAGGCTATTCCTGGAAG AATACAAAGTC (SEQ ID NO: 59) | reverse primer Hac1 gene + stop codon and AvrII site |
| ACTppFw07-007 | GGTATTGCTGAGCGTATGC AAA (SEQ ID NO: 60) | Act1 forward primer for QPCR |
| ACTppRv07-003 | CCACCGATCCATACGGAGT ACT (SEQ ID NO: 61) | Act1 reverse primer for QPCR |
| HAC1ppFw07-008 | CGACCTGGAATCTGCACTT CAA (SEQ ID NO: 62) | Hac1 forward primer QPCR |
| HAC1ppRV07-004 | CGGTACCACCTAAGGCTTC CAA (SEQ ID NO: 63) | Hac1 reverse primer QPCR |
| Kar2ppFw07-009 | CCAGCCAACTGTGTTGATTC AA (SEQ ID NO: 64) | Kar2 forward primer QPCR |
| Kar2ppRv07-005 | GGAGCTGGTGGAATACCAG TCA (SEQ ID NO: 65) | Kar2 reverse primer QPCR |

To verify the length of the unspliced *P. pastoris* HAC1 gene, PCR was performed on genomic DNA using primers HAC1-Karl and HAC1Rv06-005. The length of the obtained fragment was compared with the length of a PCR product obtained from the cDNA from an induced cell culture. The amplified fragment from the genomic DNA is about 300 bp longer than the amplicon derived from the cDNA using the same primers indicating that the intron is present in the genomic DNA sequence and absent from the spliced mRNA.

The cDNA fragment of 257 bp was isolated from the gel and cloned in a sequencing vector. The fragment was sequenced and an alignment was performed in order to identify the splice site (FIG. 17). To isolate and clone the spliced *P. pastoris* HAC1 gene, PCR primers were developed with restriction enzyme sites for cloning into an expression vector (HAC1-Karl and HAC1Rv06-009). A 10 ml culture was UPR-induced with 5 mM DTT for 1.5 hours. First strand cDNA was prepared from the isolated RNA using reverse transcriptase and PCR was subsequently performed on the cDNA template DNA using the above primers. The spliced HAC1 was isolated and cloned in pCR-blunt-TOPO cloning vector for sequencing. The spliced gene was also cloned under the control of the methanol inducible AOX1 promoter in the expression vector pBLHIS IX to obtain the vector pBLHIS IX ppHAC1spliced. The correct insertion of the HAC1 gene into the expression vector was confirmed using PCR and restriction enzyme analysis.

In *Saccharomyces cerevisiae*, upon splicing, the coding sequence of the C-terminal 10 amino acids in the non-spliced mRNA is replaced with the coding sequence of 18 amino acids. In accordance, in *Pichia pastoris* it was revealed that the coding sequence of the C-terminal 45 amino acids in the non-spliced HAC1 are replaced upon splicing by the coding sequence of again 18 amino acids which are homologous to the ones from the *S. cerevisiae* sequence (FIG. 18).

Example 7

Transformation and Induction of Spliced HAC1 Gene into *Yarrowia lipolytica*

*Yarrowia lipolytica* cells (MTLY60 strain) were transformed with the vector "PYHMAXHAC1ylspliced" containing the spliced HAC1 cDNA (above) under the expression control of the hp4d promoter and the URA3 gene as a selection marker. Integration of the vector into the yeast genome was verified using PCR. The MTLY60 strain transformed with PYHMAXHAC1ylspliced was grown in a 2 ml culture in YPG at 28° C. for 24 hours. The cultured cells were washed twice with YNB, then diluted to $OD_{600}$ 0.6 and grown for 24 hours in YTG buffered with 50 mM phosphate buffer pH: 6.8. The cells were then diluted to $OD_{600}$ 0.2 and grown for 3 more generations in order to harvest the cells in the mid-exponential phase. To the pellet, 1 ml of RNApure™ solution was added to the cells along with 1 g of glass beads. Cells were broken by vigorous shaking. RNA was extracted from the broken cells by adding 150 µl chloroform and precipitating the RNA with isopropanol. The extracted RNA was also treated with DNAse to remove any coprecipitated DNA impurities.

Figure 39A:
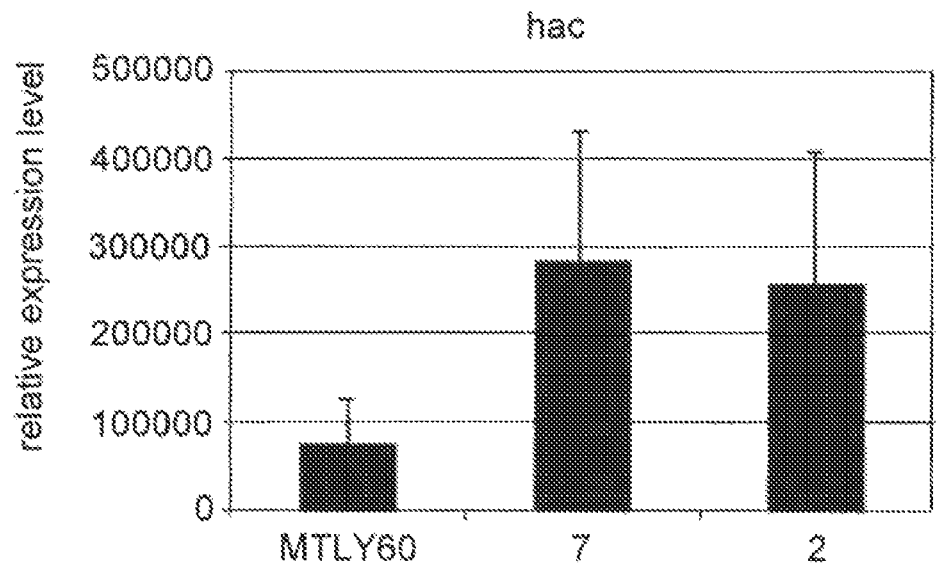
FIGS. 39A and 39B are a pair of bar graphs depicting the relative expression level (Y-axis) of the HAC1 (39A) or KAR (39B) gene in WT (MTLY60) *Yarrowia lipolytica* cells or in two clones (clone 7 and clone 2) of *Yarrowia lipolytica* cells containing a spliced form of HAC1 cDNA under the expression control of the hp4d promoter.
Figure 39B:
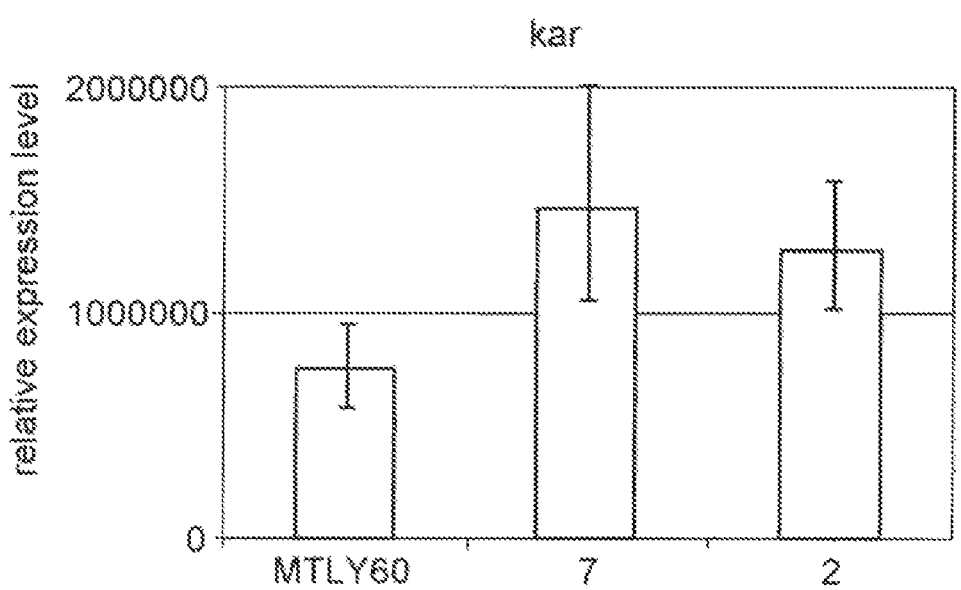

First strand cDNA was prepared from 800 ng of the RNA using the iScript™McDNA Synthesis Kit (Bio-Rad Laboratories, Hercules, Calif.) in a 20 µl total volume reaction. The equivalent of 20 ng RNA was used for real time PCR analysis to determine the amount of HAC1 mRNA in the cells. Real time PCR was run using SYBR® green as the detection reagent (fluorescent) (Eurogentec). In addition to designing primers for detecting the amount of HAC1 mRNA in the cells, primers were also designed to quantify the amount of ACT1 (household gene) and KAR2 (UPR responsive gene) genes as controls for the real time PCR. The relative amount of mRNA of each gene in the cells was calculated from the comparative threshold cycle values using Actin (a housekeeping gene) as the expression control. Induction of the UPR response by the cells was confirmed by measuring the expression of UPR. The expression levels of KAR2 as well as HAC1 are higher in the strains expressing HAC1 under control of a constitutive promoter compared to the wild type strain MTLY60 (FIG. 39).

Example 8

Transformation and Induction of Spliced HAC1 Gene into *Pichia pastoris*

Media: For the following experiments, three types of media were used: BMY (Buffered Medium for Yeast: 100 mM potassium phosphate pH:6.0/1.34% YNB without amino acids/1% Yeast extract/2% peptone); BGMY (Buffered Glycerol-complex Medium for Yeast: 100 mM potassium phosphate pH:6.0/1.34% YNB without amino acids/1% Yeast extract/2% peptone/1% glycerol); and BMMY (Buffered Methanol-complex Medium for Yeast: 100 mM potassium phosphate pH:6.0/1.34% YNB without amino acids/1% Yeast extract/2% peptone/0.5% glycerol).

Figure 19:
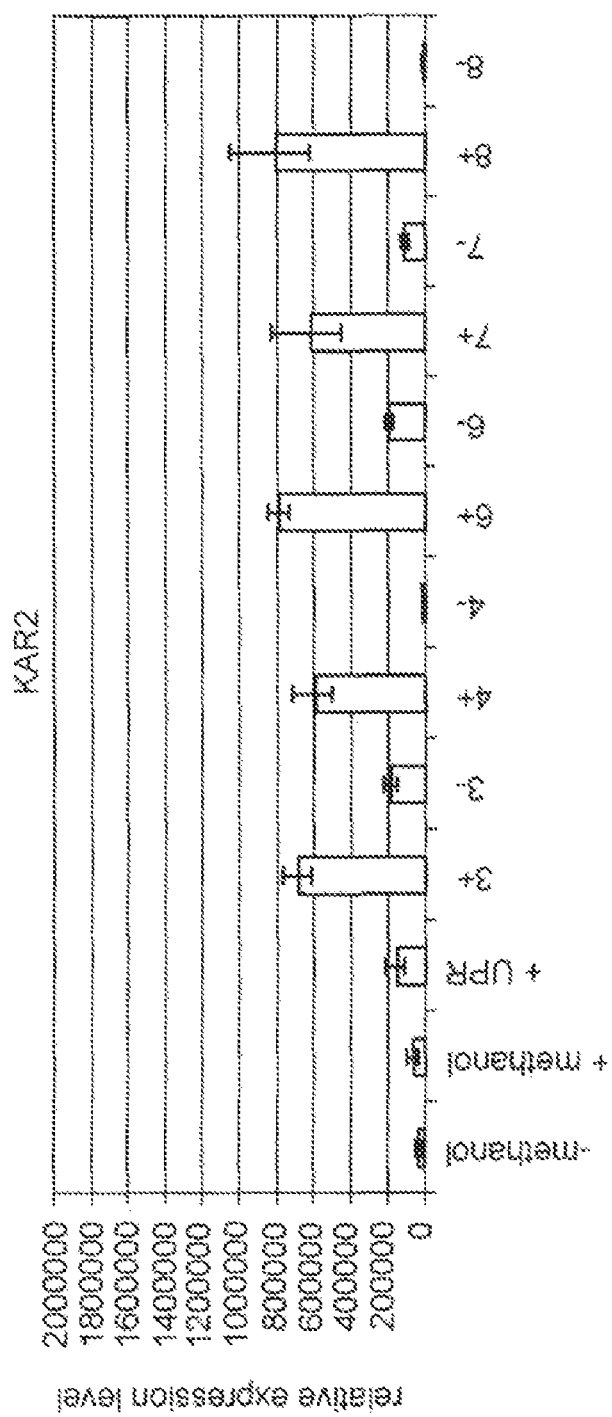
FIG. 19 is a bar graph depicting the comparison of the relative expression levels of KAR2 mRNA. Clones 3, 4, and 5 (*Pichia pastoris* GSM5 cells) were grown on methanol as carbon source. "3+," "4+," and "5+" refer to the respective clones grown on methanol as carbon source, whereas "3−," "4−," and "5−" refer to the respective clones grown on glucose as carbon source. The Y-axis represents the relative expression of the KAR2 gene using real-time PCR.

*Pichia pastoris* cells were transformed according to the electoporation protocol from the *Pichia* Expression kit (invitrogen Cat. No. K1710-01). The vector pBLHIS IX ppHAC1spliced was linearized in the HIS4 gene to target the construct to the HIS4 locus for integration. Ten micrograms of DNA was transformed into the yeast cells. The correct integration of the construct was validated using PCR on genomic DNA after isolation of single colonies (primers HAC1-Karl and HAC1Rv06-005). Fragments of 915 kb and 1237 kb were amplified from DNA obtained from the transformed cells, whereas in the non-transformants (cells without integration of the construct) a fragment of 1237 kb was amplified. Clones so identified as positive for integration of the plasmid were grown in 10 ml BMGY medium for 24 hours before induction. Cells were washed once with BMY. BMGY was added to non-induced cultures while BMY was added to the induced cultures. Every 12 hours, induced cultures were fed with 0.5% methanol (final concentration). Induction was performed for 24 hours after which cells were harvested by centrifugation. To prepare RNA, cells were combined with 1 ml RNApure™ (Genhunter Corporation, Nashville, N.Y.) and 1 g of glass beads, and lysed by vigorous shaking. RNA was extracted by the addition of 150 µl chloroform and precipitated with isopropanol. The extracted and precipitated RNA was DNAse treated with RNAse-free DNAse obtained from Qiagen (Cat No. 79254). 400 ng of total RNA was subjected to reverse transcriptase reaction using an oligodT primer and the Superscript II reverse transcriptase (Invitrogen, Cat. No. 18064-014). The equivalent of 20 ng RNA was used in a real-time PCR reaction. Primer sequences were designed by Primer Express software (Applied Biosystems) (see primer table for sequence). Real time PCR utilizing SYBR green fluorescent reagent (Eurogentec) was run in the iCycler machine from BioRad. The relative amounts of mRNA were calculated from the comparative threshold cycle values using the housekeeping gene actin as a control. Quantification of UPR is performed through expression analysis of the UPR-target gene KAR2. A 3 to 7 fold higher expression of KAR2 was obtained when comparing clones that were not induced as compared to the same clones that were induced with methanol (FIG. 19).

Figure 20:
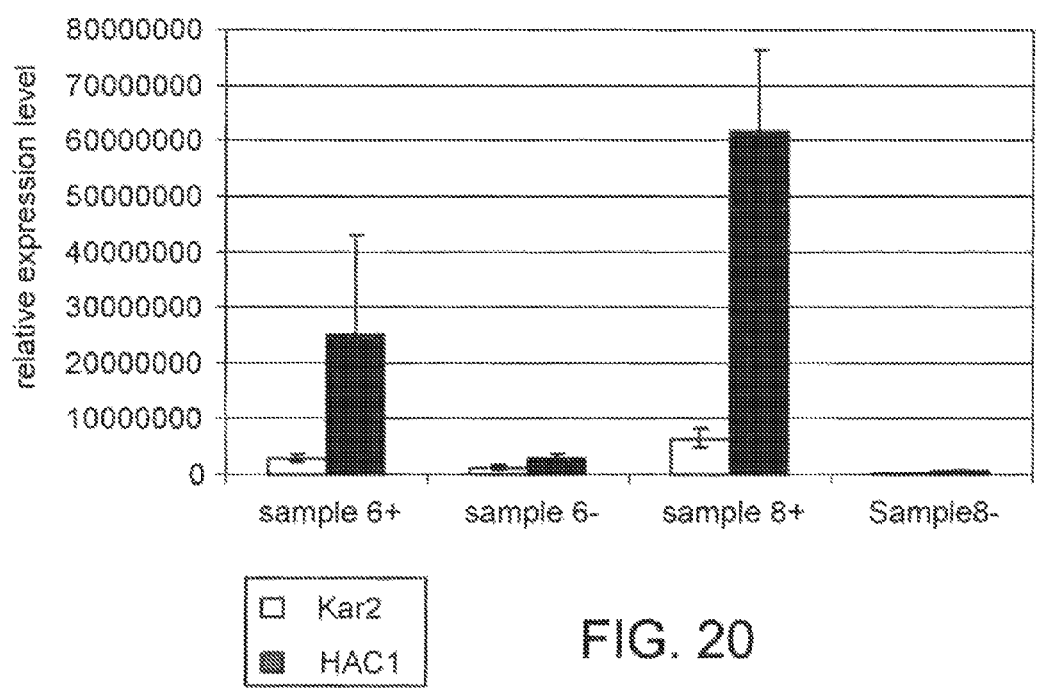
FIG. 20 is a bar graph depicting the relative expression level of Kar2 and HAC1 mRNA in two *Pichia pastoris* clones (clone 6 and 8). "6+" and "8+" refer to the respective clones grown on methanol as carbon source, whereas "6−" and "8−" refer to the respective clones grown on glucose as carbon source. The Y-axis represents the relative expression of the KAR2 gene using real-time PCR.

The relative amount of HAC1 mRNA from two additional clones 6 and clone 8 was determined by quantitative PCR and compared with the relative amount of mRNA of Kar2. A strong induction of HAC1 was observed in both clones. The relative amount of KAR2 mRNA appeared to correlate with the relative amount of HAC1 mRNA, higher expression levels of HAC1 lead to higher expression level of KAR2 (FIG. 20).

Cell death studies of the methanol-induced cultures were performed using fluorescence flow cytometry (FFC) and compared to cell death of non-induced cultures. Ten thousand cells were measured per analysis. Cells were analyzed on the FACScalibur™ (Becton Dickinson) after 12, 36 and 48 hours of induction. No cell death was observed. The GlycoSwitchM5 (GSM5) strain has as main core type glycan structures mainly $Man_5GlcNAc_2$ (structural formula IV; FIG. 4). In order to check if Hac1p induction has an influence on the N-glycan structure a DSA-FACE analysis was performed of 1 ml of the culture medium. The glycan profiles obtained after 48 hours of induction of spliced Hac1p are similar to the profile of the parental GSM5 strain.

Figure 22:
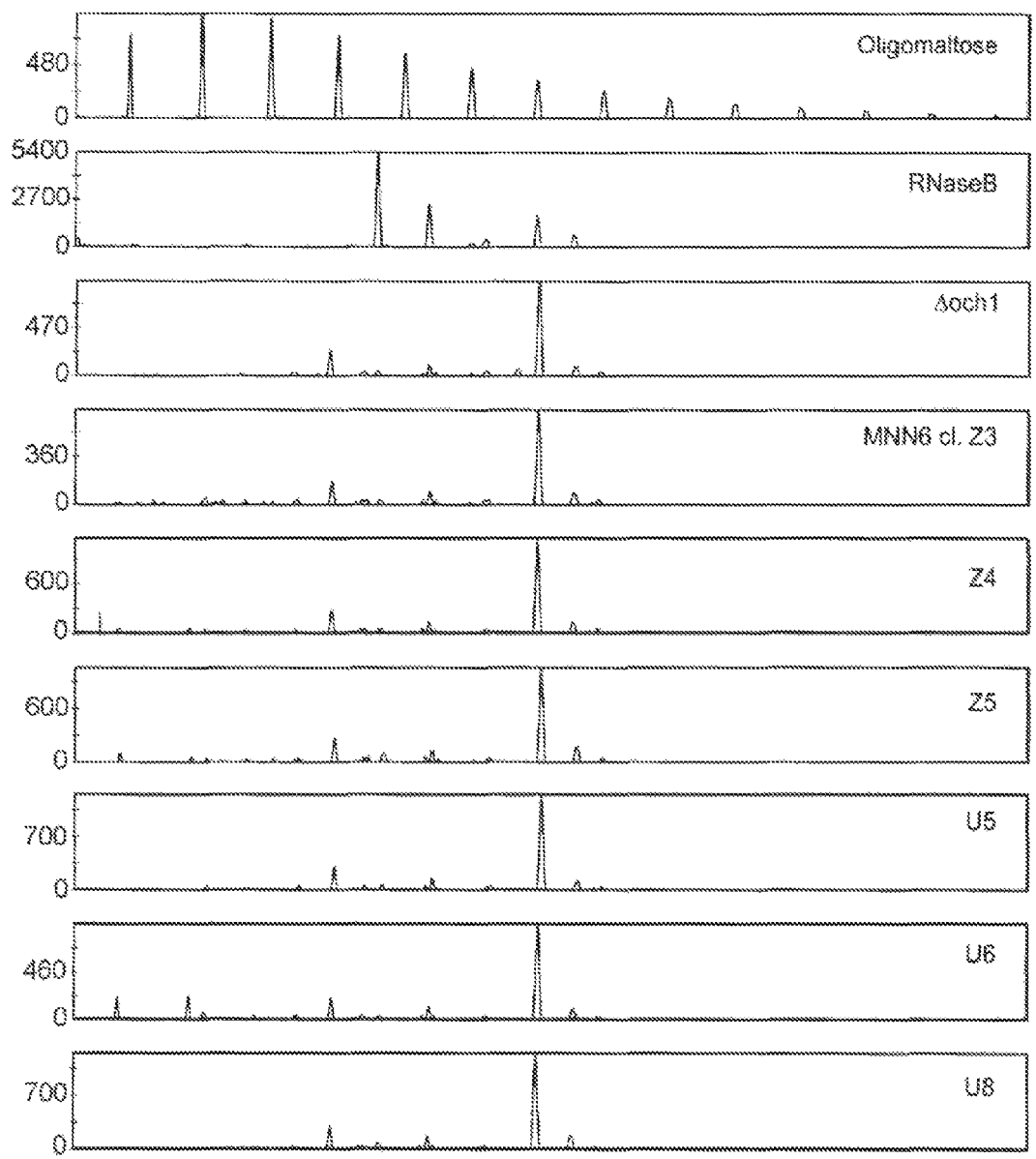
FIG. 22 is a series of electroferograms depicting N-glycan analysis of glycoproteins obtained from Δoch1 *Y. lipolytica* cells, alone, or various clones (Z3, Z4, Z5, U5, U6, and U8) of Δoch1 *Y. lipolytica* expressing YlMNN6 as indicated. Analysis was performed using DSA-FACE. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.

A growth curve was made in order to check if the induction of Hac1p impairs the growth of *P. pastoris*. No growth defect was seen of the Hac1p induced strain compared to the empty vector transformed strain (FIG. 22).

Example 9

Expression of YlMNN6

Figure 21:
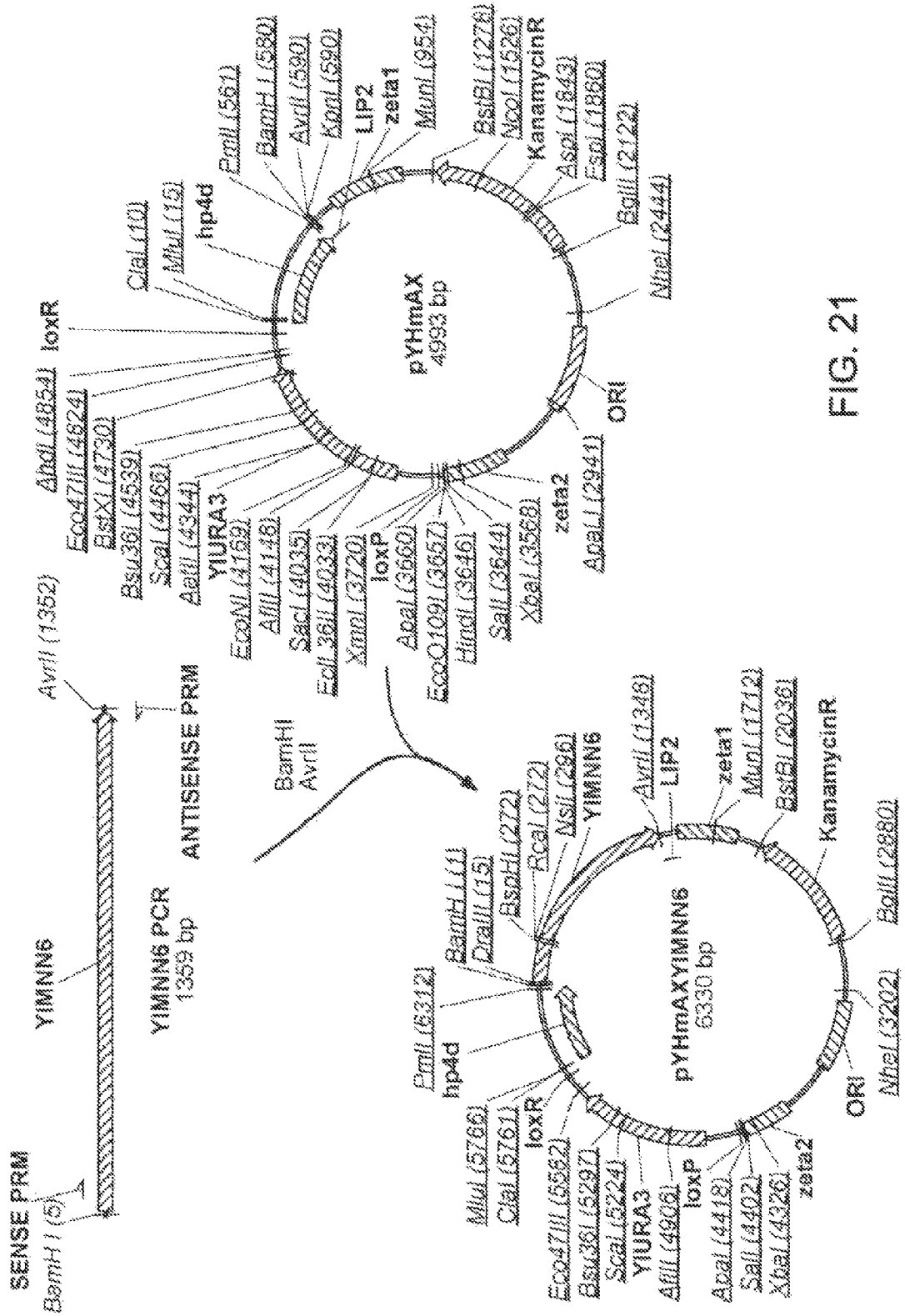
FIG. 21 is a schematic diagram depicting the cloning strategy for a YlMNN6 expression vector.

In *S. cerevisiae*, MNN6 transfers phosphomannose residues to N-glycans. Therefore, overexpression of YlMNN6 in *Y. lipolytica* could lead to increased phosphorylation. Moreover, an additional effect on phosphorylation *Y. lipolytica* be obtained by over expressing YlMNN4 and YlMNN6. The YlMNN6 coding region (Genbank® Accession No. XM_499811, Genolevures Ref: YALI0A06589g) was PCR amplified from the genome using PCR primers YlMNN6 BamHI fw (GCGGGATCCATGCACAACGTGCAC-GAAGC (SEQ ID NO:34)) and YlMNN6 AvrII rv (GCGC-CTAGGCTACCAGTCACTATAGTTCTCC (SEQ ID NO:35)) and cloned in the pYHmAX expression vector for expression under control of the hp4d promoter (FIG. 21). The plasmid was transformed to the *Y. lipolytica* strain MTLY60 using zeta sequences to improve random integration. Secreted glycoproteins were collected from cell clones that grew on medium without uracil and the composition of the glycans synthesized the glycoproteins was analyzed using DSA-FACE. However, no increased phosphorylation was observed (FIG. 22).

Example 10

Effects of Hac1p Expression

Evaluation of Hac1p overexpression on the secretion of heterologous proteins. Vectors containing the hygromycin resistance marker and the spliced HAC1 cDNA under control of the inducible AOX1 promoter (pPIChygppHAC1spliced) or under control of the constitutive GAP promoter (pGAPhygHAC1ppspliced) were transformed to a GS115 strain expressing a mIL-10 protein under the control of the inducible AOX1 promoter. *P. pastoris* cells were transformed according to the electroporation protocol from the *Pichia* Expression kit (Invitrogen Cat. No. K1710-01, Invitrogen, Carlsbad, Calif.). The vectors were linearized in the AOX1 or GAP promoter to target the integration of the Hac1p gene to respectively the AOX1 or GAP locus. Integration of the plasmid into the host genome was confirmed using PCR.

Precultures (5 ml) from positive identified clones were grown in YPD for 24 hours. The concentration (OD) at a wavelength of 600 nm ($OD_{600}$) of the cells in the cultures was measured and cultures were diluted to an $OD_{600}$ of 1 in 2 ml of BMGY media in each well of a 24 well plate. Cultures were grown in BMGY for 48 hours, washed twice with BMY, and then induced for 24 hours in BMMY. Every 8 to 12 hours, cultures were re-fed with medium containing 1% methanol (final concentration). After induction, the supernatant of the cells was harvested and the protein from 1 ml of the supernatant was precipitated using trichloroacetic acid (TCA). The precipitated protein was subjected to 15% SDS-PAGE.

Figure 40:
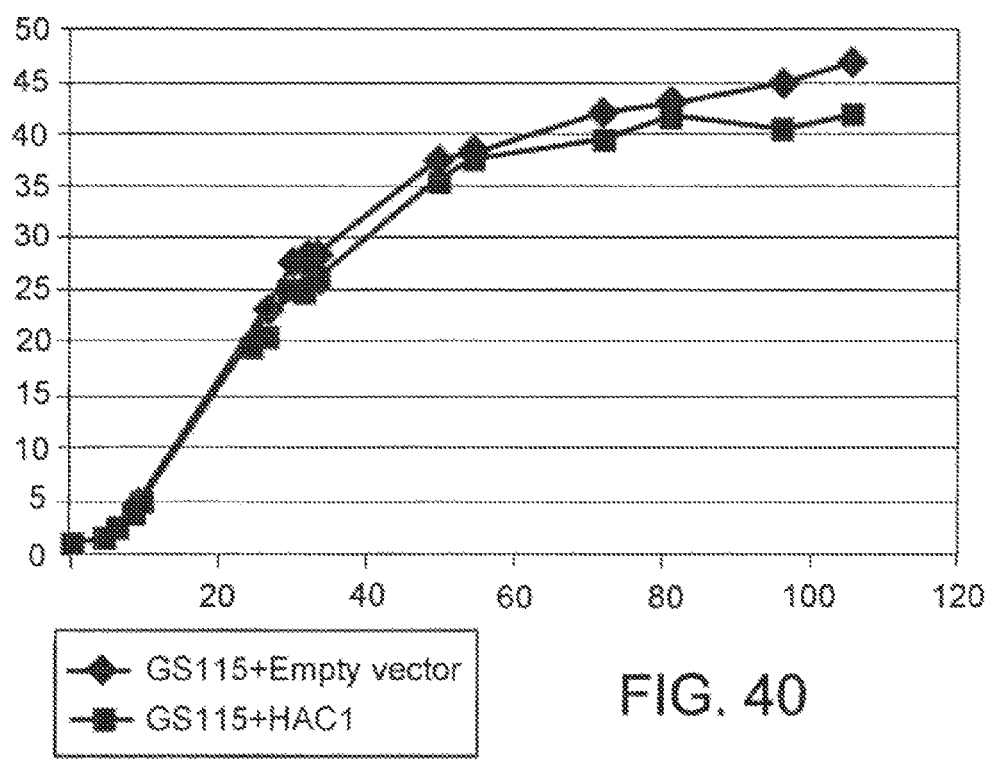
FIG. 40 is line graph depicting the growth of wild type *Pichia pastoris* GS115 cells transformed with an empty vector as compared to the growth of *Pichia pastoris* GS115 cells expressing the Hac1p protein.
Figure 41:
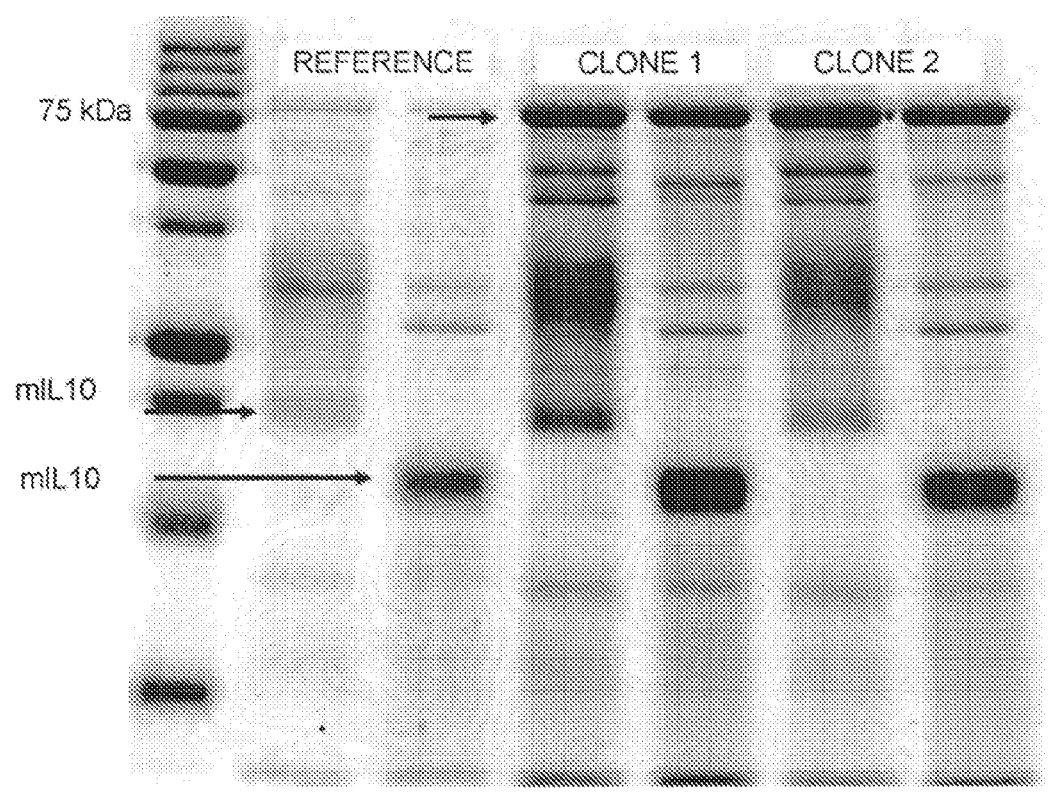
FIG. 41 is a photograph of a Coomassie blue stained polyacrylamide gel comparing the expression level of the murine IL-10 (mIL-10) protein from a culture of *Pichia pastoris* GS115 cell cells expressing mIL-10 protein with the expression of the mIL-10 protein obtained from a culture of GS115 cells expressing mIL-10 and the spliced HAC1 protein from *Pichia pastoris* under the control of an inducible promoter, AOX1. The following samples were resolved in the gel: Lane 1 ("ladder"), a combination of proteins of known molecular weight; Lane 2 ("Reference"), protein obtained from the reference mIL-10 expressing *Pichia pastoris* strain (GS115); Lane 3 ("Reference"), protein obtained from the reference mIL-10 expressing *Pichia pastoris* strain after PNGase F enzyme treatment of the proteins; Lane 4 ("Clone 1"), protein obtained from a mIL-10 expressing *Pichia pastoris* cells inducibly expressing HAC1 protein; Lane 5 ("Clone 1"), protein obtained from a mIL-10 expressing *Pichia pastoris* cells inducibly expressing HAC1 protein after treatment of the protein with PNGase F enzyme; Lane 6 ("Clone 2"), protein obtained from a mIL-10 expressing *Pichia pastoris* cells inducibly expressing HAC1 protein 1; Lane 7 ("Clone 2"), protein obtained from a mIL-10 expressing *Pichia pastoris* cells inducibly expressing HAC1 protein after treatment of the proteins with PNGase F enzyme.

From the SDS-PAGE, clonal variation in the expression of at least one protein—mIL-10—was observed between the different clones. For example, for the clones expressing the Hac1p protein constitutively (under control of GAP promoter), no improvement in expression level was observed, whereas for the clones expressing the Hac1p inducibly (AOX1 promoter), two clones could be identified that exhibited higher expression levels of the mIL-10 protein (FIG. 40 and FIG. 41). Expression of mIL-10 by each of the clones was compared to the expression of mIL-10 produced by a reference GS115 mIL-10 expressing strain.

A new induction was performed for these clones. A preculture grown for 24 hours was diluted to OD 1 in 20 ml BMGY in a baffled flask. Cells were grown for 48 hours in BMGY, washed twice, and then induced in BMMY. Cultures were re-fed with medium containing 1% methanol every 8-12 hours. After induction, the supernatant of the cells was harvested and the protein from 1 ml of the supernatant was precipitated using TCA. Prior to subjecting the precipitated protein to 15% SDS-PAGE, the protein was treated with PNGase F (or not) to remove all glycosylation (FIG. 41). SDS-PAGE resolved proteins from the supernatant of Hac1p-expressing strains contained a prominent band of 75 kDa, which is not present in the reference strain. This band was identified by means of mass spectrometry as being Kar2p, which is the most prominent UPR target gene. It could be shown using the cytokine bead array (CBA) that simultaneous inducible expression of the Hac1p and the mIL-10 protein can lead to a 2 fold higher expression of the mIL-10 protein (clone 1, FIG. 41). CBA was performed on endoH treated mIL-10 protein.

Evaluation of Hac1p overexpression on the surface expression of heterologous proteins. Vectors containing the hygromycin resistance marker and the spliced HAC1 cDNA under control of the inducible AOX1 promoter (pPIChygppHAC1spliced) or under control of the constitutive GAP promoter (pGAPhygHAC1ppspliced) were transformed to GlycoswitchMan5 strains expressing a mature human interferon-beta/alpha-agglutinin fusion protein, a mature mouse interferon gamma/alpha-agglutinin fusion protein, a mature human erythropoietin/alpha-agglutinin fusion protein, or a fusion protein of alpha-agglutinin and the lectin-like domain of mouse thrombomodulin, each of which were under the control of the inducible AOX1 promoter. *P. pastoris* cells were transformed according to the electroporation protocol from the *Pichia* Expression kit (Invitrogen Cat. No. K1710-01). The vectors were linearized in the AOX1 or GAP promoter to target the Hac1p gene to respectively the AOX1 or GAP locus for integration. Integration of the plasmid into the host genome was confirmed using PCR.

Precultures (5 ml) from positive identified clones were grown in YPD for 24 hours. The $OD_{600}$ was measured and cultures were diluted to $OD_{600}$ of 1 in 2 ml BMGY in each well of a 24 well plate. The cultures were grown in BMGY for 24 hours, washed twice with dionized water, and then induced (using culture medium containing 1% methanol) for 24 hours in BMMY. Surface expression was demonstrated by indirect immunostaining with an antibody specific for the V5-epitope, which is fused C-terminally to the $V_HH$ coding sequence. After induction, $10^7$ cells in 1 ml PBS (pH 7.2), supplemented with 0.1% bovine serum albumin (PBS/BSA), were incubated with 1 µl/ml of the anti-V5 antibody (1 µg/µl; Invitrogen), washed with PBS/BSA, and incubated with 1 µl/ml Alexa fluor 488-labeled goat anti-mouse IgG (1 µg/µl; Molecular Probes). After washing twice with PBS/BSA, the cells were analyzed by flow cytometry (Table 5).

TABLE 5

MFI values determined by flow cytometry

| Expressed Protein | Wild-type Pichia | Pichia + AOX GAP | Pichia + GAP HAC |
|---|---|---|---|
| mouse Interferon-gamma | 36.6 | 19.9 | 42.8 |
| human EPO | 59.5 | 45.8 | 66.5 |
| interferon-beta | 22.6 | 12.4 | 14.4 |
| human thrombomodulin | 95.5 | 184.1 | 67.8 |

MFI = Mean Fluorescence Intensity obtained from the flow cytometry analysis.

For the strains expressing the Hac1p protein constitutively no improvement, or very minor differences, could be observed in surface expression levels for all four proteins compared to reference strains expressing the surface protein alone. In cells expressing human interferon-beta, a significant reduction of surface expression levels was observed. For the strains overexpressing the inducible Hac1p (Table 5) the following could be observed: 1) in the human interferon-gamma surface expressing strain, a 1.8-fold lowering of the surface expression levels could be observed compared to the reference strain expressing alone the human interferon-beta a-agglutinin fusion; 2) for the strain surface-expressing human erythropoietin a-agglutinin fusion protein, a 1.3-fold lowering of the surface expression levels could be observed compared to the reference strain; 3) in the strain surface expressing human interferon-beta, no difference of the surface expression levels could be observed compared to the reference strain; and 4) in the strain surface expressing mouse thrombomodulin lectin-like domain, an 1.9-fold increase of the surface expression levels could be observed compared to the reference strain.

Figure 54:
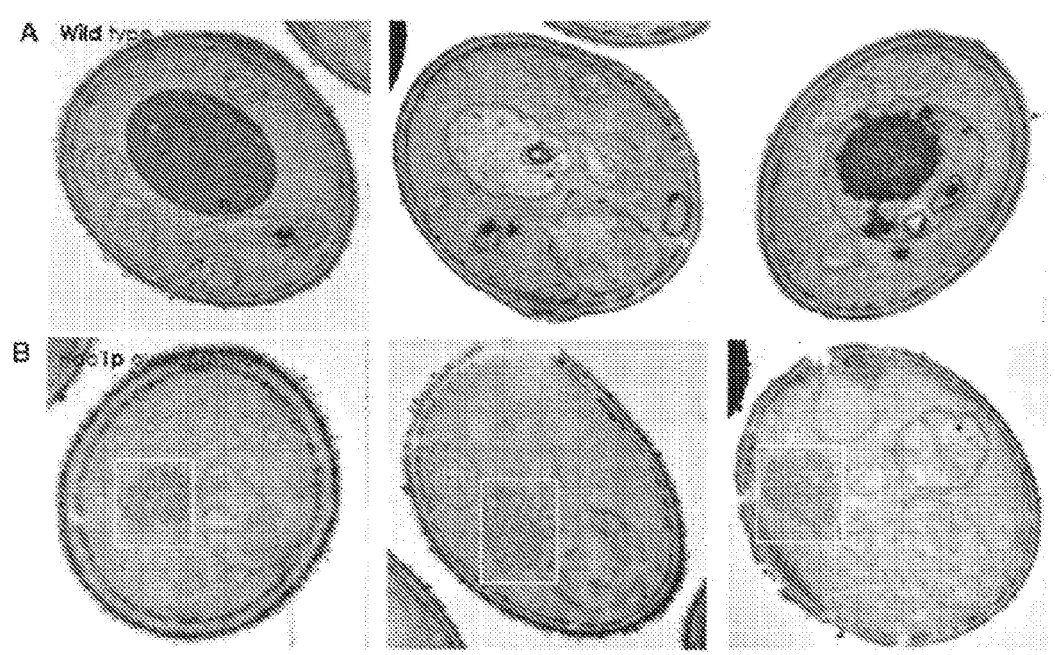
FIG. 54 is a series of electron micrographs of wild type *Pichia pastoris* cells or *Pichia pastoris* cells overexpressing the spliced form of Hac1p protein. Discrete regions of stacked lipid membranes in the cells are boxed.

Effect of overexpression of Hac1p on phospholipid synthesis. To determine whether overexpression of the Hac1p product (produced from the spliced HAC1 cDNA) had an effect of lipid metabolism in *P. pastoris*, cells were transformed with the above-described spliced HAC1 cDNA and the effect of Hac1p on lipid metabolism in the cells was determined by electron microscopy analysis. Cells were grown for 48 hours on BMGY, washed once with PBS, and then grown for another 48 hours on BMMY. The cells were next cultured in medium containing 1% methanol every 8 to 12 hours. The cells were then prepared for electron microscopy according to the method of Baharaeen (Baharaeen et al. (2004) Mycopathologia). Briefly, a primary fixative containing glutaraldehyde (3%) and para-formaldehyde (1.5% buffered in 0.05 M sodium cacodylate at pH 7.2) was contacted with the cells for 2 hours on ice. The cells were then washed three times for 20 minutes with 0.05 M sodium cacodylate. After washing, the cells were contacted with a 6% potassium permanganate solution for one hour at room temperature and then washed with 0.05 M sodium cacodylate three times for 20 minutes. The results of the experiment are presented in FIG. 54. Overexpression of the Hac1p product (produced from the spliced HAC1 cDNA) in *P. pastoris* lead to the formation of discrete regions of stacked membranes as can be shown in the electron micrograph (EM) depicted in FIG. 54. These results demonstrate that overexpression of Hac1p, by way of its transcriptional activation of genes involved in lipid metabolism, indeed has a strong effect on lipid metabolism in *P. pastoris*.

Example 11

Expression of ManHDEL

Figure 23:
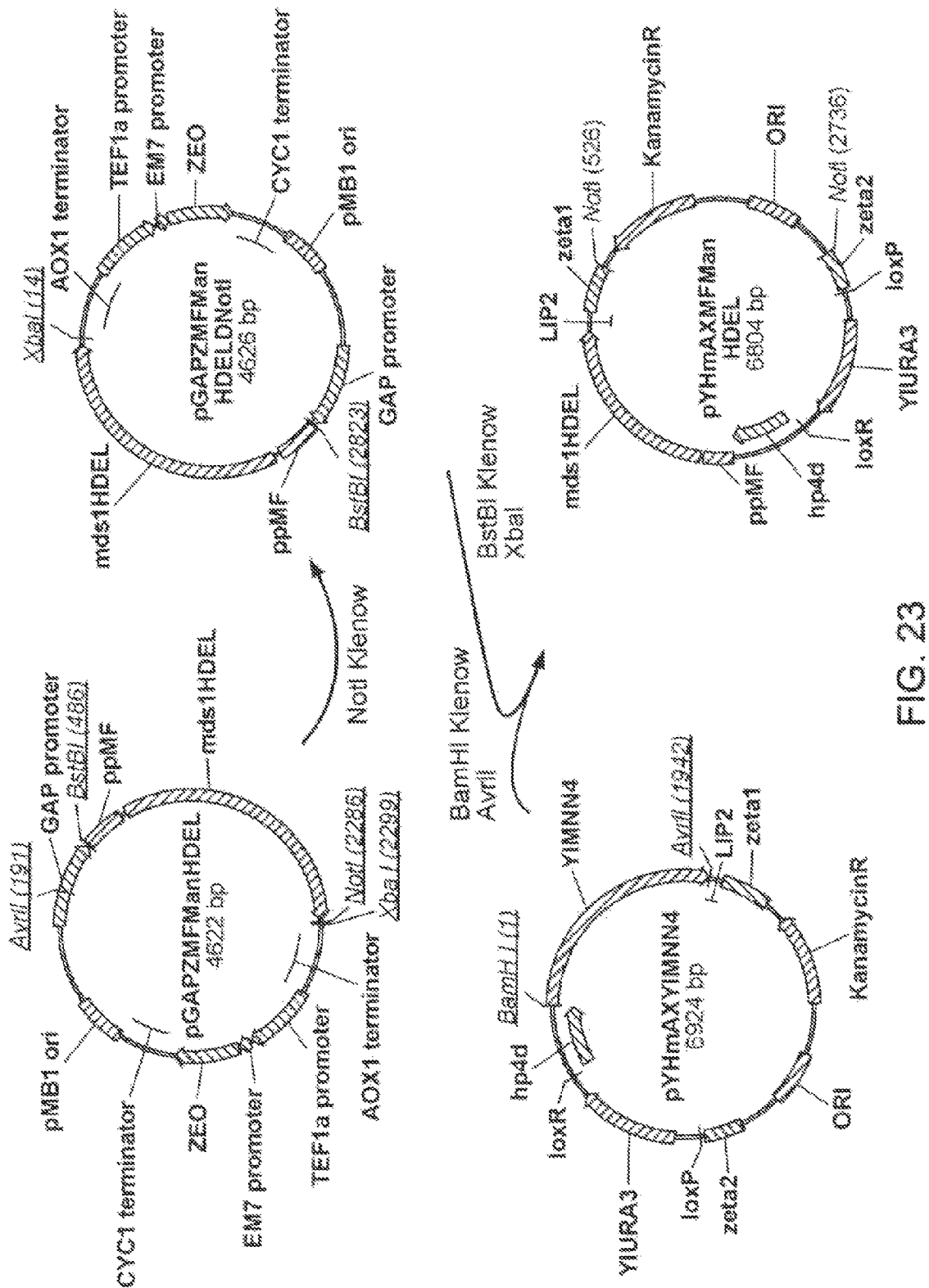
FIG. 23 is a schematic diagram depicting the cloning strategy for an MFManHDEL expression vector.

For $Man_5GlcNAc_2$ to be bound to glycoproteins expressed by the Δoch1 strain, an α-1,2-mannosidase can be expressed to cleave $Man_8GlcNAc_2$ to $Man_5GlcNAc_2$ (i.e., Golgi type α-1,2-mannosidase activity). This mannosidase should be targeted to the secretion system. *Trichoderma reesei* α-1,2-mannosidase (Genbank® accession no. AF212153), fused to the *S. cerevisiae* prepro mating factor and tagged with a HDEL sequence, is able to trim $Man_8GlcNAc_2$ to $Man_5GlcNAc_2$ in vivo in *Pichia pastoris* as well as in *Trichoderma reesei* and *Aspergillus niger*. An expression construct was made to overexpress MFManHDEL (*S. cerevisiae* α-mating factor prepro fused to *Trichoderma reesei* α-1,2-mannosidase tagged with an HDEL sequence) in *Y. lypolytica* under control of the constitutive hp4d promoter (FIG. 23). The expression cassette was transformed into the cells after digestion of the plasmid pYHmAXManHDEL with the restriction enzyme NotI, followed by isolation of the desired fragment using agarose-gel electrophoresis.

Figure 24:
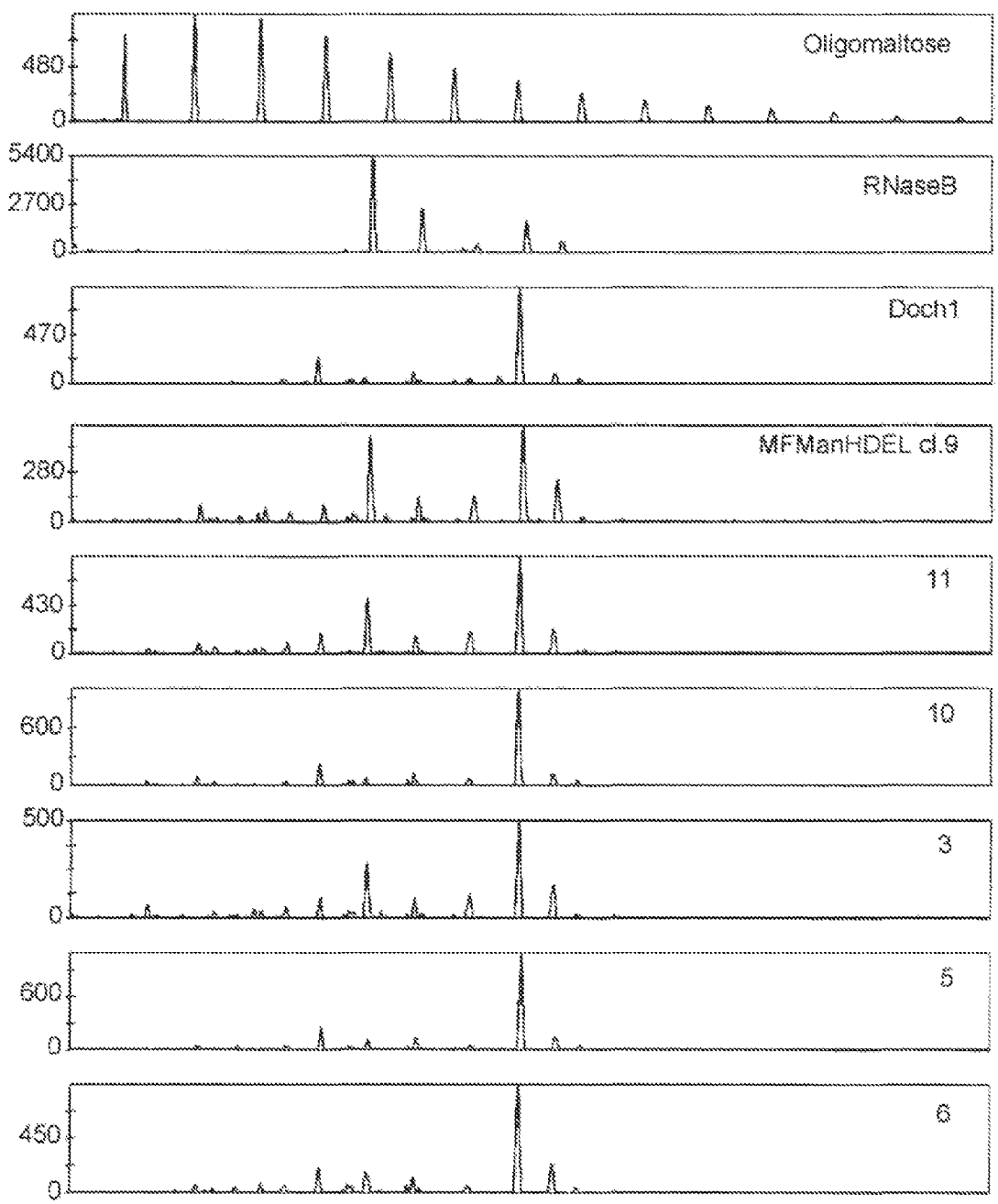
FIG. 24 is a series of electroferograms depicting N-glycan analysis of glycoproteins obtained from Δoch1 *Y. lipolytica* cells, alone, or various clones (9, 11, 10, 3, 5, and 6) of Δoch1 *Y. lipolytica* expressing MFManHDEL as indicated. Analysis was performed using DSA-FACE. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.
Figure 25A:
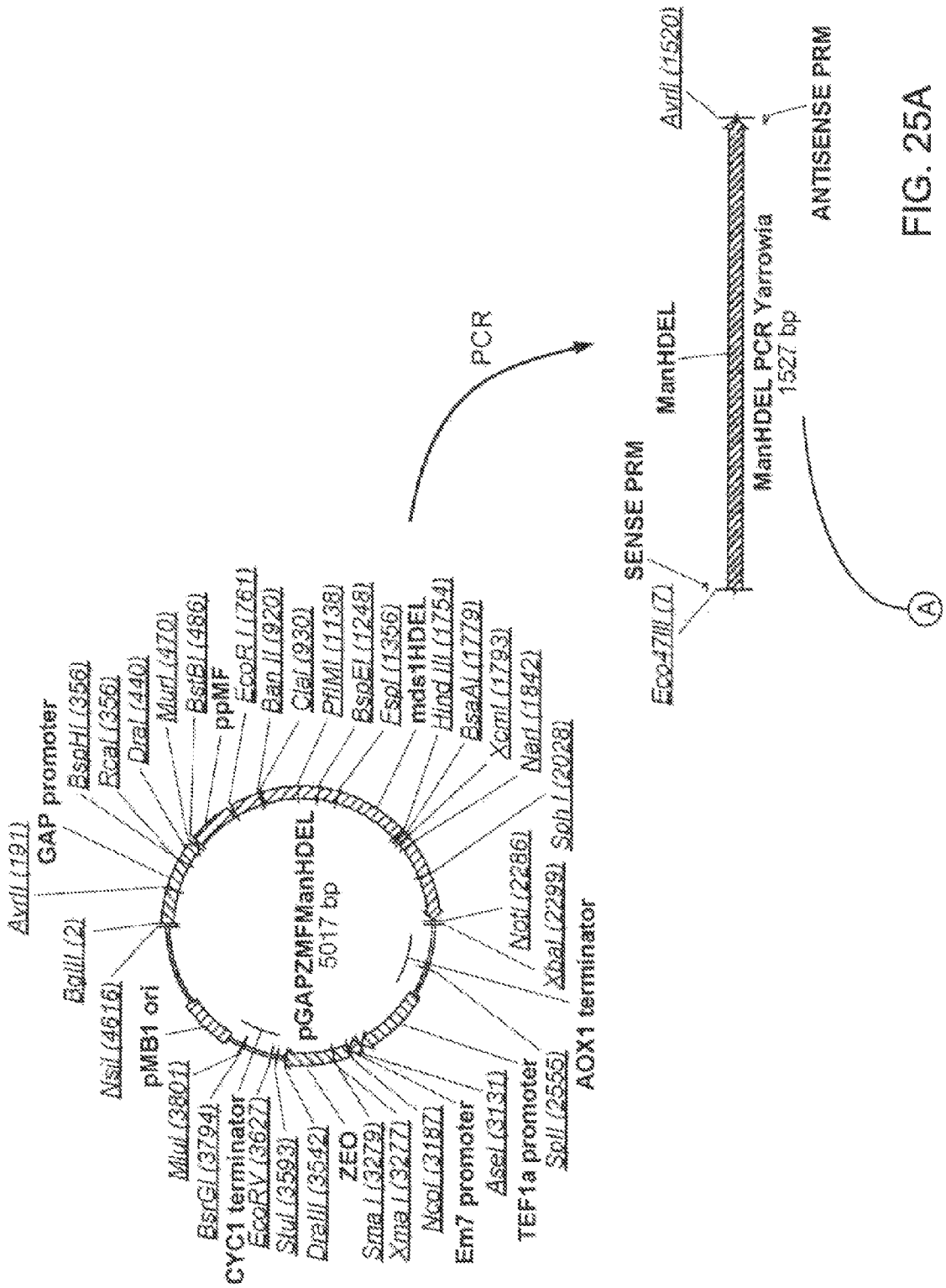
FIGS. 25A and 25B are schematic diagrams depicting the cloning strategy for an LIP2preManHDEL expression vector.
Figure 25B:
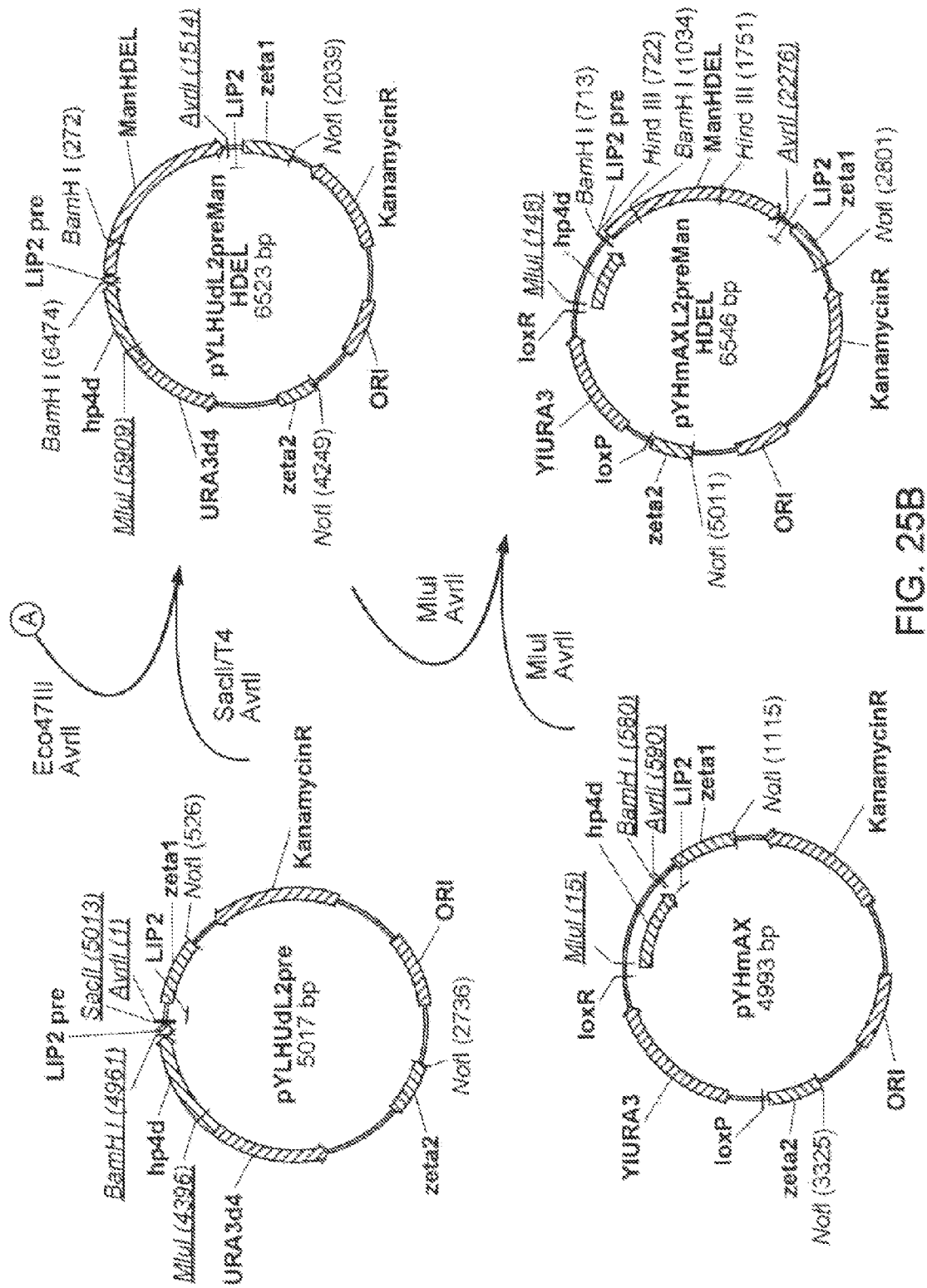
Figure 26:
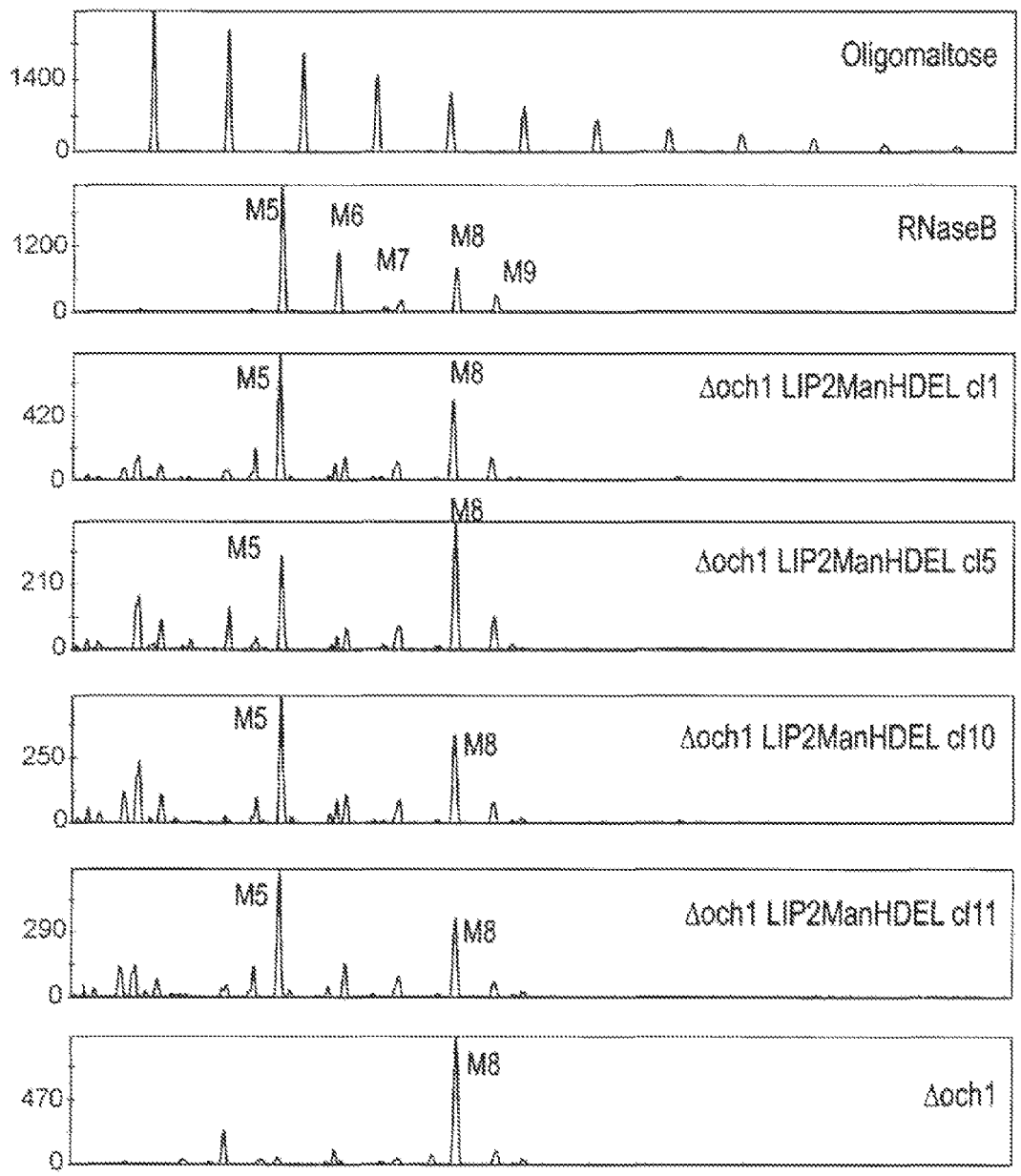
FIG. 26 is a series of electroferograms depicting N-glycan analysis of glycoproteins obtained from Δoch1 *Y. lipolytica* cells, alone, or various clones (1, 5, 10, and 11) of Δoch1 *Y. lipolytica* expressing LIP2ManHDEL as indicated. Analysis was performed using DSA-FACE. "M5," "M6," "M7," "M8," and "M9," refer to the number of mannose residues conjugated to the chitobiose core structure. The Y-axis represents the relative fluorescence units as an indication of the amount of each of the mannose structures. The X-axis represents the relative mobility of each complex mannose structure through a gel. The top electroferogram is an analysis of oligomaltose for use as a mobility standard.

Glycans derived from mannoproteins from the transformed cells were analysed using DSA-FACE. Only A minor fraction of $Man_8GlcNAc_2$ was converted to $Man_5GlcNAc_2$ (FIG. 24). Incomplete conversion of $Man_8GlcNAc_2$ to $Man_5GlcNAc_2$ could have been due to a non-optimal secretion signal. Therefore, the *Saccharomyces cerevisiae* secretion signal was replaced with the secretion signal derived from the well expressed *Yarrowia lipolytica* LIP2 (LIP2pre). The LIP2pre sequence was made by hybridizing the synthetic oligonucleotides LIP2pre fw GATCCATGAAGCTTTC-CACCATCCTCTTCACAGCCTGCGCTAC-CCTGGCCGCGGTAC (SEQ ID NO:66) and Lip2prepro rv GTACCGGCCGGCCGCTTCTGGAGAACT-GCGGCCTCAGAAGGAGTGATGGGGGAAGG GAGGGCGGC (SEQ ID NO:67) and cloning the DNA into pYLHmA vector (at the BamHI/AvrII sites) resulting in the following construct: pYLHUdL2pre. The ManHDEL coding sequence was PCR amplified from pGAPZMFManHDEL using oligonucleotides ManHDEL Eco47III fw (GGCAGCGCTACAAAACGTGGATCTCCCAAC (SEQ ID NO:68)) and ManHDEL AvrII rv (GGCCCTAGGTTA-CAACTCGTCGTGAGCAAG (SEQ ID NO:69)) and cloned in pYLHUdL2pre. The construction strategy is depicted in FIGS. 25A and 25B. The expression cassette (with L2preManHDEL under control of the constitutive promoter hp4d) was transformed to *Yarrowia lipolytica* Δoch1 strain after digestion of the plasmid with NotI and isolation of the correct fragment (see above). Glycans derived from secreted proteins were analysed via DSA FACE. Some conversion of $Man_8GlcNAc_2$ to $Man_5GlcNAc_2$ occurred, but the reaction was incomplete ($Man_8GlcNAc_2$ was present as well as intermediate products $Man_7GlcNAc_2$ and $Man_6GlcNAc_2$; FIG. 26).

To further improve the trimming of $Man_8GlcNAc_2$, $Man_7GlcNAc_2$, and $Man_6GlcNAc_2$ to $Man_5GlcNAc_2$, the *Trichoderma reesei* α-1,2 mannosidase was codon optimized for expression in *Yarrowia lipolytica* (SEQ ID NO:9; FIG. 42) and fused to the LIP2 pre signal sequence. This fusion construct was expressed under control of 4 different promoters: (i) hp4d, (ii) GAP(SEQ ID NO:10; FIG. 43), (iii) POX2, and (iv) TEF1. Final expression plasmids were named pYLHUXdL2preManHDEL (SEQ ID NO: 11; FIGS. 44A-C) pYLGUXdL2preManHDEL (SEQ ID NO:12; Figs.45A-C) pYLPUXdL2preManHDEL (SEQ ID NO:13; FIGS. 46A-C) pYLTUXdL2preManHDEL (SEQ ID NO:14; FIGS. 47A-C). All 4 plasmids were transformed to *Yarrowia lipolytica* MTLY60 Δoch1 strain (described in example 2) after cutting the plasmid with NotI and isolation of the fragment containing the ManHDEL expression cassette. Transformed strains with the ManHDEL under control of the hp4d, GAP and TEF promoter (plasmids pYLHUXdL2preManHDEL, pYLGUXdL2preManHDEL and pYLTUXdL2preManHDEL) were grown in YPD.

Figure 48:
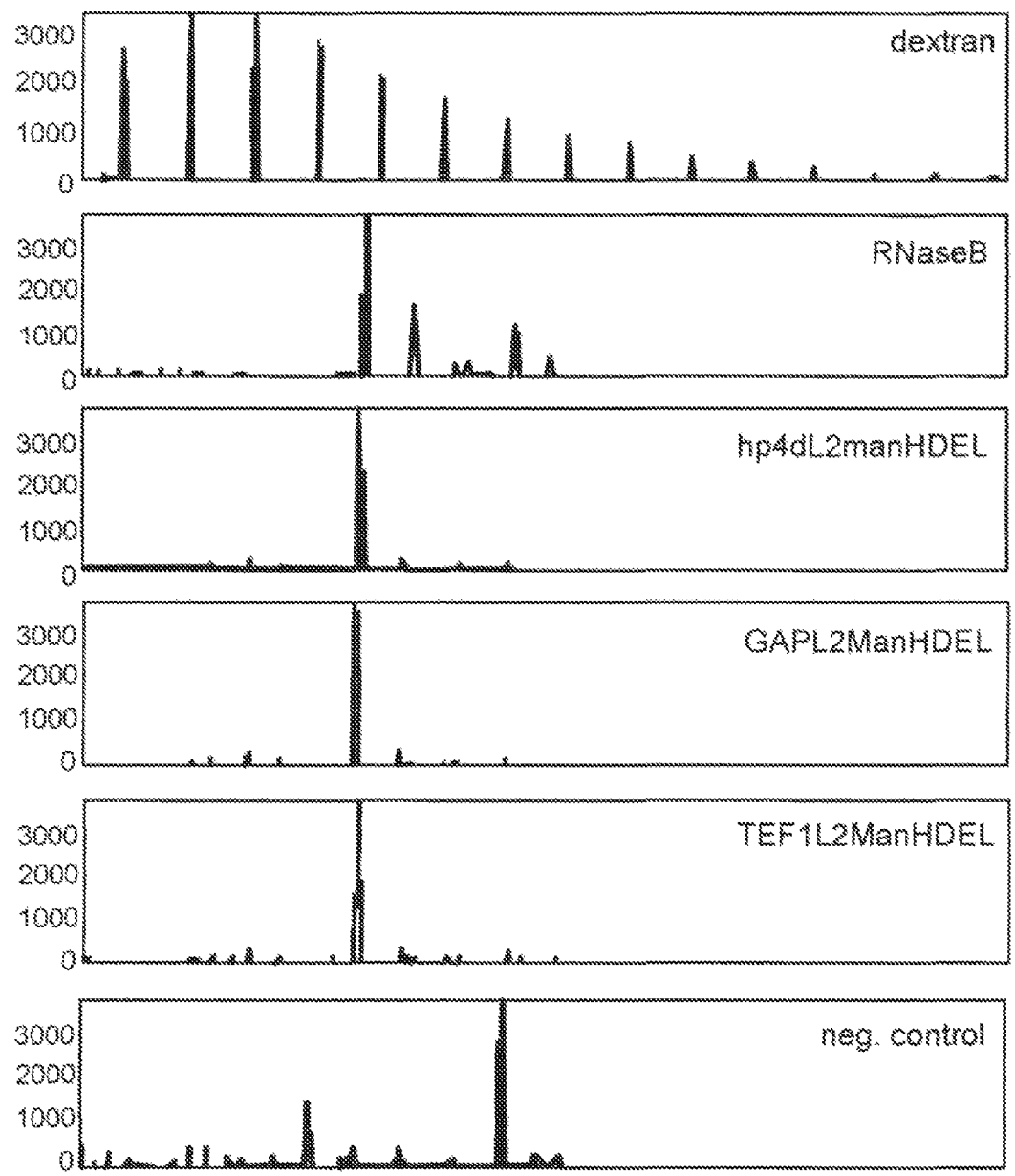
FIG. 48 is a series of electroferograms depicting N-glycan analysis of glycoproteins obtained from *Yarrowia lipolytica* cells transformed with different expression vectors as indicated: "hp4dL2ManHDEL" (pYLHUXdL2preManHDEL, FIGS. 44A-44C); "GAPL2ManHDEL" (pYLGUXdL2preManHDEL, FIGS. 45A-45C); "TEF1L2ManHDEL" (pYLTUXdL2preManHDEL, FIGS. 47A-47C). The Y-axis represents the relative fluorescence units as an indication of the amount of each of the mannose structures. The X-axis represents the relative mobility of each complex mannose structure through a gel. The top electroferogram is an analysis of dextran for use as a mobility standard. The second electroferogram in the series is an analysis of RNAse B.
Figure 49:
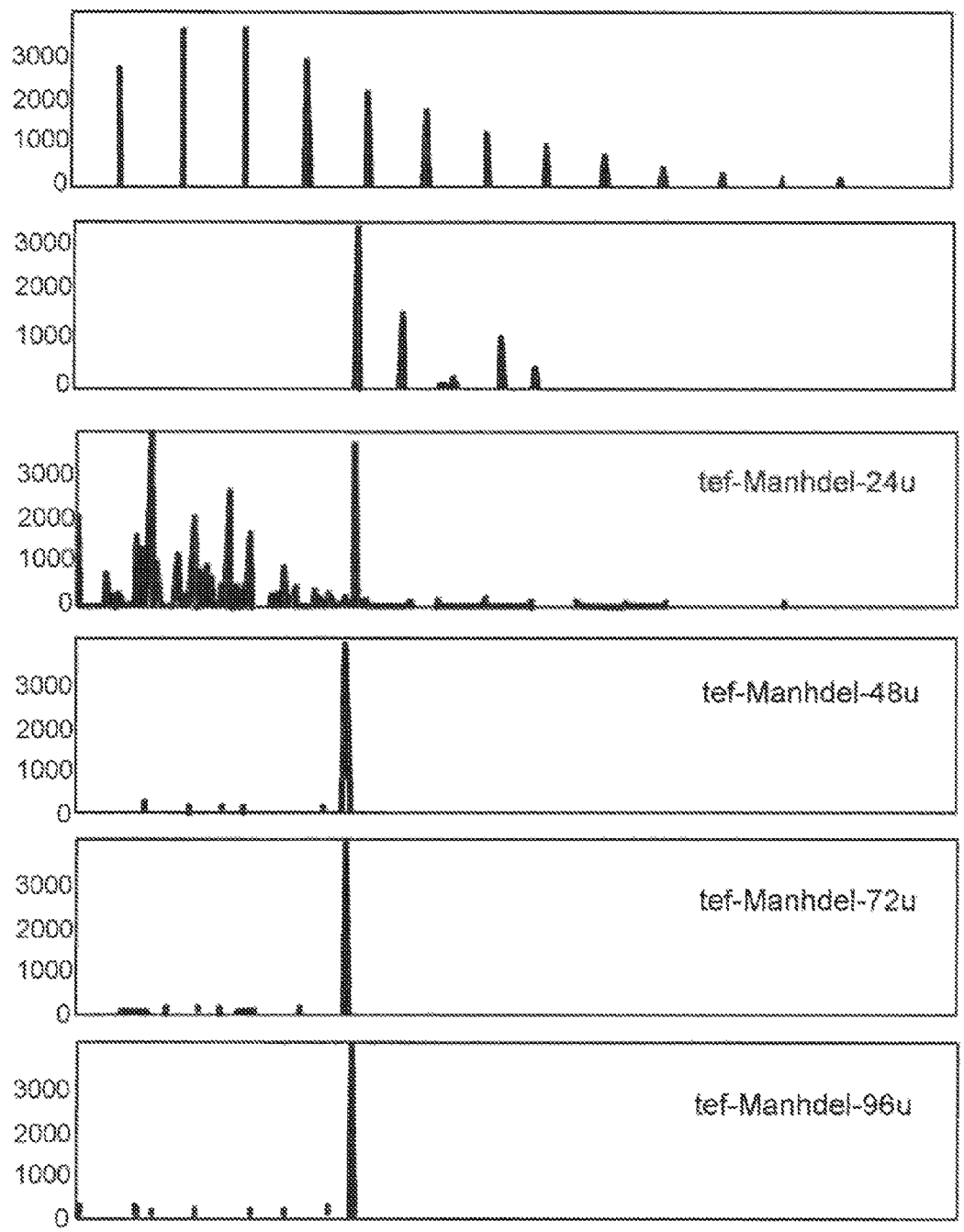
FIG. 49 is a series of electroferograms depicting N-glycan analysis of glycoproteins obtained from *Yarrowia lipolytica* MTLY60 Δoch1 cells containing a stably integrated expression vector pYLTUXdL2preManHDEL (FIGS. 47A-47C). Glycoprotein samples were obtained from cell cultures at 24, 48, 72, and 96 hours. The top electroferogram is an analysis of dextran for use as a mobility standard. The second electroferogram in the series is an analysis of RNAse B.

Glycans derived from secreted proteins of transformed strains were analyzed by DSA FACE. Results are represented in FIG. 48. Alternatively, transformants (including a transformant that had integrated the pYLPUXdL2preManHDEL plasmid) were grown in medium containing oleic acid (protein production conditions) and glycans were analysed via DSA-FACE. Data for one of the vectors, pYLTUXdL2preManHDEL, are presented in FIG. 49. As can be concluded from the data, by 48 hours of culture, almost all glycans are converted to $Man_5GlcNAc_2$.

Example 12

Culturing Conditions for POX2 Promoter Controlled Gene Expression

Cultures were started from a single colony of a fresh plate and grown overnight in 10 mL YPD at 28° C. in a 50 mL tube in an orbital shaker at 250 rpm. Next, a 250 mL shake flask containing 22 mL of production medium (including 2.5 mL oleic acid emulsion) was inoculated with the preculture at a final OD600 of 0.2. This culture was incubated at 28° C. in an orbital shaker at 250 rpm. Samples of the culture were taken at various time points over a 96 hour culture.

The Oleic Acid Emulsion (20%) was Made the Method as Follows:
Add to a sterile 50 ml vessel;
20 ml sterile water;
5 ml oleic acid; and
125 µl Tween 40.
Sonication resulting in the formation of the emulsion was performed for one minute at 75 Hz.
The Production Medium Consisted of the Following:
1% yeast extract;
2% trypton;
1% glucose; and
50 mM phosphate pH 6.8.

Example 13

Expression of Human Glucocerebrosidase

Human glucocerebrosidase (GLCM, Swiss Prot entry nr: P04062) was chemically synthesized as a codon-optimized cDNA for expression in *Yarrowia lipolytica* (SEQ ID NO:15; FIG. 50).

The coding sequence for the mature protein was fused to the coding sequence of the LIP2 pre signal sequence. This fusion construct was cloned under control of the oleic acid inducible POX2 promoter. The resulting plasmid was named pYLPUXL2preGLCM (=pRAN21)). Before transformation, the plasmid was digested with NotI and the fragment containing the expression cassette was isolated and transformed to *Yarrowia lipolytica* strain MTLY60, MTLY60Δoch1 (described in Example 2 above), and MTLY60Δoch1ManHDEL (described in Example 11). Transformants obtained in these three strains were grown as described in Example 12. Proteins were precipitated from the supernatant as described above, subjected to SDS-PAGE, and immunoblotted using a rat monoclonal anti-glucocerebrosidase antibody (Alessandrini et al. (2004) J. Invest. Dermatol 23(6):1030-6). An exemplary immunoblot analysis is depicted in FIG. 51. It can be appreciated from FIG. 51 that in a och1 disrupted strain no smearing occurs (lanes 1, 2, and 3), whereas heterogeneity of the protein is seen as a smear in WT cells (lanes 4 and 6). No smearing of protein was observed in protein obtained from a strain of yeast expressing ManHDEL. These results demonstrate that a more homogeneous population of a target protein can be obtained using the genetically engineered *Yarrowia lipolytica* cells MTLY60Δoch1 and MTLY60Δoch1ManHDEL.

Example 14

Expression of Human Erythropoietin

Human erythropoietin (Epo, Swiss Prot entry nr: P01588) encoding cDNA was chemically synthesized codon optimized for expression in *Yarrowia lipolytica* (SEQ ID NO:16; FIG. 52). The cDNA coding sequence for the mature protein was fused to the coding sequence of the LIP2 pre signal sequence. This fusion construct was cloned under control of the oleic acid inducible POX2 promoter. The resulting plasmid was named pYLPUXL2prehuEPO. Before transformation the plasmid was cut NotI and the fragment containing the expression cassette was isolated and transformed to *Yarrowia lipolytica* strain MTLY60Δoch1 (described in Example 2). Transformant candidates were grown as described in Example 12 and secreted proteins were analysed by western blot after SDS PAGE using a monoclonal mouse anti human Epo antibody obtained from R&D systems (clone AE7A5). The EPO product obtained from the cells exhibited very homogenous glycosylation.

Example 15

Expression of Human α-Galactosidase A

Human α-galactosidase A (AGAL, Swiss Prot entry nr: P06280) encoding cDNA was chemically synthesized as a codon-optimized cDNA for expression in *Yarrowia lipolytica* (SEQ ID NO:17; FIG. 53). FIGS. 12A-12H contain the cloning strategy of the galactosidase.

The cDNA coding sequence for the mature protein was fused to the coding sequence of the LIP2 pre signal sequence. This fusion construct was cloned under control of the oleic acid inducible POX2 promoter. The resulting plasmid was named pYLPUXL2preaGalase). Before transformation the plasmid was cut NotI and the fragment containing the expression cassette was isolated and transformed to *Yarrowia lipolytica* strain MTLY60 and MTLY60Δoch1MNN4 (described in Example 4). Transformants obtained in these two strains were grown as described in Example 12. Extracellular proteins obtained from transformants were analyzed by immunoblot after SDS-PAGE analysis. Two antibodies specific for α-galactosidase A (a chicken polyclonal antibody obtained from Abcam (ab28962) and a rabbit polyclonal antibody obtained from Santa Cruz Biotechnology (sc-25823)) were used to detect the expressed human α-galactosidase A protein.

Example 16

Expression of Mannosidase in WT *Yarrowia lipolytica*

Figure 55:
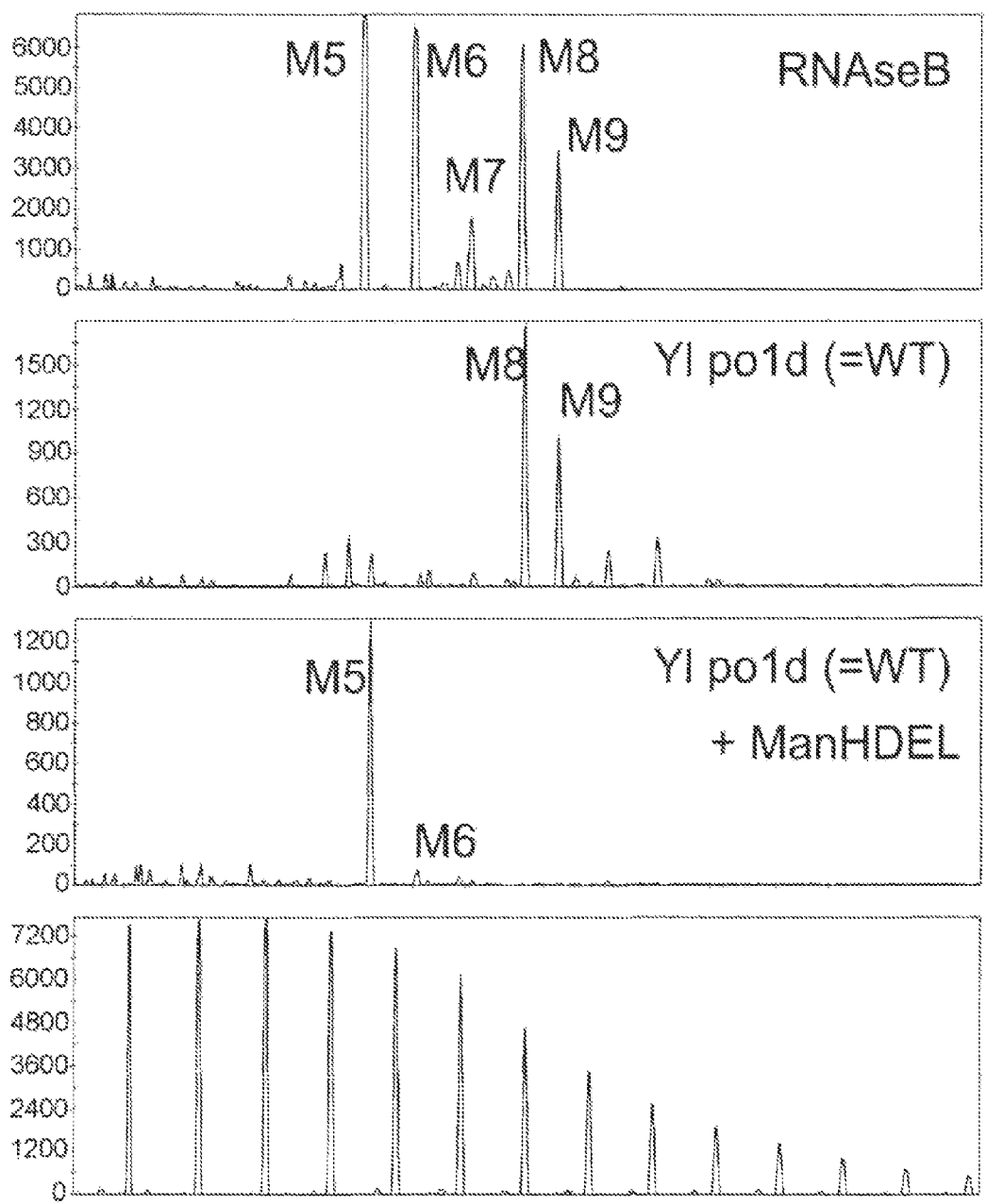
FIG. 55 is a series of electroferograms depicting N-glycan analysis of glycoproteins obtained from WT *Yarrowia lipolytica* cells (pol1d) and *Yarrowia lipolytica* cells expressing a fusion protein of alpha-1,2-mannosidase and a HDEL sequence as indicated. Analysis was performed using DSA-FACE. "M5," "M6," "M7," "M8," and "M9," refer to the number of mannose residues conjugated to the chitobiose core structure. The Y-axis represents the relative fluorescence units as an indication of the amount of each of the mannose structures. The X-axis represents the relative mobility of each complex mannose structure through a gel. The top electroferogram is an analysis of RNAse B. The bottom electroferogram is an analysis of oligomaltose for use as a mobility standard.

To determine whether expression of MannosidaseHDEL alone (that is in cells containing a functional OCH1 gene) could lead to a more homogenous glycosylation of proteins expressed by fungal cells, an expression cassette containing a nucleic acid encoding MannosidaseHDEL (see Example 11) was transformed into wild-type *Yarrowia lipolytica* po1d cells. Glycans derived from secreted proteins obtained from the cells were analysed by DSA-FACE (FIG. 55). The analyzed glycans consisted mainly of $Man_5GlcNAc_2$ and a minor part $Man_6GlcNAc_2$. These results demonstrate that expression of MannosidaseHDEL alone, in the absence of any disruption of the OCH1 gene, leads to a more homogenous glycosylation of proteins expressed by *Yarrowia lipolytica*.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising:
   (a) the nucleotide sequence set forth in SEQ ID NO:1;
   (b) a nucleotide sequence that hybridizes under highly stringent conditions to the complement of the nucleotide sequence set forth in SEQ ID NO:1; or
   (c) the complement of the nucleotide sequence set forth in SEQ ID NO:1.

2. A vector comprising the nucleic acid sequence of claim 1.

3. A cultured cell comprising the vector of claim 2.

4. The cultured cell of claim 3, wherein said cell is a fungal cell.

5. The cultured cell of claim 4, wherein said fungal cell is *Yarrowia lipolytica* or *Arxula adeninivorans*.

6. An isolated nucleic acid comprising a nucleotide sequence that is at least 90% identical to SEQ ID NO:1.

7. A vector comprising the nucleic acid of claim 6.

8. A cultured cell comprising the vector of claim 7.

9. The cultured cell of claim 8, wherein said cell is a fungal cell.

10. The cultured cell of claim 9, wherein said fungal cell is *Yarrowia lipolytica* or *Arxula adeninivorans*.

11. The nucleic acid of claim 6, wherein said nucleotide sequence is at least 95% identical to SEQ ID NO:1.

12. An isolated nucleic acid comprising:
(a) the nucleotide sequence set forth in SEQ ID NO:2;
(b) a nucleotide sequence that hybridizes under highly stringent conditions to the complement of SEQ ID NO:2; or
(c) the complement of the nucleotide sequence set forth in SEQ ID NO:2.

13. A vector comprising the nucleic acid of claim 12.

14. A cultured cell comprising the vector of claim 13.

15. The cultured cell of claim 14, wherein said cell is a fungal cell.

16. The cultured cell of claim 15, wherein said fungal cell is *Yarrowia lipolytica* or *Arxula adeninivorans*.

17. An isolated nucleic acid comprising a nucleotide sequence that is at least 90% identical to SEQ ID NO:2.

18. A vector comprising the nucleic acid of claim 17.

19. A cultured cell comprising the vector of claim 18.

20. The cultured cell of claim 19, wherein said cell is a fungal cell.

21. The cultured cell of claim 20, wherein said fungal cell is *Yarrowia lipolytica* or *Arxula adeninivorans*.

22. The isolated nucleic of claim 17, wherein said nucleotide sequence is at least 95% identical to SEQ ID NO:2.

* * * * *

UNITED STATES PATENT AND TRADEMARK OFFICE
CERTIFICATE OF CORRECTION

PATENT NO. : 8,026,083 B2  
APPLICATION NO. : 12/062469  
DATED : September 27, 2011  
INVENTOR(S) : Nico Luc Marc Callewaert et al.

Page 1 of 1

It is certified that error appears in the above-identified patent and that said Letters Patent is hereby corrected as shown below:

Column 122, line 59, Claim 2, after "acid" delete "sequence."

Column 124, line 14, Claim 22, after "nucleic" insert --acid--.

Signed and Sealed this  
Fourteenth Day of February, 2012

David J. Kappos  
*Director of the United States Patent and Trademark Office*